(12) United States Patent
Frank et al.

(10) Patent No.: US 11,634,677 B2
(45) Date of Patent: Apr. 25, 2023

(54) COATING A BIOREACTOR IN A CELL EXPANSION SYSTEM

(71) Applicant: Terumo BCT, Inc., Lakewood, CO (US)

(72) Inventors: Nathan D. Frank, Arvada, CO (US); Brian J. Nankervis, Golden, CO (US); Dennis J. Hlavinka, Arvada, CO (US); Thomas G. Dilorenzo, Arvada, CO (US)

(73) Assignee: Terumo BCT, Inc., Lakewood, CO (US)

( * ) Notice: Subject to any disclaimer, the term of this patent is extended or adjusted under 35 U.S.C. 154(b) by 0 days.

(21) Appl. No.: 16/845,791

(22) Filed: Apr. 10, 2020

(65) Prior Publication Data

US 2020/0239822 A1 Jul. 30, 2020

Related U.S. Application Data

(62) Division of application No. 15/616,876, filed on Jun. 7, 2017, now Pat. No. 11,104,874.

(Continued)

(51) Int. Cl.
*C12M 3/00* (2006.01)
*C12M 1/00* (2006.01)
(Continued)

(52) U.S. Cl.
CPC ............... *C12M 23/20* (2013.01); *B05D 7/22* (2013.01); *C12M 1/36* (2013.01); *C12M 23/50* (2013.01);
(Continued)

(58) Field of Classification Search
CPC ........ C12M 1/36; C12M 29/18; C12M 23/50; C12M 41/00; C12M 41/48; C12M 29/10;
(Continued)

(56) References Cited

U.S. PATENT DOCUMENTS 2,997,077 A 8/1961 Rodrigues
3,013,435 A 12/1961 Rodrigues
(Continued)

FOREIGN PATENT DOCUMENTS

CA 1016332 A 8/1977
CN 102406926 4/2012
(Continued)

OTHER PUBLICATIONS

Chang et al., "Membrane Bioreactors: Present and Prospects", Advances in Biochemical Engineering, 1991, pp. 27-64, vol. 44.
(Continued)

*Primary Examiner* — Nathan A Bowers
(74) *Attorney, Agent, or Firm* — Harness, Dickey & Pierce, P.L.C.

(57) ABSTRACT

Embodiments described herein generally provide for the expansion of cells in a cell expansion system using an active promotion of a coating agent(s) to a cell growth surface in some embodiments. A coating agent may be applied to a surface, such as the cell growth surface of a hollow fiber in a bioreactor, by controlling the movement of a fluid in which a coating agent is suspended, by changing flow rates, by changing flow directions, by rotation of the bioreactor, and/or combinations thereof.

18 Claims, 34 Drawing Sheets

Related U.S. Application Data

(60) Provisional application No. 62/347,012, filed on Jun. 7, 2016, provisional application No. 62/347,025, filed on Jun. 7, 2016.

(51) Int. Cl.

| | |
|---|---|
| C12M 1/36 | (2006.01) |
| C12M 1/34 | (2006.01) |
| C12Q 3/00 | (2006.01) |
| C12N 5/0775 | (2010.01) |
| C12M 1/12 | (2006.01) |
| B05D 7/22 | (2006.01) |
| C12M 3/04 | (2006.01) |

(52) U.S. Cl.
CPC ............ *C12M 25/10* (2013.01); *C12M 25/12* (2013.01); *C12M 27/10* (2013.01); *C12M 29/10* (2013.01); *C12M 29/16* (2013.01); *C12M 29/18* (2013.01); *C12M 41/00* (2013.01); *C12M 41/48* (2013.01); *C12N 5/0662* (2013.01); *C12N 5/0663* (2013.01); *C12Q 3/00* (2013.01); *B05D 2254/00* (2013.01); *B05D 2259/00* (2013.01)

(58) Field of Classification Search
CPC ...... C12M 25/10; C12M 25/12; C12M 29/16; C12M 27/10; C12M 23/20; C12N 5/0663; C12N 5/0662; C12Q 3/00; B05D 7/22; B05D 2254/00; B05D 2259/00
See application file for complete search history.

(56) References Cited

U.S. PATENT DOCUMENTS

| | | |
|---|---|---|
| 3,067,915 A | 12/1962 | Shapiro et al. |
| 3,191,807 A | 6/1965 | Rodrigues |
| 3,283,727 A | 11/1966 | Rodrigues |
| 3,701,717 A | 10/1972 | Ingvorsen |
| 3,821,087 A | 6/1974 | Knazek et al. |
| 3,896,061 A | 7/1975 | Tanzawa et al. |
| 4,173,415 A | 11/1979 | Wyatt |
| 4,301,010 A | 11/1981 | Eddleman et al. |
| 4,301,118 A | 11/1981 | Eddleman et al. |
| 4,391,912 A | 7/1983 | Yoshida et al. |
| 4,412,990 A | 11/1983 | Lundblad et al. |
| 4,418,691 A | 12/1983 | Yannas et al. |
| 4,439,322 A | 3/1984 | Sonoda et al. |
| 4,439,901 A | 4/1984 | Eddleman |
| 4,478,829 A | 10/1984 | Landaburu et al. |
| 4,486,188 A | 12/1984 | Altshuler et al. |
| 4,509,695 A | 4/1985 | Bessman |
| 4,585,654 A | 4/1986 | Landaburu et al. |
| 4,618,586 A | 10/1986 | Walker et al. |
| 4,629,686 A | 12/1986 | Gruenberg |
| 4,647,539 A | 3/1987 | Bach |
| 4,650,766 A | 3/1987 | Harm et al. |
| 4,670,544 A | 6/1987 | Schwinn et al. |
| 4,705,918 A | 11/1987 | Harmon |
| 4,722,902 A | 2/1988 | Harm et al. |
| 4,727,059 A | 2/1988 | Binder et al. |
| 4,804,628 A | 2/1989 | Cracauer et al. |
| 4,828,706 A | 5/1989 | Eddleman |
| 4,885,087 A | 12/1989 | Kopf |
| 4,889,812 A | 12/1989 | Guinn et al. |
| 4,894,342 A | 1/1990 | Guinn et al. |
| 4,897,358 A | 1/1990 | Carrasco |
| 4,918,019 A | 4/1990 | Guinn |
| 4,940,541 A | 7/1990 | Aoyagi |
| 4,960,521 A | 10/1990 | Keller |
| 4,973,558 A | 11/1990 | Wilson et al. |
| 4,988,623 A | 1/1991 | Schwarz et al. |
| 5,015,585 A | 5/1991 | Robinson |
| 5,019,054 A | 5/1991 | Clement et al. |
| 5,079,168 A | 1/1992 | Amiot |
| 5,126,238 A | 6/1992 | Gebhard et al. |
| 5,130,141 A | 7/1992 | Law et al. |
| 5,149,544 A | 9/1992 | Gentile et al. |
| 5,162,225 A | 11/1992 | Sager et al. |
| 5,169,930 A | 12/1992 | Ruoslahti et al. |
| 5,192,553 A | 3/1993 | Boyse et al. |
| 5,197,985 A | 3/1993 | Caplan et al. |
| 5,202,254 A | 4/1993 | Amiot |
| 5,225,346 A | 7/1993 | Matsumiya et al. |
| 5,226,914 A | 7/1993 | Caplan et al. |
| 5,240,614 A | 8/1993 | Ofsthun et al. |
| 5,240,861 A | 8/1993 | Bieri |
| 5,283,058 A | 2/1994 | Faustman |
| 5,310,676 A | 5/1994 | Johansson et al. |
| 5,324,428 A | 6/1994 | Flaherty |
| 5,330,915 A | 7/1994 | Wilson et al. |
| 5,342,752 A | 8/1994 | Platz et al. |
| 5,399,493 A | 3/1995 | Emerson et al. |
| 5,416,022 A | 5/1995 | Amiot |
| 5,422,197 A | 6/1995 | Zito |
| 5,436,151 A | 7/1995 | McGlave et al. |
| 5,437,994 A | 8/1995 | Emerson et al. |
| 5,439,757 A | 8/1995 | Zito |
| 5,459,069 A | 10/1995 | Palsson et al. |
| 5,460,964 A | 10/1995 | McGlave et al. |
| H1509 H | 12/1995 | Eran et al. |
| 5,478,739 A | 12/1995 | Slivka et al. |
| 5,486,359 A | 1/1996 | Caplan et al. |
| 5,496,659 A | 3/1996 | Zito |
| 5,507,949 A | 4/1996 | Ho |
| 5,510,257 A | 4/1996 | Sirkar et al. |
| 5,512,180 A | 4/1996 | Ho |
| 5,527,467 A | 6/1996 | Ofsthun et al. |
| 5,541,105 A | 7/1996 | Melink et al. |
| 5,543,316 A | 8/1996 | Zawadzka et al. |
| 5,545,492 A | 8/1996 | Zito |
| 5,549,674 A | 8/1996 | Humes et al. |
| 5,571,720 A | 11/1996 | Grandies et al. |
| 5,591,625 A | 1/1997 | Gerson et al. |
| 5,593,580 A | 1/1997 | Kopf |
| 5,595,909 A | 1/1997 | Hu et al. |
| 5,599,703 A | 2/1997 | Davis et al. |
| 5,605,822 A | 2/1997 | Emerson et al. |
| 5,605,829 A | 2/1997 | McGlave et al. |
| 5,605,835 A | 2/1997 | Hu et al. |
| 5,622,857 A | 4/1997 | Goffe |
| 5,626,731 A | 5/1997 | Cooley et al. |
| 5,627,070 A | 5/1997 | Gruenberg |
| 5,631,006 A | 5/1997 | Melink et al. |
| 5,635,386 A | 6/1997 | Palsson et al. |
| 5,635,387 A | 6/1997 | Fei et al. |
| 5,643,736 A | 7/1997 | Bruder et al. |
| 5,643,794 A | 7/1997 | Liu et al. |
| 5,646,043 A | 7/1997 | Emerson et al. |
| 5,654,186 A | 8/1997 | Cerami et al. |
| 5,656,421 A | 8/1997 | Gebhard et al. |
| 5,658,995 A | 8/1997 | Kohn et al. |
| 5,667,985 A | 9/1997 | O'Leary et al. |
| 5,670,147 A | 9/1997 | Emerson et al. |
| 5,670,351 A | 9/1997 | Emerson et al. |
| 5,674,750 A | 10/1997 | Kraus et al. |
| 5,684,712 A | 11/1997 | Goffe et al. |
| 5,686,289 A | 11/1997 | Humes et al. |
| 5,688,687 A | 11/1997 | Palsson et al. |
| 5,695,989 A | 12/1997 | Kalamasz |
| 5,700,289 A | 12/1997 | Breitbart et al. |
| 5,705,534 A | 1/1998 | D'Agostino et al. |
| 5,707,859 A | 1/1998 | Miller et al. |
| 5,712,163 A | 1/1998 | Parenteau et al. |
| 5,728,581 A | 3/1998 | Schwartz et al. |
| 5,733,541 A | 3/1998 | Taichman et al. |
| 5,733,542 A | 3/1998 | Haynesworth et al. |
| 5,736,396 A | 4/1998 | Bruder et al. |
| 5,744,347 A | 4/1998 | Wagner et al. |
| 5,750,651 A | 5/1998 | Oppermann et al. |
| 5,753,506 A | 5/1998 | Johe |
| 5,763,194 A | 6/1998 | Slowiaczek et al. |
| 5,763,197 A | 6/1998 | Tsukamoto et al. |

(56) References Cited

U.S. PATENT DOCUMENTS

| | | |
|---|---|---|
| 5,763,261 A | 6/1998 | Gruenberg |
| 5,763,266 A | 6/1998 | Palsson et al. |
| 5,766,944 A | 6/1998 | Ruiz |
| 5,772,994 A | 6/1998 | Ildstad et al. |
| 5,783,075 A | 7/1998 | Eddleman et al. |
| 5,783,216 A | 7/1998 | Faustman |
| 5,785,912 A | 7/1998 | Cooley et al. |
| 5,804,446 A | 9/1998 | Cerami et al. |
| 5,806,529 A | 9/1998 | Reisner et al. |
| 5,807,686 A | 9/1998 | Wagner et al. |
| 5,811,094 A | 9/1998 | Caplan et al. |
| 5,811,397 A | 9/1998 | Francavilla et al. |
| 5,817,773 A | 10/1998 | Wilson et al. |
| 5,821,218 A | 10/1998 | Toback et al. |
| 5,827,735 A | 10/1998 | Young et al. |
| 5,827,740 A | 10/1998 | Pittenger |
| 5,830,921 A | 11/1998 | Cooley et al. |
| 5,833,979 A | 11/1998 | Schinstine et al. |
| 5,837,258 A | 11/1998 | Grotendorst |
| 5,837,539 A | 11/1998 | Caplan et al. |
| 5,840,502 A | 11/1998 | Van Vlasselaer |
| 5,840,576 A | 11/1998 | Schinstine et al. |
| 5,840,580 A | 11/1998 | Terstappen et al. |
| 5,842,477 A | 12/1998 | Naughton et al. |
| 5,843,633 A | 12/1998 | Yin et al. |
| 5,846,796 A | 12/1998 | Cerami et al. |
| 5,853,247 A | 12/1998 | Shroyer |
| 5,853,717 A | 12/1998 | Schinstine et al. |
| 5,855,608 A | 1/1999 | Brekke et al. |
| 5,855,613 A | 1/1999 | Antanavich et al. |
| 5,855,619 A | 1/1999 | Caplan et al. |
| 5,858,747 A | 1/1999 | Schinstine et al. |
| 5,858,782 A | 1/1999 | Long et al. |
| 5,861,315 A | 1/1999 | Nakahata |
| 5,866,115 A | 2/1999 | Kanz et al. |
| 5,866,420 A | 2/1999 | Talbot et al. |
| 5,868,930 A | 2/1999 | Kopf |
| 5,882,295 A | 3/1999 | Kope |
| 5,882,918 A | 3/1999 | Goffe |
| 5,882,929 A | 3/1999 | Fofonoff et al. |
| 5,888,807 A | 3/1999 | Palsson et al. |
| 5,902,741 A | 5/1999 | Purchio et al. |
| 5,906,827 A | 5/1999 | Khouri et al. |
| 5,906,934 A | 5/1999 | Grande et al. |
| 5,908,782 A | 6/1999 | Marshak et al. |
| 5,908,784 A | 6/1999 | Johnstone et al. |
| 5,912,177 A | 6/1999 | Turner et al. |
| 5,914,108 A | 6/1999 | Tsukamoto et al. |
| 5,922,597 A | 7/1999 | Verfaillie et al. |
| 5,922,847 A | 7/1999 | Broudy et al. |
| 5,925,567 A | 7/1999 | Kraus et al. |
| 5,928,945 A | 7/1999 | Seliktar et al. |
| 5,935,849 A | 8/1999 | Schinstine et al. |
| 5,938,929 A | 8/1999 | Shimagaki et al. |
| 5,939,323 A | 8/1999 | Valentini et al. |
| 5,942,225 A | 8/1999 | Bruder et al. |
| 5,955,353 A | 9/1999 | Amiot |
| 5,958,763 A | 9/1999 | Goffe |
| 5,965,436 A | 10/1999 | Thiede et al. |
| 5,972,703 A | 10/1999 | Long et al. |
| 5,980,795 A | 11/1999 | Klotzer et al. |
| 5,981,211 A | 11/1999 | Hu et al. |
| 5,981,708 A | 11/1999 | Lawman et al. |
| 5,985,653 A | 11/1999 | Armstrong et al. |
| 5,994,129 A | 11/1999 | Armstrong et al. |
| 5,998,184 A | 12/1999 | Shi |
| 6,001,585 A | 12/1999 | Gramer |
| 6,001,643 A | 12/1999 | Spaulding |
| 6,001,647 A | 12/1999 | Peck et al. |
| 6,004,743 A | 12/1999 | Kenyon et al. |
| 6,010,696 A | 1/2000 | Caplan et al. |
| 6,015,554 A | 1/2000 | Galy |
| 6,022,540 A | 2/2000 | Bruder et al. |
| 6,022,742 A | 2/2000 | Kopf |
| 6,022,743 A | 2/2000 | Naughton et al. |
| 6,027,743 A | 2/2000 | Khouri et al. |
| 6,030,836 A | 2/2000 | Thiede et al. |
| 6,040,180 A | 3/2000 | Johe |
| 6,045,818 A | 4/2000 | Cima et al. |
| 6,048,721 A | 4/2000 | Armstrong et al. |
| 6,048,727 A | 4/2000 | Kopf |
| 6,049,026 A | 4/2000 | Muschler |
| 6,054,121 A | 4/2000 | Cerami et al. |
| 6,060,270 A | 5/2000 | Humes |
| 6,066,317 A | 5/2000 | Yang et al. |
| 6,071,691 A | 6/2000 | Hoekstra et al. |
| 6,074,366 A | 6/2000 | Rogers et al. |
| 6,082,364 A | 7/2000 | Balian et al. |
| 6,083,747 A | 7/2000 | Wong et al. |
| 6,086,643 A | 7/2000 | Clark et al. |
| 6,087,113 A | 7/2000 | Caplan et al. |
| 6,096,532 A | 8/2000 | Armstrong et al. |
| 6,096,537 A | 8/2000 | Chappel |
| 6,103,117 A | 8/2000 | Shimagaki et al. |
| 6,103,522 A | 8/2000 | Torok-Storb et al. |
| 6,110,176 A | 8/2000 | Shapira |
| 6,110,482 A | 8/2000 | Khouri et al. |
| 6,114,307 A | 9/2000 | Jaspers et al. |
| 6,117,985 A | 9/2000 | Thomas et al. |
| 6,120,491 A | 9/2000 | Kohn et al. |
| 6,127,141 A | 10/2000 | Kopf |
| 6,129,911 A | 10/2000 | Faris |
| 6,143,293 A | 11/2000 | Weiss et al. |
| 6,146,360 A | 11/2000 | Rogers et al. |
| 6,146,888 A | 11/2000 | Smith et al. |
| 6,149,902 A | 11/2000 | Artavanis-Tsakonas et al. |
| 6,149,906 A | 11/2000 | Mosca |
| 6,150,164 A | 11/2000 | Humes |
| 6,152,964 A | 11/2000 | Van Blitterswijk et al. |
| 6,162,643 A | 12/2000 | Wille, Jr. |
| 6,165,225 A | 12/2000 | Antanavich et al. |
| 6,165,785 A | 12/2000 | Ogle et al. |
| 6,174,333 B1 | 1/2001 | Kadiyala et al. |
| 6,174,526 B1 | 1/2001 | Cerami et al. |
| 6,174,666 B1 | 1/2001 | Pavlakis et al. |
| 6,179,871 B1 | 1/2001 | Halpern |
| 6,197,325 B1 | 3/2001 | MacPhee et al. |
| 6,197,575 B1 | 3/2001 | Griffith et al. |
| 6,200,606 B1 | 3/2001 | Peterson et al. |
| 6,214,369 B1 | 4/2001 | Grande et al. |
| 6,214,574 B1 | 4/2001 | Kopf |
| 6,224,860 B1 | 5/2001 | Brown |
| 6,225,119 B1 | 5/2001 | Qasba et al. |
| 6,225,368 B1 | 5/2001 | D'Agostino et al. |
| 6,228,117 B1 | 5/2001 | De Bruijn et al. |
| 6,228,607 B1 | 5/2001 | Kersten et al. |
| 6,228,635 B1 | 5/2001 | Armstrong et al. |
| 6,238,908 B1 | 5/2001 | Armstrong et al. |
| 6,239,157 B1 | 5/2001 | Mbalaviele |
| 6,242,252 B1 | 6/2001 | Reid et al. |
| 6,248,319 B1 | 6/2001 | Zsebo et al. |
| 6,248,587 B1 | 6/2001 | Rodgers et al. |
| 6,255,112 B1 | 7/2001 | Thiede et al. |
| 6,258,597 B1 | 7/2001 | Bachovchin et al. |
| 6,258,778 B1 | 7/2001 | Rodgers et al. |
| 6,261,549 B1 | 7/2001 | Fernandez et al. |
| 6,280,718 B1 | 8/2001 | Kaufman et al. |
| 6,280,724 B1 | 8/2001 | Moore |
| 6,281,012 B1 | 8/2001 | McIntosh et al. |
| 6,281,195 B1 | 8/2001 | Rueger et al. |
| 6,287,864 B1 | 9/2001 | Bagnis et al. |
| 6,291,249 B1 | 9/2001 | Mahant et al. |
| 6,297,213 B1 | 10/2001 | Oppermann et al. |
| 6,299,650 B1 | 10/2001 | Van Blitterswijk et al. |
| 6,306,424 B1 | 10/2001 | Vyakarnam et al. |
| 6,306,575 B1 | 10/2001 | Thomas et al. |
| 6,322,784 B1 | 11/2001 | Pittenger et al. |
| 6,322,786 B1 | 11/2001 | Anderson |
| 6,326,198 B1 | 12/2001 | Emerson et al. |
| 6,326,201 B1 | 12/2001 | Fung et al. |
| 6,328,765 B1 | 12/2001 | Hardwick et al. |
| 6,328,960 B1 | 12/2001 | McIntosh et al. |
| 6,333,029 B1 | 12/2001 | Vyakarnam et al. |
| 6,335,195 B1 | 1/2002 | Rodgers et al. |

(56) References Cited

U.S. PATENT DOCUMENTS

| | | |
|---|---|---|
| 6,338,942 B2 | 1/2002 | Kraus et al. |
| 6,340,592 B1 | 1/2002 | Stringer |
| 6,342,370 B1 | 1/2002 | Connolly et al. |
| 6,355,239 B1 | 3/2002 | Bruder et al. |
| 6,358,252 B1 | 3/2002 | Shapira |
| 6,361,997 B1 | 3/2002 | Huss |
| 6,365,149 B2 | 4/2002 | Vyakarnam et al. |
| 6,368,636 B1 | 4/2002 | McIntosh et al. |
| 6,372,210 B2 | 4/2002 | Brown |
| 6,372,244 B1 | 4/2002 | Antanavich et al. |
| 6,372,494 B1 | 4/2002 | Naughton et al. |
| 6,372,495 B1 | 4/2002 | Flendrig |
| 6,372,892 B1 | 4/2002 | Ballinger et al. |
| 6,376,742 B1 | 4/2002 | Zdrahala et al. |
| 6,379,953 B1 | 4/2002 | Bruder et al. |
| 6,387,367 B1 | 5/2002 | Davis-Sproul et al. |
| 6,387,369 B1 | 5/2002 | Pittenger et al. |
| 6,387,693 B2 | 5/2002 | Rieser et al. |
| 6,387,964 B1 | 5/2002 | D'Agostino et al. |
| 6,392,118 B1 | 5/2002 | Hammang et al. |
| 6,394,812 B1 | 5/2002 | Sullivan et al. |
| 6,399,580 B1 | 6/2002 | Elias et al. |
| 6,410,320 B1 | 6/2002 | Humes |
| 6,414,219 B1 | 7/2002 | Denhardt et al. |
| 6,416,496 B1 | 7/2002 | Rogers et al. |
| 6,417,205 B1 | 7/2002 | Cooke et al. |
| 6,419,829 B2 | 7/2002 | Ho et al. |
| 6,420,138 B1 | 7/2002 | Gentz et al. |
| 6,423,681 B1 | 7/2002 | Barasch et al. |
| 6,426,332 B1 | 7/2002 | Rueger et al. |
| 6,428,802 B1 | 8/2002 | Atala |
| 6,429,012 B1 | 8/2002 | Kraus et al. |
| 6,429,013 B1 | 8/2002 | Halvorsen et al. |
| 6,432,653 B1 | 8/2002 | Okarma |
| 6,432,711 B1 | 8/2002 | Dinsmore et al. |
| 6,440,407 B1 | 8/2002 | Bauer et al. |
| 6,440,734 B1 | 8/2002 | Pykett et al. |
| 6,451,562 B1 | 9/2002 | Ruben et al. |
| 6,454,811 B1 | 9/2002 | Sherwood et al. |
| 6,455,678 B1 | 9/2002 | Yin et al. |
| 6,458,585 B1 | 10/2002 | Vachula et al. |
| 6,458,589 B1 | 10/2002 | Rambhatla et al. |
| 6,461,495 B1 | 10/2002 | Morrissey et al. |
| 6,461,853 B1 | 10/2002 | Zhu |
| 6,464,983 B1 | 10/2002 | Grotendorst |
| 6,465,205 B2 | 10/2002 | Hicks, Jr. |
| 6,465,247 B1 | 10/2002 | Weissman et al. |
| 6,465,249 B2 | 10/2002 | Reya et al. |
| 6,468,794 B1 | 10/2002 | Uchida et al. |
| 6,472,200 B1 | 10/2002 | Mitrani |
| 6,475,481 B2 | 11/2002 | Talmadge |
| 6,479,064 B1 | 11/2002 | Atala |
| 6,482,231 B1 | 11/2002 | Abatangelo et al. |
| 6,482,411 B1 | 11/2002 | Ahuja et al. |
| 6,482,645 B2 | 11/2002 | Atala |
| 6,482,926 B1 | 11/2002 | Thomas et al. |
| 6,488,925 B2 | 12/2002 | Ruben et al. |
| 6,491,918 B1 | 12/2002 | Thomas et al. |
| 6,495,129 B1 | 12/2002 | Li et al. |
| 6,495,364 B2 | 12/2002 | Hammang et al. |
| 6,497,875 B1 | 12/2002 | Sorrell et al. |
| 6,498,034 B1 | 12/2002 | Strobl |
| 6,506,574 B1 | 1/2003 | Rambhatla et al. |
| 6,511,510 B1 | 1/2003 | de Bruijn et al. |
| 6,511,767 B1 | 1/2003 | Calver et al. |
| 6,511,958 B1 | 1/2003 | Atkinson et al. |
| 6,514,514 B1 | 2/2003 | Atkinson et al. |
| 6,524,452 B1 | 2/2003 | Clark et al. |
| 6,528,052 B1 | 3/2003 | Smith et al. |
| 6,528,245 B2 | 3/2003 | Sanchez-Ramos et al. |
| 6,531,445 B1 | 3/2003 | Cohen et al. |
| 6,534,084 B1 | 3/2003 | Vyakarnam et al. |
| 6,537,807 B1 | 3/2003 | Smith et al. |
| 6,541,024 B1 | 4/2003 | Kadiyala et al. |
| 6,541,249 B2 | 4/2003 | Wager et al. |
| 6,544,506 B2 | 4/2003 | Reisner |
| 6,548,734 B1 | 4/2003 | Glimcher et al. |
| 6,555,324 B1 | 4/2003 | Olweus et al. |
| 6,555,374 B1 | 4/2003 | Gimble et al. |
| 6,559,119 B1 | 5/2003 | Burgess et al. |
| 6,562,616 B1 | 5/2003 | Toner et al. |
| 6,565,843 B1 | 5/2003 | Cohen et al. |
| 6,566,126 B2 | 5/2003 | Cadwell |
| 6,569,421 B2 | 5/2003 | Hodges |
| 6,569,427 B1 | 5/2003 | Boyse et al. |
| 6,569,428 B1 | 5/2003 | Isner et al. |
| 6,569,654 B2 | 5/2003 | Shastri et al. |
| 6,576,188 B1 | 6/2003 | Rose et al. |
| 6,576,428 B1 | 6/2003 | Assenmacher et al. |
| 6,576,464 B2 | 6/2003 | Gold et al. |
| 6,576,465 B1 | 6/2003 | Long |
| 6,582,471 B1 | 6/2003 | Bittmann et al. |
| 6,582,955 B2 | 6/2003 | Martinez et al. |
| 6,586,192 B1 | 7/2003 | Peschle et al. |
| 6,589,728 B2 | 7/2003 | Csete et al. |
| 6,589,786 B1 | 7/2003 | Mangano et al. |
| 6,596,274 B1 | 7/2003 | Abatangelo et al. |
| 6,599,300 B2 | 7/2003 | Vibe-Hansen et al. |
| 6,599,520 B2 | 7/2003 | Scarborough et al. |
| 6,610,535 B1 | 8/2003 | Lu et al. |
| 6,613,798 B1 | 9/2003 | Porter et al. |
| 6,616,912 B2 | 9/2003 | Eddleman et al. |
| 6,617,070 B1 | 9/2003 | Morrissey et al. |
| 6,617,152 B2 | 9/2003 | Bryhan et al. |
| 6,617,159 B1 | 9/2003 | Cancedda et al. |
| 6,623,749 B2 | 9/2003 | Williams et al. |
| 6,623,942 B2 | 9/2003 | Ruben et al. |
| 6,624,108 B1 | 9/2003 | Clark et al. |
| 6,626,950 B2 | 9/2003 | Brown et al. |
| 6,627,191 B1 | 9/2003 | Bartelmez et al. |
| 6,632,425 B1 | 10/2003 | Li et al. |
| 6,632,620 B1 | 10/2003 | Makarovskiy |
| 6,632,934 B1 | 10/2003 | Moreadith et al. |
| 6,638,765 B1 | 10/2003 | Rosenberg |
| 6,642,019 B1 | 11/2003 | Anderson et al. |
| 6,642,048 B2 | 11/2003 | Xu et al. |
| 6,642,049 B1 | 11/2003 | Chute et al. |
| 6,642,201 B1 | 11/2003 | Khavinson et al. |
| 6,645,489 B2 | 11/2003 | Pykett et al. |
| 6,645,727 B2 | 11/2003 | Thomas et al. |
| 6,645,763 B2 | 11/2003 | Kobayashi et al. |
| 6,649,189 B2 | 11/2003 | Talmadge et al. |
| 6,649,595 B2 | 11/2003 | Clackson et al. |
| 6,649,631 B1 | 11/2003 | Orme et al. |
| 6,653,105 B2 | 11/2003 | Triglia et al. |
| 6,653,134 B2 | 11/2003 | Prockop et al. |
| 6,660,523 B2 | 12/2003 | Blom et al. |
| 6,662,805 B2 | 12/2003 | Frondoza et al. |
| 6,667,034 B2 | 12/2003 | Palsson et al. |
| 6,667,176 B1 | 12/2003 | Funk et al. |
| 6,670,169 B1 | 12/2003 | Schob et al. |
| 6,670,175 B2 | 12/2003 | Wang et al. |
| 6,673,603 B2 | 1/2004 | Baetge et al. |
| 6,673,606 B1 | 1/2004 | Tennekoon et al. |
| 6,677,306 B1 | 1/2004 | Veis et al. |
| 6,680,166 B1 | 1/2004 | Mullon et al. |
| 6,683,192 B2 | 1/2004 | Baxter et al. |
| 6,685,936 B2 | 2/2004 | McIntosh et al. |
| 6,685,971 B2 | 2/2004 | Xu |
| 6,686,198 B1 | 2/2004 | Melton et al. |
| 6,696,575 B2 | 2/2004 | Schmidt et al. |
| 6,699,716 B2 | 3/2004 | Sullivan et al. |
| 6,703,017 B1 | 3/2004 | Peck et al. |
| 6,703,209 B1 | 3/2004 | Baetscher et al. |
| 6,706,293 B1 | 3/2004 | Quintanilla Almagro et al. |
| 6,709,864 B1 | 3/2004 | Pittenger et al. |
| 6,712,850 B2 | 3/2004 | Vyakarnam et al. |
| 6,719,969 B1 | 4/2004 | Hogaboam et al. |
| 6,719,970 B1 | 4/2004 | Costantino et al. |
| 6,720,340 B1 | 4/2004 | Cooke et al. |
| 6,730,314 B2 | 5/2004 | Jeschke et al. |
| 6,730,315 B2 | 5/2004 | Usala et al. |
| 6,730,510 B2 | 5/2004 | Roos et al. |
| 6,733,746 B2 | 5/2004 | Daley et al. |

(56) References Cited

U.S. PATENT DOCUMENTS

| | | |
|---|---|---|
| 6,734,000 B2 | 5/2004 | Chin et al. |
| 6,740,493 B1 | 5/2004 | Long et al. |
| 6,759,039 B2 | 7/2004 | Tsang et al. |
| 6,759,245 B1 | 7/2004 | Toner et al. |
| 6,761,883 B2 | 7/2004 | Weissman et al. |
| 6,761,887 B1 | 7/2004 | Kavalkovich et al. |
| 6,767,699 B2 | 7/2004 | Polo et al. |
| 6,767,737 B1 | 7/2004 | Wilson et al. |
| 6,767,738 B1 | 7/2004 | Gage et al. |
| 6,767,740 B2 | 7/2004 | Sramek et al. |
| 6,770,478 B2 | 8/2004 | Crowe et al. |
| 6,777,227 B2 | 8/2004 | Ricci et al. |
| 6,777,231 B1 | 8/2004 | Katz et al. |
| 6,780,612 B1 | 8/2004 | Ford et al. |
| 6,787,355 B1 | 9/2004 | Miller et al. |
| 6,790,455 B2 | 9/2004 | Chu et al. |
| 6,793,939 B2 | 9/2004 | Badylak |
| 6,797,269 B2 | 9/2004 | Mosca et al. |
| 6,797,514 B2 | 9/2004 | Berenson et al. |
| 6,800,480 B1 | 10/2004 | Bodnar et al. |
| 6,802,971 B2 | 10/2004 | Gorsuch et al. |
| 6,805,860 B1 | 10/2004 | Alt |
| 6,809,117 B2 | 10/2004 | Enikolopov et al. |
| 6,811,773 B1 | 11/2004 | Gentz et al. |
| 6,811,776 B2 | 11/2004 | Kale et al. |
| 6,814,961 B1 | 11/2004 | Jensen et al. |
| 6,821,513 B1 | 11/2004 | Fleming |
| 6,821,790 B2 | 11/2004 | Mahant et al. |
| 6,828,145 B2 | 12/2004 | Avital et al. |
| 6,833,269 B2 | 12/2004 | Carpenter |
| 6,835,377 B2 | 12/2004 | Goldberg et al. |
| 6,835,566 B2 | 12/2004 | Smith et al. |
| 6,838,284 B2 | 1/2005 | de Bruijn et al. |
| 6,841,150 B2 | 1/2005 | Halvorsen et al. |
| 6,841,151 B2 | 1/2005 | Stringer |
| 6,841,294 B1 | 1/2005 | Morrissey et al. |
| 6,841,355 B2 | 1/2005 | Livant |
| 6,841,386 B2 | 1/2005 | Kraus et al. |
| 6,841,542 B2 | 1/2005 | Bartelmez et al. |
| 6,844,011 B1 | 1/2005 | Faustman |
| 6,844,187 B1 | 1/2005 | Weschler et al. |
| 6,849,051 B2 | 2/2005 | Sramek et al. |
| 6,849,255 B2 | 2/2005 | Gazit et al. |
| 6,849,454 B2 | 2/2005 | Kelly et al. |
| 6,849,662 B2 | 2/2005 | Enikolopov et al. |
| 6,852,308 B2 | 2/2005 | Kohn et al. |
| 6,852,321 B2 | 2/2005 | Colucci et al. |
| 6,852,533 B1 | 2/2005 | Rafii et al. |
| 6,855,242 B1 | 2/2005 | Comninellis et al. |
| 6,855,542 B2 | 2/2005 | DiMilla et al. |
| 6,863,900 B2 | 3/2005 | Kadiyala et al. |
| 6,866,843 B2 | 3/2005 | Habener et al. |
| 6,872,389 B1 | 3/2005 | Faris |
| 6,875,430 B2 | 4/2005 | McIntosh et al. |
| 6,887,600 B2 | 5/2005 | Morrissey et al. |
| 6,887,704 B2 | 5/2005 | Peled et al. |
| 6,908,763 B1 | 6/2005 | Akashi et al. |
| 6,911,201 B1 | 6/2005 | Merchav et al. |
| 6,914,279 B2 | 7/2005 | Lu et al. |
| 6,939,955 B2 | 9/2005 | Rameshwar |
| 6,943,008 B1 | 9/2005 | Ma |
| 6,965,018 B2 | 11/2005 | Mikesell et al. |
| 6,969,308 B2 | 11/2005 | Doi et al. |
| 6,979,308 B1 | 12/2005 | MacDonald et al. |
| 6,979,321 B2 | 12/2005 | Geis et al. |
| 6,988,004 B2 | 1/2006 | Kanno et al. |
| 7,008,394 B2 | 3/2006 | Geise et al. |
| 7,015,037 B1 | 3/2006 | Furcht et al. |
| 7,029,666 B2 | 4/2006 | Bruder et al. |
| 7,033,339 B1 | 4/2006 | Lynn |
| 7,033,823 B2 | 4/2006 | Chang |
| 7,041,493 B2 | 5/2006 | Rao |
| 7,045,098 B2 | 5/2006 | Stephens |
| 7,052,517 B2 | 5/2006 | Murphy et al. |
| 7,056,493 B2 | 6/2006 | Kohn et al. |
| 7,112,441 B2 | 9/2006 | Uemura et al. |
| 7,118,672 B2 | 10/2006 | Husain et al. |
| 7,122,178 B1 | 10/2006 | Simmons et al. |
| 7,160,719 B2 | 1/2007 | Nyberg |
| 7,169,295 B2 | 1/2007 | Husain et al. |
| 7,172,696 B1 | 2/2007 | Martinez et al. |
| 7,175,763 B2 | 2/2007 | Husain et al. |
| 7,192,776 B2 | 3/2007 | Stephens |
| 7,195,711 B2 | 3/2007 | Gorsuch et al. |
| 7,250,154 B2 | 7/2007 | Kohn et al. |
| 7,270,996 B2 | 9/2007 | Cannon et al. |
| 7,271,234 B2 | 9/2007 | Kohn et al. |
| 7,294,259 B2 | 11/2007 | Cote et al. |
| 7,300,571 B2 | 11/2007 | Cote et al. |
| 7,303,676 B2 | 12/2007 | Husain et al. |
| 7,303,677 B2 | 12/2007 | Cote et al. |
| 7,341,062 B2 | 3/2008 | Chachgues et al. |
| 7,358,001 B2 | 4/2008 | Morrissey et al. |
| 7,361,493 B1 | 4/2008 | Hammond et al. |
| 7,368,169 B2 | 5/2008 | Kohn et al. |
| 7,378,271 B2 | 5/2008 | Bader |
| 7,399,872 B2 | 7/2008 | Webster et al. |
| 7,416,884 B2 | 8/2008 | Gemmiti et al. |
| 7,425,440 B2 | 9/2008 | Malinge et al. |
| 7,435,586 B2 | 10/2008 | Bartlett et al. |
| 7,438,902 B2 | 10/2008 | Habener et al. |
| 7,439,057 B2 | 10/2008 | Frangos et al. |
| 7,452,529 B2 | 11/2008 | Brown, Jr. et al. |
| 7,491,388 B1 | 2/2009 | Mc Intosh et al. |
| 7,494,811 B2 | 2/2009 | Wolfinbarger, Jr. et al. |
| 7,514,074 B2 | 4/2009 | Pittenger et al. |
| 7,514,075 B2 | 4/2009 | Hedrick et al. |
| 7,524,676 B2 | 4/2009 | Reiter et al. |
| 7,531,351 B2 | 5/2009 | Marx et al. |
| 7,534,601 B2 | 5/2009 | Wikswo et al. |
| 7,534,609 B2 | 5/2009 | Merchav et al. |
| 7,572,374 B2 | 8/2009 | Gorsuch et al. |
| 7,579,179 B2 | 8/2009 | Bryhan et al. |
| 7,585,412 B2 | 9/2009 | Gorsuch et al. |
| 7,588,938 B2 | 9/2009 | Ma |
| 7,598,075 B2 | 10/2009 | Smith et al. |
| 7,608,447 B2 | 10/2009 | Cohen et al. |
| 7,659,118 B2 | 2/2010 | Furcht et al. |
| 7,678,573 B2 | 3/2010 | Merchav et al. |
| 7,682,822 B2 | 3/2010 | Noll et al. |
| 7,682,823 B1 | 3/2010 | Runyon |
| 7,718,430 B2 | 5/2010 | Antwiler |
| 7,722,896 B2 | 5/2010 | Kohn et al. |
| D620,732 S | 8/2010 | Andrews |
| 7,838,122 B2 | 11/2010 | Kohn et al. |
| 7,838,289 B2 | 11/2010 | Furcht et al. |
| 7,892,829 B2 | 2/2011 | Pittenger et al. |
| 7,919,307 B2 | 4/2011 | Klaus et al. |
| 7,927,587 B2 | 4/2011 | Blazer et al. |
| 7,989,851 B2 | 8/2011 | Lu et al. |
| 8,008,528 B2 | 8/2011 | Kohn et al. |
| 8,034,365 B2 | 10/2011 | Baluca |
| 8,075,881 B2 | 12/2011 | Verfaillie et al. |
| 8,147,824 B2 | 4/2012 | Maziarz et al. |
| 8,147,863 B2 | 4/2012 | Kohn et al. |
| 8,158,120 B2 | 4/2012 | Pittenger et al. |
| 8,158,121 B2 | 4/2012 | Pittenger et al. |
| 8,252,280 B1 | 8/2012 | Verfaillie et al. |
| 8,252,887 B2 | 8/2012 | Bolikal et al. |
| 8,288,159 B2 | 10/2012 | Warren et al. |
| 8,288,590 B2 | 10/2012 | Kohn et al. |
| 8,298,823 B2 | 10/2012 | Warren et al. |
| 8,309,347 B2 | 11/2012 | Antwiler |
| 8,361,453 B2 | 1/2013 | Uhrich et al. |
| 8,377,683 B2 | 2/2013 | Lu et al. |
| 8,383,397 B2 | 2/2013 | Wojciechowski et al. |
| 8,383,806 B2 | 2/2013 | Rameshwar |
| 8,399,245 B2 | 3/2013 | Leuthaeuser et al. |
| 8,415,449 B2 | 4/2013 | Kohn et al. |
| 8,435,781 B2 | 5/2013 | Kodama |
| 8,461,289 B2 | 6/2013 | Kohn et al. |
| 8,476,399 B2 | 7/2013 | Bolikal et al. |
| 8,486,621 B2 | 7/2013 | Luo et al. |
| 8,486,695 B2 | 7/2013 | Danilkovitch et al. |

(56) References Cited

U.S. PATENT DOCUMENTS

| | | |
|---|---|---|
| 8,492,140 B2 | 7/2013 | Smith et al. |
| 8,492,150 B2 | 7/2013 | Parker et al. |
| 8,524,496 B2 | 9/2013 | Meiron et al. |
| 8,529,888 B2 | 9/2013 | Meiron et al. |
| 8,540,499 B2 | 9/2013 | Page et al. |
| 8,551,511 B2 | 10/2013 | Brandom et al. |
| 8,580,249 B2 | 11/2013 | Blazar et al. |
| 8,678,638 B2 | 3/2014 | Wong |
| 8,785,181 B2 | 7/2014 | Antwiler |
| 8,852,570 B2 | 10/2014 | Pittenger et al. |
| 8,852,571 B2 | 10/2014 | Pittenger et al. |
| 8,852,572 B2 | 10/2014 | Pittenger et al. |
| 8,852,573 B2 | 10/2014 | Pittenger et al. |
| 8,852,574 B2 | 10/2014 | Pittenger et al. |
| 8,852,575 B2 | 10/2014 | Pittenger et al. |
| 8,895,291 B2 | 11/2014 | DiLorenzo et al. |
| 9,057,045 B2 | 6/2015 | Gibbons et al. |
| 9,109,193 B2 | 8/2015 | Galliher et al. |
| 9,175,259 B2 | 11/2015 | Nankervis |
| 9,220,810 B2 | 12/2015 | Ma et al. |
| 9,441,195 B2 | 9/2016 | Wojciechowski et al. |
| 9,534,198 B2 | 1/2017 | Page et al. |
| 9,732,313 B2 | 8/2017 | Hirschel et al. |
| 10,093,956 B2 | 10/2018 | Hirschel et al. |
| 10,494,421 B2 | 12/2019 | Castillo |
| 10,577,575 B2 | 3/2020 | Frank |
| 2001/0017188 A1 | 8/2001 | Cooley et al. |
| 2001/0020086 A1 | 9/2001 | Hubbell et al. |
| 2001/0021516 A1 | 9/2001 | Wei et al. |
| 2001/0029046 A1 | 10/2001 | Beaulieu |
| 2001/0033834 A1 | 10/2001 | Wilkison et al. |
| 2001/0036663 A1 | 11/2001 | Kraus et al. |
| 2001/0041687 A1 | 11/2001 | Mruk |
| 2001/0044413 A1 | 11/2001 | Pierce et al. |
| 2001/0049139 A1 | 12/2001 | Lagasse et al. |
| 2002/0015724 A1 | 2/2002 | Yang et al. |
| 2002/0018804 A1 | 2/2002 | Austin et al. |
| 2002/0028510 A1 | 3/2002 | Sanberg et al. |
| 2002/0031757 A1 | 3/2002 | Ohgushi et al. |
| 2002/0037278 A1 | 3/2002 | Ueno et al. |
| 2002/0045260 A1 | 4/2002 | Hung et al. |
| 2002/0064869 A1 | 5/2002 | Ebner et al. |
| 2002/0076400 A1 | 6/2002 | Katz et al. |
| 2002/0077687 A1 | 6/2002 | Ahn |
| 2002/0082698 A1 | 6/2002 | Parenteau et al. |
| 2002/0116054 A1 | 8/2002 | Lundell et al. |
| 2002/0128581 A1 | 9/2002 | Vishnoi et al. |
| 2002/0128582 A1 | 9/2002 | Farrell et al. |
| 2002/0128583 A1 | 9/2002 | Min et al. |
| 2002/0128584 A1 | 9/2002 | Brown et al. |
| 2002/0130100 A1 | 9/2002 | Smith |
| 2002/0132343 A1 | 9/2002 | Lum |
| 2002/0139743 A1 | 10/2002 | Critz et al. |
| 2002/0142457 A1 | 10/2002 | Umezawa et al. |
| 2002/0146678 A1 | 10/2002 | Benvenisty |
| 2002/0146817 A1 | 10/2002 | Cannon et al. |
| 2002/0150989 A1 | 10/2002 | Greene et al. |
| 2002/0151056 A1 | 10/2002 | Sasai et al. |
| 2002/0159981 A1 | 10/2002 | Peled et al. |
| 2002/0160032 A1 | 10/2002 | Long et al. |
| 2002/0160510 A1 | 10/2002 | Hariri |
| 2002/0168765 A1 | 11/2002 | Prockop et al. |
| 2002/0169408 A1 | 11/2002 | Beretta et al. |
| 2002/0182241 A1 | 12/2002 | Borenstein et al. |
| 2002/0182664 A1 | 12/2002 | Dolecek et al. |
| 2002/0188962 A1 | 12/2002 | Denhardt et al. |
| 2002/0197240 A1 | 12/2002 | Chiu |
| 2003/0021850 A1 | 1/2003 | Xu |
| 2003/0022390 A1 | 1/2003 | Stephens |
| 2003/0027330 A1 | 2/2003 | Lanza et al. |
| 2003/0027331 A1 | 2/2003 | Yan et al. |
| 2003/0032143 A1 | 2/2003 | Neff et al. |
| 2003/0036168 A1 | 2/2003 | Ni et al. |
| 2003/0040113 A1 | 2/2003 | Mizuno et al. |
| 2003/0049236 A1 | 3/2003 | Kassem et al. |
| 2003/0054331 A1 | 3/2003 | Fraser et al. |
| 2003/0059851 A1 | 3/2003 | Smith |
| 2003/0059939 A1 | 3/2003 | Page et al. |
| 2003/0078345 A1 | 4/2003 | Morrisey |
| 2003/0082795 A1 | 5/2003 | Shuler et al. |
| 2003/0086915 A1 | 5/2003 | Rader et al. |
| 2003/0089471 A1 | 5/2003 | Gehr et al. |
| 2003/0092101 A1 | 5/2003 | Ni et al. |
| 2003/0101465 A1 | 5/2003 | Lawman et al. |
| 2003/0103957 A1 | 6/2003 | McKerracher |
| 2003/0104568 A1 | 6/2003 | Lee |
| 2003/0113813 A1 | 6/2003 | Heidaran et al. |
| 2003/0113910 A1 | 6/2003 | Levanduski |
| 2003/0124091 A1 | 7/2003 | Tuse et al. |
| 2003/0124721 A1 | 7/2003 | Cheatham et al. |
| 2003/0130593 A1 | 7/2003 | Gonzalez |
| 2003/0133918 A1 | 7/2003 | Sherley |
| 2003/0138950 A1 | 7/2003 | McAllister et al. |
| 2003/0143727 A1 | 7/2003 | Chang |
| 2003/0148152 A1 | 8/2003 | Morrisey |
| 2003/0149011 A1 | 8/2003 | Ackerman et al. |
| 2003/0152558 A1 | 8/2003 | Luft et al. |
| 2003/0157078 A1 | 8/2003 | Hall et al. |
| 2003/0157709 A1 | 8/2003 | DiMilla et al. |
| 2003/0161817 A1 | 8/2003 | Young et al. |
| 2003/0166272 A1 | 9/2003 | Abuljadayel |
| 2003/0170214 A1 | 9/2003 | Bader |
| 2003/0180296 A1 | 9/2003 | Salcedo et al. |
| 2003/0185817 A1 | 10/2003 | Thomas et al. |
| 2003/0202938 A1 | 10/2003 | Rameshwar |
| 2003/0203483 A1 | 10/2003 | Seshi |
| 2003/0204323 A1 | 10/2003 | Morrisey |
| 2003/0211602 A1 | 11/2003 | Atala |
| 2003/0211603 A1 | 11/2003 | Earp et al. |
| 2003/0216718 A1 | 11/2003 | Hamblin et al. |
| 2003/0219898 A1 | 11/2003 | Sugaya et al. |
| 2003/0223968 A1 | 12/2003 | Yang |
| 2003/0224420 A1 | 12/2003 | Hellerstein et al. |
| 2003/0224510 A1 | 12/2003 | Yamaguchi et al. |
| 2003/0225010 A1 | 12/2003 | Rameshwar |
| 2003/0232432 A1 | 12/2003 | Bhat |
| 2003/0232752 A1 | 12/2003 | Freeman et al. |
| 2003/0235909 A1 | 12/2003 | Hariri et al. |
| 2004/0009158 A1 | 1/2004 | Sands et al. |
| 2004/0009589 A1 | 1/2004 | Levenberg et al. |
| 2004/0010231 A1 | 1/2004 | Leonhardt et al. |
| 2004/0014209 A1 | 1/2004 | Lassar et al. |
| 2004/0018174 A1 | 1/2004 | Palasis |
| 2004/0018617 A1 | 1/2004 | Hwang |
| 2004/0023324 A1 | 2/2004 | Sakano et al. |
| 2004/0023370 A1 | 2/2004 | Yu et al. |
| 2004/0027914 A1 | 2/2004 | Vrane |
| 2004/0033214 A1 | 2/2004 | Young et al. |
| 2004/0033599 A1 | 2/2004 | Rosenberg |
| 2004/0037811 A1 | 2/2004 | Penn et al. |
| 2004/0037815 A1 | 2/2004 | Clarke et al. |
| 2004/0038316 A1 | 2/2004 | Kaiser et al. |
| 2004/0053869 A1 | 3/2004 | Andrews et al. |
| 2004/0062753 A1 | 4/2004 | Rezania et al. |
| 2004/0063205 A1 | 4/2004 | Xu |
| 2004/0067585 A1 | 4/2004 | Wang et al. |
| 2004/0071668 A1 | 4/2004 | Bays et al. |
| 2004/0072259 A1 | 4/2004 | Scadden et al. |
| 2004/0077079 A1 | 4/2004 | Storgaard et al. |
| 2004/0079248 A1 | 4/2004 | Mayer et al. |
| 2004/0087016 A1 | 5/2004 | Keating et al. |
| 2004/0091936 A1 | 5/2004 | West |
| 2004/0096476 A1 | 5/2004 | Uhrich et al. |
| 2004/0097408 A1 | 5/2004 | Leder et al. |
| 2004/0101959 A1 | 5/2004 | Marko et al. |
| 2004/0107453 A1 | 6/2004 | Furcht et al. |
| 2004/0110286 A1 | 6/2004 | Bhatia |
| 2004/0115804 A1 | 6/2004 | Fu et al. |
| 2004/0115806 A1 | 6/2004 | Fu |
| 2004/0120932 A1 | 6/2004 | Zahner |
| 2004/0121461 A1 | 6/2004 | Honmou et al. |
| 2004/0121464 A1 | 6/2004 | Rathjen et al. |
| 2004/0126405 A1 | 7/2004 | Sahatjian et al. |
| 2004/0128077 A1 | 7/2004 | Koebler et al. |

(56) References Cited

U.S. PATENT DOCUMENTS

| | | |
|---|---|---|
| 2004/0131601 A1 | 7/2004 | Epstein et al. |
| 2004/0132184 A1 | 7/2004 | Dennis et al. |
| 2004/0136967 A1 | 7/2004 | Weiss et al. |
| 2004/0137612 A1 | 7/2004 | Baksh |
| 2004/0137613 A1 | 7/2004 | Vacanti et al. |
| 2004/0143174 A1 | 7/2004 | Brubaker |
| 2004/0143863 A1 | 7/2004 | Li et al. |
| 2004/0151700 A1 | 8/2004 | Harlan et al. |
| 2004/0151701 A1 | 8/2004 | Kim et al. |
| 2004/0151706 A1 | 8/2004 | Shakhov et al. |
| 2004/0151729 A1 | 8/2004 | Michalopoulos et al. |
| 2004/0152190 A1 | 8/2004 | Sumita |
| 2004/0161419 A1 | 8/2004 | Strom et al. |
| 2004/0171533 A1 | 9/2004 | Zehentner et al. |
| 2004/0180347 A1 | 9/2004 | Stanton et al. |
| 2004/0191902 A1 | 9/2004 | Hambor et al. |
| 2004/0197310 A1 | 10/2004 | Sanberg et al. |
| 2004/0197375 A1 | 10/2004 | Rezania et al. |
| 2004/0208786 A1 | 10/2004 | Kevy et al. |
| 2004/0214275 A1 | 10/2004 | Soejima et al. |
| 2004/0219134 A1 | 11/2004 | Naughton et al. |
| 2004/0219136 A1 | 11/2004 | Hariri |
| 2004/0219563 A1 | 11/2004 | West et al. |
| 2004/0224403 A1 | 11/2004 | Bhatia |
| 2004/0229351 A1 | 11/2004 | Rodriguez et al. |
| 2004/0234972 A1 | 11/2004 | Owens et al. |
| 2004/0235158 A1 | 11/2004 | Bartlett et al. |
| 2004/0235160 A1 | 11/2004 | Nishikawa et al. |
| 2004/0235166 A1 | 11/2004 | Prockop et al. |
| 2004/0242469 A1 | 12/2004 | Lee et al. |
| 2004/0258669 A1 | 12/2004 | Dzau et al. |
| 2004/0259242 A1 | 12/2004 | Malinge et al. |
| 2004/0259254 A1 | 12/2004 | Honmou et al. |
| 2004/0260058 A1 | 12/2004 | Scheek et al. |
| 2004/0260318 A1 | 12/2004 | Hunter et al. |
| 2004/0265996 A1 | 12/2004 | Schwarz et al. |
| 2005/0002914 A1 | 1/2005 | Rosen et al. |
| 2005/0003460 A1 | 1/2005 | Nilsson et al. |
| 2005/0003527 A1 | 1/2005 | Lang et al. |
| 2005/0003534 A1 | 1/2005 | Huberman et al. |
| 2005/0008624 A1 | 1/2005 | Peled et al. |
| 2005/0008626 A1 | 1/2005 | Fraser et al. |
| 2005/0009178 A1 | 1/2005 | Yost et al. |
| 2005/0009179 A1 | 1/2005 | Gemmiti et al. |
| 2005/0009181 A1 | 1/2005 | Black et al. |
| 2005/0013804 A1 | 1/2005 | Kato et al. |
| 2005/0014252 A1 | 1/2005 | Chu et al. |
| 2005/0014253 A1 | 1/2005 | Ehmann et al. |
| 2005/0014254 A1 | 1/2005 | Kruse |
| 2005/0014255 A1 | 1/2005 | Tang et al. |
| 2005/0019801 A1 | 1/2005 | Rubin et al. |
| 2005/0019908 A1 | 1/2005 | Hariri |
| 2005/0019910 A1 | 1/2005 | Takagi et al. |
| 2005/0019911 A1 | 1/2005 | Gronthos et al. |
| 2005/0026836 A1 | 2/2005 | Dack et al. |
| 2005/0031587 A1 | 2/2005 | Tsutsui et al. |
| 2005/0031595 A1 | 2/2005 | Peled et al. |
| 2005/0031598 A1 | 2/2005 | Levenberg et al. |
| 2005/0032122 A1 | 2/2005 | Hwang et al. |
| 2005/0032207 A1 | 2/2005 | Wobus et al. |
| 2005/0032209 A1 | 2/2005 | Messina et al. |
| 2005/0032218 A1 | 2/2005 | Gerlach |
| 2005/0036980 A1 | 2/2005 | Chaney et al. |
| 2005/0037488 A1 | 2/2005 | Mitalipova et al. |
| 2005/0037490 A1 | 2/2005 | Rosenberg et al. |
| 2005/0037492 A1 | 2/2005 | Xu et al. |
| 2005/0037493 A1 | 2/2005 | Mandalam et al. |
| 2005/0037949 A1 | 2/2005 | O'Brien et al. |
| 2005/0106119 A1 | 5/2005 | Brandom et al. |
| 2005/0106127 A1 | 5/2005 | Kraus et al. |
| 2005/0112447 A1 | 5/2005 | Fletcher et al. |
| 2005/0112762 A1 | 5/2005 | Hart et al. |
| 2005/0118712 A1 | 6/2005 | Tsai et al. |
| 2005/0130297 A1 | 6/2005 | Sarem et al. |
| 2005/0136093 A1 | 6/2005 | Denk |
| 2005/0137517 A1 | 6/2005 | Blickhan et al. |
| 2005/0142162 A1 | 6/2005 | Hunter et al. |
| 2005/0149157 A1 | 7/2005 | Hunter et al. |
| 2005/0152946 A1 | 7/2005 | Hunter et al. |
| 2005/0158289 A1 | 7/2005 | Simmons et al. |
| 2005/0172340 A1 | 8/2005 | Logvinov et al. |
| 2005/0175665 A1 | 8/2005 | Hunter et al. |
| 2005/0175703 A1 | 8/2005 | Hunter et al. |
| 2005/0178395 A1 | 8/2005 | Hunter et al. |
| 2005/0178396 A1 | 8/2005 | Hunter et al. |
| 2005/0180957 A1 | 8/2005 | Scharp et al. |
| 2005/0181502 A1 | 8/2005 | Furcht et al. |
| 2005/0182463 A1 | 8/2005 | Hunter et al. |
| 2005/0183731 A1 | 8/2005 | Hunter et al. |
| 2005/0186244 A1 | 8/2005 | Hunter et al. |
| 2005/0186671 A1 | 8/2005 | Cannon et al. |
| 2005/0187140 A1 | 8/2005 | Hunter et al. |
| 2005/0196421 A1 | 9/2005 | Hunter et al. |
| 2005/0208095 A1 | 9/2005 | Hunter et al. |
| 2005/0244963 A1 | 11/2005 | Teplyashin |
| 2005/0249731 A1 | 11/2005 | Aslan et al. |
| 2005/0255118 A1 | 11/2005 | Wehner |
| 2005/0261674 A1 | 11/2005 | Nobis et al. |
| 2005/0277577 A1 | 12/2005 | Hunter et al. |
| 2005/0281790 A1 | 12/2005 | Simmons et al. |
| 2005/0282733 A1 | 12/2005 | Prins et al. |
| 2005/0283844 A1 | 12/2005 | Furcht et al. |
| 2006/0002900 A1 | 1/2006 | Binder et al. |
| 2006/0008452 A1 | 1/2006 | Simmons et al. |
| 2006/0019388 A1 | 1/2006 | Hutmacher et al. |
| 2006/0019389 A1 | 1/2006 | Yayon et al. |
| 2006/0054941 A1 | 3/2006 | Lu et al. |
| 2006/0083720 A1 | 4/2006 | Fraser et al. |
| 2006/0099198 A1 | 5/2006 | Thomson et al. |
| 2006/0166364 A1 | 7/2006 | Senesac |
| 2006/0172008 A1 | 8/2006 | Yayon et al. |
| 2006/0193840 A1 | 8/2006 | Gronthos et al. |
| 2006/0228798 A1 | 10/2006 | Verfaillie et al. |
| 2006/0233834 A1 | 10/2006 | Guehenneux et al. |
| 2006/0239909 A1 | 10/2006 | Anderson et al. |
| 2006/0258586 A1 | 11/2006 | Sheppard et al. |
| 2006/0258933 A1 | 11/2006 | Ellis et al. |
| 2006/0259998 A1 | 11/2006 | Brumbley et al. |
| 2006/0280748 A1 | 12/2006 | Buckheit |
| 2006/0286077 A1 | 12/2006 | Gronthos et al. |
| 2007/0005148 A1 | 1/2007 | Barofsky et al. |
| 2007/0011752 A1 | 1/2007 | Paleyanda |
| 2007/0042462 A1 | 2/2007 | Hildinger |
| 2007/0065938 A1 | 3/2007 | Gronthos et al. |
| 2007/0105222 A1 | 5/2007 | Wolfinbarger et al. |
| 2007/0116612 A1 | 5/2007 | Williamson |
| 2007/0117180 A1 | 5/2007 | Morikawa et al. |
| 2007/0122904 A1 | 5/2007 | Nordon |
| 2007/0123996 A1 | 5/2007 | Sugaya et al. |
| 2007/0160583 A1 | 7/2007 | Lange et al. |
| 2007/0166834 A1 | 7/2007 | Williamson et al. |
| 2007/0178071 A1 | 8/2007 | Westenfelder |
| 2007/0196421 A1 | 8/2007 | Hunter et al. |
| 2007/0197957 A1 | 8/2007 | Hunter et al. |
| 2007/0198063 A1 | 8/2007 | Hunter et al. |
| 2007/0202485 A1 | 8/2007 | Nees et al. |
| 2007/0203330 A1 | 8/2007 | Kretschmar et al. |
| 2007/0208134 A1 | 9/2007 | Hunter et al. |
| 2007/0231305 A1 | 10/2007 | Noll et al. |
| 2007/0238169 A1 | 10/2007 | Abilez et al. |
| 2007/0258943 A1 | 11/2007 | Penn et al. |
| 2007/0274970 A1 | 11/2007 | Gordon et al. |
| 2007/0275457 A1 | 11/2007 | Granchelli et al. |
| 2007/0295651 A1 | 12/2007 | Martinez et al. |
| 2007/0298015 A1 | 12/2007 | Beer et al. |
| 2007/0298497 A1 | 12/2007 | Antwiler |
| 2008/0003663 A1 | 1/2008 | Bryhan et al. |
| 2008/0009458 A1 | 1/2008 | Dornan et al. |
| 2008/0032398 A1 | 2/2008 | Cannon et al. |
| 2008/0050770 A1 | 2/2008 | Zhang et al. |
| 2008/0063600 A1 | 3/2008 | Aguzzi et al. |
| 2008/0064649 A1 | 3/2008 | Rameshwar |
| 2008/0069807 A1 | 3/2008 | Jy et al. |
| 2008/0095676 A1 | 4/2008 | Andretta |

(56) References Cited

U.S. PATENT DOCUMENTS

| | | |
|---|---|---|
| 2008/0095690 A1 | 4/2008 | Liu |
| 2008/0103412 A1 | 5/2008 | Chin |
| 2008/0110827 A1 | 5/2008 | Cote et al. |
| 2008/0113426 A1 | 5/2008 | Smith et al. |
| 2008/0113440 A1 | 5/2008 | Gurney et al. |
| 2008/0153077 A1 | 6/2008 | Henry |
| 2008/0160597 A1 | 7/2008 | van der Heiden et al. |
| 2008/0166808 A1 | 7/2008 | Nyberg |
| 2008/0181879 A1 | 7/2008 | Catelas et al. |
| 2008/0190857 A1 | 8/2008 | Beretta et al. |
| 2008/0194017 A1 | 8/2008 | Esser et al. |
| 2008/0206831 A1 | 8/2008 | Coffey et al. |
| 2008/0220522 A1 | 9/2008 | Antwiler |
| 2008/0220523 A1 | 9/2008 | Antwiler |
| 2008/0220524 A1 | 9/2008 | Noll et al. |
| 2008/0220526 A1 | 9/2008 | Ellison et al. |
| 2008/0221443 A1 | 9/2008 | Ritchie et al. |
| 2008/0227189 A1 | 9/2008 | Bader |
| 2008/0227190 A1 | 9/2008 | Antwiler |
| 2008/0248572 A1 | 10/2008 | Antwiler |
| 2008/0254533 A1 | 10/2008 | Antwiler |
| 2008/0268165 A1 | 10/2008 | Fekety et al. |
| 2008/0306095 A1 | 12/2008 | Crawford |
| 2009/0004738 A1 | 1/2009 | Merchav et al. |
| 2009/0011399 A1 | 1/2009 | Fischer |
| 2009/0047289 A1 | 2/2009 | Denhardt et al. |
| 2009/0074728 A1 | 3/2009 | Gronthos et al. |
| 2009/0075881 A1 | 3/2009 | Catelas et al. |
| 2009/0076481 A1 | 3/2009 | Stegmann et al. |
| 2009/0081770 A1 | 3/2009 | Srienc et al. |
| 2009/0081797 A1 | 3/2009 | Fadeev et al. |
| 2009/0092608 A1 | 4/2009 | Ni et al. |
| 2009/0098103 A1 | 4/2009 | Madison et al. |
| 2009/0098645 A1 | 4/2009 | Fang et al. |
| 2009/0100944 A1 | 4/2009 | Newby |
| 2009/0104163 A1 | 4/2009 | Deans et al. |
| 2009/0104692 A1 | 4/2009 | Bartfeld et al. |
| 2009/0104699 A1 | 4/2009 | Newby et al. |
| 2009/0118161 A1 | 5/2009 | Cruz |
| 2009/0181087 A1 | 7/2009 | Kraus et al. |
| 2009/0183581 A1 | 7/2009 | Wilkinson et al. |
| 2009/0191627 A1 | 7/2009 | Fadeev et al. |
| 2009/0191632 A1 | 7/2009 | Fadeev et al. |
| 2009/0191634 A1 | 7/2009 | Martin et al. |
| 2009/0203065 A1 | 8/2009 | Gehman et al. |
| 2009/0203129 A1 | 8/2009 | Furcht et al. |
| 2009/0203130 A1 | 8/2009 | Furcht et al. |
| 2009/0214382 A1 | 8/2009 | Burgess et al. |
| 2009/0214481 A1 | 8/2009 | Muhs et al. |
| 2009/0214652 A1 | 8/2009 | Hunter et al. |
| 2009/0215022 A1 | 8/2009 | Page et al. |
| 2009/0227024 A1 | 9/2009 | Baker et al. |
| 2009/0227027 A1 | 9/2009 | Baker et al. |
| 2009/0233334 A1 | 9/2009 | Hildinger et al. |
| 2009/0233353 A1 | 9/2009 | Furcht et al. |
| 2009/0233354 A1 | 9/2009 | Furcht et al. |
| 2009/0258379 A1 | 10/2009 | Klein et al. |
| 2009/0269841 A1 | 10/2009 | Wojciechowski et al. |
| 2009/0270725 A1 | 10/2009 | Leimbach et al. |
| 2009/0280153 A1 | 11/2009 | Hunter et al. |
| 2009/0280565 A1 | 11/2009 | Jolicoeur et al. |
| 2009/0291890 A1 | 11/2009 | Madison et al. |
| 2010/0009409 A1 | 1/2010 | Hubbell et al. |
| 2010/0021954 A1 | 1/2010 | Deshayes et al. |
| 2010/0021990 A1 | 1/2010 | Edwards et al. |
| 2010/0028311 A1 | 2/2010 | Motlagh et al. |
| 2010/0042260 A1 | 2/2010 | Antwiler |
| 2010/0075410 A1 | 3/2010 | Desai et al. |
| 2010/0086481 A1 | 4/2010 | Baird et al. |
| 2010/0092536 A1 | 4/2010 | Hunter et al. |
| 2010/0093607 A1 | 4/2010 | Dickneite |
| 2010/0105138 A1 | 4/2010 | Dodd et al. |
| 2010/0111910 A1 | 5/2010 | Rakoczy |
| 2010/0129376 A1 | 5/2010 | Denhardt et al. |
| 2010/0129912 A1 | 5/2010 | Su et al. |
| 2010/0136091 A1 | 6/2010 | Moghe et al. |
| 2010/0144037 A1 | 6/2010 | Antwiler |
| 2010/0144634 A1 | 6/2010 | Zheng et al. |
| 2010/0183561 A1 | 7/2010 | Sakthivel et al. |
| 2010/0183585 A1 | 7/2010 | Van Zant et al. |
| 2010/0203020 A1 | 8/2010 | Ghosh |
| 2010/0230203 A1 | 9/2010 | Karayianni |
| 2010/0248366 A1 | 9/2010 | Fadeev et al. |
| 2010/0278933 A1 | 11/2010 | Sayeski et al. |
| 2010/0285453 A1 | 11/2010 | Goodrich |
| 2010/0285590 A1 | 11/2010 | Verfaillie et al. |
| 2010/0291180 A1 | 11/2010 | Uhrich |
| 2010/0291181 A1 | 11/2010 | Uhrich et al. |
| 2010/0297234 A1 | 11/2010 | Sugino et al. |
| 2010/0304427 A1 | 12/2010 | Faris et al. |
| 2010/0304482 A1 | 12/2010 | Deshayes et al. |
| 2010/0310524 A1 | 12/2010 | Bechor et al. |
| 2010/0316446 A1 | 12/2010 | Runyon |
| 2011/0085746 A1 | 4/2011 | Wong et al. |
| 2011/0111498 A1 | 5/2011 | Oh et al. |
| 2011/0129447 A1 | 6/2011 | Meretzki et al. |
| 2011/0129486 A1 | 6/2011 | Meiron |
| 2011/0143433 A1 | 6/2011 | Oh et al. |
| 2011/0159584 A1 | 6/2011 | Gibbons et al. |
| 2011/0171182 A1 | 7/2011 | Abelman |
| 2011/0171659 A1 | 7/2011 | Furcht et al. |
| 2011/0177595 A1 | 7/2011 | Furcht et al. |
| 2011/0212493 A1 | 9/2011 | Hirschel et al. |
| 2011/0256108 A1 | 10/2011 | Meiron et al. |
| 2011/0256160 A1 | 10/2011 | Meiron et al. |
| 2011/0293583 A1 | 12/2011 | Aberman |
| 2012/0028352 A1 | 2/2012 | Oh et al. |
| 2012/0051976 A1 | 3/2012 | Lu et al. |
| 2012/0058554 A1 | 3/2012 | Deshayes et al. |
| 2012/0064047 A1 | 3/2012 | Verfaillie et al. |
| 2012/0064583 A1 | 3/2012 | Edwards et al. |
| 2012/0086657 A1 | 4/2012 | Stanton, IV et al. |
| 2012/0118919 A1 | 5/2012 | Cianciolo |
| 2012/0122220 A1 | 5/2012 | Merchav et al. |
| 2012/0135043 A1 | 5/2012 | Maziarz et al. |
| 2012/0145580 A1 | 6/2012 | Paruit et al. |
| 2012/0156779 A1 | 6/2012 | Anneren et al. |
| 2012/0178885 A1 | 7/2012 | Kohn et al. |
| 2012/0189713 A1 | 7/2012 | Kohn et al. |
| 2012/0208039 A1 | 8/2012 | Barbaroux et al. |
| 2012/0219531 A1 | 8/2012 | Oh et al. |
| 2012/0219737 A1 | 8/2012 | Sugino et al. |
| 2012/0226013 A1 | 9/2012 | Kohn et al. |
| 2012/0231519 A1 | 9/2012 | Bushman et al. |
| 2012/0237557 A1 | 9/2012 | Lewitus et al. |
| 2012/0295352 A1 | 11/2012 | Antwiler |
| 2012/0308531 A1 | 12/2012 | Pinxteren et al. |
| 2012/0315696 A1 | 12/2012 | Luitjens et al. |
| 2013/0004465 A1 | 1/2013 | Aberman |
| 2013/0039892 A1 | 2/2013 | Aberman |
| 2013/0058907 A1 | 3/2013 | Wojciechowski et al. |
| 2013/0059383 A1 | 3/2013 | Borgart et al. |
| 2013/0101561 A1 | 4/2013 | Sabaawy |
| 2013/0143313 A1 | 6/2013 | Niazi |
| 2013/0157353 A1 | 6/2013 | Borgart et al. |
| 2013/0259843 A1 | 10/2013 | Duda et al. |
| 2013/0319575 A1 | 12/2013 | Mendyk |
| 2013/0323213 A1 | 12/2013 | Meiron et al. |
| 2013/0337558 A1 | 12/2013 | Meiron et al. |
| 2014/0004553 A1 | 1/2014 | Parker et al. |
| 2014/0017209 A1 | 1/2014 | Aberman et al. |
| 2014/0030805 A1 | 1/2014 | Kasuto et al. |
| 2014/0051162 A1 | 2/2014 | Nankervis |
| 2014/0051167 A1 | 2/2014 | Nankervis et al. |
| 2014/0112893 A1 | 4/2014 | Tom et al. |
| 2014/0186937 A1 | 7/2014 | Smith et al. |
| 2014/0193895 A1 | 7/2014 | Smith et al. |
| 2014/0193911 A1 | 7/2014 | Newby et al. |
| 2014/0242039 A1 | 8/2014 | Meiron et al. |
| 2014/0248244 A1 | 9/2014 | Danilkovitch et al. |
| 2014/0315300 A1 | 10/2014 | Oh et al. |
| 2014/0342448 A1 | 11/2014 | Nagels |
| 2015/0004693 A1 | 1/2015 | Danilkovitch et al. |
| 2015/0104431 A1 | 4/2015 | Pittenger et al. |

(56) References Cited

U.S. PATENT DOCUMENTS

| | | |
|---|---|---|
| 2015/0111252 A1 | 4/2015 | Hirschel et al. |
| 2015/0125138 A1 | 5/2015 | Karnieli et al. |
| 2015/0140653 A1 | 5/2015 | Jones et al. |
| 2015/0175950 A1 | 6/2015 | Hirschel et al. |
| 2015/0225685 A1 | 8/2015 | Hirschel et al. |
| 2015/0247122 A1 | 9/2015 | Tom et al. |
| 2015/0259749 A1 | 9/2015 | Santos et al. |
| 2015/0275170 A1 | 10/2015 | Nankervis |
| 2016/0090569 A1 | 3/2016 | Vang |
| 2016/0362650 A1 | 12/2016 | Wojciechowski et al. |
| 2016/0362652 A1 | 12/2016 | Page et al. |
| 2017/0349869 A1 | 12/2017 | Frank et al. |
| 2017/0349872 A1 | 12/2017 | Frank |
| 2017/0349873 A1 | 12/2017 | Frank et al. |
| 2018/0010082 A1 | 1/2018 | Jaques et al. |
| 2018/0030398 A1 | 2/2018 | Castillo |
| 2018/0155668 A1 | 6/2018 | Hirschel et al. |
| 2019/0194628 A1 | 6/2019 | Rao et al. |

FOREIGN PATENT DOCUMENTS

| | | |
|---|---|---|
| DE | 3833925 | 9/1989 |
| DE | 4007703 A1 | 9/1991 |
| DE | 10244859 | 4/2004 |
| DE | 10327988 A1 | 7/2004 |
| DE | 102012200939 A1 | 7/2013 |
| EP | 0220650 A2 | 5/1987 |
| EP | 750938 A1 | 1/1997 |
| EP | 906415 A1 | 4/1999 |
| EP | 959980 A1 | 12/1999 |
| EP | 1007631 A1 | 6/2000 |
| EP | 1028737 A1 | 8/2000 |
| EP | 1028991 A1 | 8/2000 |
| EP | 1066052 A2 | 1/2001 |
| EP | 1066060 A2 | 1/2001 |
| EP | 1084230 A2 | 3/2001 |
| EP | 1147176 A1 | 10/2001 |
| EP | 1220611 A1 | 7/2002 |
| EP | 1223956 A1 | 7/2002 |
| EP | 1325953 A1 | 7/2003 |
| EP | 1437404 A1 | 7/2004 |
| EP | 1437406 A2 | 7/2004 |
| EP | 1447443 A1 | 8/2004 |
| EP | 1452594 A1 | 9/2004 |
| EP | 1062321 B1 | 12/2004 |
| EP | 1484080 A1 | 12/2004 |
| EP | 1498478 A1 | 1/2005 |
| EP | 1538196 A1 | 6/2005 |
| EP | 1036057 B1 | 10/2005 |
| EP | 1605044 A2 | 12/2005 |
| EP | 1756262 A1 | 2/2007 |
| EP | 1771737 A1 | 4/2007 |
| EP | 1882030 A1 | 1/2008 |
| EP | 1908490 A1 | 4/2008 |
| EP | 1971679 A2 | 9/2008 |
| EP | 1991668 A2 | 11/2008 |
| EP | 2200622 A1 | 6/2010 |
| EP | 2208782 A2 | 7/2010 |
| EP | 2264145 A1 | 12/2010 |
| EP | 2027247 B1 | 1/2011 |
| EP | 2303293 A1 | 4/2011 |
| EP | 2311938 A1 | 4/2011 |
| EP | 2331957 A1 | 6/2011 |
| EP | 2334310 A2 | 6/2011 |
| EP | 2334783 A2 | 6/2011 |
| EP | 2361968 A1 | 8/2011 |
| EP | 2366775 A1 | 9/2011 |
| EP | 2465922 A2 | 6/2012 |
| EP | 2481819 | 8/2012 |
| EP | 2548951 A1 | 1/2013 |
| EP | 2561066 A1 | 2/2013 |
| EP | 2575831 A1 | 4/2013 |
| EP | 2591789 A2 | 5/2013 |
| EP | 2624845 A2 | 8/2013 |
| EP | 2626417 A1 | 8/2013 |
| EP | 2641606 A1 | 9/2013 |
| EP | 2689008 A1 | 1/2014 |
| EP | 2694639 A1 | 2/2014 |
| EP | 2697362 A2 | 2/2014 |
| EP | 2739720 A1 | 6/2014 |
| EP | 2807246 A1 | 12/2014 |
| GB | 1414671 A | 11/1975 |
| GB | 2297980 A | 8/1996 |
| GB | 2360789 A | 10/2001 |
| HU | 3285 U | 5/2007 |
| JP | H02245177 A | 9/1990 |
| JP | 2003/052360 A | 2/2003 |
| JP | 2003510068 A | 3/2003 |
| JP | 2005278564 A | 10/2005 |
| JP | 2006223273 A | 8/2006 |
| JP | 2007000038 A | 1/2007 |
| JP | 2012-506257 | 3/2012 |
| JP | 5548207 | 7/2014 |
| JP | 2019-516029 | 6/2019 |
| JP | 2019-525765 | 9/2019 |
| KR | 101228026 | 1/2013 |
| KR | 10-2015-0002762 | 1/2015 |
| KR | 101504392 | 3/2015 |
| KR | 101548790 | 8/2015 |
| KR | 101553040 | 9/2015 |
| KR | 10-2017-0076679 | 7/2017 |
| KR | 10-2018-0027501 | 3/2018 |
| KR | 102027596 | 10/2019 |
| KR | 10-2020-0034790 | 3/2020 |
| KR | 10-2020-0058433 | 5/2020 |
| MY | 115206 A | 4/2003 |
| WO | 86/02379 A1 | 4/1986 |
| WO | 88/01643 A1 | 3/1988 |
| WO | WO 89/12676 | 12/1989 |
| WO | 90/02171 A1 | 3/1990 |
| WO | WO-9013306 A2 | 11/1990 |
| WO | WO-9105238 A1 | 4/1991 |
| WO | 91/07485 A1 | 5/1991 |
| WO | WO-9106641 A1 | 5/1991 |
| WO | WO-9109194 A1 | 6/1991 |
| WO | 92/10564 A1 | 6/1992 |
| WO | WO-94/25571 A1 | 11/1994 |
| WO | 95/04813 A1 | 2/1995 |
| WO | 95/21911 A1 | 8/1995 |
| WO | WO 95/24468 | 9/1995 |
| WO | WO-96/29395 A1 | 9/1996 |
| WO | WO-96/39035 A1 | 12/1996 |
| WO | WO-97/05826 A1 | 2/1997 |
| WO | 97/16527 A1 | 5/1997 |
| WO | WO-97/29792 A1 | 8/1997 |
| WO | WO-97/39104 A1 | 10/1997 |
| WO | WO-1997-040137 A1 | 10/1997 |
| WO | WO 98/22588 | 5/1998 |
| WO | WO-98/31403 A1 | 7/1998 |
| WO | 98/53046 A1 | 11/1998 |
| WO | WO-98/51317 A1 | 11/1998 |
| WO | WO-98/51785 A1 | 11/1998 |
| WO | WO-99/05180 A1 | 2/1999 |
| WO | WO-99/24391 A1 | 5/1999 |
| WO | WO-99/24490 A1 | 5/1999 |
| WO | WO-99/27167 A1 | 6/1999 |
| WO | WO-99/49015 A2 | 9/1999 |
| WO | WO-00/06704 A2 | 2/2000 |
| WO | WO-0009018 A1 | 2/2000 |
| WO | WO-00/16420 A1 | 3/2000 |
| WO | WO-00/17326 A1 | 3/2000 |
| WO | WO-00/29002 A2 | 5/2000 |
| WO | WO-0032225 A1 | 6/2000 |
| WO | WO-00/44058 A2 | 7/2000 |
| WO | WO 00/46354 | 8/2000 |
| WO | WO-0054651 A2 | 9/2000 |
| WO | WO-0056405 A2 | 9/2000 |
| WO | WO-00/59933 A2 | 10/2000 |
| WO | WO-00/69449 A2 | 11/2000 |
| WO | 00/75275 A2 | 12/2000 |
| WO | WO-00/75196 A1 | 12/2000 |
| WO | WO-00/77236 A2 | 12/2000 |
| WO | WO-2001/000783 A2 | 1/2001 |
| WO | WO-2001/011011 A2 | 2/2001 |

(56) References Cited

FOREIGN PATENT DOCUMENTS

| | | |
|---|---|---|
| WO | WO-2001/018174 A2 | 3/2001 |
| WO | WO-2001/021766 A2 | 3/2001 |
| WO | 01/23520 A1 | 4/2001 |
| WO | WO-2001/025402 A1 | 4/2001 |
| WO | WO-2001/029189 A2 | 4/2001 |
| WO | WO-0122810 A2 | 4/2001 |
| WO | WO-2001/034167 A1 | 5/2001 |
| WO | WO-2001/049851 A1 | 7/2001 |
| WO | WO-2001/054706 A2 | 8/2001 |
| WO | WO-2001-094541 A2 | 12/2001 |
| WO | 02/28996 A1 | 4/2002 |
| WO | WO-2002/042422 A2 | 5/2002 |
| WO | WO-2002/057430 A2 | 7/2002 |
| WO | WO-2002/092794 A2 | 11/2002 |
| WO | WO-2002/101385 A1 | 12/2002 |
| WO | WO-2003/010303 A1 | 2/2003 |
| WO | WO-2003/014313 A2 | 2/2003 |
| WO | WO-2003/016916 A1 | 2/2003 |
| WO | WO-2003/023018 A2 | 3/2003 |
| WO | WO-2003/023019 A1 | 3/2003 |
| WO | WO-2003/025167 A2 | 3/2003 |
| WO | WO-2003/029402 A2 | 4/2003 |
| WO | WO 03/039459 | 5/2003 |
| WO | WO-2003/040336 A2 | 5/2003 |
| WO | WO-2003/042405 A2 | 5/2003 |
| WO | WO-2003/046161 A2 | 6/2003 |
| WO | WO-2003/055989 A2 | 7/2003 |
| WO | WO-2003/061685 A1 | 7/2003 |
| WO | WO-2003/061686 A1 | 7/2003 |
| WO | WO-2003/068961 A2 | 8/2003 |
| WO | WO-2003/072064 A2 | 9/2003 |
| WO | WO-2003/078609 A1 | 9/2003 |
| WO | WO-2003/078967 A2 | 9/2003 |
| WO | WO-2003/080816 A2 | 10/2003 |
| WO | WO-2003/082145 A2 | 10/2003 |
| WO | WO-2003/085099 A2 | 10/2003 |
| WO | WO-2003/089631 A1 | 10/2003 |
| WO | WO-2003/091398 A2 | 11/2003 |
| WO | WO-2003/095631 A1 | 11/2003 |
| WO | 03/105663 A2 | 12/2003 |
| WO | WO-2004/001697 A1 | 12/2003 |
| WO | WO-2004/012226 A2 | 2/2004 |
| WO | WO-2004/016779 A1 | 2/2004 |
| WO | 2004024303 A2 | 3/2004 |
| WO | WO-2004/018526 A1 | 3/2004 |
| WO | WO-2004/018655 A2 | 3/2004 |
| WO | WO-2004/026115 A2 | 4/2004 |
| WO | WO-2004/029231 A1 | 4/2004 |
| WO | WO-2004/042023 A2 | 5/2004 |
| WO | WO-2004/042033 A2 | 5/2004 |
| WO | WO-2004/042040 A1 | 5/2004 |
| WO | WO-2004/044127 A2 | 5/2004 |
| WO | WO-2004/044158 A2 | 5/2004 |
| WO | WO-2004/046304 A1 | 6/2004 |
| WO | WO-2004/050826 A2 | 6/2004 |
| WO | WO-2004/053096 A2 | 6/2004 |
| WO | WO-2004/055155 A2 | 7/2004 |
| WO | WO-2004/056186 A1 | 7/2004 |
| WO | WO-2004/065616 A2 | 8/2004 |
| WO | WO-2004/069172 A2 | 8/2004 |
| WO | WO-2004/070013 A2 | 8/2004 |
| WO | WO-2004/072264 A2 | 8/2004 |
| WO | WO-2004/073633 A2 | 9/2004 |
| WO | WO-2004/074464 A1 | 9/2004 |
| WO | WO-2004/076642 A2 | 9/2004 |
| WO | WO-2004/076653 A1 | 9/2004 |
| WO | 2004/090112 A2 | 10/2004 |
| WO | WO-2004/087870 A2 | 10/2004 |
| WO | WO-2004/094588 A2 | 11/2004 |
| WO | WO-2004/096975 A2 | 11/2004 |
| WO | WO-2004/104166 A2 | 12/2004 |
| WO | WO-2004/106499 A1 | 12/2004 |
| WO | WO-2004/113513 A2 | 12/2004 |
| WO | WO-2005/001033 A2 | 1/2005 |
| WO | WO-2005/001081 A1 | 1/2005 |
| WO | WO-2005/003320 A2 | 1/2005 |
| WO | WO-2005/007799 A2 | 1/2005 |
| WO | WO-2005/010172 A2 | 2/2005 |
| WO | WO-2005/011524 A1 | 2/2005 |
| WO | WO-2005/012480 A2 | 2/2005 |
| WO | WO-2005/012510 A1 | 2/2005 |
| WO | WO-2005/012512 A1 | 2/2005 |
| WO | WO-05014775 A2 | 2/2005 |
| WO | WO-2005/028433 A2 | 3/2005 |
| WO | WO-05044972 A2 | 5/2005 |
| WO | WO-2005/056747 A2 | 6/2005 |
| WO | WO-05051316 A2 | 6/2005 |
| WO | WO-2005/063303 A1 | 7/2005 |
| WO | WO-2005/075636 A1 | 8/2005 |
| WO | 2005087915 A2 | 9/2005 |
| WO | WO 2005/104755 | 11/2005 |
| WO | WO-2005/107760 A1 | 11/2005 |
| WO | WO-2006/009291 A1 | 1/2006 |
| WO | WO-2006/032075 A1 | 3/2006 |
| WO | WO-2006/032092 A1 | 3/2006 |
| WO | WO 2006/037022 | 4/2006 |
| WO | WO-2006/108229 A1 | 10/2006 |
| WO | WO-2006/113881 A2 | 10/2006 |
| WO | WO-2006/121445 A2 | 11/2006 |
| WO | WO-06124021 A1 | 11/2006 |
| WO | WO-06129312 A2 | 12/2006 |
| WO | WO 2007/038572 | 4/2007 |
| WO | WO 2007/059473 | 5/2007 |
| WO | WO-2007/115367 A1 | 10/2007 |
| WO | WO-2007/115368 A1 | 10/2007 |
| WO | WO 2007/117765 | 10/2007 |
| WO | 2007/136821 A1 | 11/2007 |
| WO | WO-2007/136760 A2 | 11/2007 |
| WO | 2007/139742 A1 | 12/2007 |
| WO | 2007/139746 A1 | 12/2007 |
| WO | 2007/139747 A1 | 12/2007 |
| WO | 2007/139748 A2 | 12/2007 |
| WO | WO-2008/006168 A1 | 1/2008 |
| WO | WO-2008/011664 A1 | 1/2008 |
| WO | WO-2008/017128 A1 | 2/2008 |
| WO | WO-2008/028241 A1 | 3/2008 |
| WO | WO-08040812 A1 | 4/2008 |
| WO | WO 2008/073635 | 6/2008 |
| WO | 2008/109674 A2 | 9/2008 |
| WO | WO-2008/116261 A1 | 10/2008 |
| WO | WO-2008/149129 A1 | 12/2008 |
| WO | 2009/034186 A2 | 3/2009 |
| WO | WO-2009/026635 A1 | 3/2009 |
| WO | WO-09058146 A1 | 5/2009 |
| WO | WO-09080054 A1 | 7/2009 |
| WO | WO-09081408 A2 | 7/2009 |
| WO | WO-2009/140452 A2 | 11/2009 |
| WO | WO-09132457 A1 | 11/2009 |
| WO | WO-2009/144720 A1 | 12/2009 |
| WO | WO-10005527 A1 | 1/2010 |
| WO | WO-2010/019886 A1 | 2/2010 |
| WO | WO-10014253 A2 | 2/2010 |
| WO | WO-10019997 A1 | 2/2010 |
| WO | WO-2010/026573 A1 | 3/2010 |
| WO | WO-2010/026574 A2 | 3/2010 |
| WO | WO-2010/026575 A2 | 3/2010 |
| WO | WO 2010/036760 | 4/2010 |
| WO | WO-2010/059487 A1 | 5/2010 |
| WO | WO-10061377 A2 | 6/2010 |
| WO | WO-10068710 A2 | 6/2010 |
| WO | WO-10071826 A2 | 6/2010 |
| WO | WO-10083385 A2 | 7/2010 |
| WO | WO-10111255 A1 | 9/2010 |
| WO | WO-10119036 A1 | 10/2010 |
| WO | WO-10123594 A2 | 10/2010 |
| WO | WO-2011/025445 A1 | 3/2011 |
| WO | WO 2011/098592 | 8/2011 |
| WO | WO 2011/130617 | 10/2011 |
| WO | WO-2011/132087 A1 | 10/2011 |
| WO | WO-2011/147967 A1 | 12/2011 |
| WO | WO-2012/072924 A1 | 6/2012 |
| WO | WO-2012/127320 A1 | 9/2012 |
| WO | WO-2012/140519 A2 | 10/2012 |
| WO | WO-2012/138968 A1 | 10/2012 |

(56) References Cited

FOREIGN PATENT DOCUMENTS

| | | |
|---|---|---|
| WO | 2012/171026 A2 | 12/2012 |
| WO | 2012/171030 A2 | 12/2012 |
| WO | WO 2013/085682 | 6/2013 |
| WO | WO-2013/110651 A1 | 8/2013 |
| WO | WO-2014/037862 A1 | 3/2014 |
| WO | WO-2014/037863 A1 | 3/2014 |
| WO | WO-2014/068508 A2 | 5/2014 |
| WO | WO-2014/128306 A1 | 8/2014 |
| WO | WO-2014/128634 A1 | 8/2014 |
| WO | WO-2014/131846 A1 | 9/2014 |
| WO | WO-2014/141111 A1 | 9/2014 |
| WO | WO-2015/004609 A2 | 1/2015 |
| WO | WO 2015/059714 | 4/2015 |
| WO | 2015/073913 A1 | 5/2015 |
| WO | WO 2015/069943 | 5/2015 |
| WO | WO 2015/118148 | 8/2015 |
| WO | WO 2015/118149 | 8/2015 |
| WO | WO-2015/131143 A1 | 9/2015 |
| WO | WO 2016/130940 | 8/2016 |
| WO | WO 2017/072201 | 5/2017 |
| WO | WO 2017/158611 | 9/2017 |
| WO | WO 2017/207822 | 12/2017 |
| WO | WO 2018/183426 | 10/2018 |
| WO | WO 2019/155032 | 8/2019 |
| WO | WO 2019/238919 | 12/2019 |
| WO | WO 2020/020569 | 1/2020 |
| WO | WO 2020/079274 | 4/2020 |

OTHER PUBLICATIONS

Chang, Ho Nam, "Membrane Bioreactors: Engineering Aspects", Biotech. Adv., 1987, pp. 129-145, vol. 5.
Edgington, Stephen M., "New Horizons for Stem-Cell Bioreactors", Biotechnology, Oct. 1992, pp. 1099-1106, vol. 10.
Gastens et al., "Good Manufacturing Practice-Compliant Expansion of Marrow-Derived Stem and Progenitor Cells for Cell Therapy", Cell Transplantation, 2007, pp. 685-696, vol. 16.
Gramer et al., "Screening Tool for Hollow-Fiber Bioreactor Process Development", Biotechnol. Prog., 1998, pp. 203-209, vol. 14.
Hirschel et al., "An Automated Hollow Fiber System for the Large Scale Manufacture of Mammalian Cell Secreted Product", Large Scale Cell Culture Technology, ed. Bjorn K. Lydersen, 1987, pp. 113-144, Hanser Publishers.
Infanger et al., "Simulated weightlessness changes the cytoskeleton and extracellular matrix proteins in papillary thyroid carcinoma cells", Cell and Tissue Research, 2006, 324(2): 267-277.
Jones et al., "Genetic stability of bone marrow-derived human mesenchymal stromal cells in the Quantum System", Cytotherapy, 2013; 15: 1323-1339.
Liu et al., "Ex vivo Expansion of Hematopoietic Stem Cells Derived from Umbilical Cord Blood in Rotating Wall Vessel", Journal of Biotechnology, 2006, 124:592-601.
Nankervis et al., "Shear Stress Conditions in the Quantum Cell Expansion System", Poster Session—TERMIS AM Annual Conference 2013, Nov. 12, 2013.
Nguyen et al., "QUANTUM® Cell Expansion System: Automated Expansion of Human Mesenchymal Stem Cells from Precultured Cells Using the Quantum Cell Expansion System", Terumo BCT, Inc., 2012.
Nielsen, Lars Keld, "Bioreactors for Hematopoietic Cell Culture", Annu. Rev. Biomed. Eng., 1999, vol. 1, pp. 129-152.
Pörtner et al., "An Overview on Bioreactor Design, Prototyping and Process Control for Reproducible Three-Dimensional Tissue Culture", Drug Testing in Vitro: Breakthroughs and Trends in Cell Culture Technology, ed. Uwe Marx and Volker Sandig, 2007, Wiley-VCH, pp. 53-78.
Zhao et al., "Perfusion Bioreactor System for Human Mesenchymal Stem Cell Tissue Engineering: Dynamic Cell Seeding and Construct Development", Biotechnology and Bioengineering, Aug. 20, 2005, vol. 91, No. 4, pp. 482-493.
Biovest International, "AutovaxIDTM: advanced hollow fibre bioreactors with automated lactate control yield higher density monoclonal antibody production", VWRbioMarke, No. 21, Sep. 2008, pp. 10-11.
Clausen et al., "Lactate as an Indicator of Terminating Time in Insect Cell Culture Baculovirus Expression Vector Systems", Biotechnology Techniques, vol. 10, No. 10, Oct. 1996, pp. 721-726.
Gerlach, J.C. et al., "Comparison of hollow fibre membranes for hepatocyte immobilization in bioreactors," The International Journal of Artificial Organs, 1996, vol. 19 No. 10, pp. 610-616.
Gloeckner et al., "New Miniaturized Hollow-Fiber Bioreacter for in Vivo Like Cell Culture, Cell Expansion, and Production of Cell-Derived Products", Biotechnol. Prog., Aug. 21, 2001, vol. 17, No. 5, pp. 828-831.
Grayson et al., "Effects of Hypoxia on Human Mesenchymal Stem Cell Expansion and Plasticity in 3D Constructs", J. Cellular Physiology, 2006, 207:331-339.
Lloyd, J.R. et al., "Hollow-Fibre bioreactors compared to batch and chemostat culture for the production of a recombinant toxoid by a marine Vibrio," Appl. Microbiol Biotechnol, Aug. 1997, vol. 48, pp. 155-161.
Neumann, Detlef et al., "Bioreaktorsteurung mit grafischer Bedienoberflache," ATP Automatisierungstechnische Praxis, Mar. 1995, pp. 16-23, vol. 37, No. 3, Munchen, DE. (English language translation provided).
Notice of Allowance and Fee(s) Due, U.S. Appl. No. 15/616,635, dated Feb. 5, 2020.
Notice of Allowance and Fee(s) Due, U.S. Appl. No. 15/616,635, dated Apr. 22, 2020.
Notice of Allowance and Fee(s) Due, U.S. Appl. No. 15/616,745, dated Nov. 14, 2019.
Notice of Allowance and Fee(s) Due, U.S. Appl. No. 15/616,876, dated Jan. 2, 2020.
Office Action, U.S. Appl. No. 15/616,635, dated Jun. 24, 2019.
Office Action, U.S. Appl. No. 15/616,745, dated Jun. 10, 2019.
Office Action, U.S. Appl. No. 15/616,876, dated Apr. 18, 2019.
Ozturk et al., "Real-Time Monitoring and Control of Glucose and Lactate Concentrations in a Mammalian Cell Perfusion Reactor", Biotechnology and Bioengineering, vol. 53, No. 4, Feb. 20, 1997, pp. 372-378.
Sauer, I. et al., "Extracorporeal liver support based on primary human liver cells and albumin dialysis-treatment of patient with primary graft non function," Journal of Hepatology, Oct. 2003, vol. 39 No. 4, pp. 649-653.
Wang et al., "Influence of Oxygen on the Proliferation and Metabolism of Adipose Derived Adult Stem Cells", J. Cellular Physiology, 2005, 204:184-161.
Zhao et al., "Effects of Oxygen Transport on 3-D human Mesenchymal Stem Cell Metabolic Activity in Perfusion and Static Cultures: Experiments and Mathematical Model", Biotechnol. Prog, 2005, 27, 1269-1280.
"The Effect of Rocking Rate and Angle on T Cell Cultures Grown in XuriTM Cell Expansion Systems," GE Healthcare UK Limited, Cell therapy bioreactor systems, Application note 29-1166-55 AA, Aug. 2014, www.gelifesciences.com/xuri.
Abumiya et al., "Shear Stress Induces Expression of Vascular Endothelial Growth Factor Receptor Flk-1/KDR Through the CT-Rich Sp1 Binding Site," Ateriosclerosis, Thrombosis, and Vascular Biology, vol. 22, Jun. 2002, pp. 907-913.
Akiyama et al., "Ultrathin Poly(N-isopropylacrylamide) Grafted Layer on Polystyrene Surfaces for Cell Adhesion/Detachment Control," Langmuir, vol. 20, No. 13, May 26, 2004, pp. 5506-5511.
Akram et al., "Mesenchymal Stem Cells Promote Alveolar Epithelial Cell Wound Repair in vitro through Distinct Migratory and Paracrine Mechanisms," Respiratory Research, vol. 14, No. 9, 2013, pp. 1-16.
Alenazi et al., "Modified Polyether-sulfone Membrane: a Mini Review," Designed Monomers And Polymers, vol. 20, No. 1, 2017, pp. 532-546.
Anamelechi et al., "Streptavidin Binding and Endothelial Cell Adhesion to Biotinylated Fibronectin," Langmuir, vol. 23, No. 25, Dec. 4, 2007, pp. 12583-12588.

(56) References Cited

OTHER PUBLICATIONS

Azar et al., "Heart Rates of Male and Female Sprague-Dawley and Spontaneously Hypertensive Rats Housed Singly or in Groups," Journal of the American Association for Laboratory Animal Science, vol. 50, No. 2, Mar. 2011, pp. 175-184.
Baecher-Allan et al., "CD4+CD25high Regulatory Cells in Human Peripheral Blood," The Journal of Immunology, vol. 167, 2001, pp. 1245-1253.
Bai et al., "Expansion of Primitive Human Hematopoietic Stem Cells by Culture in a Zwitterionic Hydrogel," Nature Medicine, vol. 25, Oct. 2019, pp. 1566-1575.
Barker et al., "CD34+ Cell Content of 126 341 Cord Blood Units in the US Inventory: Implications for Transplantation and Banking," Blood Advances, vol. 3, No. 8, Apr. 23, 2019, pp. 1267-1271.
Boitano et al., "Aryl Hydrocarbon Receptor Antagonists Promote the Expansion of Human Hematopoietic Stem Cells," Science, vol. 329, No. 5997, published Sep. 10, 2010. corrected May 6, 2011, pp. 1345-1348.
Brunstein et al., "Infusion of ex vivo Expanded T Regulatory Cells in Adults Transplanted with Umbilical Cord Blood: Safety Profile and Detection Kinetics," Blood, vol. 117, No. 3, Jan. 20, 2011, pp. 1061-1070.
Bryce et al., "In vitro micronucleus assay scored by flow cytometry provides a comprehensive evaluation of cytogenetic damage and cytotoxicity," Mutation Research, vol. 630, Mar. 19, 2007, pp. 78-91.
Bryce et al., "Interlaboratory Evaluation of a Flow Cytometric, High Content in vitro Micronucleus Assay," Mutation Research, vol. 650, Jan. 7, 2008, pp. 181-195.
Camacho Villa et al., "CD133+CD34+ and CD133+CD38+ Blood Progenitor Cells as Predictors of Platelet Engraftment in Patients Undergoing Autologous Peripheral Blood Stem Cell Transplantation," Transfusion and Apheresis Science, vol. 46, 2012, pp. 239-244.
Cano et al., "Immobilization of endo-1,4-β-xylanase on Polysulfone Acrylate Membranes: Synthesis and Characterization," Journal of Membrane Science, vol. 280, Feb. 28, 2006, pp. 383-388.
Carvell et al., "Monitoring Live Biomass in Disposable Bioreactors," BioProcess International, vol. 14, No. 3, Mar. 2016, pp. 40-48.
Carvell et al., "On-line Measurements and Control of Viable Cell Density in Cell Culture Manufacturing Processes Using Radio Frequency Impedance," Cytotechnology, 2006, vol. 50, pp. 35-48.
Cuchiara et al., "Covalent Immobilization of SCF and SDF1α for in vitro Culture of Hematopoietic Progenitor Cells," Acta Biomaterials, vol. 9, No. 12, Dec. 2013, pp. 9258-9269.
Da Silva et al., "Smart Thermoresponsive Coatings and Surfaces for Tissue Engineering: Switching Cell-Material Boundaries," Trends in Biotechnology, vol. 15, No. 12, 2007, pp. 577-583.
Garlie et al., "T Cells Coactivated with Immobilized Anti-CD3 and Anti-CD28 as Potential Immunotherapy for Cancer," Journal of Immunotherapy, vol. 22, No. 4, 1999, pp. 336-345.
Hao et al., "A Functional Comparison of CD34+ CD38-Cells in Cord Blood and Bone Marrow," Blood, vol. 86, No. 10, Nov. 15, 1995, pp. 3745-3753.
Harimoto et al., "Novel Approach for Achieving Double-Layered Cell Sheets Co-Culture: Overlaying Endothelial Cell Sheets onto Monolayer Hepatocytes Utilizing Temperature-Responsive Culture Dishes," Journal of Biomedical Material Research, vol. 62, 2002, pp. 464-470.
Högstedt et al., "Frequency and Size Distribution of Micronuclei in Lymphocytes Stimulated with Phytohemagglutinin and Pokeweed Mitogen in Workers Exposed to Piperazine," Hereditas, vol. 109, 1998, pp. 139-142.
Horwitz et al., "Phase I/II Study of Stem-Cell Transplantation Using a Single Cord Blood Unit Expanded Ex Vivo with Nicotinamide," Journal of Clinical Oncology, vol. 37, No. 5, Dec. 4, 2018, pp. 367-376.
Itkin et al., "SDF-1 Keeps HSC Quiescent at Home," Blood, vol. 117, No. 2, Jan. 13, 2011, pp. 373-374.
Jang et al., "Syndecan-4 Proteoliposomes Enhance Fibroblast Growth Factor-2 (FGF-2)-Induced Proliferation, Migration, and Neovascularization of Ischemic Muscle," PNAS, vol. 109, No. 5, Jan. 31, 2012, pp. 1679-1684.
Johansson et al., "Pancreatic Islet Survival and Engraftment Is Promoted by Culture on Functionalized Spider Silk Matrices," PLoS ONE, Jun. 19, 2015, pp. 1-21.
Klein et al., "Affinity Membranes Prepared from Hydrophilic Coatings on Microporous Polysulfone Hollow Fibers," Journal of Membrane Science, vol. 90, 1994, pp. 69-80.
Koestenbauer et al., "Protocols for Hematopoietic Stem Cell Expansion from Umbilical Cord Blood," Cell Transplantation, vol. 18, May 6, 2009, pp. 1059-1068.
Koller et al., "Clinical-scale Human Umbilical Cord Blood Cell Expansion in a Novel Automated Perfusion Culture System," Bone Marrow Transplantation, vol. 21, 1998, pp. 653-663.
Lang et al., "Generation of Hematopoietic Humanized Mice in the Newborn BALB/C-Rag2null Il2rγnull Mouse Model: A Multivariable Optimization Approach," Clinical Immunology, vol. 140, Apr. 14, 2011, pp. 102-116.
Lataillade et al., "Chemokine SDF-1 Enhances Circulating CD341 Cell Proliferation in Synergy with Cytokines: Possible Role in Progenitor Survival," Blood, vol. 95, No. 3, Feb. 1, 2000, pp. 756-768.
Lee et al., "Long-Term Outcomes Following CD19 CAR T Cell Therapy for B-ALL Are Superior in Patients Receiving a Fludarabine/Cyclophosphamide Preparative Regimen and Post-CAR Hematopoietic Stem Cell Transplantation," Blood, vol. 128, No. 22, Dec. 2, 2016, Ab. 218.
Li et al., "Heparin-induced Conformation Changes of Fibronectin within the Extracellular Matrix Promote hMSC Osteogenic Differentiation," Biomaterials Science, vol. 3, 2015, pp. 73-84.
Malin et al., "Noninvasive Prediction of Glucose by Near-Infrared Diffuse Reflectance Spectroscopy," Clinical Chemistry, vol. 45, No. 9, 1999, pp. 1651-1658.
Marek-Trzonkowska et al., "Administration of CD4+ CD25high CD127- Regulatory T Cells Preserves β-Cell Function in Type 1 Diabetes in Children," Diabetes Care, vol. 35, No. 9, Sep. 2012, pp. 1817-1820.
Murugappan et al., "Human Hematopoietic Progenitor Cells Grow Faster under Rotational Laminar Flows," Biotechnology Progress—Cell Culture & Tissue Engineering, Online, Apr. 22, 2010.
Nelson et al., "Emergent Patterns of Growth Controlled by Multicellular Form and Mechanics," PNAS, vol. 102, No. 33, Aug. 16, 2005, pp. 11594-11599.
Nicolette et al., "In Vitro Micronucleus Screening of Pharmaceutical Candidates by Flow Cytometry in Chinese Hamster V79 Cells," Environmental and Molecular Mutagenesis, vol. 52, Oct. 20, 2010, pp. 355-362.
Nugent et al., "Adventitial Endothelial Implants Reduce Matrix Metalloproteinase-2 Expression and Increase Luminal Diameter in Porcine Arteriovenous Grafts," Journal of Vascular Surgery, vol. 46, No. 3, Sep. 2007, pp. 548-556.e2.
Okano et al., "Mechanism of Cell Detachment from Temperature-Modulated, Hydrophilic-Hydrophobic Polymer Surfaces," Biomaterials, vol. 16, No. 4, 1995, pp. 297-303.
Putnam et al., "Expansion of Human Regulatory T-Cells from Patients with Type 1 Diabetes," Diabetes, vol. 58, Mar. 2009, pp. 652-662.
Rahmahwati et al., "The Synthesis of Polyethersulfone (PES) Derivatives for the Immobilization of Lipase Enzyme," Key Engineering Materials, vol. 811, Jul. 8, 2019, pp. 14-21.
Rodrigues et al., "Stem Cell Cultivation in Bioreactors," Biotechnology Advances, vol. 29, Jun. 25, 2011, pp. 815-829.
Ronco et al., "Blood and Dialysate Flow Distributions in Hollow-Fiber Hemodialyzers Analyzed by Computerized Helical Scanning Technique," Journal of the American Society of Nephrology, vol. 13, 2002, pp. S53-S61.
Ryu et al., "Near-infrared Light Responsive Synthetic c-di-GMP Module for Optogenetic Applications," ACS Synthetic Biology, vol. 3, Jan. 28, 2014, pp. 802-810.
Shimizu et al., "Fabrication of Pulsatile Cardiac Tissue Grafts Using a Novel 3-Dimensional Cell Sheet Manipulation Technique and

(56) References Cited

OTHER PUBLICATIONS

Temperature-Responsive Cell Culture Surfaces," Circulation Research, vol. 90, Feb. 22, 2002, e40-e48, pp. 1-9.

Smith et al., "Expansion of Neutrophil Precursors and Progenitors in Suspension Cultures of CD34+ Cells Enriched from Human Bone Marrow," Experimental Hematology, vol. 21, 1993, pp. 870-877.

Streltsova et al., "Recurrent Stimulation of Natural Killer Cell Clones with K562 Expressing Membrane-Bound Interleukin-21 Affects Their Phenotype, Interferon-γ Production, and Lifespan," International Journal of Molecular Sciences, vol. 20, No. 443, 2019, pp. 1-18.

Takezawa et al., "Cell Culture on a Thermo-responsive Polymer Surface," Nature, Bio/Technology, vol. 8, Sep. 1990, pp. 854-856.

Tiziani et al., "Metabolomic Profiling of Drug Response in Acute Myeloid Leukaemia Cell lines," PLoS ONE, vol. 4, Issue 1, Jan. 22, 2009, e4251.

Ueda et al., "Interaction of Natural Killer Cells with Neutrophils Exerts a Significant Antitumor Immunity in Hematopoietic Stem Cell Transplantation Recipients," Cancer Medicine, vol. 5, No. 1, 2016 pp. 49-60.

Urbich et al., "Fluid Shear Stress-induced Transcriptional Activation of the Vascular Endothelial Growth Factor Receptor-2 Gene Requires Sp1-Dependent DNA Binding," FEBS Letters, 535, 2003, pp. 87-93.

Von Laer, "Loss of CD38 Antigen on CD34 CD38 Cells during Short-term Culture," Leukemia, Correspondence, 1999 pp. 947-948.

Wagner et al., "Phase I/II Trial of StemRegenin-1 Expanded Umbilical Cord Blood Hematopoietic Stem Cells Supports Testing as a Stand-alone Graft," Cell Stem Cell, Jan. 7, 2016, vol. 18, pp. 144-155.

Weaver et al., "An Analysis of Engraftment Kinetics as a Function of the CD34 Content of the Peripheral Blood Progenitor Cell Collections in 692 Patients after the Administration of Myeloblative Chemotherapy," Blood, vol. 86, No. 10, Nov. 15, 1995, pp. 3691-3969.

Yang et al., "Suspension Culture of Mammalian Cells Using Thermosensitive Microcarrier that Allows Cell Detachment without Proteolytic Enzyme Treatment," Cell Transplantation, vol. 19, Aug. 18, 2010, pp. 1123-1132.

Yi et al., "A Readily Modified Polyethersulfone with Amino-Substituted Groups: Its Amphiphilic Copolymer Synthesis and Membrane Application," Polymer, vol. 53, Dec. 2, 2011, pp. 350-358.

Zheng et al., "Differential Effects of Cyclic and Static Stretch on Coronary Microvascular Endothelial Cell Receptors and Vasculogenic/Angiogenic Responses," American Journal of Physiology—Heart and Circulatory Physiology, vol. 295, Aug. 2008, H794-H800.

Notice of Allowance for U.S. Appl. No. 15/616,876, dated Mar. 22, 2021, 9 pages.

U.S. Appl. No. 15/616,745, 2017/0349872 (U.S. Pat. No. 10,577,575).

U.S. Appl. No. 15/616,635, 2017/0349869.

U.S. Appl. No. 16/845,686.

Abumiya, et al. at National Cardiovascular Center Research Institute in Japan, suggest that subjecting human umbilical vein endothelial cells (HUVECs) to laminar shear stress for a period of 8 hours increased the relative expression of VEGFR-2 mRNA (Ateriosclerosis, Thrombosis, and Vascular Biology, 2002).

Afzali B, Edozie FC, Fazekasova H, Scotta C, Mitchell PJ, Canavan JB, Kordasti SY, Chana PS, Ellis R, Lord GM, John S, Hilton R, Lechler RI, Lombardi G. Comparison of regulatory T cells in hemodialysis patients and healthy controls: implications for cell therapy in transplantation. Clin J Am Soc Nephrol. 2013;8(8):1396-405.

Alberts B, Johnson A, Lewis J, et al. Molecular Biology of the Cell. 4th edition. New York: Garland Science; 2002. Fibroblasts and Their Transformations: The Connective-Tissue Cell Family. Available from: https://www.ncbi.nlm.nih.gov/books/NBK26889.

Almeida L, Lochner M, Berod L, Sparwasser T. Metabolic pathways in T cell activation and lineage differentiation. Semin Immunol. 2016;28(5):514-524.

Amy Putnam, Todd M. Brusko, Michael R. Lee, Weihong Liu, Gregory L. Szot, Taumoha Ghosh, Mark A. Atkinson, and Jeffrey A. Bluestone. Expansion of human regulatory T-Cells from patients with Type 1 Diabetes. Diabetes, 58: 652-662, 2009.

Anurathapan et al., "Engineered T cells for cancer treatment," Cytotherapy, vol. 16, pp. 713-733, 2014.

Aronowski J, Samways E, Strong R, Rhoades HM, Grotta JC. An alternative method for the quantitation of neuronal damage after experimental middle cerebral artery occlusion in rats: Analysis of behavioral deficit. Journal of cerebral blood flow and metabolism : official journal of the International Society of Cerebral Blood Flow and Metabolism. 1996;16:705-713.

Arrigoni, Chiara, et al. "Rotating versus perfusion bioreactor for the culture of engineered vascular constructs based on hyaluronic acid." Biotechnology and bioengineering 100.5 (2008): 988-997.

Bai/Delaney (Nohla Therapeutics) showed that expanding Cord Blood-derived CD34+CD38-CD45RA- HSPCs in a biodegradable zwitterionic hydrogel with a rNotch ligand cocktail for 24 days mitigated HSPC differentiation and promoted self-renewal of lymphoid and myeloid cell phenotypes in an NSG mouse model (Nature Medicine, 2019).

Ballas CB, Zielske SP, Gerson SL (2002) Adult bone marrow stem cells for cell and gene therapies: implications for greater use. J Cell Biochem Suppl 38: 20-28.

Ballke C, Gran E, Baekkevold ES, Jahnsen FL. Characterization of Regulatory T-Cell Markers in CD4+ T Cells of the Upper Airway Mucosa. PLoS One. 2016;11(2):e0148826.

Baraniak PR, McDevitt TC (2010) Stem cell paracrine actions and tissue regeneration. Regen Med 5(1): 121-143.

Barckhausen C, Rice B, Baila S, et al. (2016) GMP-Compliant Expansion of Clinical-Grade Human Mesenchymal Stromal/Stem Cells Using a Closed Hollow Fiber Bioreactor. Methods Mol Biol 1416: 389-412.

Barker, Juliet N., et al. "CD34+ cell content of 126 341 cord blood units in the US inventory: implications for transplantation and banking." Blood advances 3.8 (2019): 1267-1271.

Bazarian JJ, Cernak I, Noble-Haeusslein L, Potolicchio S, Temkin N. Long-term neurologic outcomes after traumatic brain injury. The Journal of head trauma rehabilitation. 2009;24:439-451.

Bending D, Pesenacker AM, Ursu S, Wu Q, Lom H, Thirugnanabalan B, Wedderburn LR. Hypomethylation at the regulatory T cell-specific demethylated region in CD25hi T cells is decoupled from FOXP3 expression at the inflamed site in childhood arthritis. J Immunol 2014;193(6):2699-708.

Berendse M, Grounds MD, Lloyd CM (2003) Myoblast structure affects subsequent skeletal myotube morphology and sarcomere assembly. Exp Cell Res 291(2): 435-450.

Bernard, A., Payton, Mar. 1995. "Fermentation and Growth of Escherichia coli for Optimal Protein Production".

Berney SM, Schaan T, Wolf RE, van der Heyde H, Atkinson TP. CD2 (OKT11) augments CD3-mediated intracellular signaling events in human T lymphocytes. J Investig Med. 2000;48(2):102-9.

Bioheart Clinical Trial Clinica 1302 Apr. 18, 2008.

Biomolecular and Cellular Interactions with the Hollow Fiber Membrane Currently Used in the Quantum® Cell Expansion System. 12th NJ Symposium on Biomaterials Science, Oct. 6-7, 2014, New Brunswick, NJ.

Blache C, Chauvin JM, Marie-Cardine A, Contentin N, Pommier P, Dedreux I, Francois S, Jacquot S, Bastit D, Boyer 0. Reduced frequency of regulatory T cells in peripheral blood stem cell compared to bone marrow transplantations. Biol Blood Marrow Transplant. 2010;16(3):430-4.

Bluestone et al. Type 1 diabetes immunotherapy using polyclonal regulatory! cells. Science Translational Medicine 7(315):1-34, 2015.

Bluestone JA, Tang Q. Treg cells-the next frontier of cell therapy. Science. 2018;362(6411):154-155.

Bluestone, Jeffrey A., et al. "Type 1 diabetes immunotherapy using polyclonal regulatory T cells." *Science translational medicine* 7.315 (2015): 315ra189-315ra189.

(56) References Cited

OTHER PUBLICATIONS

Blum S, Moore AN, Adams F, Dash PK. A mitogen-activated protein kinase cascade in the ca1/ca2 subfield of the dorsal hippocampus is essential for long-term spatial memory. The Journal of neuroscience : the official journal of the Society for Neuroscience. 1999;19:3535-3544.
Bojun Li et al. Heparin-induced conformation changes of fibronectin within the extracellular matrix promote hMSC osteogenic differentiation. Biomaterials Science 3: 73-84, 2015.
Boquest AC, Shahdadfar A, Brinchmann JE, Collas P. Isolation of Stromal Stem Cells from Human Adipose Tissue. Methods Mol Biol. 2006;325:35-46. doi: 10.1385/1-59745-005-7:35. PMID: 16761717.
Borden, M. and Longo, M., "Dissolution Behavior of Lipid Monolayer-Coated, Air-Filled Microbubbles: Effect of Lipid Hydrophobic Chain Length," Langmuir, vol. 18, pp. 9225-9233, 2002.
Bourke, Sharon L., and Joachim Kohn. "Polymers derived from the amino acid L-tyrosine: polycarbonates, polyarylates and copolymers with poly (ethylene glycol)." Advanced drug delivery reviews 55.4 (2003): 447-466.
Brand, K. and Hermfisse, U., "Aerobic Glycolysis by Proliferating Cells: a Protective Strategy against Reactive Oxygen Species," The FASEB Journal, vol. 11, pp. 388-395, Apr. 1997.
Brentjens et al., "CD19-Targeted T Cells Rapidly Induce Molecular Remission in Adults with Chemotherapy-Refractory Acute Lympohblastic Leukemia," Science Iranslational Medicine, vol. 5, Issue 177, pp. 1-9, Mar. 20, 2013.
Brentjens et al., "Safety and Persistance of Adoptively Transferred Autologous CD19-Target T Cells in Patients with Relapsed or Chemotherapy Refractory B-Cell Leukemias," Blood, vol. 118, No. 18, pp. 4817-4828, Nov. 3, 2011.
C. H. Weaver, et al. An Analysis of Engraftment Kinetics as a function of the CD34 Content of the Peripheral Blood Progenitor Cell Collections in 692 Patients After the Administration of Myeloblative Chemotherapy. Blood 86(10): 3691-3969, 1995.
Carswell, K. and Papoutsakis, E. "Culture of Human T Cells in Stirred Bioreactors for Cellular Immunotherapy Applications: Shear, Proliferation, and the IL-2 Receptor," Biotechnology and Bioengineering, vol. 68, No. 3, pp. 329-338, May 5, 2000.
Celeste Nelson et al., Emergent patterns of growth controlled by multicellular form and mechanics, (in Christopher Chen's Lab demonstrated, in separate experiments, that curved surfaces with a radius of curvature (200 ?m) that is greater than the cell diameter and surfaces that have undulating special patterning (depressions) increase the patterned growth of ECs), [PNAS 102(33): 11594-11599, 2005].
Chapman NM, Chi H. mTOR signaling, Tregs and immune modulation. Immunotherapy. 2014;6(12):1295-311.
Chaudhry A, Samstein RM, Treuting P, Liang Y, Pils MC, Heinrich JM, Jack RS, Wunderlich FT, Bruning JC, Muller W, Rudensky AY. Interleukin-10 signaling in regulatory T cells is required for suppression of Th17 cell-mediated inflammation. Immunity. 2011;34(4):566-78.
Chen, C. and Broden, M., "The Role of Poly(theylene glycol) Brush Architecture in Complement Activation on Targeted Microbubble Surfaces," Biomaterials, vol. 32, No. 27, pp. 6579-6587, Jun. 17, 2011.
Choi W, Kwon SJ, Jin HJ, et al. (2017) Optimization of culture conditions for rapid clinical-scale expansion of human umbilical cord blood-derived mesenchymal stem cells. Clin Transl Med 6(1): 38.
Chullikana A, Majumdar AS, Gottipamula S, et al. (2015) Randomized, double-blind, phase I/II study of intravenous allogeneic mesenchymal stromal cells in acute myocardial infarction. Cytotherapy 17(3): 250-261.
Claudio G. Brunstein, Jeffrey S. Miller, Qing Cao, Daivd H. McKenna, Keli L. Hippen, Julie Curtsinger, Todd Defor, Bruce L. Levine, Carl H. June, Pablo Rubinstein, Philip B. McGlave, Bruce R. Blazar, and John E. Wagner. Infusion of ex vivo expanded T regulatory cells in adults transplanted with umbilical cord blood: safety profile and detection kinetics. Blood, 117(3): 1061-1070, 2010.
Coeshott C, Vang B, Jones M, Nankervis B. Large-scale expansion and characterization of CD3(+) T-cells in the Quantum((R)) Cell Expansion System. J Transl Med. 2019;17(1):258.
Coombes JL, Robinson NJ, Maloy KJ, Uhlig HH, Powrie F. Regulatory T cells and intestinal homeostasis. Immunol Rev. 2005;204:184-94.
Coquillard C. mTOR Signaling in Regulatory T cell Differentiation and Expansion. SOJ Immunology. 2015;3(1):1-10.
Creed JA, DiLeonardi AM, Fox DP, Tessier AR, Raghupathi R. Concussive brain trauma in the mouse results in acute cognitive deficits and sustained impairment of axonal function. Journal of neurotrauma. 2011;28:547-563.
Dash PK, Hochner B, Kandel ER. Injection ofthe camp-responsive element into the nucleus of aplysia sensory neurons blocks long-term facilitation. Nature. 1990;345:718-721.
Dash PK, Johnson D, Clark J, Orsi SA, Zhang M, Zhao J, Grill RJ, Moore AN, Pati S. Involvement of the glycogen synthase kinase-3 signaling pathway in tbi pathology and neurocognitive outcome. PloS one. 2011;6:e24648.
Dash PK, Mach SA, Blum S, Moore AN. Intrahippocampal wortmannin infusion enhances long-term spatial and contextual memories. Learn Mem. 2002;9:167-177.
Dash PK, Orsi SA, Zhang M, Grill RJ, Pati S, Zhao J, Moore AN. Valproate administered after traumatic brain injury provides neuroprotection and improves cognitive function in rats. PloS one. 2010;5:e11383.
Dash PK, Zhao J, Orsi SA, Zhang M, Moore AN. Sulforaphane improves cognitive function administered following traumatic brain injury. Neuroscience letters. 2009;460:103-107.
Davila et al., "Efficacy and Toxicity Management of 19-28z CAR T Cell Therapy in B cell Acute Lymphoblastic Leukemia," Science Translational Medicine, vol. 6, No. 224, pp. 1-10, Feb. 19, 2014.
Dejana E, Orsenigo F, Lampugnani MG. The role of adherens junctions and ve-cadherin in the control of vascular permeability. Journal of cell science. 2008;121:2115-2122.
Dejana E, Spagnuolo R, Bazzoni G. Interendothelial junctions and their role in the control of angiogenesis, vascular permeability and leukocyte transmigration. Thrombosis and haemostasis. 2001;86:308-315.
Dejana E, Tournier-Lasserve E, Weinstein BM. The control of vascular integrity by endothelial cell junctions: Molecular basis and pathological implications. Developmental cell. 2009;16:209-221.
Del Pino A, Ligero G, Lopez MB, et al. (2015) Morphology, cell viability, karyotype, expression of surface markers and plasticity of three primary cell line cultures before and after the cryostorage in LN2 and GN2. Cryobiology 70(1): 1-8.
Delaney, Colleen, et al. "Notch-mediated expansion of human cord blood progenitor cells capable of rapid myeloid reconstitution." Nature medicine 16.2 (2010): 232-236.
Ding, Zhongli, Guohua Chen, and Allan S. Hoffman. "Synthesis and purification of thermally sensitive oligomer? enzyme conjugates of poly (N-isopropylacrylamide)? trypsin." Bioconjugate chemistry 7.1 (1996): 121-125.
Dixon CE, Clifton GL, Lighthall JW, Yaghmai AA, Hayes RL. A controlled cortical impact model of traumatic brain injury in the rat. Journal of neuroscience methods. 1991;39:253-262.
Dominici M, Le Blanc K, Mueller I, et al. (2006) Minimal criteria for defining multipotent mesenchymal stromal cells. The International Society for Cellular Therapy position statement. Cytotherapy 8(4): 315-317.
Durrani S, Konoplyannikov M, Ashraf M, Haider KH (2010) Skeletal myoblasts for cardiac repair. Regen Med 5(6): 919-932.
Esensten JH, Muller YD, Bluestone JA, Tang Q. Regulatory T-cell therapy for autoimmune and autoinflammatory diseases: The next frontier. J Allergy Clin Immunol. 2018;142(6):1710-1718.
Fakin R, Hamacher J, GuggerM, Gazdhar A, Moser H, Schmid RA. Prolonged amelioration of acute lung allograft rejection by sequential overexpression of human interleukin-10 and hepatocyte growth factor in rats. Exp Lung Res. 2011;37(9):555-62.

(56) References Cited

OTHER PUBLICATIONS

Fedorov et al., "PD-1- and CTLA-4-Based Inhibitory Chimeric Antigen Receptors (iCARs) Divert Off-Target Immunotherapy Responses," Science Translational Medicine, vol. 5, No. 215, pp. 1-12, Dec. 11, 2013.
Ferreira LMR, Muller YD, Bluestone JA, Tang Q. Next-generation regulatory T cell therapy. Nat Rev Drug Discov. 2019;18(10):749-769.
Fischbach, Michael A., Jeffrey A. Bluestone, and Wendell A. Lim. "Cell-based therapeutics: the next pillar of medicine." Science translational medicine 5.179 (2013): 179ps7-179ps7.
Fisk, Nicholas M., et al. "Can routine commercial cord blood banking be scientifically and ethically justified?." PLoS medicine 2.2 (2005): e44.
Forbes Jun. 23, 2014 article "Will this man cure cancer?".
Fowler DH. Rapamycin-resistant effector T-cell therapy. Immunol Rev. 2014;257(1):210-25.
Fraser H, Safinia N, Grageda N, Thirkell S, Lowe K, Fry LJ, Scotta C, Hope A, Fisher C, Hilton R, Game D, Harden P, Bushell A, Wood K, Lechler RI, Lombardi G. A Rapamycin-Based GMP-Compatible Process for the Isolation and Expansion of Regulatory T Cells for Clinical Trials. Mol Ther Methods Clin Dev. 2018;8:198-209.
Frauwirth KA, Riley JL, Harris MH, Parry RV, Rathmell JC, Plas DR, Elstrom RL, June CH, Thompson CB. The CD28 signaling pathway regulates glucose metabolism. Immunity. 2002;16(6):769-777.
Fuchs A, Gliwinski M, Grageda N, Spiering R, Abbas AK, Appel S, Bacchetta R, Battaglia M, Berglund D, Blazar B, Bluestone JA, Bornhauser M, Ten Brinke A, Brusko TM, Cools N, Cuturi MC, Geissler E, Giannoukakis N, Golab K, Hafler DA, van Ham SM, Hester J et al. Minimum Information about T Regulatory Cells: A Step toward Reproducibility and Standardization. Front Immunol. 2017;8:1844.
G0211: Study for Gamma Irradiation of Bioreactor Membranes, undated, author unknown, 3 pages.
Galgani M, De Rosa V, La Cava A, Matarese G. Role of Metabolism in the Immunobiology of Regulatory T Cells. J Immunol. 2016;197(7):2567-75.
Gedaly R, De Stefano F, Turcios L, Hill M, Hidalgo G, Mitov Ml, Alstott MC, Butterfield DA, Mitchell HC, Hart J, Ai-Attar A, Jennings CD, Marti F. mTOR Inhibitor Everolimus in Regulatory T Cell Expansion for Clinical Application in Transplantation. Transplantation. 2019;103(4):705-715.
Gimble, Jeffrey M., Adam J. Katz, and Bruce A. Bunnell. "Adipose-derived stem cells for regenerative medicine." Circulation research 100.9 (2007): 1249-1260.
Gingras AC, Raught B, Sonenberg N. Regulation of translation initiation by FRAP/mTOR. Genes Dev. 2001;15(7):807-26.
Godin, Michel, et al. "Measuring the mass, density, and size of particles and cells using a suspended microchannel resonator." Applied physics letters 91.12 (2007): 123121.
Goh, Celeste, Sowmya Narayanan, and Young S. Hahn. "Myeloid-derived suppressor cells: the dark knight or the joker in viral infections?." Immunological reviews 255A (2013): 210-221.
Golab K, Leveson-Gower D, Wang XJ, Grzanka J, Marek-Trzonkowska N, Krzystyniak A, Millis JM, Trzonkowski P, Witkowski P. Challenges in cryopreservation of regulatory T cells (Tregs) for clinical therapeutic applications. Int Immunopharmacol. 2013;16(3):371-5.
Goldring CE, Duffy PA, Benvenisty N, Andrews PW, Ben-David U, Eakins R, French N, Hanley NA, Kelly L, Kitteringham NR, Kurth J, Ladenheim D, Laverty H, McBlane J, Narayanan G, Patel S, Reinhardt J, Rossi A, Sharpe M, Park BK. Assessing the safety of stem cell therapeutics. Cell stem cell. 2011;8:618-628.
Griesche, Nadine, et al. "A simple modification of the separation method reduces heterogeneity of adipose-derived stem cells." cells tissues organs 192.2 (2010): 106-115.
Gutcher I, Donkor MK, Ma Q, Rudensky AY, Flavell RA, Li MO. Autocrine transforming growth factor-betal promotes in vivo Th17 cell differentiation. Immunity. 2011;34(3):396-408.

Haack-Sorensen M, Follin B, Juhl M, et al. (2016) Culture expansion of adipose derived stromal cells. A closed automated Quantum Cell Expansion System compared with manual flask-based culture. J Transl Med 14(1): 319.
Hall ED, Sullivan PG, Gibson TR, Pavel KM, Thompson BM, Scheff SW. Spatial and temporal characteristics of neurodegeneration after controlled cortical impact in mice: More than a focal brain injury. Journal of neurotrauma. 2005;22:252-265.
Hami et al., "GMP Production and Testing of Xcellerated T Cells for the Treatment of Patients with CLL," Cytotherapy, pp. 554-562, 2004.
Hamm RJ, Dixon CE, Gbadebo DM, Singha AK, Jenkins LW, Lyeth BG, Hayes RL. Cognitive deficits following traumatic brain injury produced by controlled cortical impact. Journal of neurotrauma. 1992;9:11-20.
Hanley PJ, Mei Z, Durett AG, et al. (2014) Efficient manufacturing of therapeutic mesenchymal stromal cells with the use of the Quantum Cell Expansion System. Cytotherapy 16(8): 1048-1058.
He N, Fan W, Henriquez B, Yu RT, Atkins AR, Liddle C, Zheng Y, Downes M, Evans RM. Metabolic control of regulatory T cell (Treg) survival and function by Lkb1. Proc Natl Acad Sci USA. 2017;114(47):12542-12547.
He X, Landman S, Bauland SC, van den Dolder J, Koenen HJ, Joosten I. A TNFR2-Agonist Facilitates High Purity Expansion of Human Low Purity Treg Cells. PLoS One. 2016;11(5):e0156311.
Heskins, Michael, and James E. Guillet. "Solution properties of poly(N-isopropylacrylamide)." Journal of Macromolecular Science—Chemistry 2.8 (1968): 1441-1455.
Hill JA, Feuerer M, Tash K, Haxhinasto S, Perez J, Melamed R, Mathis D, Benoist C. Foxp3 Transcription-factor-dependent and -independent regulation of the regulatory T cell transcriptional signature. Immunity. 2007;27(5):786-800.
Högstedt, Benkt, Anita Karlsson, and Anders Holmén. "Frequency and size distribution of micronuclei in lymphocytes stimulated with phytohemagglutinin and pokeweed mitogen in workers exposed to piperazine." Hereditas 109.(1988): 139-142.
Hollyman et al., "Manufacturing Validation of Biologicall Functional T Cells Targeted to CD19 Antigen for Autologous Adoptive Cell Therapy," J Immunother, vol. 32, No. 2, pp. 169-180, Feb.-Mar. 2009.
http://www.ucdenver.edu/academics/colleges/medicalschool/centers/cancercenter/Research/sharedresources/AnimalImaging/smal-lanimalimaging/Pages/MRI.aspx.
ISCT Webinar "Volume Reduction technology for Large Scale Harvest or Post-thaw Manipulation of Cellular Therapeutics".
Iwashima, Shigejiro, et al. "Novel culture system of mesenchymal stromal cells from human subcutaneous adipose tissue." Stem cells and development 18.4 (2009): 533-544.
Jarocha D, Stangel-Wojcikiewicz K, Basta A, Majka M (2014) Efficient myoblast expansion for regenerative medicine use. Int J Mol Med 34(1): 83-91.
Jin, H., and J. Bae. "Neuropeptide Y regulates the hematopoietic stem cell microenvironment and prevents nerve injury in the bone marrow." 22nd Annual ISCT Meeting (2016): S29.
Jo CH, Lee YG, Shin WH, et al. (2014) Intra-articular injection of mesenchymal stem cells for the treatment of osteoarthritis of the knee: a proof-of-concept clinical trial. Stem Cells 32(5): 1254-1266.
John Carvell, et al. Monitoring Live Biomass in Disposable Bioreactors, BioProcess International 14(3)s, Mar. 2016.
John Nicolette, et al. (Abbott Laboratories). In Vitro Micronucleus Screening of Pharmaceutical Candidates by Flow Cyto9metry in Chinese Hamster V79 Cells, Environmental and Molecular Mutagenesis 00:000-000, 2010.
John P. Carvell and Jason E. Dowd. On-line measurements and control of viable cell density in cell culture manufacturing processes using radio frequency impedance. Cytotechnology 50: 35-48, 2006.
Johnson, Patrick A., et al. "Interplay of anionic charge, poly (ethylene glycol), and iodinated tyrosine incorporation within tyrosine? derived polycarbonates: Effects on vascular smooth muscle cell adhesion, proliferation, and motility." Journal of Biomedical Materials Research Part A: An Official Journal of The Society for Biomaterials, The Japanese Society for Biomaterials, and The

(56) References Cited

OTHER PUBLICATIONS

Australian Society for Biomaterials and the Korean Society for Biomaterials 93.2 (2010): 505-514.
Johnston LC, Su X, Maguire-Zeiss K, Horovitz K, Ankoudinova I, Guschin D, Hadaczek P, Federoff HJ, Bankiewicz K, Forsayeth J. Human interleukin-10 gene transfer is protective in a rat model of Parkinson's disease. Mol Ther. 2008;16(8):1392-9.
Jones2016ISCT 2016 Poster 69.
Joy, Abraham, et al. "Control of surface chemistry, substrate stiffness, and cell function in a novel terpolymer methacrylate library." Langmuir 27.5 (2011): 1891-1899.
Kalamasz et al., "Optimization of Human T-Cell Expansion Ex Vivo Using Magnetic Beads Conjugated with Anti-CD3 and Anti-CD28 Antibodies," J Immunother, vol. 27, No. 5, pp. 405-418, Sep.-Oct. 2004.
Kim, Do-Hyung, et al. "mTOR interacts with raptor to form a nutrient-sensitive complex that signals to the cell growth machinery." Cell 110.2 (2002): 163-175.
Kishore M, Cheung KCP, Fu H, Bonacina F, Wang G, Coe D, Ward EJ, Colamatteo A, Jangani M, Baragetti A, Matarese G, Smith DM, Haas R, Mauro C, Wraith DC, Okkenhaug K, Catapano AL, De Rosa V, Norata GD, Marelli-Berg FM. Regulatory T Cell Migration Is Dependent on Glucokinase-Mediated Glycolysis. Immunity. 2017;47(5):875-889 e10.
Klapper et al., "Single-Pass, Closed-System Rapid Expansion of Lymphocyte Cultures for Adoptive Cell Therapy," Journal of Immunological Methods, 345, pp. 90-99, Apr. 21, 2009.
Klysz D, Tai X, Robert PA, Craveiro M, Cretenet G, Oburoglu L, Mongellaz C, Floess S, Fritz V, Matias Ml, Yong C, Surh N, Marie JC, Huehn J, Zimmermann V, Kinet S, Dardalhon V, Taylor N. Glutamine-dependent alpha-ketoglutarate production regulates the balance between T helper 1 cell and regulatory T cell generation. Sci Signal. 2015;8(396):ra97.
Korpanty et al., "Tageting Vascular Enothelium with Avidin Microbubbles," Ultrasound in Medicine and Biology, vol. 31, No. 9, pp. 1279-1283, May 24, 2005.
Krauss et al., "Signaling Takes a Breath—New Quantitative Perspectives on Bioenergetics and Signal Transduction," Immunity, vol. 15, pp. 497-502, Oct. 2001.
Kulikov, A. V., et al. "Application of multipotent mesenchymal stromal cells from human adipose tissue for compensation of neurological deficiency induced by 3-nitropropionic acid in rats." Bulletin of experimental biology and medicine 145.4 (2008): 514-519.
Kumar P, Marinelarena A, Raghunathan D, Ragothaman VK, Saini S, Bhattacharya P, Fan J, Epstein AL, Maker AV, Prabhakar BS. Critical role of OX40 signaling in the TCR-independent phase of human and murine thymic Treg generation. Cell Mol Immunol. 2019;16(2):138-153.
Kwan, J. and Borden, M., "Lipid Monolayer Collapse and Microbubble Stability," Advances in Colloid and Interface Science, vols. 183-184, pp. 82-99, Aug. 21, 2012.
Lampugnani MG, Caveda L, Breviario F, Del Maschio A, Dejana E. Endothelial cell-to-cell junctions. Structural characteristics and functional role in the regulation of vascular permeability and leukocyte extravasation. Bailliere's clinical haematology. 1993;6:539-558.
Lee et al., "Continued Antigen Stimulation Is Not Required During CD4+ T Cell Clonal Expansion," The Journal of Immunology, 168, pp. 1682-1689, 2002.
Lee, Jae W., et al. "Allogeneic human mesenchymal stem cells for treatment of E. coli endotoxin-induced acute lung injury in the ex vivo perfused human lung." Proceedings of the national academy of Sciences 106.38 (2009): 16357-16362.
Levine, B., "T Lymphocyte Engineering ex vivo for Cancer and Infectious Disease," Expert Opinion on Biological Therapy, vol. 4, No. 4, pp. 475-489, 2008.
Lindstein, Tullia, et al. "Regulation of lymphokine messenger RNA stability by a surface-mediated T cell activation pathway." Science 244.4902 (1989): 339-343.
Liotta, Francesco, et al. "Frequency of regulatory T cells in peripheral blood and in tumour-infiltrating lymphocytes correlates with poor prognosis in renal cell carcinoma." *BJU international* 107.9 (2011): 1500-1506.
Liu W, Putnam AL, Xu-Yu Z, Szot GL, Lee MR, Zhu S, Gottlieb PA, Kapranov P, Gingeras TR, Fazekas de St Groth B, Clayberger C, Soper DM, Ziegler SF, Bluestone Ja. CD127 expression inversely correlates with FoxP3 and suppressive function of human CD4+ T reg cells. J Exp Med. 2006;203(7):1701-1711.
Lum et al., "Ultrasound Radiation Force Enables Targeted Deposition of Model Drug Carriers Loaded on Microbubbles," Journal of Controlled Release, 111, pp. 128-134, 2006.
M. R. Koller, et al. Clinical-scale human umbilical cord blood cell expansion in a novel automated perfusion culture system. Bone Marrow Transplantion 21:653-663, 1998.
Malone et al., "Characterization of Human Tumor-Infiltrating Lymphocytes Expanded in Hollow-Fiber Bioreactors for Immunotherapy of Cancer," Cancer Biotherapy & Radiopharmaceuticals, vol. 16, No. 5, pp. 381-390, 2001.
Mao AS, Mooney DJ (2015) Regenerative medicine: current therapies and future directions. Proc Natl Acad Sci USA 112(47): 14452-14459.
Maria Streltsova, Dean Lee (Nationwide Children's Hospital, OSU, Columbus, OH) et al. (Int'l Journal of Molecular Sciences, 2019).
Markgraf CG, Clifton GL, Aguirre M, Chaney SF, Knox-Du Bois C, Kennon K, Verma N. Injury severity and sensitivity to treatment after controlled cortical impact in rats. Journal of Neurotrauma. 2001;18:175-186.
Mathew, James M., et al. "A phase I clinical trial with ex vivo expanded recipient regulatory T cells in living donor kidney transplants." Scientific reports 8.1 (2018): 1-12.
Matthay, Michael A., et al. "Therapeutic potential of mesenchymal stem cells for severe acute lung injury." Chest 138.4 (2010): 965-972.
Maynard CL, Harrington LE, Janowski KM, Oliver JR, Zindl CL, Rudensky AY, Weaver CT. Regulatory T cells expressing interleukin 10 develop from Foxp3+ and Foxp3- precursor cells in the absence of interleukin 10. Nat Immunol. 2007;8(9):931-41.
McKenna DH, Jr., Sumstad D, Kadidlo DM, et al. Optimization of cGMP purification and expansion of umbilical cord blood-derived T-regulatory cells in support of first-in-human clinical trials. Cytotherapy 2017;19:250-62.
McLimans W, Kinetics of Gas Diffusion in Mammalian Cell Culture Systems. Biotechnology and Bioengineering 1968; 10:725-740.
McMurtrey, Richard J. "Analytic models of oxygen and nutrient diffusion, metabolism dynamics, and architecture optimization in three-dimensional tissue constructs with applications and insights in cerebral organoids." Tissue Engineering Part C: Methods 22.3 (2016): 221-249.
Menge, Tyler, et al. "Mesenchymal stem cells regulate blood-brain barrier integrity through TIMP3 release after traumatic brain injury." Science translational medicine 4.161 (2012): 161ra150-161ra150.
Miska J, Lee-Chang C, Rashidi A, Muroski ME, Chang AL, Lopez-Rosas A, Zhang P, Panek WK, Cordero A, Han Y, Ahmed AU, Chandel NS, Lesniak MS. HIF-1alpha Is a Metabolic Switch between Glycolytic-Driven Migration and Oxidative Phosphorylation-Driven Immunosuppression of Tregs in Glioblastoma. Cell Rep. 2019;27(1):226-237 e4.
Miyara M, Yoshioka Y, Kitoh A, Shima T, Wing K, Niwa A, Parizot C, Taflin C, Heike T, Valeyre D, Mathian A, Nakahata T, Yamaguchi T, Nomura T, Ono M, Amoura Z, Gorochov G, Sakaguchi S. Functional delineation and differentiation dynamics of human CD4+ T cells expressing the FoxP3 transcription factor. Immunity. 2009;30(6):899-911.
Nankervis B, Jones M, Vang B et al. (2018) Optimizing T Cell Expansion in a Hollow-Fiber Bioreactor. Curr Stem Cell Rep. Advanced online publication, https://doi.org/10.1007/s40778-018-0116-x.
Nankervis, Brian, et al. "Optimizing T cell expansion in a hollow-fiber bioreactor." Current Stem Cell Reports 4.1 (2018): 46-51.
Nedoszytko B, Lange M, Sokolowska-Wojdylo M, Renke J, Trzonkowski P, Sobjanek M, Szczerkowska-Dobosz A, Niedoszytko M, Gorska A, Romantowski J, Czarny J, Skokowski J, Kalinowski

(56) References Cited

OTHER PUBLICATIONS

L, Nowicki R. The role of regulatory T cells and genes involved in their differentiation in pathogenesis of selected inflammatory and neoplastic skin diseases. Part II: The Treg role in skin diseases pathogenesis. Postepy Dermatol Alergol. 2017;34(5):405-417.

Nehlin JO, Just M, Rustan AC (2011) Human myotubes from myoblast cultures undergoing senescence exhibit defects in glucose and lipid metabolism. Biogerontology 12: 349-365.

New victories for adult Stem Cell Research New York Feb. 6, 2007.

Newton R, Priyadharshini B, Turka LA. Immunometabolism of regulatory T cells. Nat Immunol. 2016;17(6):618-25.

Ng TH, Britton GJ, Hill EV, Verhagen J, Burton BR, Wraith DC. Regulation of adaptive immunity; the role of interleukin-10. Front Immunol. 2013;4:129.

Nikolaychik, V. V., M. M. Samet, and P. L Lelkes. "A New, Cryoprecipitate Based Coating For Improved Endothelial Cell Attachment And Growth On Medical Grade Artificial Surfaces." ASAIO Journal (American Society for Artificial Internal Organs: 1992) 40.3 (1994): M846-52.

Nish SA, Schenten D, Wunderlich FT, Pope SD, Gao Y, Hoshi N, Yu S, Yan X, Lee HK, Pasman L, Brodsky I, Yordy B, Zhao H, Bruning J, Medzhitov R. T cell-intrinsic role of IL-6 Signaling in primary and memory responses. Elife. 2014;3:e01949.

Niwayama, Jun, et al. "Analysis of hemodynamics during blood purification therapy using a newly developed noninvasive continuous monitoring method." Therapeutic Apheresis and Dialysis 10.4 (2006): 380-386.

Okano et al. (Tokyo Women's Medical College, Japan) demonstrated the recovery of endothelial cells and hepatocytes from plasma-treated polystyrene dishes grafted with PNIAAm (Journal of Biomedical Materials Research, 1993).

Onishi Y, Fehervari Z, Yamaguchi T, Sakaguchi S. Foxp3+ natural regulatory T cells preferentially form aggregates on dendritic cells in vitro and actively inhibit their maturation. Proc Natl Acad Sci U S A. 2008;105(29):10113-8.

Onyszchuk G, LeVine SM, Brooks WM, Berman NE. Post-acute pathological changes in the thalamus and internal capsule in aged mice following controlled cortical impact injury: A magnetic resonance imaging, iron histochemical, and glial immunohistochemical study. Neuroscience letters. 2009;452:204-208.

Pacella I, Procaccini C, Focaccetti C, Miacci S, Timperi E, Faicchia D, Severa M, Rizzo F, Coccia EM, Bonacina F, Mitro N, Norata GD, Rossetti G, Ranzani V, Pagani M, Giorda E, Wei Y, Matarese G, Barnaba V, Piconese S. Fatty acid metabolism complements glycolysis in the selective regulatory T cell expansion during tumor growth. Proc Natl Acad Sci U S A. 2018;115(28):E6546-E6555.

Parhi, Purnendu, Avantika Golas, and Erwin A. Vogler. "Role Of Proteins And Water In The Initial Attachment Of Mammalian Cells To Biomedical Surfaces: A Review." Journal of Adhesion Science and Technology 24.5 (2010): 853-888.

Pati S, Gerber MH, Menge TD, Wataha KA, Zhao Y, Baumgartner JA, Zhao J, Letourneau PA, Huby MP, Baer LA, Salsbury JR, Kozar RA, Wade CE, Walker PA, Dash PK, Cox CS, Jr., Doursout MF, Holcomb JB. Bone marrow derived mesenchymal stem cells inhibit inflammation and preserve vascular endothelial integrity in the lungs after hemorrhagic shock. PLoS one. 2011;6:e25171.

Pati S, Khakoo AY, Zhao J, Jimenez F, Gerber MH, Harting M, Redell JB, Grill R, Matsuo Y, Guha S, Cox CS, Reitz MS, Holcomb JB, Dash PK. Human mesenchymal stem cells inhibit vascular permeability by modulating vascular endothelial cadherin/beta-catenin signaling. Stem cells and development. 2011;20:89-101.

Pati, Shibani, and Todd E. Rasmussen. "Cellular therapies in trauma and critical care medicine: Looking towards the future." *PLoS Medicine* 14.7 (2017): e1002343.

Pati, Shibani, et al. "Lyophilized plasma attenuates vascular permeability, inflammation and lung injury in hemorrhagic shock." PloS one 13.2 (2018): e0192363.

Peters JH, Preijers FW, Woestenenk R, Hilbrands LB, Koenen HJ, Joosten I. Clinical grade Treg: GMP isolation, improvement of purity by CD127 Depletion, Treg expansion, and Treg cryopreservation. PLoS One. 2008;3(9):e3161.

Peters, R.; Jones, M.; Brecheisen, M.; Startz, T.; Vang, B.; Nankervis, B.; Frank, N.; Nguyen, K. (2012) TerumoBCT. https://www.terumobct.com/location/north-america/products-and-services/Pages/Quantum-Materials.aspx.

Porter CM, Horvath-Arcidiacono JA, Singh AK, Horvath KA, Bloom ET, Mohiuddin MM. Characterization and expansion of baboon CD4+CD25+ Treg cells for potential use in a non-human primate xenotransplantation model. Xenotransplantation. 2007;14(4):298-308.

Povsictj, O'Connor CM, Henry T, et al. (2011) A double-blind, randomized, controlled, multicenter study to assess the safety and cardiovascular effects of skeletal myoblast implantation by catheter delivery in patients with chronic heart failure after myocardial infarction. Am Heart J 162(4): 654-662.

Prockop, Darwin J., Carl A. Gregory, and Jeffery L. Spees. "One strategy for cell and gene therapy: harnessing the power of adult stem cells to repair tissues." Proceedings of the National Academy of Sciences 10Q.suppl_1 (2003): 11917-11923.

Q. L. Hao, et al. A functional comparison of CD34+ CD38= cells in cord blood and bone marrow. Blood 86:3745-3753, 1995.

Rey-Jurado, Emma, et al. "Assessing the importance of domestic vaccine manufacturing centers: an overview of immunization programs, vaccine manufacture, and distribution." Frontiers in immunology 9 (2018): 26.

Roballo KC, Dhungana S, Z. J, Oakey J, Bushman J. Localized delivery of immunosuppressive regulatory 7 cells to peripheral nerve allografts promotes regeneration of branched segmental defects. Biomaterials. 2019;209:1-9.

Ronco C1, Levin N, Brendolan A, Nalesso F, Cruz D, Ocampo C, Kuang D, Bonello M, De Cal M, Corradi V, Ricci Z. Flow distribution analysis by helical scanning in polysulfone hemodialyzers: effects of fiber structure and design on flow patterns and solute clearances. Hemodial Int. Oct. 2006; 10(4):380-8.

Rosenblum MD, Way SS, Abbas AK. Regulatory 7 cell memory. Nat Rev Immunol. 2016;16(2):90-101.

Rubtsov YP, Rasmussen JP, Chi EY, Fontenot J, Castelli L, Ye X, Treuting P, Siewe L, Roers A, Henderson WR, Jr., Muller W, Rudensky AY. Regulatory 7 cell-derived interleukin-10 limits inflammation at environmental interfaces. Immunity. 2008;28(4):546-58.

Rudensky, Alexander Y. "Regulatory T cells and Foxp3." Immunological reviews 241.1 (2011): 260-268.

S. Koestenbauer, et al. Protocols for Hematopoietic Stem Cell Expansion from Umbilical Cord Blood. Cell Transplantation 18: 1059-1068, 2009.

S. L. Smith, et al. Expansion of neutrophil precursors and progenitors in suspension cultures of CD34+ cells enriched from human bone marrow. Experimental Hematology 21:870-877, 1993.

Safinia N, Grageda N, Scotta C, Thirkell S, Fry LJ, Vaikunthanathan T, Lechler RI, Lombardi G. Cell Therapy in Organ Transplantation: Our Experience on the Clinical Translation of Regulatory T Cells. Front Immunol. 2018;9:354.

Sahay A, Scobie KN, Hill AS, O'Carroll CM, Kheirbek MA, Burghardt NS, Fenton AA, Dranovsky A, Hen R. Increasing adult hippocampal neurogenesis is sufficient to improve pattern separation. Nature. 2011;472:466-470.

Sakaguchi S, Sakaguchi N, Asano M, Itoh M, Toda M. Immunologic self-tolerance maintained by activated 7 cells expressing IL-2 receptor alpha-chains (CD25). Breakdown of a single mechanism of self-tolerance causes various autoimmune diseases. J Immunol. 1995;155(3):1151-64.

Sakaguchi S, Sakaguchi N, Shimizu J, Yamazaki S, Sakihama T, Itoh M, Kuniyasu Y, Nomura T, Toda M, Takahashi T. Immunologic tolerance maintained by CD25+ CD4+ regulatory T cells: their common role in controlling autoimmunity, tumor immunity, and transplantation tolerance. Immunol Rev. 2001;182:18-32.

Schild, Howard G. "Poly (N-isopropylacrylamide): experiment, theory and application." Progress in polymer science 17.2 (1992): 163-249.

(56) References Cited

OTHER PUBLICATIONS

Schmitz R, Alessio A, Kina P. The Physics of PET/CT scanners. Imaging Research Laboratory, Department of Radiology, University of Washington http://depts.washington.edu/imreslab/education/Physics%20of%20PET.pdf.
Schwartz RH. T cell anergy. Annu Rev Immunol. 2003;21:305-34.
Shevkoplyas et al., "The Force Acting on a Superparamagnetic Bead due to an Applied Magnetic Field," Lab on a Chip , 7, pp. 1294-1302, 2007.
Shimazu Y, Shimazu Y, Hishizawa M, Hamaguchi M, Nagai Y, Sugino N, Fujii S, Kawahara M, Kadowaki N, Nishikawa H, Sakaguchi S, Takaori-Kondo A. Hypomethylation of the Treg-Specific Demethylated Region in FOXP3 Is a Hallmark ofthe Regulatory T-cell Subtype in Adult T-cell Leukemia. Cancer Immunol Res. 2016;4(2):136-45.
Shimizu et al. (TWMU & Heart Institute of Japan) described the detachment of avian card io myocytes from PIPAAm matrixes that were observed to pulse spontaneously with neovascularization in layered sheets three (3) weeks after transplantation (Circulation Research, 2002).
Sigma-Aldrich Cheimcals Mitomycin C (M4287) MSDS, v4.4, Jul. 7, 2011.
Sirsi, S. and Borden, M., "Microbubble Composition, Properties, and Biomedical Applications," Bubble Science, Engineering STechnology, vol. 1, No. 1-2, pp. 3-17, 2009.
Smith C, Okern G, Rehan S, et al. Ex vivo expansion of human T cells for adoptive immunotherapy using the novel Xeno-free CTS Immune Cell Serum Replacement. Clinical S Translational Immunology 2015;4:e31.
Somerville et al., "Clinical Scale Rapid Expansion of Lymphocytes for Adoptive Cell Transfer Therapy in the WAVE® Bioreactor," Journal of Translational Medicine, vol. 10, No. 69, pp. 1-11, 2012.
Somerville, R. and Dudley, M., "Bioreactors Get Personal," Oncolmmunology, vol. 1, No. 8, pp. 1435-1437, Nov. 2012.
Spectrum Labs KrosFlo Research IIi TFF System, undated, Spectrum Laboratories, Inc., 4 pages.
Stafano Tiziani, et al. Metabolomic Profiling of Drug Response in Acute Myeloid Leukaemia Cell lines. PLOSone 4(1): e4251 (Jan. 22, 2009).
StAR_Abstract, undated, author unknown, 1 page.
Startz et al. May 2016 TBCT T-cell White Paper.
Startz, T., et al. "Maturation of dendritic cells from CD14+ monocytes in an automated functionally closed hollow fiber bioreactor system." Cytotherapy 16.4 (2014): S29.
Steven M. Bryce, et al. (Litron Laboratories). In vitro micronucleus assay scored by flow cytometry provides a comprehensive evaluation of cytogenetic damage and cytotoxicity. Mutation Research 630(1-2): 78-91, 2007.
Steven M. Bryce, et al. (Novartis Pharma AG, Johnson & Johnson Pharmaceutical Research, GlaxoSmithKline). Interlaboratory evaluation of a flow cytometric, high content in vitro micronucleus assay. Genetic Toxicology and Environmental Mutagenesis 650:181-195, 2008.
Stuart, Martien A. Cohen, et al. "Emerging applications of stimuli-responsive polymer materials." Nature materials 9.2 (2010): 101-113.
Su LF, Del Alcazar D, Stelekati E, Wherry EJ, Davis MM. Antigen exposure shapes the ratio between antigen-specific Tregs and conventional T cells in human peripheral blood. Proc Natl Acad Sci U S A. 2016;113(41):E6192-E6198.
The effect of rocking rate and angle on T cell cultures grown in Xuri™ Cell Expansion Systems, Aug. 2014, GE Healthcare UK Limited, 4 pages.
Trzonkowski et al., "Ex Vivo Expansion of CD4+ CD25+ T Regulatory Cells for Immunosuppressive Therapy," Cytometry Part A, 75A, pp. 175-188, 2009.
Trzonkowski, Piotr, et al. "First-in-man clinical results of the treatment of patients with graft versus host disease with human ex vivo expanded CD4+ CD25+ CD127? T regulatory cells." Clinical immunology 133.1 (2009): 22-26.
Tsvetkov, Ts, et al. "Isolation and cryopreservation of human peripheral blood monocytes." Cryobiology 23.6 (1986): 531-536.
Underwood, P. Anne, et al. "Effects of base material, plasma proteins and FGF2 on endothelial cell adhesion and growth." Journal of Biomaterials Science, Polymer Edition 13.8 (2002): 845-862.
Urbich, et al. from the Goethe-Universität, demonstrated that human endothelial cells increased VEGFR-2 mRNA expression when exposed to 5-15 dynes/cm2 of constant shear force for a Period of 6-24 hours (FEBS, 2002).
van der Net JB, Bushell A, Wood KJ, Harden PN. Regulatory T cells: first steps of clinical application in solid organ transplantation. Transpl Int. 2016;29(1):3-11.
van der Windt GJ, Pearce EL. Metabolic switching and fuel choice during T-cell differentiation and memory development. Immunol Rev. 2012;249(1):27-42.
Vera et al., "Accelerated Production of Antigen-Specific T-Cells for Pre-Clinical and Clinical Applications Using Gas-Permeable Rapid Expansion Cultureware (G-Rex)," J Immunother, vol. 33, No. 3, pp. 305-315, Apr. 2010.
Villa, Alma Y. Camacho, et al. "CD133+ CD34+ and CD133+ CD38+ blood progenitor cells as predictors of platelet engraftment in patients undergoing autologous peripheral blood stem cell transplantation." Transfusion and Apheresis Science 46.3 (2012): 239-244.
Visser EP1, Disselhorst JA, Brom M, Laverman P, Gotthardt M, Oyen WJ, Boerman OC. Spatial resolution and sensitivity ofthe Inveon small-animal PET scanner. J Nucl Med. Jan. 2009;50(1):139-47.
Walker, Peter A., et al. "Direct intrathecal implantation of mesenchymal stromal cells leads to enhanced neuroprotection via an NF?B-mediated increase in interleukin-6 production." Stem cells and development 19.6 (2010): 867-876.
Wang R, Dillon CP, Shi LZ, Milasta S, Carter R, Finkelstein D, McCormick LL, Fitzgerald P, Chi H, Munger J, Green DR. The transcription factor Myc controls metabolic reprogramming upon T lymphocyte activation. Immunity. 2011;35(6):871-82.
Wang, Jiamian, John A. Jansen, and Fang Yang. "Electrospraying: possibilities and challenges of engineering carriers for biomedical applications—a mini review." Frontiers in Chemistry 7 (2019): 258.
Ward H, Vigues S, Poole S, Bristow AF. The rat interleukin 10 receptor: cloning and sequencing of cDNA coding for the alpha-chain protein sequence, and demonstration by western blotting of expression in the rat brain. Cytokine. 2001;15(5):237-2340.
Wawman, Rebecca Ellen, Helen Bartlett, and Ye Htun Oo. "Regulatory T cell metabolism in the hepatic microenvironment." Frontiers in immunology 8 (2018): 1889.
Weber et al., "White Paper on Adoptive Cell Therapy for Cancer with Tumor-Infiltrating Lymphocytes: A Report ofthe CTEP Sub-committee on Adoptive Cell Therapy," Clinical Cancer Research, vol. 17, No. 7, pp. 1664-1673, Apr. 1, 2011.
Weiss RA, Weiss MA, Beasley KL, Munavalli G (2007) Autologous cultured fibroblast injection for facial contour deformities: a prospective, placebo-controlled, Phase III clinical trial. Dermatol Surg 33(3): 263-268.
Widdel, F. 2010. "Theory and measurement of bacterial growth" http://www.mpi-bremen.de/Binaries/Binary13037/Wachstumsversuch.pdf.
Yamada, Noriko, et al. "Thermo?responsive polymeric surfaces; control of attachment and detachment of cultured cells." Die Makromolekulare Chemie, Rapid Communications 11.11 (1990): 571-576.
Yoshinari, Masao, et al. "Effect of cold plasma-surface modification on surface wettability and initial cell attachment." International Journal of Biomedical and Biological Engineering 3.10 (2009): 507-511.
Zappasodi et al., "The Effect Of Artificial Antigen-Presenting Cells with Preclustered Anit-CD28/-CD3/LFA-1 Monoclonal Antibodies on the Induction of ex vivo Expansion of Functional Human Antitumor T Cells," Haematologica, vol. 93, No. 10, pp. 1523-1534, 2008.

(56) References Cited

OTHER PUBLICATIONS

Zemmour D, Zilionis R, Kiner E, Klein AM, Mathis D, Benoist C. Publisher Correction: Singlecell gene expression reveals a landscape of regulatory T cell phenotypes shaped by the TCR. Nat Immunol. 2018;19(6):645.

Zeng B, Kwak-Kim J, Liu Y, Liao AH. Treg cells are negatively correlated with increased memory B cells in pre-eclampsia while maintaining suppressive function on autologous B-cell. Proliferation. Am J Reprod Immunol. 2013;70(6):454-63.

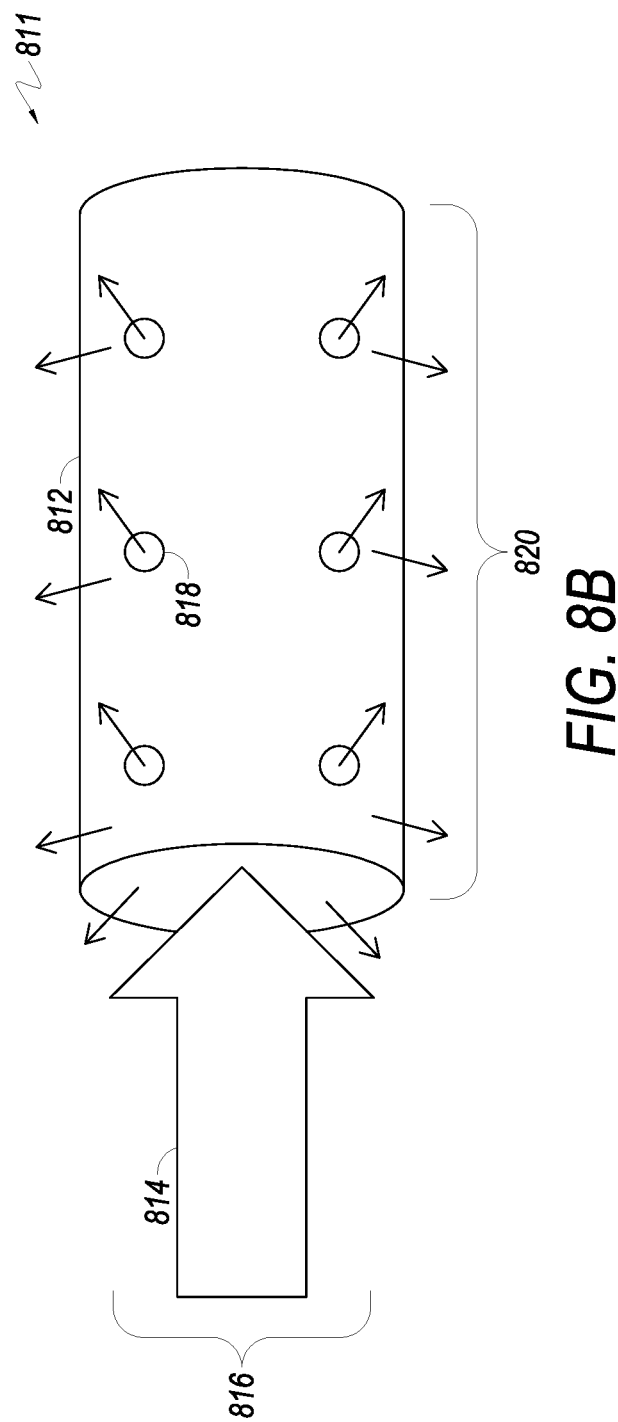

| IC Inlet: (100mL SDE CPPT) | Step 1 | Step 2 | Step 3 |
|---|---|---|---|
| IC Inlet Rate (mL/min) | Reagent | Wash | Wash |
| IC Circulation Rate (mL/min) | 10 | 10 | 50 |
| EC Inlet | 100 | 100 | -25 |
| EC Inlet Rate (mL/min) | None | None | Wash |
| EC Circulation Rate (mL/min) | 0 | 0 | 0.1 |
| Outlet | 30 | 30 | 30 |
| Rocker Control | EC Outlet | EC Outlet | EC Outlet |
| Stop Condition | Stationary (0) | Stationary (0) | Stationary (0) |
| | Empty Bag | IC Volume: 22mL | Time: 10.0 min |

FIG. 8C

COATING A BIOREACTOR IN A CELL EXPANSION SYSTEM

CROSS-REFERENCE TO RELATED APPLICATION

This application is a divisional application of, and claims priority to, U.S. patent application Ser. No. 15/616,876, entitled, "Coating a Bioreactor," filed on Jun. 7, 2017, now U.S. Pat. No. 11,104,874, issued on Aug. 31, 2021, which claims priority to, and the benefit of, U.S. Provisional Application Ser. No. 62/347,025, filed on Jun. 7, 2016, and entitled, "Growth Surface Coating," and U.S. Provisional Application Ser. No. 62/347,012, filed on Jun. 7, 2016, and entitled, "Coating a Bioreactor." The disclosures of the above-identified applications are hereby incorporated by reference in their entireties as if set forth herein in full for all that they teach and for all purposes.

BACKGROUND

Cell Expansion Systems (CESs) may be used to expand and differentiate cells. Cell expansion systems may be used to expand, e.g., grow, a variety of adherent and suspension cells. For example, cell expansion systems may be used to expand mesenchymal stem cells (MSCs) and other types of cells, such as bone marrow cells. Stem cells which are expanded from donor cells may be used to repair or replace damaged or defective tissues and have broad clinical applications for a wide range of diseases. Cells, of both adherent and non-adherent type, may be grown in a bioreactor in a cell expansion system.

SUMMARY

Embodiments of the present disclosure generally relate to a cell expansion system for expanding cells. Such expansion may occur through the use of a bioreactor or cell growth chamber comprising a hollow fiber membrane. In embodiments, a hollow fiber membrane comprises a plurality of hollow fibers. Such hollow fiber membrane may include an extracapillary (EC) space and an intracapillary (IC) space. A cell expansion system may expand a variety of cell types, such as mesenchymal stem cells, cancer cells, T-cells, fibroblasts, and myoblasts. In expanding cells, a compound or coating agent may be applied to a cell growth surface. For example, an adherence-promoting compound may be applied to a cell growth surface to promote contact, e.g., adherence, and subsequent expansion of cells, such as a cell line including human mesenchymal stem cells (hMSCs). In embodiments, for cells to adhere to the surface of the hollow fibers, the surface may be modified in some way, such as by coating at least the cell growth surface with a protein, for example. In embodiments, a coating agent may be applied to the inner surface or inner aspect of bioreactor fibers. For example, a coating agent may be applied to the intracapillary (IC) surface of a hollow fiber(s). In another embodiment, a coating agent may be applied to the extracapillary (EC) surface of a hollow fiber(s). As non-limiting examples of coating agent(s), cryoprecipitate (CPPT), fibronectin (FN), human fibronectin (hFN), and/or combinations of such coating agents may be used. In other embodiments, a plurality of coating agents, or a combination of coating agent(s), may be used.

Embodiments provide for fluid movement in a cell growth chamber or bioreactor to be controlled to actively promote a coating agent(s) to a cell growth surface, e.g., to a surface of a hollow fiber(s). For example, such fluid movement may be controlled so as to move fluid from one side, e.g., IC side, of a hollow fiber to the other side, e.g., EC side, of the hollow fiber. In an embodiment, ultrafiltration may be used to move fluid in a bioreactor. For example, positive ultrafiltration may be used to move fluid from the IC side of a bioreactor to the EC side of the bioreactor. In another embodiment, negative ultrafiltration may be used to move fluid from the EC side of a bioreactor to the IC side of the bioreactor. In embodiments, other types of ultrafiltration or directions of fluid movement may be used. The direction of fluid movement may depend on the surface upon which cells are being expanded.

By controlling fluid movement, a coating solution, e.g., a fluid(s) and a coating agent(s), may be actively pushed to the IC (or EC) loop, and the fluid(s) may be pushed through the pores, for example, of a hollow fiber(s), leaving a residual layer of adherence-promoting protein(s), for example, on the IC (or EC) side of the hollow fiber(s) and therefore facilitating the contact, e.g., attachment, of cells, e.g., adherent cells. Such fluid movement, e.g., ultrafiltration, may decrease the time required for a chemical reaction between a coating agent and the growth surface of the bioreactor to occur to coat the fiber(s). Such fluid movement may be controlled through the adjusting of one or more valve(s), pump(s), or other type of fluid flow control device(s).

Embodiments of the present disclosure provide for implementing such coating procedure(s) through the use of one or more protocols or tasks for use with a cell expansion system. Such protocols or tasks may include pre-programmed protocols or tasks for use with an automated CES, for example. In embodiments, a pre-programmed, default, or otherwise previously saved task may be selected. A task may comprise one or more steps. In other embodiments, such protocols or tasks may include custom or user-defined protocols or tasks for use with an automated CES, for example. Through a user interface (UI) and graphical user interface (GUI) elements, a custom or user-defined protocol or task may be created. In embodiments, a combination of pre-programmed, default, custom, and/or user-defined tasks, for example, may be used.

In addition, ultrafiltration may be combined with other processes for coating a cell growth surface, e.g., a surface of a hollow fiber. For example, some coating processes referred to as a bulls-eye coat process may provide for changing flow rates, flow directions, and rotation of a bioreactor during a coating process to improve distribution of the coating agent throughout the bioreactor. Embodiments provide for combining ultrafiltration, such as by continuously introducing a wash fluid into the bioreactor, while other steps (e.g., changing flow rates, flow directions, and rotation of a bioreactor) are performed.

Other embodiments provide for combining processes of coating a cell growth surface, e.g., a surface of a hollow fiber with processes for loading and attaching cells. For example, a bulls-eye coat process may be combined with a bulls-eye load process. The coating process may provide for changing flow rates, flow directions, and rotation of a bioreactor during a coating process, while the bulls-eye load may provide for changing flow rates, flow directions, and rotation of a bioreactor during a process of loading and attaching cells.

This Summary is included to provide a selection of concepts in a simplified form, in which such concepts are further described below in the Detailed Description. This Summary is not intended to be used in any way to limit the claimed subject matter's scope. Features, including equivalents and variations thereof, may be included in addition to those provided herein.

BRIEF DESCRIPTION OF THE DRAWINGS

Embodiments of the present disclosure may be described by referencing the accompanying figures. In the figures, like numerals refer to like items.

FIG. 8B depicts a schematic of applying an agent to a cell growth surface of a hollow fiber in accordance with embodiments of the present disclosure.

FIG. 8C illustrates example steps and parameters for applying an agent to a cell growth surface in accordance with an embodiment of the present disclosure.

DETAILED DESCRIPTION

Figure 1A:
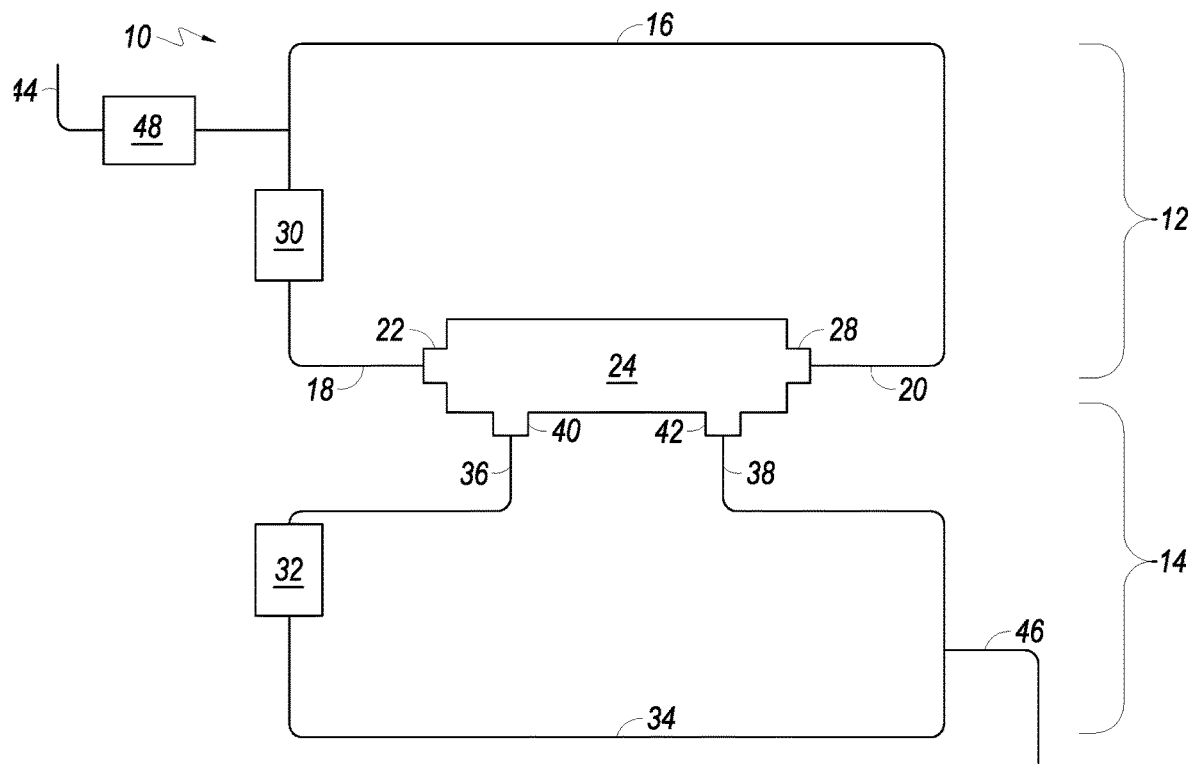
FIG. 1A depicts an embodiment of a cell expansion system (CES).

The following Detailed Description provides a discussion of illustrative embodiments with reference to the accompanying drawings. The inclusion of specific embodiments herein should not be construed as limiting or restricting the present disclosure. Further, while language specific to features, acts, and/or structures, for example, may be used in describing embodiments herein, the claims are not limited to the features, acts, and/or structures described. A person of skill in the art will appreciate that other embodiments, including improvements, are within the spirit and scope of the present disclosure. Further, any alternatives or additions, including any listed as separate embodiments, may be used or incorporated with any other embodiments herein described.

Embodiments of the present disclosure are generally directed to methods and systems for applying a coating agent or reagent to a cell growth surface to promote cell contact, e.g., adherence, and subsequent expansion of cells. In an embodiment, such application comprises an active promotion of a coating agent or reagent to the cell growth surface, such as the cell growth surface of a hollow fiber(s) where a hollow fiber bioreactor may be used for cell expansion in a cell expansion system. Controlling fluid movement in a bioreactor or cell growth chamber allows for the active promotion of a coating agent or reagent to a cell growth surface.

Passive coating processes may involve the passive application of a coating agent to a cell growth surface, in which a coating agent(s) may be passively applied to a cell growth chamber of an automated cell expansion system using circulating flow, for example. A coating agent(s) may be loaded into an intracapillary or extracapillary side of a bioreactor, for example. The coating agent(s) may then be circulated in the intracapillary or extracapillary loop for a particular, e.g., first, time period. As such, the bioreactor may be passively coated using circulating flow in the IC (or EC) loop, in which such process may take multiple hours, for example. Such coating procedure may take from about four (4) hours to about twenty-four (24) hours, for example, of circulation of a coating agent to achieve coating of the cell growth surface. As an example, a bioreactor coating protocol may load a coating agent into the intracapillary side of a bioreactor in a cell expansion system. The coating agent may then be circulated in the intracapillary circulation loop for a minimum of sixteen (16) hours. A user utilizing such process may therefore use at least two cell expansion systems, in which the user may begin, in a second cell expansion system, any additional expansion of a population of cells harvested from a first cell expansion system (where cells may not be stored in a non-cryopreserved state for up to sixteen (16) hours, for example).

Embodiments herein provide for the active pushing or active promotion of a coating agent solution to a cell growth surface. Rather than passively coating the bioreactor using circulating flow in the IC loop, for example, for many hours, a coating solution, e.g., a fluid(s) and a coating agent(s), can be actively pushed into the IC loop, and the fluid(s) may be pushed through the pores of the bioreactor, leaving a residual layer of adherence promoting proteins on the IC side of the bioreactor fibers to facilitate the attachment of adherent cells. In an embodiment, ultrafiltration may be used to allow a coating agent or reagent to be promoted to the growth surface of a hollow fiber, for example. Ultrafiltration, e.g., positive ultrafiltration, may be used to move fluid from a first side of a hollow fiber to a second side of a hollow fiber. For example, utilizing positive ultrafiltration of a fluid, the fluid may be moved from the IC side of a hollow fiber or hollow fiber membrane to the EC side of the hollow fiber or hollow fiber membrane. Such fluid movement may decrease the time it takes for a chemical reaction to occur between a coating agent or reagent and a growth surface of the bioreactor to coat the cell growth surface. The molecular barrier created by the specified construction of the hollow fibers in the bioreactor may be such that the coating agent or reagent may not be able to pass through the fiber wall along with the fluid in which it is suspended. The adherence promoting proteins of the coating agent may remain in a residual layer on a first side of the hollow fiber(s) as the solution is pushed through the pores of the fibers to a second side of the hollow fiber(s). Moving the fluid using ultrafiltration, e.g., positive ultrafiltration, may thus result in "actively" promoting the coating agent or reagent to the surface of the hollow fiber(s), according to embodiments.

For example, a coating agent(s) may be introduced to the fibers of a hollow fiber bioreactor on the IC (or EC) side. Such coating agent(s) may be suspended in a solution, e.g., coating solution. The IC outlet or waste valve may be closed, with the EC outlet or waste valve open. The IC inlet rate may be set to wash the IC side with media, such as phosphate buffered saline (PBS), for example. Such fluid may have no pathway but through the pores of the fibers (IC outlet valve closed). Accordingly, the solution may flow through the pores of the fibers from the IC side to the EC side. The coating agent, e.g., CPPT, may be hydrostatically deposited onto the inner wall(s) of the bioreactor fiber for a defined time period. For example, such time period may be about ten (10) minutes, according to an embodiment. Such membrane ultrafiltration method allows adherence promoting proteins to be physisorbed on the bioreactor fibers as the solution flows through the pores of the fiber from the IC side to the EC side, for example.

In an embodiment, such active moving of the coating agent to the cell growth surface(s) may significantly decrease the amount of time it may take to coat the cell growth surface as compared to other methods of coating a cell growth surface. In embodiments, such coating procedure using ultrafiltration may be referred to as an expedited coating procedure. Such expedited coating procedure using active moving of the coating agent to the cell growth surface(s) through ultrafiltration may use less time to coat the cell growth surface than procedures using passive coating procedures which may take overnight or about twelve (12) hours to about sixteen (16) hours to coat the bioreactor. For example, such expedited coating procedure may take less than or equal to about four (4) hours. In embodiments, such expedited coating procedure may take any time period in a range from above or equal to about five (5) minutes to less than or equal to about sixty (60) minutes, or any other range therein, depending on the procedure. For example, such coating procedure may take less than or equal to about ten (10) minutes, less than or equal to about twelve (12) minutes, less than or equal to about fifteen (15) minutes, less than or equal to about twenty (20) minutes, less than or equal to about thirty (30) minutes, less than or equal to about forty-five (45) minutes, less than or equal to about sixty (60) minutes, etc.

Embodiments are directed to a cell expansion system, as described above. In embodiments, such cell expansion system is closed, in which a closed cell expansion system comprises contents that are not directly exposed to the atmosphere. Such cell expansion system may be automated. In embodiments, cells, of both adherent and non-adherent or suspension type, may be grown in a bioreactor in the cell expansion system. According to embodiments, the cell expansion system may include base media or other type of media. Methods for replenishment of media are provided for cell growth occurring in a bioreactor of the closed cell expansion system. In embodiments, the bioreactor used with such systems is a hollow fiber bioreactor. Many types of bioreactors may be used in accordance with embodiments of the present disclosure.

The system may include, in embodiments, a bioreactor that further includes a first fluid flow path having at least opposing ends, a first opposing end of the first fluid flow path fluidly associated with a first port of a hollow fiber membrane and a second end of the first fluid flow path fluidly associated with a second port of the hollow fiber membrane, in which the first fluid flow path comprises an intracapillary portion of the hollow fiber membrane. In embodiments, a hollow fiber membrane comprises a plurality of hollow fibers. The system may further include a fluid inlet path fluidly associated with the first fluid flow path, in which a plurality of cells are introduced into the first fluid flow path through a first fluid inlet path. A first pump for circulating fluid in the first fluid flow path of the bioreactor may also be included. In embodiments, the system includes a controller for controlling operation of the first pump. In an embodiment, the controller is a computing system, including a processor, for example. The controller is configured, in embodiments, to control the pump to circulate a fluid at a first rate within the first fluid flow path. In some embodiments, a second pump for transferring intracapillary inlet fluid from an intracapillary media bag to the first fluid flow path and a second controller for controlling operation of the second pump are included. The second controller, in embodiments, controls the second pump to transfer cells from a cell inlet bag to the first fluid flow path, for example. Additional controllers, e.g., third controller, fourth controller, fifth controller, sixth controller, etc., may be used in accordance with embodiments. Further, additional pumps, e.g., third pump, fourth pump, fifth pump, sixth pump, etc., may be used in accordance with embodiments of the present disclosure. In addition, while the present disclosure may refer to a media bag, a cell inlet bag, etc., multiple bags, e.g., a first media bag, a second media bag, a third media bag, a first cell inlet bag, a second cell inlet bag, a third cell inlet bag, etc., and/or other types of containers, may be used in embodiments. In other embodiments, a single media bag, a single cell inlet bag, etc., may be used. Further, additional or other fluid paths, e.g., a second fluid flow path, a second fluid inlet path, etc., may be included in embodiments.

In other embodiments, the system is controlled by, for example: a processor coupled to the cell expansion system; a display device, in communication with the processor, and operable to display data; and a memory, in communication with and readable by the processor, and containing a series of instructions. In embodiments, when the instructions are executed by the processor, the processor receives an instruction to coat the bioreactor, for example. In response to the instruction to coat the bioreactor, the processor may execute a series of steps to coat the bioreactor and may next receive an instruction to load cells into the bioreactor, for example. In response to the instruction to load cells, the processor may execute a series of steps to load the cells from a cell inlet bag, for example, into the bioreactor.

A schematic of an example cell expansion system (CES) is depicted in FIG. 1A, in accordance with embodiments of the present disclosure. CES 10 includes first fluid circulation path 12 and second fluid circulation path 14. First fluid flow path 16 has at least opposing ends 18 and 20 fluidly associated with a hollow fiber cell growth chamber 24 (also referred to herein as a "bioreactor"), according to embodiments. Specifically, opposing end 18 may be fluidly associated with a first inlet 22 of cell growth chamber 24, and opposing end 20 may be fluidly associated with first outlet 28 of cell growth chamber 24. Fluid in first circulation path 12 flows through the interior of hollow fibers 116 (see FIG. 1B) of hollow fiber membrane 117 (see FIG. 1B) disposed in cell growth chamber 24 (cell growth chambers and hollow fiber membranes are described in more detail infra). Further, first fluid flow control device 30 may be operably connected to first fluid flow path 16 and may control the flow of fluid in first circulation path 12.

Second fluid circulation path 14 includes second fluid flow path 34, cell growth chamber 24, and a second fluid flow control device 32. The second fluid flow path 34 has at least opposing ends 36 and 38, according to embodiments. Opposing ends 36 and 38 of second fluid flow path 34 may be fluidly associated with inlet port 40 and outlet port 42 respectively of cell growth chamber 24. Fluid flowing through cell growth chamber 24 may be in contact with the outside of hollow fiber membrane 117 (see FIG. 1B) in the cell growth chamber 24, in which a hollow fiber membrane comprises a plurality of hollow fibers. Second fluid circulation path 14 may be operably connected to second fluid flow control device 32.

Figure 1B:
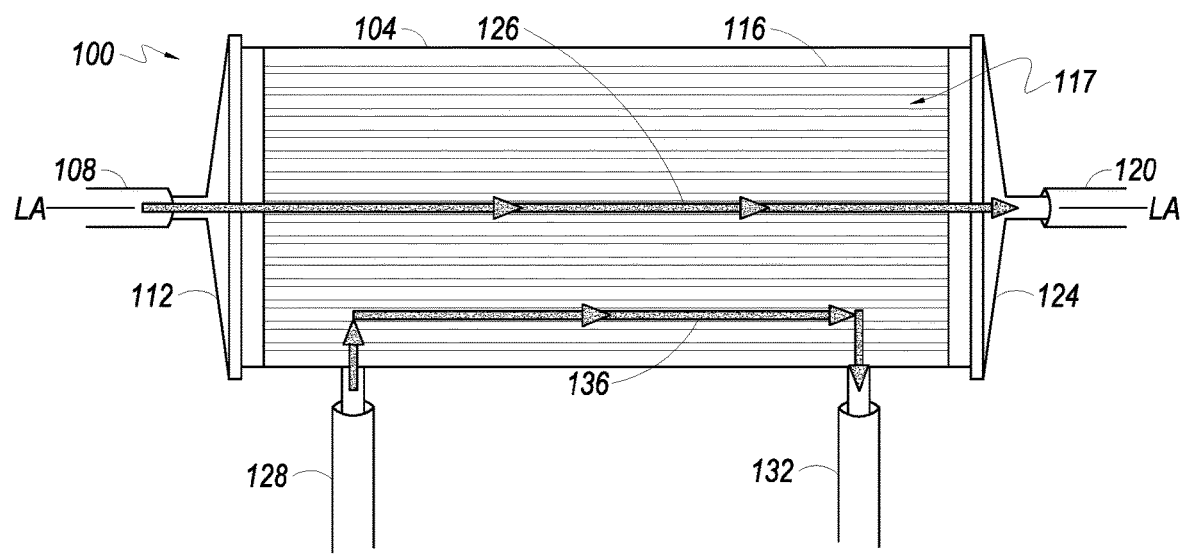
FIG. 1B illustrates a front elevation view of an embodiment of a bioreactor showing circulation paths through the bioreactor.

First and second fluid circulation paths 12 and 14 may thus be separated in cell growth chamber 24 by a hollow fiber membrane 117 (see FIG. 1B). Fluid in first fluid circulation path 12 flows through the intracapillary ("IC") space of the hollow fibers in the cell growth chamber 24. First circulation path 12 may be referred to as the "IC loop." Fluid in second circulation path 14 flows through the extracapillary ("EC") space in the cell growth chamber 24. Second fluid circulation path 14 may be referred to as the "EC loop." Fluid in first fluid circulation path 12 may flow in either a co-current or counter-current direction with respect to the flow of fluid in second fluid circulation path 14, according to embodiments.

Fluid inlet path 44 may be fluidly associated with first fluid circulation path 12. Fluid inlet path 44 allows fluid into first fluid circulation path 12, while fluid outlet path 46 allows fluid to leave CES 10. Third fluid flow control device 48 may be operably associated with fluid inlet path 44. Alternatively, third fluid flow control device 48 may alternatively be associated with first outlet path 46.

Fluid flow control devices as used herein may comprise a pump, valve, clamp, or combination thereof, according to embodiments. Multiple pumps, valves, and/or clamps can be arranged in any combination. In various embodiments, the fluid flow control device is or includes a peristaltic pump. In embodiments, fluid circulation paths, inlet ports, and outlet ports may be constructed of tubing of any material.

Various components are referred to herein as "operably associated." As used herein, "operably associated" refers to components that are linked together in operable fashion and encompasses embodiments in which components are linked directly, as well as embodiments in which additional components are placed between the two linked components. "Operably associated" components can be "fluidly associated." "Fluidly associated" refers to components that are linked together such that fluid can be transported between them. "Fluidly associated" encompasses embodiments in which additional components are disposed between the two fluidly associated components, as well as components that are directly connected. Fluidly associated components can include components that do not contact fluid, but contact other components to manipulate the system (e.g., a peristaltic pump that pumps fluids through flexible tubing by compressing the exterior of the tube).

Generally, any kind of fluid, including buffers, protein containing fluid, and cell-containing fluid, for example, can flow through the various circulations paths, inlet paths, and outlet paths. As used herein, "fluid," "media," and "fluid media" are used interchangeably.

Turning to FIG. 1B, an example of a hollow fiber cell growth chamber 100 which may be used with the present disclosure is shown in front side elevation view. Cell growth chamber 100 has a longitudinal axis LA-LA and includes cell growth chamber housing 104. In at least one embodiment, cell growth chamber housing 104 includes four openings or ports: IC inlet port 108, IC outlet port 120, EC inlet port 128, and EC outlet port 132.

According to embodiments of the present disclosure, fluid in a first circulation path enters cell growth chamber 100 through IC inlet port 108 at a first longitudinal end 112 of the cell growth chamber 100, passes into and through the intracapillary side (referred to in various embodiments as the intracapillary ("IC") side or "IC space" of a hollow fiber membrane) of a plurality of hollow fibers 116 comprising hollow fiber membrane 117, and out of cell growth chamber 100 through IC outlet port 120 located at a second longitudinal end 124 of the cell growth chamber 100. The fluid path between the IC inlet port 108 and the IC outlet port 120 defines the IC portion 126 of the cell growth chamber 100. Fluid in a second circulation path flows in the cell growth chamber 100 through EC inlet port 128, comes in contact with the extracapillary side or outside (referred to as the "EC side" or "EC space" of the membrane) of the hollow fibers 116, and exits cell growth chamber 100 via EC outlet port 132. The fluid path between the EC inlet port 128 and the EC outlet port 132 comprises the EC portion 136 of the cell growth chamber 100. Fluid entering cell growth chamber 100 via the EC inlet port 128 may be in contact with the outside of the hollow fibers 116. Small molecules (e.g., ions, water, oxygen, lactate, etc.) may diffuse through the hollow fibers 116 from the interior or IC space of the hollow fiber to the exterior or EC space, or from the EC space to the IC space. Large molecular weight molecules, such as growth factors, are typically too large to pass through the hollow fiber membrane, and may remain in the IC space of the hollow fibers 116. The media may be replaced as needed, in embodiments. Media may also be circulated through an oxygenator or gas transfer module to exchange gasses as needed. Cells may be contained within a first circulation path and/or a second circulation path, as described below, and may be on either the IC side and/or EC side of the membrane, according to embodiments.

The material used to make the hollow fiber membrane 117 may be any biocompatible polymeric material which is capable of being made into hollow fibers. One material which may be used is a synthetic polysulfone-based material, according to an embodiment of the present disclosure. In order for the cells to adhere to the surface of the hollow fibers, the surface may be modified in some way, either by coating at least the cell growth surface with a protein such as fibronectin or collagen, for example, or by exposing the surface to radiation, according to embodiments. Gamma treating the membrane surface allows for attachment of adherent cells without additionally coating the membrane with fibronectin, cryoprecipitate, or the like. Bioreactors made of gamma treated membranes may be reused. Other coatings and/or treatments for cell attachment may be used in accordance with embodiments of the present disclosure.

Figure 1C:
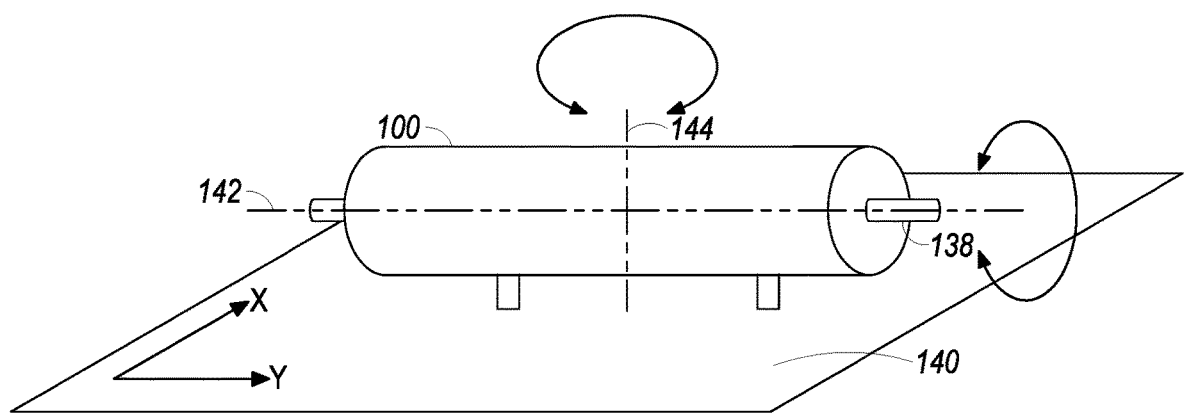
FIG. 1C depicts a rocking device for moving a cell growth chamber rotationally or laterally during operation of a cell expansion system, according to embodiments of the present disclosure.

In embodiments, the CES (such as CES 500 (see FIG. 5) and/or CES 600 (see FIG. 6), for example) may include a device configured to move or "rock" the cell growth chamber relative to other components of the cell expansion system by attaching it to a rotational and/or lateral rocking device. FIG. 1C shows one such device, in which a bioreactor 100 may be rotationally connected to two rotational rocking components and to a lateral rocking component, according to an embodiment.

A first rotational rocking component 138 rotates the bioreactor 100 around central axis 142 of the bioreactor 100. Rotational rocking component 138 may be rotationally associated with bioreactor 100. In embodiments, bioreactor 100 may be rotated continuously in a single direction around central axis 142 in a clockwise or counterclockwise direction. Alternatively, bioreactor 100 may rotate in alternating fashion, first clockwise, then counterclockwise, for example, around central axis 142, according to embodiments.

The CES may also include a second rotational rocking component that rotates bioreactor 100 around rotational axis 144. Rotational axis 144 may pass through the center point of bioreactor 100 and may be normal to central axis 142. Bioreactor 100 may be rotated continuously in a single direction around rotational axis 144 in a clockwise or counterclockwise direction, in embodiments. Alternatively, bioreactor 100 may be rotated around rotational axis 144 in an alternating fashion, first clockwise, then counterclockwise, for example. In various embodiments, bioreactor 100 may also be rotated around rotational axis 144 and positioned in a horizontal or vertical orientation relative to gravity.

In embodiments, lateral rocking component 140 may be laterally associated with bioreactor 100. The plane of lateral rocking component 140 moves laterally in the -x and -y directions, in embodiments. The settling of cells in the bioreactor may be reduced by movement of cell-containing media within the hollow fibers, according to embodiments.

The rotational and/or lateral movement of a rocking device may reduce the settling of cells within the device and reduce the likelihood of cells becoming trapped within a portion of the bioreactor. The rate of cells settling in the cell growth chamber is proportional to the density difference between the cells and the suspension media, according to Stoke's Law. In some embodiments, a 180 degree rotation (fast) with a pause (having a total combined time of 30 seconds, for example) repeated as described above keeps non-adherent red blood cells suspended. A minimum rotation of about 180 degrees would be preferred in an embodiment; however, one could use rotation of up to 360 degrees or greater. Different rocking components may be used separately, or may be combined in any combination. For example, a rocking component that rotates bioreactor 100 around central axis 142 may be combined with the rocking component that rotates bioreactor 100 around axis 144. Likewise, clockwise and counterclockwise rotation around different axes may be performed independently in any combination.

Figure 2:
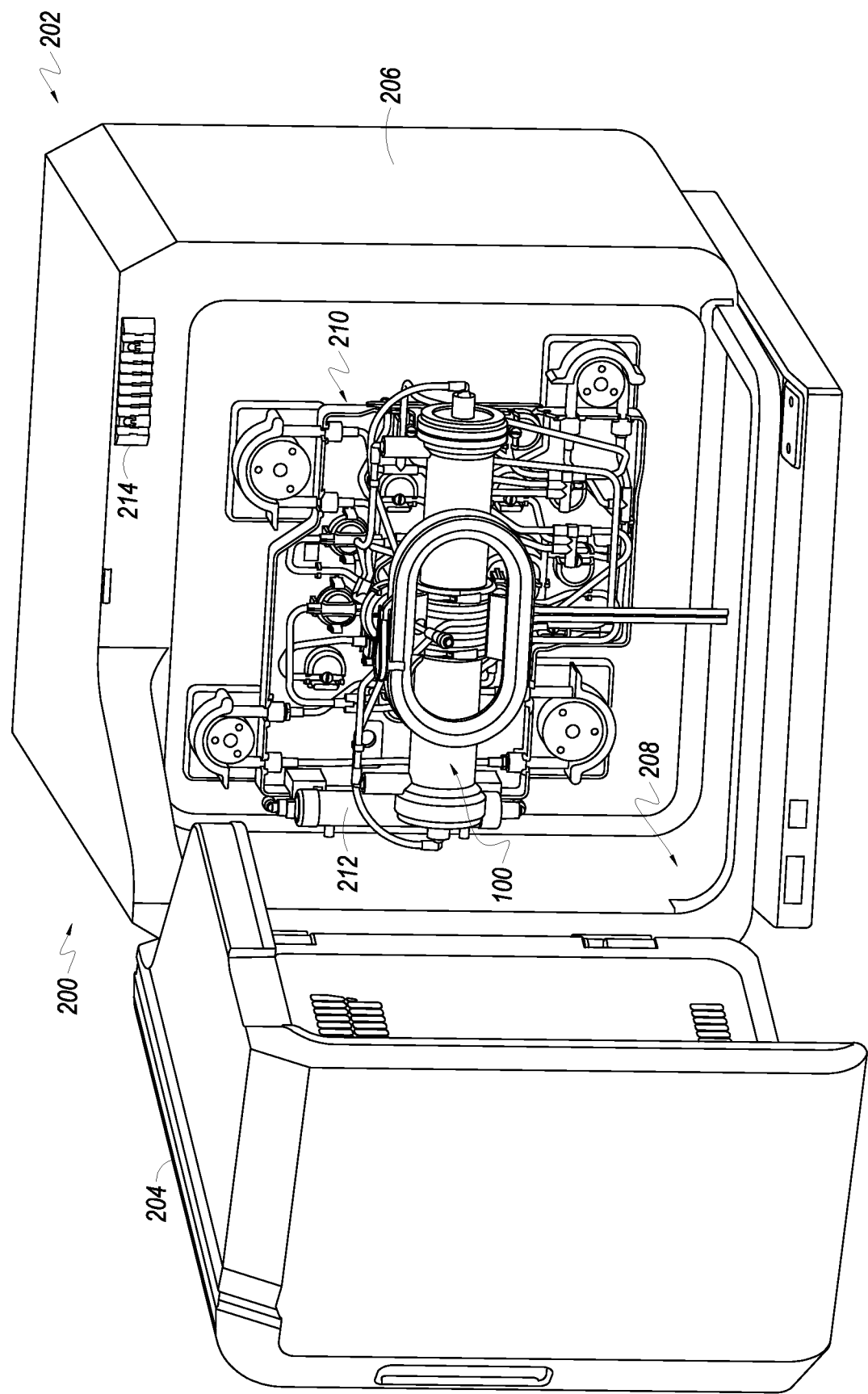
FIG. 2 illustrates a perspective view of a cell expansion system with a pre-mounted fluid conveyance device, in accordance with embodiments of the present disclosure.

Turning to FIG. 2, an embodiment of a cell expansion system 200 with a pre-mounted fluid conveyance assembly is shown in accordance with embodiments of the present disclosure. The CES 200 includes a cell expansion machine 202 that comprises a hatch or closable door 204 for engagement with a back portion 206 of the cell expansion machine 202. An interior space 208 within the cell expansion machine 202 includes features adapted for receiving and engaging a pre-mounted fluid conveyance assembly 210. The pre-mounted fluid conveyance assembly 210 is detachably-attachable to the cell expansion machine 202 to facilitate relatively quick exchange of a new or unused pre-mounted fluid conveyance assembly 210 at a cell expansion machine 202 for a used pre-mounted fluid conveyance assembly 210 at the same cell expansion machine 202. A single cell expansion machine 202 may be operated to grow or expand a first set of cells using a first pre-mounted fluid conveyance assembly 210 and, thereafter, may be used to grow or expand a second set of cells using a second pre-mounted fluid conveyance assembly 210 without needing to be sanitized between interchanging the first pre-mounted fluid conveyance assembly 210 for the second pre-mounted fluid conveyance assembly 210. The pre-mounted fluid conveyance assembly 210 includes a bioreactor 100 and an oxygenator or gas transfer module 212 (also see FIG. 4). Tubing guide slots are shown as 214 for receiving various media tubing connected to pre-mounted fluid conveyance assembly 210, according to embodiments.

Figure 3:
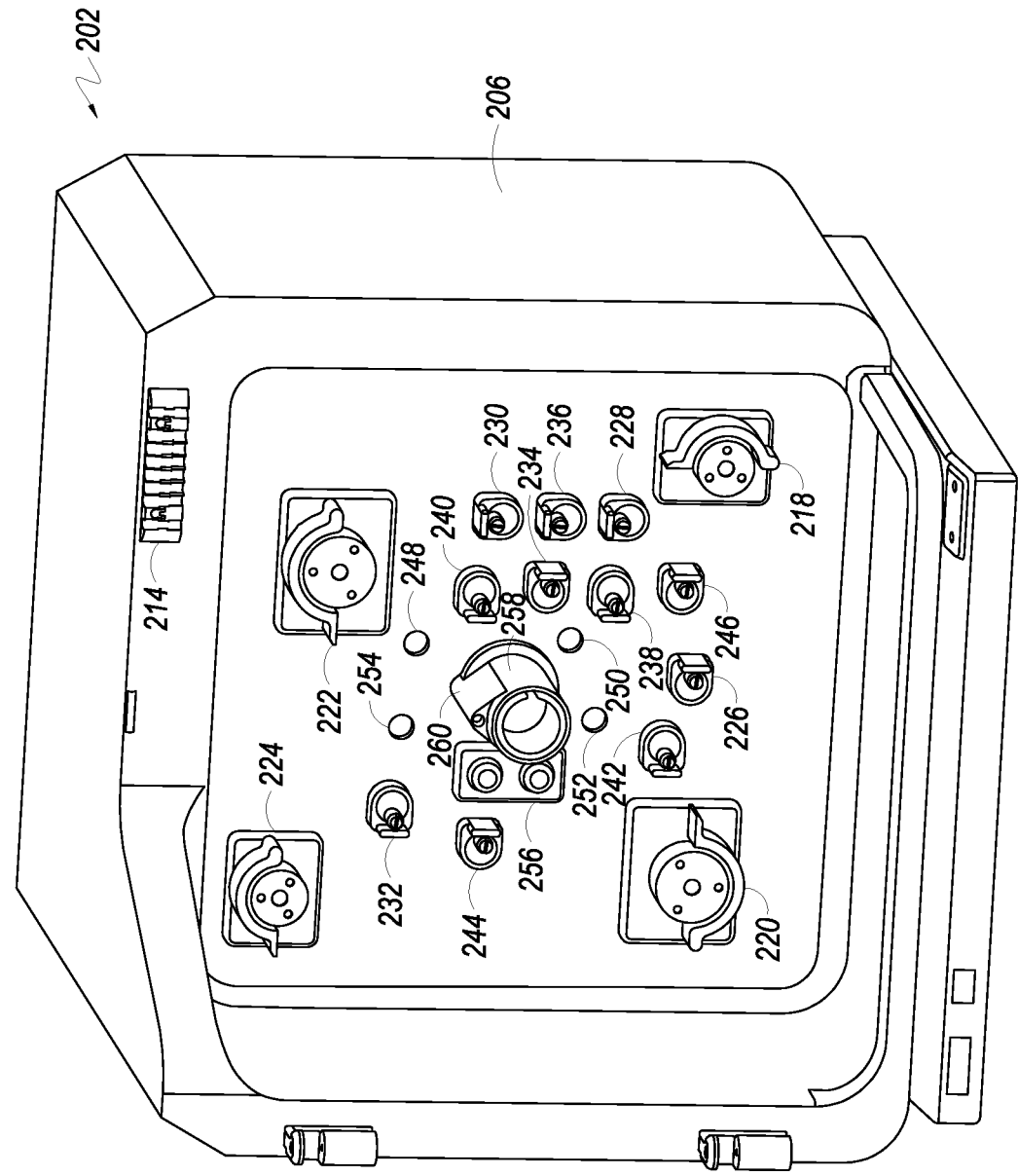
FIG. 3 depicts a perspective view of a housing of a cell expansion system, in accordance with embodiments of the present disclosure.

Next, FIG. 3 illustrates the back portion 206 of cell expansion machine 202 prior to detachably-attaching a pre-mounted fluid conveyance assembly 210 (FIG. 2), in accordance with embodiments of the present disclosure. The closable door 204 (shown in FIG. 2) is omitted from FIG. 3. The back portion 206 of the cell expansion machine 202 includes a number of different structures for working in combination with elements of a pre-mounted fluid conveyance assembly 210. More particularly, the back portion 206 of the cell expansion machine 202 includes a plurality of peristaltic pumps for cooperating with pump loops on the pre-mounted fluid conveyance assembly 210, including the IC circulation pump 218, the EC circulation pump 220, the IC inlet pump 222, and the EC inlet pump 224. In addition, the back portion 206 of the cell expansion machine 202 includes a plurality of valves, including the IC circulation valve 226, the reagent valve 228, the IC media valve 230, the air removal valve 232, the cell inlet valve 234, the wash valve 236, the distribution valve 238, the EC media valve 240, the IC waste or outlet valve 242, the EC waste or outlet valve 244, and the harvest valve 246. Several sensors are also associated with the back portion 206 of the cell expansion machine 202, including the IC outlet pressure sensor 248, the combination IC inlet pressure and temperature sensors 250, the combination EC inlet pressure and temperature sensors 252, and the EC outlet pressure sensor 254. Also shown is an optical sensor 256 for an air removal chamber, according to an embodiment.

In accordance with embodiments, a shaft or rocker control 258 for rotating the bioreactor 100 is shown. Shaft fitting 260 associated with the shaft or rocker control 258 allows for proper alignment of a shaft access aperture, see e.g., 424 (FIG. 4) of a tubing-organizer, see e.g., 300 (FIG. 4) of a pre-mounted conveyance assembly 210 or 400 with the back portion 206 of the cell expansion machine 202. Rotation of shaft or rocker control 258 imparts rotational movement to shaft fitting 260 and bioreactor 100. Thus, when an operator or user of the CES 200 attaches a new or unused pre-mounted fluid conveyance assembly 400 (FIG. 4) to the cell expansion machine 202, the alignment is a relatively simple matter of properly orienting the shaft access aperture 424 (FIG. 4) of the pre-mounted fluid conveyance assembly 210 or 400 with the shaft fitting 260.

Figure 4:
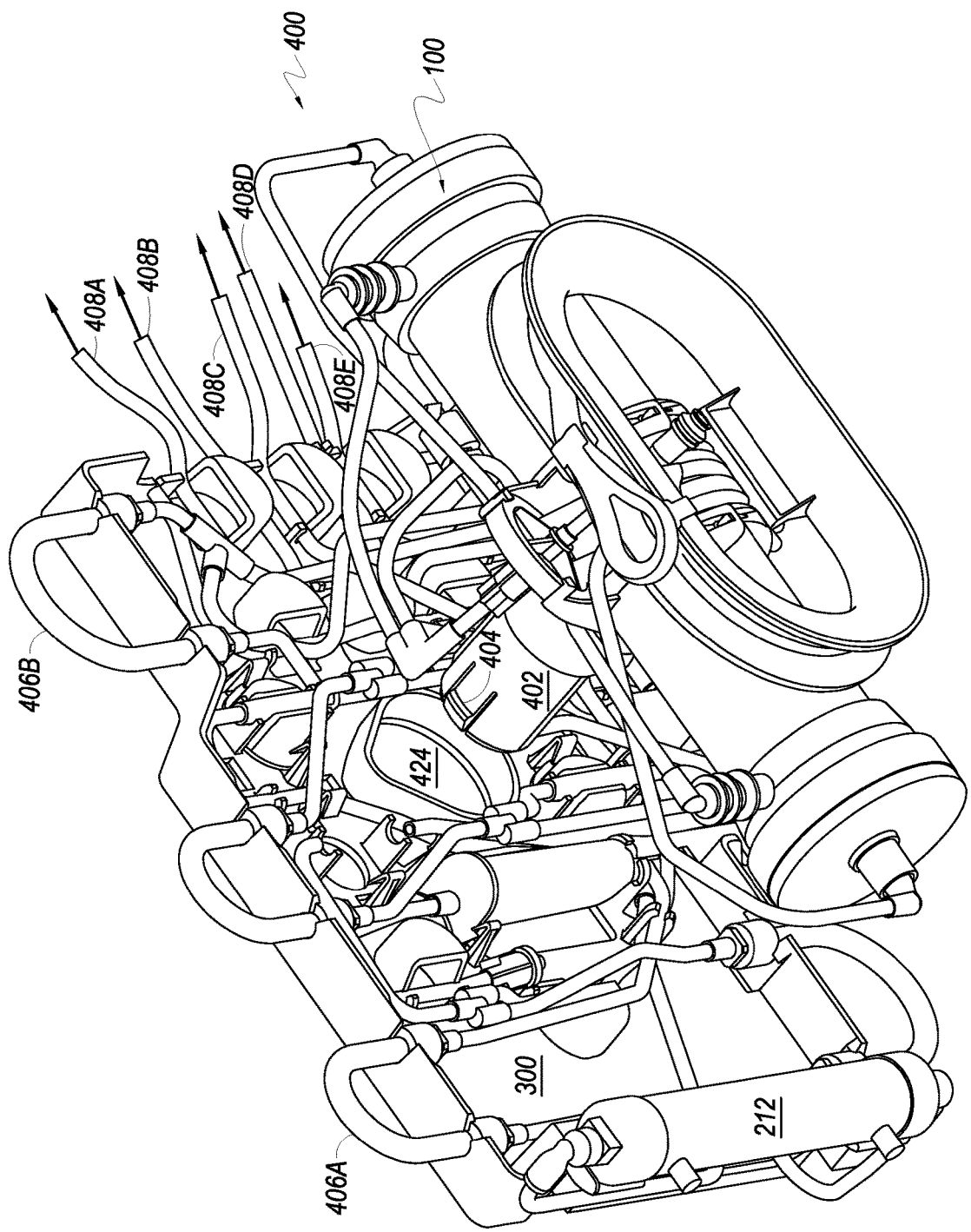
FIG. 4 illustrates a perspective view of a pre-mounted fluid conveyance device, in accordance with embodiments of the present disclosure

Turning to FIG. 4, a perspective view of a detachably-attachable pre-mounted fluid conveyance assembly 400 is shown. The pre-mounted fluid conveyance assembly 400 may be detachably-attachable to the cell expansion machine 202 (FIGS. 2 and 3) to facilitate relatively quick exchange of a new or unused pre-mounted fluid conveyance assembly 400 at a cell expansion machine 202 for a used pre-mounted fluid conveyance assembly 400 at the same cell expansion machine 202. As shown in FIG. 4, the bioreactor 100 may be attached to a bioreactor coupling that includes a shaft fitting 402. The shaft fitting 402 includes one or more shaft fastening mechanisms, such as a biased arm or spring member 404 for engaging a shaft, e.g., 258 (shown in FIG. 3), of the cell expansion machine 202.

According to embodiments, the pre-mounted fluid conveyance assembly 400 includes tubing 408A, 408B, 408C, 408D, 408E, etc., and various tubing fittings to provide the fluid paths shown in FIGS. 5 and 6, as described below. Pump loops 406A and 406B may also be provided for the pump(s). In embodiments, although the various media may be provided at the site where the cell expansion machine 202 is located, the pre-mounted fluid conveyance assembly 400 may include sufficient tubing length to extend to the exterior of the cell expansion machine 202 and to enable welded connections to tubing associated with media bag(s) or container(s), according to embodiments.

Figure 5:
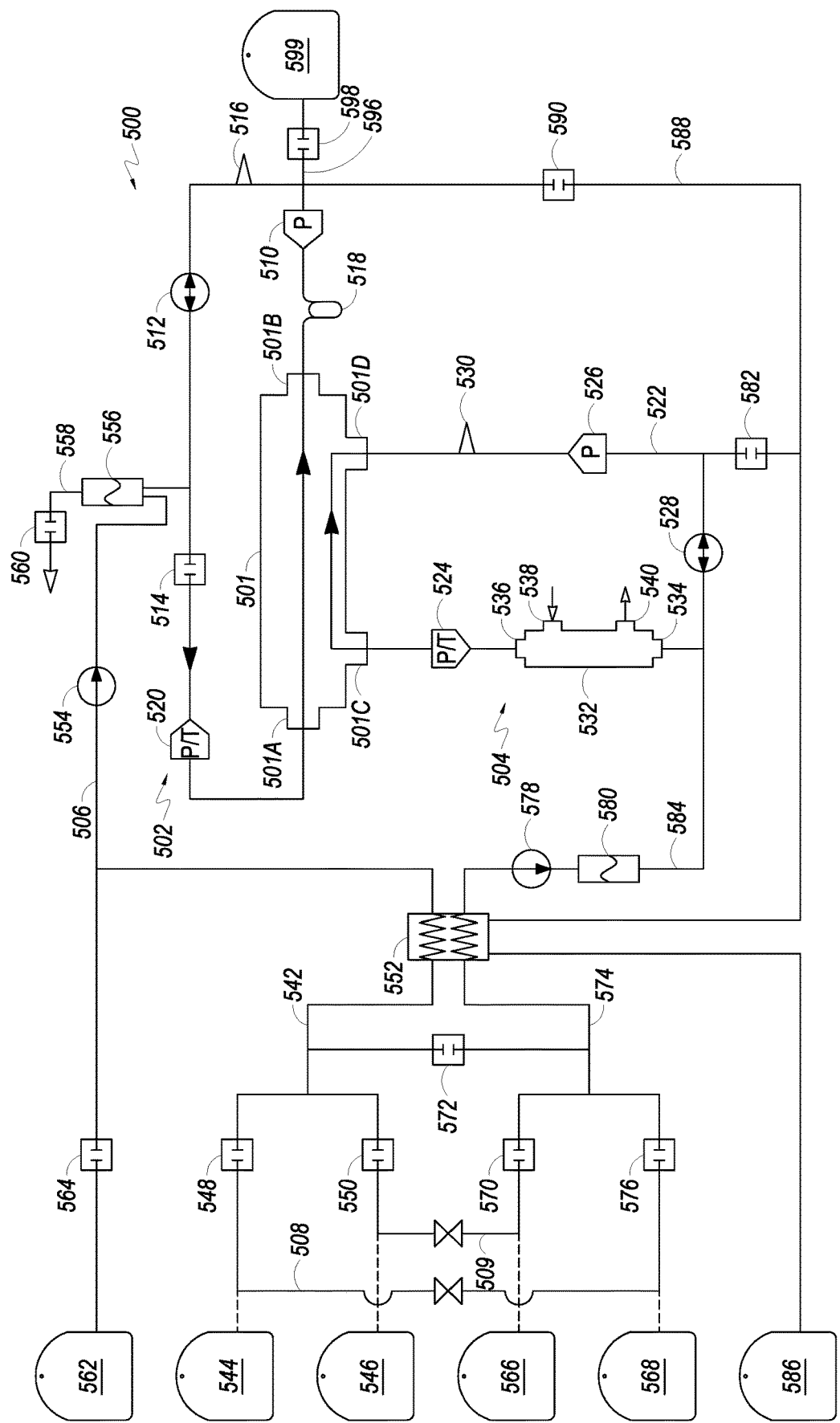
FIG. 5 depicts a schematic of a cell expansion system, in accordance with an embodiment of the present disclosure.
Figure 6:
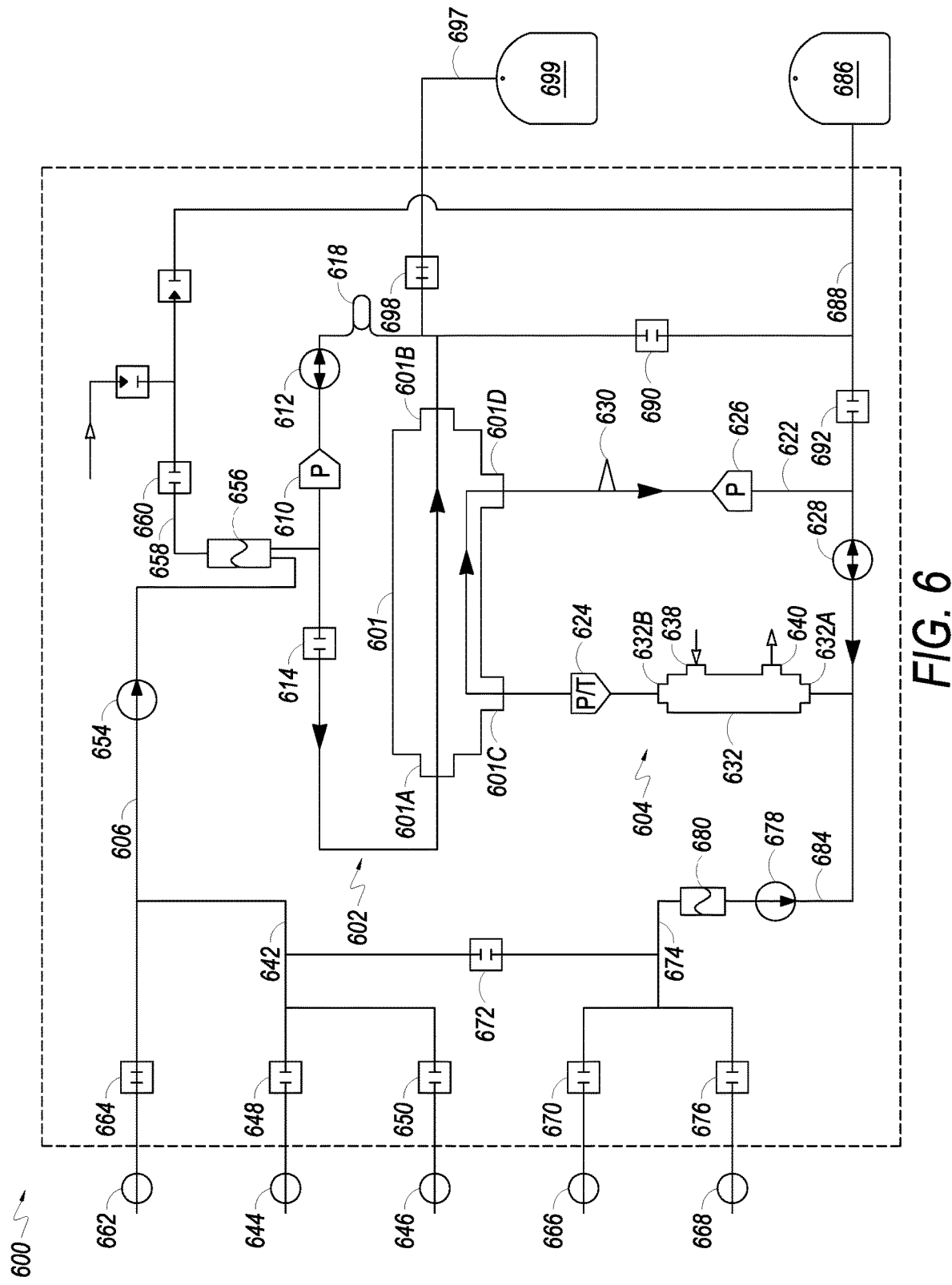
FIG. 6 illustrates a schematic of a cell expansion system, in accordance with another embodiment of the present disclosure.

Next, FIG. 5 illustrates a schematic of an embodiment of a cell expansion system 500, and FIG. 6 illustrates a schematic of another embodiment of a cell expansion system 600. In the embodiments shown in FIGS. 5 and 6, and as described below, the cells are grown in the IC space. However, the disclosure is not limited to such examples and may in other embodiments provide for cells to be grown in the EC space.

FIG. 5 illustrates a CES 500, which includes first fluid circulation path 502 (also referred to as the "intracapillary loop" or "IC loop") and second fluid circulation path 504 (also referred to as the "extracapillary loop" or "EC loop"), according to embodiments. First fluid flow path 506 may be fluidly associated with cell growth chamber 501 to form first fluid circulation path 502. Fluid flows into cell growth chamber 501 through IC inlet port 501A, through hollow fibers in cell growth chamber 501, and exits via IC outlet port 501B. Pressure gauge 510 measures the pressure of media leaving cell growth chamber 501. Media flows through IC circulation pump 512 which may be used to control the rate of media flow. IC circulation pump 512 may pump the fluid in a first direction or second direction opposite the first direction. Exit port 501B may be used as an inlet in the reverse direction. Media entering the IC loop may enter through valve 514. As those skilled in the art will appreciate, additional valves, pressure gauges, pressure/temperature sensors, ports, and/or other devices may be placed at various locations to isolate and/or measure characteristics of the media along portions of the fluid paths. Accordingly, it is to be understood that the schematic shown represents one possible configuration for various elements of the CES 500, and modifications to the schematic shown are within the scope of the one or more present embodiments.

With regard to the IC loop 502, samples of media may be obtained from sample port 516 or sample coil 518 during operation. Pressure/temperature gauge 520 disposed in first fluid circulation path 502 allows detection of media pressure and temperature during operation. Media then returns to IC inlet port 501A to complete fluid circulation path 502. Cells grown/expanded in cell growth chamber 501 may be flushed out of cell growth chamber 501 into harvest bag 599 through valve 598 or redistributed within the hollow fibers for further growth.

Fluid in second fluid circulation path 504 enters cell growth chamber 501 via EC inlet port 501C, and leaves cell growth chamber 501 via EC outlet port 501D. Media in the EC loop 504 may be in contact with the outside of the hollow fibers in the cell growth chamber 501, thereby allowing diffusion of small molecules into and out of the hollow fibers.

Pressure/temperature gauge 524 disposed in the second fluid circulation path 504 allows the pressure and temperature of media to be measured before the media enters the EC space of the cell growth chamber 501, according to an embodiment. Pressure gauge 526 allows the pressure of media in the second fluid circulation path 504 to be measured after it leaves the cell growth chamber 501. With regard to the EC loop, samples of media may be obtained from sample port 530 or a sample coil during operation.

In embodiments, after leaving EC outlet port 501D of cell growth chamber 501, fluid in second fluid circulation path 504 passes through EC circulation pump 528 to oxygenator or gas transfer module 532. EC circulation pump 528 may also pump the fluid in opposing directions. Second fluid flow path 522 may be fluidly associated with oxygenator or gas transfer module 532 via oxygenator inlet port 534 and oxygenator outlet port 536. In operation, fluid media flows into oxygenator or gas transfer module 532 via oxygenator inlet port 534, and exits oxygenator or gas transfer module 532 via oxygenator outlet port 536. Oxygenator or gas transfer module 532 adds oxygen to, and removes bubbles from, media in the CES 500, for example. In various embodiments, media in second fluid circulation path 504 may be in equilibrium with gas entering oxygenator or gas transfer module 532. The oxygenator or gas transfer module 532 may be any appropriately sized oxygenator or gas transfer device. Air or gas flows into oxygenator or gas transfer module 532 via filter 538 and out of oxygenator or gas transfer device 532 through filter 540. Filters 538 and 540 reduce or prevent contamination of oxygenator or gas transfer module 532 and associated media. Air or gas purged from the CES 500 during portions of a priming sequence may vent to the atmosphere via the oxygenator or gas transfer module 532.

In the configuration depicted for CES 500, fluid media in first fluid circulation path 502 and second fluid circulation path 504 flows through cell growth chamber 501 in the same direction (a co-current configuration). The CES 500 may also be configured to flow in a counter-current conformation.

In accordance with at least one embodiment, media, including cells (from bag 562), and fluid media from bag 546 may be introduced to first fluid circulation path 502 via first fluid flow path 506. Fluid container 562 (e.g., Cell Inlet Bag or Saline Priming Fluid for priming air out of the system) may be fluidly associated with the first fluid flow path 506 and the first fluid circulation path 502 via valve 564.

Fluid containers, or media bags, 544 (e.g., Reagent) and 546 (e.g., IC Media) may be fluidly associated with either first fluid inlet path 542 via valves 548 and 550, respectively, or second fluid inlet path 574 via valves 570 and 576. First and second sterile sealable input priming paths 508 and 509 are also provided. An air removal chamber (ARC) 556 may be fluidly associated with first circulation path 502. The air removal chamber 556 may include one or more ultrasonic sensors including an upper sensor and lower sensor to detect air, a lack of fluid, and/or a gas/fluid interface, e.g., an air/fluid interface, at certain measuring positions within the air removal chamber 556. For example, ultrasonic sensors may be used near the bottom and/or near the top of the air removal chamber 556 to detect air, fluid, and/or an air/fluid interface at these locations. Embodiments provide for the use of numerous other types of sensors without departing from the spirit and scope of the present disclosure. For example, optical sensors may be used in accordance with embodiments of the present disclosure. Air or gas purged from the CES 500 during portions of the priming sequence or other protocols may vent to the atmosphere out air valve 560 via line 558 that may be fluidly associated with air removal chamber 556.

EC media (e.g., from bag 568) or wash solution (e.g., from bag 566) may be added to either the first or second fluid flow paths. Fluid container 566 may be fluidly associated with valve 570 that may be fluidly associated with first fluid circulation path 502 via distribution valve 572 and first fluid inlet path 542. Alternatively, fluid container 566 may be fluidly associated with second fluid circulation path 504 via second fluid inlet path 574 and EC inlet path 584 by opening valve 570 and closing distribution valve 572. Likewise, fluid container 568 may be fluidly associated with valve 576 that may be fluidly associated with first fluid circulation path 502 via first fluid inlet path 542 and distribution valve 572. Alternatively, fluid container 568 may be fluidly associated with second fluid inlet path 574 by opening valve 576 and closing distribution valve 572.

An optional heat exchanger 552 may be provided for media reagent or wash solution introduction.

In the IC loop, fluid may be initially advanced by the IC inlet pump 554. In the EC loop, fluid may be initially advanced by the EC inlet pump 578. An air detector 580, such as an ultrasonic sensor, may also be associated with the EC inlet path 584.

In at least one embodiment, first and second fluid circulation paths 502 and 504 are connected to waste or outlet line 588. When valve 590 is opened, IC media may flow through waste line 588 and to waste or outlet bag 586. Likewise, when valve 582 is opened, EC media may flow through waste line 588 to waste or outlet bag 586.

In embodiments, cells may be harvested via cell harvest path 596. Here, cells from cell growth chamber 501 may be harvested by pumping the IC media containing the cells through cell harvest path 596 and valve 598 to cell harvest bag 599.

Various components of the CES 500 may be contained or housed within a machine or housing, such as cell expansion machine 202 (FIGS. 2 and 3), wherein the machine maintains cells and media, for example, at a predetermined temperature.

Turning to FIG. 6, a schematic of another embodiment of a cell expansion system 600 is shown. CES 600 includes a first fluid circulation path 602 (also referred to as the "intracapillary loop" or "IC loop") and second fluid circulation path 604 (also referred to as the "extracapillary loop" or "EC loop"). First fluid flow path 606 may be fluidly associated with cell growth chamber 601 to form first fluid circulation path 602. Fluid flows into cell growth chamber 601 through IC inlet port 601A, through hollow fibers in cell growth chamber 601, and exits via IC outlet port 601B. Pressure sensor 610 measures the pressure of media leaving cell growth chamber 601. In addition to pressure, sensor 610 may, in embodiments, also be a temperature sensor that detects the media pressure and temperature during operation. Media flows through IC circulation pump 612 which may be used to control the rate of media flow. IC circulation pump 612 may pump the fluid in a first direction or second direction opposite the first direction. Exit port 601B may be used as an inlet in the reverse direction. Media entering the IC loop may enter through valve 614. As those skilled in the art will appreciate, additional valves, pressure gauges, pressure/temperature sensors, ports, and/or other devices may be placed at various locations to isolate and/or measure characteristics of the media along portions of the fluid paths. Accordingly, it is to be understood that the schematic shown represents one possible configuration for various elements of the CES 600, and modifications to the schematic shown are within the scope of the one or more present embodiments.

With regard to the IC loop, samples of media may be obtained from sample coil 618 during operation. Media then returns to IC inlet port 601A to complete fluid circulation path 602. Cells grown/expanded in cell growth chamber 601 may be flushed out of cell growth chamber 601 into harvest bag 699 through valve 698 and line 697. Alternatively, when valve 698 is closed, the cells may be redistributed within chamber 601 for further growth.

Fluid in second fluid circulation path 604 enters cell growth chamber 601 via EC inlet port 601C and leaves cell growth chamber 601 via EC outlet port 601D. Media in the EC loop may be in contact with the outside of the hollow fibers in the cell growth chamber 601, thereby allowing diffusion of small molecules into and out of the hollow fibers that may be within chamber 601, according to an embodiment.

Pressure/temperature sensor 624 disposed in the second fluid circulation path 604 allows the pressure and temperature of media to be measured before the media enters the EC space of the cell growth chamber 601. Sensor 626 allows the pressure and/or temperature of media in the second fluid circulation path 604 to be measured after it leaves the cell growth chamber 601. With regard to the EC loop, samples of media may be obtained from sample port 630 or a sample coil during operation.

After leaving EC outlet port 601D of cell growth chamber 601, fluid in second fluid circulation path 604 passes through EC circulation pump 628 to oxygenator or gas transfer module 632. EC circulation pump 628 may also pump the fluid in opposing directions, according to embodiments. Second fluid flow path 622 may be fluidly associated with oxygenator or gas transfer module 632 via an inlet port 632A and an outlet port 632B of oxygenator or gas transfer module 632. In operation, fluid media flows into oxygenator or gas transfer module 632 via inlet port 632A, and exits oxygenator or gas transfer module 632 via outlet port 632B. Oxygenator or gas transfer module 632 adds oxygen to, and removes bubbles from, media in the CES 600, for example. In various embodiments, media in second fluid circulation path 604 may be in equilibrium with gas entering oxygenator or gas transfer module 632. The oxygenator or gas transfer module 632 may be any appropriately sized device useful for oxygenation or gas transfer. Air or gas flows into oxygenator or gas transfer module 632 via filter 638 and out of oxygenator or gas transfer device 632 through filter 640. Filters 638 and 640 reduce or prevent contamination of oxygenator or gas transfer module 632 and associated media. Air or gas purged from the CES 600 during portions of a priming sequence may vent to the atmosphere via the oxygenator or gas transfer module 632.

In the configuration depicted for CES 600, fluid media in first fluid circulation path 602 and second fluid circulation path 604 flows through cell growth chamber 601 in the same direction (a co-current configuration). The CES 600 may also be configured to flow in a counter-current conformation, according to embodiments.

In accordance with at least one embodiment, media, including cells (from a source such as a cell container, e.g., a bag) may be attached at attachment point 662, and fluid media from a media source may be attached at attachment point 646. The cells and media may be introduced into first fluid circulation path 602 via first fluid flow path 606. Attachment point 662 may be fluidly associated with the first fluid flow path 606 via valve 664, and attachment point 646 may be fluidly associated with the first fluid flow path 606 via valve 650. A reagent source may be fluidly connected to point 644 and be associated with fluid inlet path 642 via valve 648, or second fluid inlet path 674 via valves 648 and 672.

Air removal chamber (ARC) 656 may be fluidly associated with first circulation path 602. The air removal chamber 656 may include one or more sensors including an upper sensor and lower sensor to detect air, a lack of fluid, and/or a gas/fluid interface, e.g., an air/fluid interface, at certain measuring positions within the air removal chamber 656. For example, ultrasonic sensors may be used near the bottom and/or near the top of the air removal chamber 656 to detect air, fluid, and/or an air/fluid interface at these locations. Embodiments provide for the use of numerous other types of sensors without departing from the spirit and scope of the present disclosure. For example, optical sensors may be used in accordance with embodiments of the present disclosure. Air or gas purged from the CES 600 during portions of a priming sequence or other protocol(s) may vent to the atmosphere out air valve 660 via line 658 that may be fluidly associated with air removal chamber 656.

An EC media source may be attached to EC media attachment point 668, and a wash solution source may be attached to wash solution attachment point 666, to add EC media and/or wash solution to either the first or second fluid flow path. Attachment point 666 may be fluidly associated with valve 670 that may be fluidly associated with first fluid circulation path 602 via valve 672 and first fluid inlet path 642. Alternatively, attachment point 666 may be fluidly associated with second fluid circulation path 604 via second fluid inlet path 674 and second fluid flow path 684 by opening valve 670 and closing valve 672. Likewise, attachment point 668 may be fluidly associated with valve 676 that may be fluidly associated with first fluid circulation path 602 via first fluid inlet path 642 and valve 672. Alternatively, fluid container 668 may be fluidly associated with second fluid inlet path 674 by opening valve 676 and closing distribution valve 672.

In the IC loop, fluid may be initially advanced by the IC inlet pump 654. In the EC loop, fluid may be initially advanced by the EC inlet pump 678. An air detector 680, such as an ultrasonic sensor, may also be associated with the EC inlet path 684.

In at least one embodiment, first and second fluid circulation paths 602 and 604 are connected to waste or outlet line 688. When valve 690 is opened, IC media may flow through waste line 688 and to waste or outlet bag 686. Likewise, when valve 692 is opened, EC media may flow to waste or outlet bag 686.

After cells have been grown in cell growth chamber 601, they may be harvested via cell harvest path 697. Here, cells from cell growth chamber 601 may be harvested by pumping the IC media containing the cells through cell harvest path 697, with valve 698 open, into cell harvest bag 699.

Various components of the CES 600 may be contained or housed within a machine or housing, such as cell expansion machine 202 (FIGS. 2 and 3), wherein the machine maintains cells and media, for example, at a predetermined temperature. It is further noted that, in embodiments, components of CES 600 and CES 500 (FIG. 5) may be combined. In other embodiments, a CES may include fewer or additional components than those shown in FIGS. 5 and 6 and still be within the scope of the present disclosure. An example of a cell expansion system that may incorporate features of the present disclosure is the QUANTUM® Cell Expansion System (the "QUANTUM® System"), manufactured by Terumo BCT, Inc. in Lakewood, Colo.

Examples and further description of cell expansion systems are provided in U.S. patent application Ser. No. 12/042, 798 (U.S. Pat. No. 8,309,347), entitled, "Cell Expansion System and Methods of Use," issued on Nov. 13, 2012, which is hereby incorporated by reference herein in its entirety for all that it teaches and for all purposes.

Figure 7:
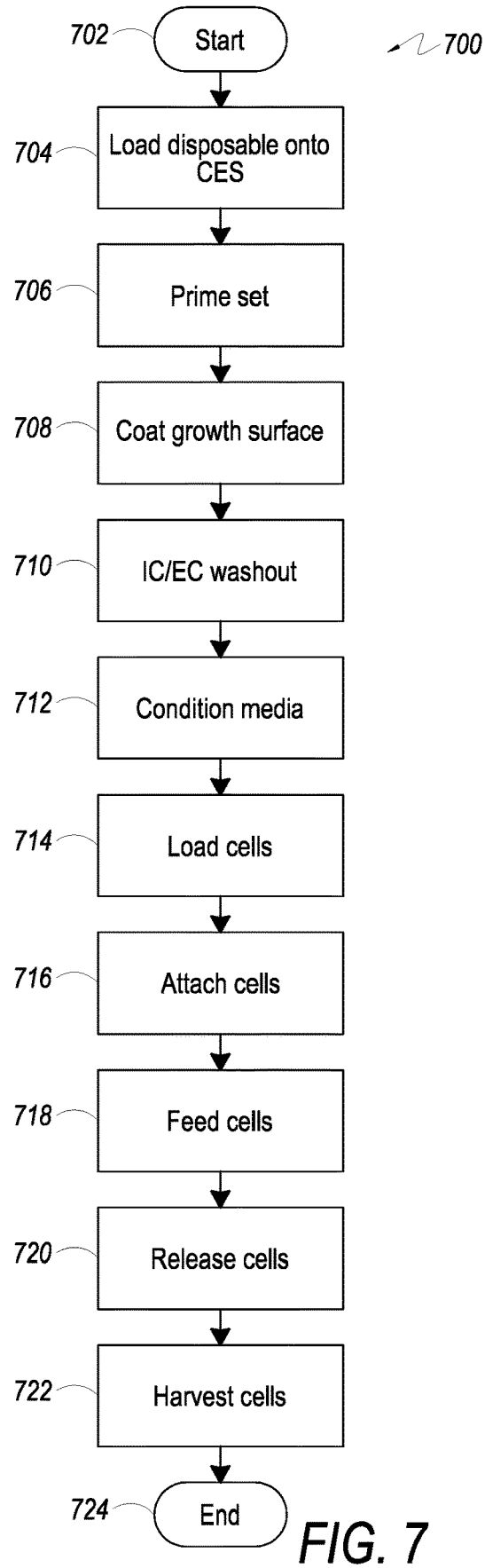
FIG. 7 depicts a flow diagram illustrating the operational characteristics of a process for applying an agent to a cell growth surface in accordance with embodiments of the present disclosure.

While various example embodiments of a cell expansion system and methods associated therewith have been described, FIG. 7 illustrates example operational steps 700 of a process for applying an agent to a cell growth surface that may be used with a cell expansion system, such as CES 500 (FIG. 5) or CES 600 (FIG. 6), in accordance with embodiments of the present disclosure. FIG. 7 will be described in conjunction with example settings and media introduction. However, the embodiments presented herein are not limited to this example; rather, the embodiments can be modified to meet other system designs or configurations. START operation is initiated 702, and process 700 proceeds to load the disposable tubing set 704 onto the cell expansion system. Next, the system may be primed 706. In an embodiment, a user or an operator, for example, may provide an instruction to the system to prime by selecting a task for priming, for example. In an embodiment, such task for priming may be a pre-programmed task. The system 500 (FIG. 5) or 600 (FIG. 6) may be primed, for example, with phosphate-buffered saline (PBS). To prime the bioreactor 501, 601, a bag (e.g., 546) may be attached (for example, to connection point 646) to the system 500, 600. When referring to numerals in the Figures, for example, such as "Numeral, Numeral" (e.g., 500, 600), such nomenclature can mean "Numeral and/or Numeral" (e.g., 500 and/or 600). Valve 550, 650 may be opened. The PBS can then be directed into the first fluid circulation path 502, 602 by the IC inlet pump 554, 654 set to pump the PBS into the first fluid circulation path 502, 602. Valve 514, 614 may be opened while the PBS enters the bioreactor 501, 601 through the inlet 501A, 601A and out the outlet 501B, 601B. Once the bioreactor 501, 601 and/or the first fluid circulation path 502, 602 have media therein with air removed by the air removal chamber 556, 656, the bioreactor 501, 601 is primed, according to an embodiment.

In an embodiment, to further prime the bioreactor 501, 601, a bag (e.g., 568) may be attached (for example, to connection point 668) to the system 500, 600. Valve 576, 676 may be opened. A media, e.g., PBS, can then be directed into the second fluid circulation path 504, 604 by the EC inlet pump 578, 678 set to pump the media into the second fluid circulation path 504, 604. Valve 582, 692 may be closed while the media enters the bioreactor 501, 601 through the inlet 501C, 601C and out the outlet 501D, 601D of the EC loop. Once the bioreactor 501, 601 and/or the second fluid circulation path 504, 604 have media therein with air removed, e.g., by an air removal chamber, the bioreactor 501, 601 is primed, according to an embodiment.

Process 700 then proceeds to coat the cell growth surface, e.g., bioreactor 501, 601, in step 708, in which the cell growth surface may be coated with a coating agent or reagent. Any coating agent(s) or reagent(s), such as fibronectin or cryoprecipitate, for example, understood by those of skill in the art may be used. In embodiments, any combination of coating agent(s) or reagent(s) may be used. In an embodiment, an outlet or waste valve 590, 690 to one of the circulation loops, e.g., IC loop 502, 602, may be closed, while the outlet or waste valve 582, 692 to the other circulation loop, e.g., EC loop 504, 604, may be opened or remains open. For example, the IC waste or outlet valve 590, 690 may be closed while the EC waste or outlet valve 582, 692 is open. In embodiments, a coating agent or reagent may be loaded into a circulation loop, e.g., IC loop 502, 602, of the cell expansion system 500, 600 until the reagent bag (e.g., 544) or container is empty. Next, the reagent may be chased from an air removal chamber 556, 656 into the circulation loop, e.g., IC loop 502, 602. The bioreactor 501, 601, e.g., cell growth surface of hollow fibers where a hollow fiber bioreactor is used, may then be coated by controlling the fluid movement in the bioreactor 501, 601. In embodiments, such control of the fluid movement uses ultrafiltration, e.g., positive ultrafiltration, to move fluid from one side (e.g., the IC side 502, 602) of the bioreactor 501, 601 to the other side (e.g., the EC side 504, 604). For example, where the IC outlet or waste valve 590, 690 may be closed, with the EC outlet or waste valve open 582, 692, a fluid in the bioreactor 501, 601 may have no pathway but through the pores of the fibers (IC outlet valve 590, 690 closed). In an embodiment, the IC inlet rate may be set to wash the IC side 502, 602 with media or a fluid, such as phosphate buffered saline (PBS), for example. Accordingly, the solution may then flow through the pores of the fibers from the IC side 502, 602 to the EC side 504, 604. The coating agent, e.g., CPPT, may be hydrostatically deposited onto the wall(s), e.g., inner wall(s), of the bioreactor fiber for a defined time period. For example, such time period may be about ten (10) minutes, according to an embodiment. Other time periods may apply according to other embodiments of the present disclosure. Such membrane ultrafiltration method allows adherence promoting proteins to be physisorbed on the bioreactor fibers as the solution flows through the pores of the fiber from the IC side 502, 602 to the EC side 504, 604.

An example of the solutions being introduced to the system 500, 600 to coat the bioreactor may be as shown below:

TABLE 1

| Bag (Connection Point) | Solution in Bag | Volume (estimation based on factory default values) |
| --- | --- | --- |
| Cell Inlet 562 (662) | None | N/A |
| Reagent 544 (644) | Reagent (e.g., CPPT or Fibronectin) | e.g., 6-25 mL CPPT in 100 mL total volume w/PBS |
| IC Media 546 (646) | None | N/A |
| Wash 566 (666) | PBS | 1 L |
| EC Media 568 (668) | None | N/A |

The coating of the bioreactor may occur in three stages. An example of the settings for the system 500, 600 for the first stage of introducing the solution(s) above may be as shown below:

TABLE 2

| Component | Setting |
| --- | --- |
| IC Inlet valve configuration | Reagent (e.g., valves 548, 648, 514, 614 open) |
| IC Inlet Rate for Pump 554, 654 | 10 mL/min |
| IC Circulation Rate for Pump 512, 612 | 100 mL/min |
| EC Inlet valve configuration | None |
| EC Inlet Rate for Pump 578, 678 | 0 mL/min |
| EC Circulation Rate for Pump 528, 628 | 30 mL/min |
| Outlet valve configuration | EC Outlet (e.g., valve 582, 692 open) |
| Rocker Control | Stationary (0°) |
| Stop Condition | Empty Bag for bag 544 |

An example of the settings for the system 500, 600 for the second stage of coating the bioreactor, which chases or washes reagent from the air removal chamber 556, 656, may be as shown below:

TABLE 3

| Component | Setting |
| --- | --- |
| IC Inlet valve configuration | Wash (e.g., valves 570, 670, 572, 672, 514, 614, 560, 660 open) |
| IC Inlet Rate for Pump 554, 654 | 10 mL/min |
| IC Circulation Rate for Pump 512, 612 | 100 mL/min |
| EC Inlet valve configuration | None |
| EC Inlet Rate for Pump 578, 678 | 0 mL/min |
| EC Circulation Rate for Pump 528, 628 | 30 mL/min |
| Outlet valve configuration | EC Outlet (e.g., valve 582, 692 open) |
| Rocker Control | Stationary (0°) |
| Stop Condition | IC Volume (e.g., 22 mL) |

An example of the settings for the system 500, 600 for the third stage of coating the bioreactor, which causes ultrafiltration from the IC side 502, 602 to the EC side 504, 604, for example, may be as shown below:

TABLE 4

| Component | Setting |
| --- | --- |
| IC Inlet valve configuration | Wash (e.g., valves 570, 670, 572, 672, 514, 614 open) |
| IC Inlet Rate for Pump 554, 654 | 50 mL/min |
| IC Circulation Rate for Pump 512, 612 | −25 mL/min |
| EC Inlet valve configuration | Wash |
| EC Inlet Rate for Pump 578, 678 | 0.1 mL/min |
| EC Circulation Rate for Pump 528, 628 | 30 mL/min |
| Outlet valve configuration | EC Outlet (e.g., valve 582, 692 open) |
| Rocker Control | Stationary (0°) |
| Stop Condition | 10 Min |

In an embodiment, such active promoting of the coating agent to a cell growth surface, as described above, may significantly decrease the amount of time to coat the cell growth surface as compared to other methods of coating a cell growth surface. In embodiments, such coating procedure using ultrafiltration may be referred to as an expedited coating procedure. Such expedited coating procedure using active moving of the coating agent to the cell growth surface(s) through ultrafiltration may use less time to coat the cell growth surface than procedures using passive coating procedures which may take overnight or about twelve (12) hours to about sixteen (16) hours to coat the bioreactor. For example, such expedited coating procedure may take less than or equal to about four (4) hours. In embodiments, such expedited coating procedure may take any time period in a range from above or equal to about five (5) minutes to less than or equal to about sixty (60) minutes, or any other range therein, depending on the procedure. For example, such coating procedure may take less than or equal to about ten (10) minutes, less than or equal to about twelve (12) minutes, less than or equal to about fifteen (15) minutes, less than or equal to about twenty (20) minutes, less than or equal to about thirty (30) minutes, less than or equal to about forty-five (45) minutes, less than or equal to about sixty (60) minutes, etc. As described above, passive coating procedures may take about sixteen (16) hours to coat the bioreactor, for example. A significant time savings may be realized by using ultrafiltration for coating the bioreactor.

Returning to FIG. 7, once the bioreactor is coated, the IC/EC Washout task may be performed in step 710, in which fluid on the IC circulation loop 502, 602 and on the EC circulation loop 504, 604 may be replaced. The replacement volume may be determined by the number of IC Volumes and EC Volumes exchanged. An example of the solutions being introduced to the system 500, 600 during the IC/EC Washout task may be as shown below:

TABLE 5

| Bag (Connection Point) | Solution in Bag | Volume (estimation based on factory default values) |
| --- | --- | --- |
| Cell Inlet 562 (662) | None | N/A |
| Reagent 544 (644) | None | N/A |
| IC Media 546 (646) | Media with Protein | 1.4 L |
| Wash 566 (666) | None | N/A |
| EC Media 568 (668) | None | N/A |

An example of the settings for an IC/EC Washout task of the system 500, 600 may be as shown below:

TABLE 6

| Component | Setting |
| --- | --- |
| IC Inlet valve configuration | IC Media (e.g., valves 550, 650, 514, 614 open) |
| IC Inlet Rate for Pump 554, 654 | 100 mL/min |
| IC Circulation Rate for Pump 512, 612 | −17 mL/min |
| EC Inlet valve configuration | IC Media (e.g., valves 550, 650, 572, 672 open) |
| EC Inlet Rate for Pump 578, 678 | 148 mL/min |
| EC Circulation Rate for Pump 528, 628 | −1.7 mL/min |
| Outlet valve configuration | IC and EC Outlet (e.g., valves 590, 690 and 582, 692 open) |
| Rocker Control | In Motion (−90°, 180°, in 1 sec intervals) |
| Stop Condition | Exchange (2.5 IC Volumes; 2.5 EC Volumes) |

Next, to maintain the proper or desired gas concentration across the fibers in the bioreactor membrane, the condition media task 712 may be executed to allow the media to reach equilibrium with the provided gas supply before cells are loaded into the bioreactor. For example, rapid contact between the media and the gas supply provided by the gas transfer module or oxygenator 532, 632 may be provided by using a high EC circulation rate. The system 500, 600 may then be maintained in a proper or desired state until a user or operator, for example, is ready to load cells into the bioreactor 501, 601. In an embodiment, the system 500, 600 may be conditioned with complete media, for example. Complete media may be any media source used for cell growth. In an embodiment, complete media may comprise alpha-MEM (a-MEM) and fetal bovine serum (FBS), for example. Any type of media known to those of skill in the art may be used.

The condition media task 712 may be a two-step process where, in the first step, the system 500, 600 provides rapid contact between the media and the gas supply by using a high EC circulation rate.

In the second step, the system 500, 600 maintains the bioreactor 501, 601 in a proper state until an operator, for example, is ready to load the cells. An example of the solutions being introduced to the system 500, 600 during the condition media task 712 may be as shown below.

While an example media is shown in Table 7, any type of media known to those of skill in the art may be used.

TABLE 7

| Bag (Connection Point) | Solution in Bag | Volume (estimation based on factory default values) |
|---|---|---|
| Cell Inlet 562 (662) | None | N/A |
| Reagent 544 (644) | None | N/A |
| IC Media 546 (646) | None | N/A |
| Wash 566 (666) | None | N/A |
| EC Media 568 (668) | Media with Protein (e.g., αMEM with GlutaMAX plus 10% FBS) | 0.1 L plus 6 mL/hour |

An example of the settings for a first step of the condition media task 712 may be as shown below:

TABLE 8

| Component | Setting |
|---|---|
| IC Inlet valve configuration | None |
| IC Inlet Rate for Pump 554, 654 | 0 mL/min |
| IC Circulation Rate for Pump 512, 612 | 100 mL/min |
| EC Inlet valve configuration | EC Media (and/or IC Media) (e.g., valve 576, 676 open) |
| EC Inlet Rate for Pump 578, 678 | 0.1 mL/min |
| EC Circulation Rate for Pump 528, 628 | 250 mL/min |
| Outlet valve configuration | EC Outlet (e.g., valve 582, 692 open) |
| Rocker Control | Stationary |
| Stop Condition | Time (e.g., 10 min) |

An example of the settings for a second step of the condition media task 712 may be as shown below:

TABLE 9

| Component | Setting |
|---|---|
| IC Inlet valve configuration | None |
| IC Inlet Rate for Pump 554, 654 | 0 mL/min |
| IC Circulation Rate for Pump 512, 612 | 100 mL/min |
| EC Inlet valve configuration | EC Media (and/or IC Media) (e.g., valve 576, 676 open) |
| EC Inlet Rate for Pump 578, 678 | 0.1 mL/min |
| EC Circulation Rate for Pump 528, 628 | 30 mL/min |
| Outlet valve configuration | EC Outlet (e.g., valve 582, 692 open) |
| Rocker Control | Stationary |
| Stop Condition | Manual |

Process 700 next proceeds to loading cells 714 into the bioreactor 501, 601 from a cell inlet bag 562 (at connection point 662), for example. In an embodiment, the cells are loaded with uniform suspension 714. In an embodiment, the cells may be loaded into the bioreactor 501, 601 from the cell inlet bag 562 (at connection point 662) until the bag 562 is empty. Cells may then be chased or washed from the air removal chamber 556, 656 to the bioreactor 501, 601, according to an embodiment. In embodiments that utilize larger chase volumes, cells may be spread and move toward the IC outlet port 501B, 601B. The distribution of cells may be promoted across the membrane via IC circulation, such as through an IC circulation pump 512, 612, with no IC inlet, for example. Examples and further description of loading and distributing cells are provided in U.S. patent application Ser. No. 13/971,500 (U.S. Pat. No. 9,175,259), entitled, "Method of Loading and Distributing Cells in a Bioreactor of a Cell Expansion System," issued Nov. 3, 2015, which is hereby incorporated by reference herein in its entirety for all that it teaches and for all purposes.

In another embodiment, the cells may be loaded 714 using another type of cell loading, such as a high flux cell load. In yet another embodiment, the cells may be loaded 714 using another type of loading, such as a bulls-eye cell loading technique. Examples and further description of bulls-eye cell loading procedure(s) are provided in U.S. patent application Ser. No. 14/542,276 (U.S. Pat. No. 9,617,506), entitled, "Expanding Cells in a Bioreactor," issued on Apr. 11, 2017, which is hereby incorporated by reference herein in its entirety for all that it teaches and for all purposes.

An example of the solutions being introduced to the system 500, 600 to load cells 714 may be as shown below:

TABLE 10

| Bag (Connection Point) | Solution in Bag | Volume (estimation based on factory default values) |
|---|---|---|
| Cell Inlet 562 (662) | Cells | Cells (e.g., mesenchymal stem cells (MSC)) in 100 mL complete media |
| Reagent 544 (644) | None | N/A |
| IC Media 546 (646) | Media with Protein | 0.1 L |
| Wash 566 (666) | None | N/A |
| EC Media 568 (668) | None | N/A |

The loading of cells 714 may occur in stages. An example of the settings for the system 500, 600 for an example first stage may be as shown below:

TABLE 11

| Component | Setting |
|---|---|
| IC Inlet valve configuration | Cell Inlet (e.g., valves 564, 664, 514, 614 open) |
| IC Inlet Rate for Pump 554, 654 | 50 mL/min |
| IC Circulation Rate for Pump 512, 612 | 200 mL/min |
| EC Inlet valve configuration | None |
| EC Inlet Rate for Pump 578, 678 | 0 mL/min |
| EC Circulation Rate for Pump 528, 628 | 30 mL/min |
| Outlet valve configuration | EC Outlet (e.g., valve 582, 692 open) |
| Rocker Control | In Motion (−90°, 180°, in 1 sec intervals) |
| Stop Condition | ARC stop |

An example of the settings for the system 500, 600 for an example second stage may be as shown below:

TABLE 12

| Component | Setting |
|---|---|
| IC Inlet valve configuration | IC Media (e.g., valves 550, 650, 514, 614 open) |
| IC Inlet Rate for Pump 554, 654 | 50 mL/min |
| IC Circulation Rate for Pump 512, 612 | 200 mL/min |
| EC Inlet valve configuration | None |
| EC Inlet Rate for Pump 578, 678 | 0 mL/min |
| EC Circulation Rate for Pump 528, 628 | 30 mL/min |

TABLE 12-continued

| Component | Setting |
| --- | --- |
| Outlet valve configuration | EC Outlet (e.g., valve 582, 692 open) |
| Rocker Control | In Motion (−90°, 180°, in 1 sec intervals) |
| Stop Condition | IC Volume (e.g., 22 mL) |

An example of the settings for the system 500, 600 for an example third stage may be as shown below:

TABLE 13

| Component | Setting |
| --- | --- |
| IC Inlet valve configuration | None |
| IC Inlet Rate for Pump 554, 654 | 0 mL/min |
| IC Circulation Rate for Pump 512, 612 | 200 mL/min |
| EC Inlet valve configuration | None |
| EC Inlet Rate for Pump 578, 678 | 0 mL/min |
| EC Circulation Rate for Pump 528, 628 | 30 mL/min |
| Outlet valve configuration | EC Outlet (e.g., valve 582, 692 open) |
| Rocker Control | In Motion (−90°, 180°, in 1 sec intervals) |
| Stop Condition | Time (2.0 Min) |

Further, the cells, e.g., adherent cells, may be allowed to attach 716 to the hollow fibers. In an embodiment, in allowing the cells to attach 716, adherent cells are enabled to attach to the bioreactor membrane while allowing flow on the EC circulation loop 504, 604, with the pump (e.g., 512, 612, 554, 654) flow rate to the IC loop 502, 602 set to zero. An example of the solutions being introduced to the system 500, 600 during the process of cells attaching to the membrane 716 may be as shown below:

TABLE 14

| Bag (Connection Point) | Solution in Bag | Volume (estimation based on factory default values) |
| --- | --- | --- |
| Cell Inlet 562 (662) | None | N/A |
| Reagent 544 (644) | None | N/A |
| IC Media 546 (646) | Media with Protein | 6 mL/hour |
| Wash 566 (666) | None | N/A |
| EC Media 568 (668) | None | N/A |

An example of the settings for attaching to the membrane 716 in the system 500, 600 may be as shown below:

TABLE 15

| Component | Setting |
| --- | --- |
| IC Inlet valve configuration | None |
| IC Inlet Rate for Pump 554, 654 | 0 mL/min |
| IC Circulation Rate for Pump 512, 612 | 0 mL/min |
| EC Inlet valve configuration | IC Media (e.g., valves 550, 650, 572, 672 open) |
| EC Inlet Rate for Pump 578, 678 | 0.1 mL/min |
| EC Circulation Rate for Pump 528, 628 | 30 mL/min |
| Outlet valve configuration | EC Outlet (e.g., valve 582, 692 open) |
| Rocker Control | Stationary (at 180°) |
| Stop Condition | Manual |

Next, the cells may be fed in step 718, in which a flow rate, e.g., low flow rate in an embodiment, is continuously added to the IC circulation loop 502, 602 and/or the EC circulation loop 504, 604. In an embodiment, the cells may be fed with media, such as media with protein, for example. Outlet settings allow for the removal of fluid added to the system, in accordance with embodiments. An example of the solutions being introduced to the system 500, 600 during the feed step 718 may be as shown below:

TABLE 16

| Bag (Connection Point) | Solution in Bag | Volume (estimation based on factory default values) |
| --- | --- | --- |
| Cell Inlet 562 (662) | None | N/A |
| Reagent 544 (644) | None | N/A |
| IC Media 546 (646) | Media with Protein | 6 mL/hour |
| Wash 566 (666) | None | N/A |
| EC Media 568 (668) | None | N/A |

An example of the settings for the feed step 718 in the system 500, 600 may be as shown below:

TABLE 17

| Component | Setting |
| --- | --- |
| IC Inlet valve configuration | IC Media (e.g., valves 550, 650, 514, 614 open) |
| IC Inlet Rate for Pump 554, 654 | 0.1 mL/min |
| IC Circulation Rate for Pump 512, 612 | 20 mL/min |
| EC Inlet valve configuration | None |
| EC Inlet Rate for Pump 578, 678 | 0 mL/min |
| EC Circulation Rate for Pump 528, 628 | 30 mL/min |
| Outlet valve configuration | IC Outlet (e.g., valve 590, 690 open) |
| Rocker Control | Stationary (at 0°) |
| Stop Condition | Manual |

When it is determined to harvest the expanded cells, such as after the cells have reached confluence, after a defined period of time, according to user preference, etc., process 700 proceeds to release cells 720, in which the cells may be released from the membrane of the bioreactor 501, 601 and may be suspended in the IC loop 502, 602. Following the release of any adherent cells, harvest operation 722 transfers the cells in suspension from the IC circulation loop 502, 602, including any cells remaining in the bioreactor 501, 601, to a harvest bag 599, 699 or other container. Process 700 then terminates at END operation 724.

The releasing of cells 720 and harvesting of those cells 722 may be a five-step process, according to embodiments. An example of the solutions being introduced to the system 500, 600 during the release/harvest steps 720, 722 may be as shown below:

TABLE 18

| Bag (Connection Point) | Solution in Bag | Volume (estimation based on factory default values) |
| --- | --- | --- |
| Cell Inlet 562 (662) | None | N/A |
| Reagent 544 (644) | Trypsin | 180 mL |
| IC Media 546 (646) | Media with Protein | 0.6 L |
| Wash 566 (666) | PBS | 1.4 L |
| EC Media 568 (668) | None | N/A |

A first step in the releasing of cells 720 may perform an IC/EC Washout task in preparation for adding a reagent. For example, IC/EC media may be replaced with a phosphate buffered saline (PBS) to remove protein, calcium (Ca2+), and magnesium (Mg2+) in preparation for adding trypsin, or another chemical-releasing agent, to release any adherent cells. An example of the settings for an example first step of the release step 720 with the system 500, 600 may be as shown below:

TABLE 19

| Component | Setting |
| --- | --- |
| IC Inlet valve configuration | Wash (e.g., valves 570, 670, 572, 672, 514, 614 open) |
| IC Inlet Rate for Pump 554, 654 | 100 mL/min |
| IC Circulation Rate for Pump 512, 612 | −17 mL/min |
| EC Inlet valve configuration | Wash |
| EC Inlet Rate for Pump 578, 678 | 148 mL/min |
| EC Circulation Rate for Pump 528, 628 | −1.7 mL/min |
| Outlet valve configuration | IC Outlet (e.g., valve 590, 690 open) and EC outlet (e.g., valve 582, 692 open) |
| Rocker Control | In Motion (−90°, 180°, 1 second interval) |
| Stop Condition | Exchange (2.5 IC volumes; 2.5 EC volumes) |

A second step of the releasing cell process 720 includes loading a reagent into the system 500, 600 until the reagent bag 544 is empty. An example of the settings for an example second step of the release step 720 with the system 500, 600 may be as shown below:

TABLE 20

| Component | Setting |
| --- | --- |
| IC Inlet valve configuration | Reagent (e.g., valves 548, 648, 514, 614 open) |
| IC Inlet Rate for Pump 554, 654 | 50 mL/min |
| IC Circulation Rate for Pump 512, 612 | 300 mL/min |
| EC Inlet valve configuration | None |
| EC Inlet Rate for Pump 578, 678 | 0 mL/min |
| EC Circulation Rate for Pump 528, 628 | 30 mL/min |
| Outlet valve configuration | EC outlet (e.g., valve 582, 692 open) |
| Rocker Control | In Motion (−90°, 180°, 1 second interval) |
| Stop Condition | Empty Bag (Reagent Bag 544 empty) |

A third step in the releasing cell process can chase the reagent into the IC loop 502, 602. An example of the settings for an example third step of the release step 720 with the system 500, 600 may be as shown below:

TABLE 21

| Component | Setting |
| --- | --- |
| IC Inlet valve configuration | Wash (e.g., valves 570, 670, 572, 672, 514, 614 open) |
| IC Inlet Rate for Pump 554, 654 | 50 mL/min |
| IC Circulation Rate for Pump 512, 612 | 300 mL/min |
| EC Inlet valve configuration | None |
| EC Inlet Rate for Pump 578, 678 | 0 mL/min |
| EC Circulation Rate for Pump 528, 628 | 30 mL/min |
| Outlet valve configuration | EC outlet (e.g., valve 582, 692 open) |
| Rocker Control | In Motion (−90°, 180°, 1 second interval) |
| Stop Condition | IC Volume (22 mL) |

A fourth step in the releasing cell process 720 can mix the reagent within the IC loop 502, 602. An example of the settings for an example fourth step of the release step 720 with the system 500, 600 may be as shown below:

TABLE 22

| Component | Setting |
| --- | --- |
| IC Inlet valve configuration | None |
| IC Inlet Rate for Pump 554, 654 | 0 mL/min |
| IC Circulation Rate for Pump 512, 612 | 300 mL/min |
| EC Inlet valve configuration | None |
| EC Inlet Rate for Pump 578, 678 | 0 mL/min |
| EC Circulation Rate for Pump 528, 628 | 30 mL/min |
| Outlet valve configuration | EC outlet (e.g., valve 582, 692 open) |
| Rocker Control | In Motion (−90°, 180°, 1 second interval) |
| Stop Condition | Time (4 Minutes) |

An example of the settings for an example fifth step, which may generally be a harvest step 722, with the system 500, 600 may be as shown below:

TABLE 23

| Component | Setting |
| --- | --- |
| IC Inlet valve configuration | IC Media (e.g., valves 550, 650, 514, 614 open) |
| IC Inlet Rate for Pump 554, 654 | 400 mL/min |
| IC Circulation Rate for Pump 512, 612 | −70 mL/min |
| EC Inlet valve configuration | IC Media (e.g., valves 550, 650, 572, 672 open) |
| EC Inlet Rate for Pump 578, 678 | 60 mL/min |
| EC Circulation Rate for Pump 528, 628 | 30 mL/min |
| Outlet valve configuration | Harvest (e.g., valve 598, 698 open) |
| Rocker Control | In Motion (−90°, 180°, 1 second interval) |
| Stop Condition | IC Volume (378 mL) |

As described above, following release step 720 and harvest step 722, process 700 terminates at END operation 724.

Figure 8A:
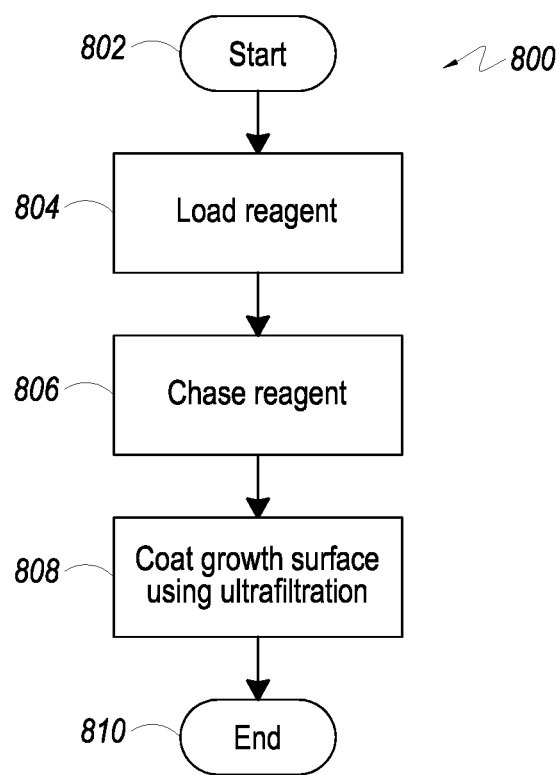
FIG. 8A illustrates a flow diagram depicting the operational characteristics of a process for applying a reagent to a cell growth surface in accordance with embodiments of the present disclosure.

Turning to FIG. 8A, example operational steps 800 of a process for applying an agent or reagent to a cell growth surface that may be used with a cell expansion system, such as CES 500 (FIG. 5) or CES 600 (FIG. 6), are provided in accordance with embodiments of the present disclosure. START operation is initiated 802, and process 800 proceeds to load a reagent, or coating agent, 804 into a circulation loop, e.g., IC loop 502, 602, of a cell expansion system 500, 600. In an embodiment, such loading proceeds until a bag (e.g., 544) or container including the reagent or coating agent is empty. In another embodiment, such loading proceeds for a defined period of time or other condition as understood by a person of skill in the art. Example parameters 822 and 828 for such loading step 804 may be found in FIG. 8C, in which Table 821 provides example parameters or settings 828 for various steps 822, 824, and 826 of applying an agent to a cell growth surface in accordance with an embodiment of the present disclosure. Such example parameters or settings 828 include an example IC inlet of about 100 mL SDE CPPT, as an example coating solution. In an embodiment, CPPT may be prepared so as to create about 25 mL "single donor equivalent (SDE)" aliquots: (1) unprocessed CPPT may be obtained from a blood center; (2) CPPT may be diluted in PBS to a final volume of about 100 mL for every donor represented by the product (e.g.: 5 donors for CPPT product=about 500 mL of total solution); (3) this stock solution may be divided into about 25 mL aliquots. In an embodiment, each aliquot may be sufficient to coat one cell expansion system, e.g., QUANTUM System®, bioreactor, for example. Other volumes and/or proportions may be used in accordance with embodiments of the present disclosure.

In an embodiment, prior to loading such reagent or coating agent, an outlet or waste valve 590, 690 to one of the circulation loops, e.g., IC loop 502, 602, may be closed, while the outlet or waste valve 582, 692 to the other circulation loop, e.g., EC loop 504, 604, remains open. For example, the IC waste or outlet valve 590, 690 may be closed while the EC waste or outlet valve 582, 692 may be open, according to an embodiment. In another embodiment, such closing of an outlet or waste valve, e.g., IC waste or outlet valve 590, 690, while keeping another outlet or waste valve, e.g., EC waste or outlet valve 582, 692, open may occur after loading the reagent into the circulation loop 502, 602. In other embodiments, other types of fluid flow control device(s) to control fluid movement may be used as understood by a person of skill in the art.

Next, the reagent may be chased or washed 806 from an air removal chamber 556, 656 into the circulation loop, e.g., IC loop 502, 602. Example parameters 824 and 828 for such chase step 806 may be found in FIG. 8C.

The cell growth surface of the bioreactor 501, 601, e.g., cell growth surface of hollow fibers where a hollow fiber bioreactor is used, may then be coated 808 by controlling the fluid movement, e.g., ultrafiltration, in the bioreactor 501, 601. Example parameters 826 and 828 for such coating step 808 may be found in FIG. 8C. As shown in FIG. 8C, coating step 808 and example parameters 826, 828 may include a stop condition of about ten (10) minutes, according to an embodiment. Steps 822, 824, and 826 for applying an agent to a growth surface may be followed by an IC/EC Washout step, for example, and/or other steps, where it is desired to continue with a process for expanding cells in a cell expansion system 500, 600, according to an embodiment.

As described above, control of the fluid movement may use ultrafiltration, such as positive ultrafiltration, to move fluid from one side (the IC side 502, 602) of the bioreactor 501, 601 to the other side (the EC side 504, 604), according to embodiments. For example, where the IC outlet or waste valve 590, 690 may be closed, with the EC outlet or waste valve 582, 692 open, a fluid in the bioreactor 501, 601 may have no pathway but through the pores of the fibers (IC outlet valve 590,690 closed). In an embodiment, the IC inlet rate may be set to wash the IC side 502, 602 with media or a fluid, such as phosphate buffered saline (PBS), for example. Accordingly, the solution may flow through the pores of the fibers from the IC side 502, 602 to the EC side 504, 604. Such coating agent, e.g., CPPT, may be hydrostatically deposited onto the inner wall(s) of the bioreactor fiber for a defined time period. For example, such time period may be about ten (10) minutes, according to an embodiment. Such membrane ultrafiltration method allows adherence promoting proteins to be physisorbed on the bioreactor fibers as the coating solution flows through the pores of the fiber from the IC side to the EC side, for example.

As described above, the active promoting of the coating agent to a cell growth surface may significantly decrease the amount of time it may take to coat the growth surface as compared to other methods of coating a growth surface. In embodiments, such coating procedure using ultrafiltration may be referred to as an expedited coating procedure. Such expedited coating procedure using active moving of the coating agent to the cell growth surface(s) through ultrafiltration may use less time to coat the cell growth surface than procedures using passive coating procedures which may take overnight or about twelve (12) hours to about sixteen (16) hours to coat the bioreactor. For example, such expedited coating procedure may take less than or equal to about four (4) hours. In embodiments, such expedited coating procedure may take any time period in a range from above or equal to about five (5) minutes to less than or equal to about sixty (60) minutes, or any other range therein, depending on the procedure. For example, such coating procedure may take less than or equal to about ten (10) minutes, less than or equal to about twelve (12) minutes, less than or equal to about fifteen (15) minutes, less than or equal to about twenty (20) minutes, less than or equal to about thirty (30) minutes, less than or equal to about forty-five (45) minutes, less than or equal to about sixty (60) minutes, etc.

Following the application of the reagent or coating agent to the cell growth surface, process 800 then terminates at END operation 810.

While FIG. 8A illustrates a method for applying a coating agent or reagent to a cell growth surface, FIG. 8B depicts a schematic of applying an agent to a growth surface of a hollow fiber, in accordance with embodiments of the present disclosure. In embodiments, schematic 811 depicts the flow of a coating agent or reagent solution, such as cryoprecipitate solution 814, through a single fiber 812, e.g., hollow fiber, of a bioreactor during an active coating procedure. In schematic 811, a coating agent and/or coating solution, e.g., a cryoprecipitate solution, may be introduced to the fibers of a bioreactor, e.g., a hollow fiber bioreactor 501, 601, on the intracapillary (IC) side 816, for example. In such embodiment, an IC waste valve or IC outlet valve 590, 690 may be closed, while an EC waste valve or EC outlet valve 582, 692 may be open. In embodiments, the IC inlet rate for a chase step, e.g., step 824 (FIG. 8C), may be set. The IC inlet rate may then be set for a Wash step, e.g., step 826 (FIG. 8C), according to an embodiment. For example, the IC inlet rate may be set to about 50 mL/minute for a wash task with media or a fluid, such as phosphate buffered saline (PBS). In embodiments, the IC inlet rate may be set to any rate in a range including a value greater than or equal to about 5 mL/minute to less than or equal to about 100 mL/minute. For example, the IC inlet rate may be set to a value greater than or equal to about 40 mL/minute to less than or equal to about 60 mL/minute.

Returning to FIG. 8B, the coating agent in the coating solution, e.g., cryoprecipitate solution 814, may be hydrostatically deposited onto the inner wall of bioreactor fiber 812 for a specified time period, e.g., about ten (10) minutes. Various time periods may be used based on the CES 500, 600 configurations, for example. Such membrane ultrafiltration process allows adherence promoting protein(s) to be physisorbed on the bioreactor fibers as the reagent solution or coating solution flows through the pores 818 of the fiber 812 from the IC side of the fiber 816 to the EC side of the fiber 820.

Figure 9A:
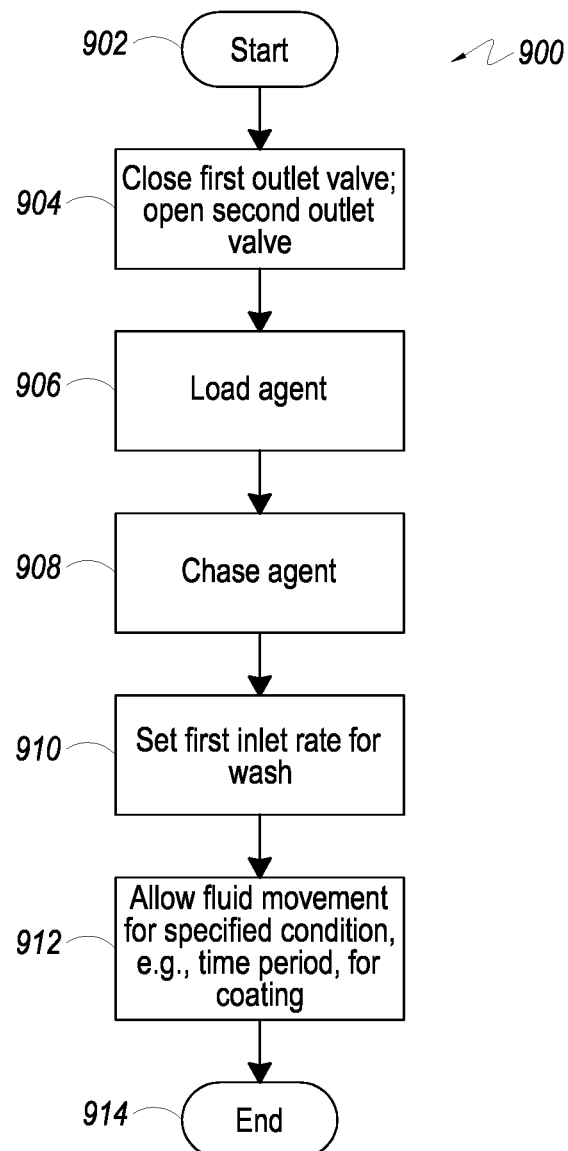
FIG. 9A depicts a flow diagram illustrating the operational characteristics of a process for applying an agent to a cell growth surface in accordance with embodiments of the present disclosure.

Turning to FIG. 9A, example operational steps 900 of a process for applying an agent or reagent to a cell growth surface that may be used with a cell expansion system, such as CES 500 (FIG. 5) or CES 600 (FIG. 6), are provided in accordance with embodiments of the present disclosure. In embodiments, such CES is automated, and various steps and/or parameters may be pre-programmed, set, and/or created to execute one or more tasks to expand cells. START operation is initiated 902, and process 900 proceeds to close 904 a first outlet or waste valve 590, 690, and open (or leave/remain open) a second outlet or waste valve 582, 692, where the first 590, 690 and second 582, 682 outlet valves are different. In an embodiment, such as where cells may be grown on the IC side, for example, an IC outlet valve or IC waste valve 590, 690 may be closed, while an EC outlet valve or EC waste valve 582, 692 may be open or remain open. In another embodiment, such as where cells may be grown on the EC side, for example, an EC outlet valve or EC waste valve 582, 692 may be closed, while an IC outlet valve or IC waste valve 590, 690 may be open or remain opened. In an embodiment, step 904 occurs before loading a coating agent or reagent into the cell expansion system 500, 600. In another embodiment, step 904 occurs after the loading of a coating agent. In an embodiment, step 904 may occur at any time during process 900. Process 900 is offered for illustrative purposes and may be rearranged, combined into other steps, etc. Further, additional or fewer steps may be used in other embodiments.

Returning to FIG. 9, process 900 proceeds to load an agent 906 or agent solution, e.g., coating agent or coating solution, into a cell expansion system, such as cell expansion system 500, 600, for example. In an embodiment, a coating agent or coating agent solution is loaded into a circulation loop, e.g., IC loop 502, 602, of a cell expansion system 500, 600. In an embodiment, such loading proceeds until a bag (e.g., 544) or container including the reagent or coating agent is empty. In another embodiment, such loading proceeds for a defined period of time or other condition as understood by a person of skill in the art.

Next, the agent or reagent may be chased or washed 908 from an air removal chamber 556, 656 into the circulation loop, e.g., IC loop 502, 602. Process 900 next proceeds to set a first inlet rate 910, e.g., IC inlet rate, to wash a first side, e.g., IC side 816 (FIG. 8B), with media or a fluid, such as phosphate buffered saline (PBS), for example. For example, the IC inlet rate may be set to about 50 mL/minute for a wash task with media or a fluid, such as phosphate buffered saline (PBS). In embodiments, the IC inlet rate may be set to any rate in a range including a value greater than or equal to about 5 mL/minute to less than or equal to about 100 mL/minute. For example, the IC inlet rate may be set to a value greater than or equal to about 40 mL/minute to less than or equal to about 60 mL/minute. In embodiments, the IC inlet rate may be set to about 51 mL/minute; about 52 mL/minute; about 53 mL/minute; about 54 mL/minute; about 55 mL/minute; about 56 mL/minute; about 57 mL/minute; about 58 mL/minute; about 59 mL/minute; about 60 mL/minute; about 49 mL/minute; about 48 mL/minute; about 47 mL/minute; about 46 mL/minute; about 45 mL/minute; about 44 mL/minute; about 43 mL/minute; about 42 mL/minute; about 41 mL/minute; about 40 mL/minute; etc.

Such washing, or increased inlet rate, promotes the movement of fluid 912 from a first side 816 (FIG. 8B) of a hollow fiber 812 to a second side 820 of the hollow fiber 812, e.g., from the IC side 816 to the EC side 820, in which ultrafiltration allows proteins or molecules that are too large to pass through the pores 818 of a hollow fiber 812 to adhere to the bioreactor fiber 812 and thus coat the walls while the fluid in which the coating agent is suspended flows through the pores 818. Where the fluid flows through the pores 818 of the fiber 812 from the IC 816 to the EC side 820, positive ultrafiltration may result in the deposit of the coating agent or reagent on the inner walls, or IC side 816, of the fiber(s). On the other hand, in an embodiment where cells are grown on an EC side 820 and where the solution flows through the pores 818 of the fiber 812 from the EC side 820 to the IC side 816, negative ultrafiltration may result in the deposit of the coating agent or reagent on the outer walls, or EC side 820, of the fiber(s) 812. In an embodiment, such fluid movement may occur for a specified time period, e.g., about ten (10) minutes, to allow for such coating. In an embodiment, such active promoting of the coating agent to a cell growth surface may significantly decrease the amount of time it may take to coat the cell growth surface as compared to other methods of coating a cell growth surface. In embodiments, such coating procedure using ultrafiltration may be referred to as an expedited coating procedure. Such expedited coating procedure using active moving of the coating agent to the cell growth surface(s) through ultrafiltration may use less time to coat the cell growth surface than procedures using passive coating procedures which may take overnight or about twelve (12) hours to about sixteen (16) hours to coat the bioreactor. For example, such expedited coating procedure may take less than or equal to about four (4) hours. In embodiments, such expedited coating procedure may take any time period in a range from above or equal to about five (5) minutes to less than or equal to about sixty (60) minutes, or any other range therein, depending on the procedure. For example, such coating procedure may take less than or equal to about ten (10) minutes, less than or equal to about twelve (12) minutes, less than or equal to about fifteen (15) minutes, less than or equal to about twenty (20) minutes, less than or equal to about thirty (30) minutes, less than or equal to about forty-five (45) minutes, less than or equal to about sixty (60) minutes, etc. In other embodiments, other conditions may be used to determine when to stop or decrease the active promotion of the fluid. For example, such active promotion may be stopped or decreased when a media bag (e.g., 566) containing a wash solution is empty. Other conditions may be used according to embodiments. Process 900 then terminates at END operation 914.

Figure 9B:
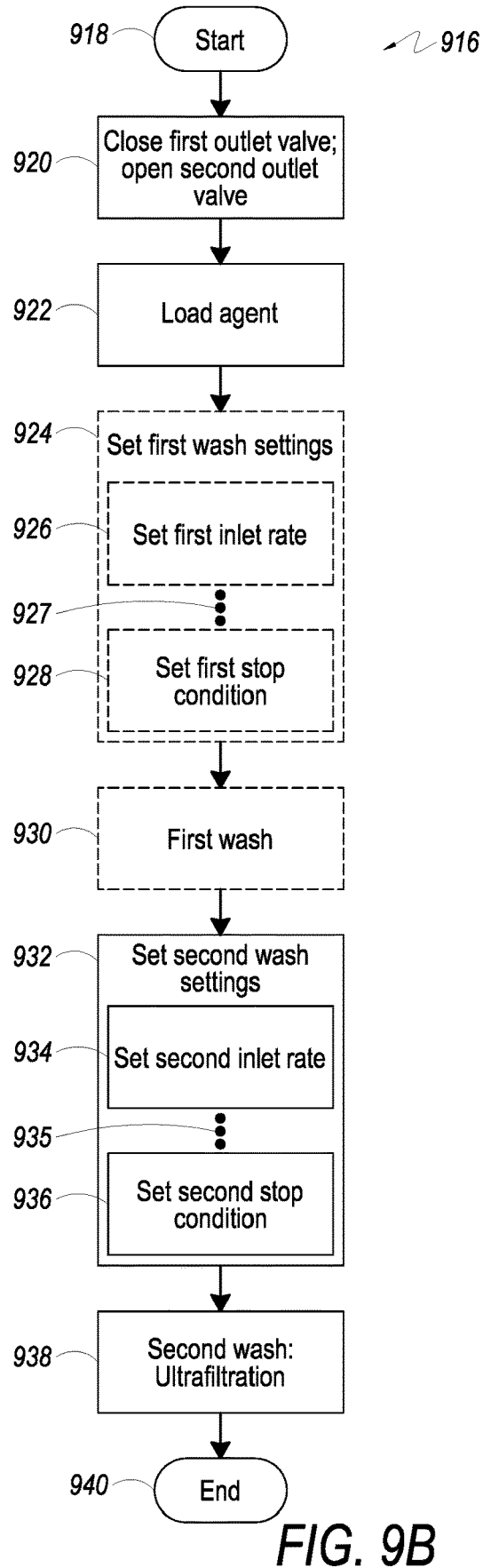
FIG. 9B depicts a flow diagram illustrating the operational characteristics of a process for applying an agent to a cell growth surface in accordance with embodiments of the present disclosure.

Turning to FIG. 9B, example operational steps 916 of a process for applying an agent to a cell growth surface that may be used with a cell expansion system, such as CES 500 (FIG. 5) or CES 600 (FIG. 6), are provided in accordance with embodiments of the present disclosure. In embodiments, such CES is automated, and various steps and/or parameters may be pre-programmed, set, and/or created as custom or user-defined tasks to expand cells. START operation is initiated 918, and process 916 proceeds to close 920 a first outlet or waste valve 590, 690, and open (or leave/remain open) a second outlet or waste valve 582, 692, where the first 590, 690 and second 582, 692 outlet valves are different. In an embodiment, such as where cells may be grown on the IC side, for example, an IC outlet valve or IC waste valve 590, 690 may be closed, while an EC outlet valve or EC waste valve 582, 692 may be open or remain open. In another embodiment, such as where cells may be grown on the EC side, for example, an EC outlet valve or EC waste valve 582, 692 may be closed, while an IC outlet valve or IC waste valve 590, 690 may be open or remain opened. In an embodiment, step 920 occurs before loading a coating agent or reagent into the cell expansion system 500, 600. In another embodiment, step 920 occurs after the loading of a coating agent. In an embodiment, step 920 may occur at any time during process 916. Process 916 is offered for illustrative purposes and may be rearranged, combined into other steps, etc. Further, additional or fewer steps may be used in other embodiments.

Returning to FIG. 9B, process 916 proceeds to load an agent 922 or agent solution, e.g., coating agent or coating solution, into a cell expansion system, such as cell expansion system 500, 600, for example. In an embodiment, a coating agent or coating agent solution is loaded into a circulation loop, e.g., IC loop 502, 602, of a cell expansion system 500, 600. In an embodiment, such loading proceeds until a bag (e.g., 544) or container including the reagent or coating agent is empty. In another embodiment, such loading proceeds for a defined period of time or other condition as understood by a person of skill in the art.

Next, process 916 proceeds to optional step 924, in which the settings for a first wash may be set. During such first wash, the agent may be chased or washed from an air removal chamber 556, 656 into the circulation loop, e.g., IC loop 502, 602. The settings may include, for example, optionally setting a first inlet rate 926 and/or optionally setting a first stop condition 928. An example of a first stop condition may include a particular volume, e.g., an IC volume. Optional settings 926 and 928 are offered merely for illustrative purposes. Other settings and/or subsets of settings to control a first wash may be included. There may be fewer or more settings as represented by ellipsis 927. When settings for a first wash are set, process 916 next proceeds to optional first wash 930.

Following optional first wash 930 (or where no first wash is desired, following load agent 922), process 916 proceeds to set second wash settings 932. For example, a second inlet rate, e.g., IC inlet rate, may be set 934 to wash a first side, e.g., IC side 816 (FIG. 8B), with media or a fluid, such as phosphate buffered saline (PBS), for example. For example, the IC inlet rate may be set to about 50 mL/minute for a wash task with media or a fluid, such as phosphate buffered saline (PBS). In embodiments, the IC inlet rate may be set to any rate in a range including a value greater than or equal to about 5 mL/minute to less than or equal to about 100 mL/minute. For example, the IC inlet rate may be set to a value greater than or equal to about 40 mL/minute to less than or equal to about 60 mL/minute.

Additional or other settings may also be set to control such second wash. For example, a second stop condition may be set 936. Such stop condition may include a time period, or time interval, in which the second wash may be stopped when such stop condition is reached. As an example, a ten (10) minute time period may be set as a second stop condition for a second wash. Any time period may be used in accordance with embodiments of the present disclosure. Settings 934 and 936 are offered merely for illustrative purposes. Other settings and/or subsets of settings to control a second wash may be included. There may be fewer or more settings as represented by ellipsis 935.

Following the entering of the second wash settings at step 932, process 916 next proceeds to conducting a second wash 938. Such washing, or increased inlet rate, promotes the movement of fluid from a first side 816 (FIG. 8B) of a hollow fiber 812 to a second side 820 of the hollow fiber 812, e.g., from the IC side 816 to the EC side 820, in which ultrafiltration allows proteins or molecules that are too large to pass through the pores 818 of a hollow fiber 812 to adhere to the bioreactor fiber 812 and thus coat the walls while the solution flows through the pores 818. Where the solution flows through the pores 818 of the fiber 812 from the IC 816 to the EC side 820, positive ultrafiltration may result in the deposit of the coating agent or reagent on the inner walls, or IC side 816, of the fiber(s). On the other hand, in an embodiment where cells are grown on an EC side 820 and where the solution flows the pores 818 of the fiber 812 from the EC side 820 to the IC side 816, negative ultrafiltration may result in the deposit of the coating agent or reagent on the outer walls, or EC side 820, of the fiber(s) 812.

Active promoting of the coating agent to a cell growth surface may significantly decrease the amount of time it may take to coat the growth surface as compared to other methods of coating a growth surface. In embodiments, such coating procedure using ultrafiltration may be referred to as an expedited coating procedure. For example, such expedited coating procedure may take less than or equal to about four (4) hours. In an embodiment, such fluid movement may occur for a specified time period, e.g., about ten (10) minutes, to allow for such coating. For example, such coating procedure may take any time period in a range from above or equal to about five (5) minutes to less than or equal to about sixty (60) minutes, or any other range therein, depending on the procedure. For example, such coating procedure may take less than or equal to about ten (10) minutes, less than or equal to about twelve (12) minutes, less than or equal to about fifteen (15) minutes, less than or equal to about twenty (20) minutes, less than or equal to about thirty (30) minutes, less than or equal to about forty-five (45) minutes, less than or equal to about sixty (60) minutes, etc. Any time period may be used in accordance with embodiments of the present disclosure. In an embodiment, such time period may be based on a stop condition, such as a second stop condition set in step 936. For example, a stop condition may be set where an automated CES is used to expand cells. In other embodiments, other conditions may be used to determine when to stop or decrease the active promotion of the fluid. For example, such active promotion may be stopped or decreased when a media bag (e.g., 566) containing the wash solution is empty. Other conditions may be used according to embodiments. Process 916 then terminates at END operation 940.

Figure 10:
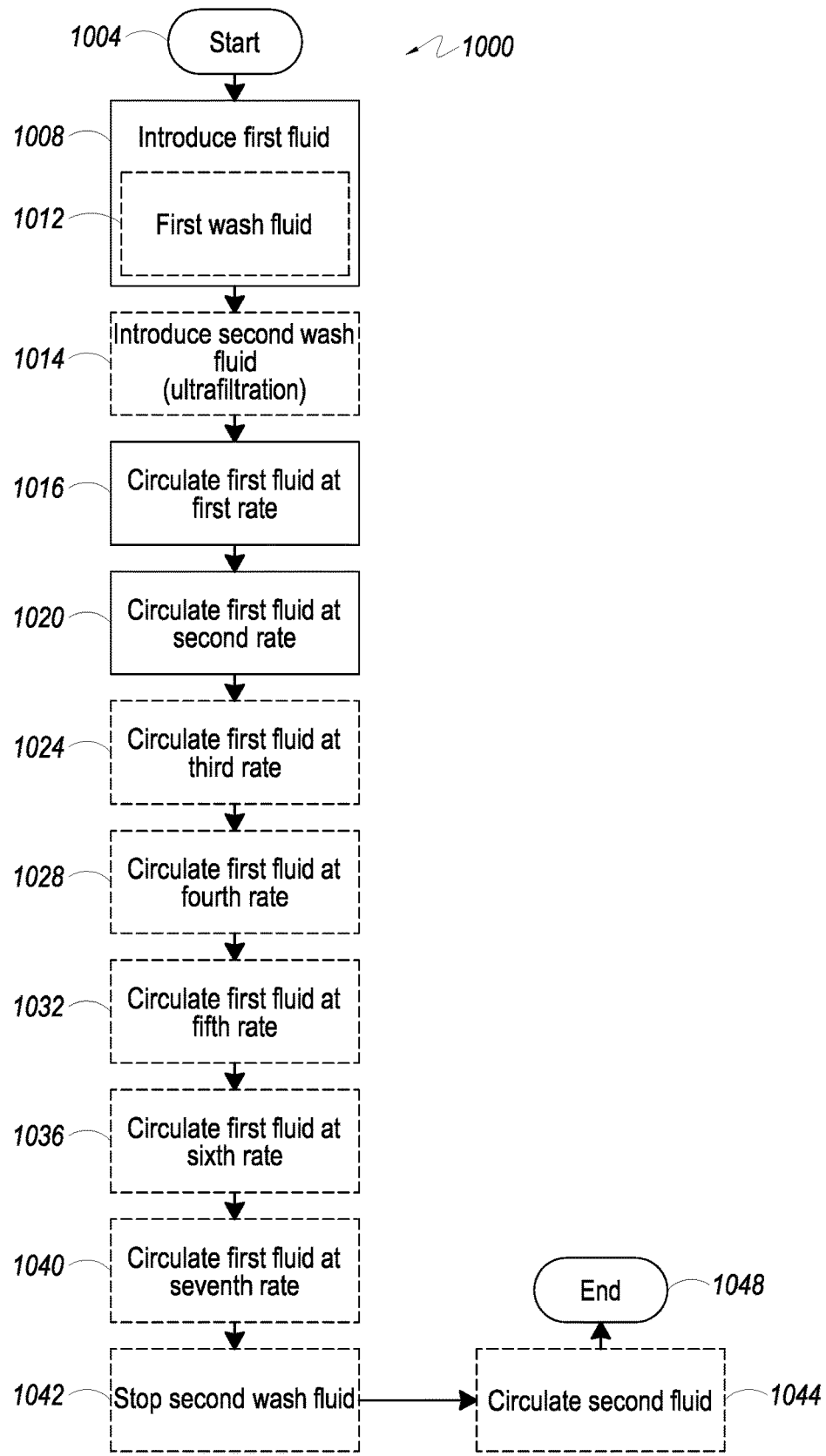
FIG. 10 illustrates a flow for a process of coating a bioreactor according to an embodiment.

Referring now to FIG. 10, flow 1000 illustrates yet another embodiment of a process for coating a cell growth surface, e.g., such as a surface of a hollow fiber. Flow 1000 starts at step 1004 and proceeds to step 1008 where fluid that includes a reagent may be introduced into a cell expansion system and a bioreactor such as bioreactors 100, 501, and/or 601. In embodiments, step 1008 may involve activating one or more pumps (554, 654) to introduce fluid with the reagent from a bag (562) or connection point (662) into a fluid flow path.

As part of introducing the fluid with the reagent into the cell expansion system, step 1008 may involve optional step 1012, where a wash fluid (e.g., PBS) may be used to chase the reagent from parts of the CES. For example, the wash fluid may move any reagent left behind in an ARC, such as ARC 556/656. The wash fluid may chase any lingering reagent into the bioreactor and/or a fluid flow path associated with the bioreactor e.g., 502/602.

Flow 1000 then passes to step 1014 where a second wash fluid may be introduced into the bioreactor. In embodiments, step 1014 may involve activating a pump, such as pumps 554,654 to introduce the second wash fluid from a bag (562) or connection point (662) into a fluid flow path and into the bioreactor (100, 501, and/or 601). In embodiments, the second wash fluid is introduced to create conditions for ultrafiltration, as described above. Ultrafiltration allows proteins or molecules (e.g., the coating reagent) that are too large to pass through the pores 818 (FIG. 8) of a hollow fiber 812 (FIG. 8) to adhere to the bioreactor fiber 812 and thus coat the walls while the solution flows through the pores 818. Where the solution flows through the pores 818 of the fiber 812 from the IC 816 to the EC side 820, positive ultrafiltration may result in the deposit of the coating agent or reagent on the inner walls, or IC side 816, of the fibers. In embodiments, the second wash fluid introduced at step 1014 may be continuously introduced as steps 1016 through 1040 are performed.

Flow 1000 then passes to step 1016 where fluid that includes the coating reagent may be circulated through the bioreactor such as bioreactors 100, 501, and/or 601. In embodiments, step 1016 may involve activating one or more pumps to circulate fluid with the reagent through the bioreactor. For example, an IC circulation pump (e.g., 512 or 612) may be activated to circulate fluid through the IC side of a bioreactor at a first circulation flow rate. In at least one embodiment, fluid may pass through hollow fibers (e.g., the lumen).

In embodiments, the first rate may be a relatively high flow rate. In embodiments, the first circulation flow rate may be less than about 500 ml/min, less than about 400 ml/min, or even less than about 300 ml/min. In other embodiments, the first circulation rate may be greater than about 50 ml/min, greater than about 100 ml/min, or even greater than about 150 ml/min. In one embodiment, the first circulation flow rate is between about 100 ml/min and about 500 ml/min, such as about 300 ml/min.

Step 1016 may be performed for a first predetermined period of time. In one specific example, the first period of time may be about 4 minutes, about 8 minutes, about 12 minutes, or even about 16 minutes. In other embodiments, the first predetermined period of time may be less than about 20 minutes, less than about 15 minutes, less than about 10 minutes, or even less than about 5 minutes. In some embodiments, the first predetermined period of time may be greater than about 2 minutes, greater than about 4 minutes, greater than about 6 minutes, greater than about 8 minutes, greater than about 10 minutes, greater than about 12 minutes, greater than about 14 minutes, greater than about 16 minutes, greater than about 18 minutes, or even greater than about 20 minutes. Step 1016 may be performed in embodiments to provide time to allow the reagent to coat portions of the bioreactor. For example, when the bioreactor comprises hollow fibers, step 1016 may be performed to allow the reagent time to coat interior surfaces of the hollow fibers.

Flow 1000 passes to step 1020, wherein fluid with the reagent is circulated at a second flow rate, which may be less than the first flow rate. In embodiments, the second flow rate may be less than about 400 ml/min, less than about 300 ml/min, or even less than about 200 ml/min. In other embodiments, the second circulation rate may be greater than about 25 ml/min, greater than about 50 ml/min, or even greater than about 75 ml/min. In one embodiment, the second circulation flow rate is between about 100 ml/min and about 300 ml/min, such as about 250 ml/min.

Step 1020 may be performed for a second predetermined period of time. In one specific example, the second period of time may be about 4 minutes, about 8 minutes, about 12 minutes, or even about 16 minutes. In other embodiments, the second predetermined period of time may be less than about 20 minutes, less than about 15 minutes, less than about 10 minutes, or even less than about 5 minutes. In some embodiments, the second predetermined period of time may be greater than about 2 minutes, greater than about 4 minutes, greater than about 6 minutes, greater than about 8 minutes, greater than about 10 minutes, greater than about 12 minutes, greater than about 14 minutes, greater than about 16 minutes, greater than about 18 minutes, or even greater than about 20 minutes. Step 1020 may be performed in embodiments to provide time to allow the reagent to coat portions of the bioreactor. For example, when the bioreactor comprises hollow fibers, step 1020 may be performed to allow the reagent time to coat interior surfaces of the hollow fibers.

Flow 1000 passes to optional step 1024, wherein fluid with the reagent is circulated at a third flow rate, which may be less than the first flow rate. In embodiments, the third flow rate may be less than the second flow rate. In embodiments, the third flow rate may be less than about 350 ml/min, less than about 300 ml/min, or even less than about 250 ml/min. In other embodiments, the second circulation rate may be greater than about 25 ml/min, greater than about 50 ml/min, or even greater than about 75 ml/min. In one embodiment, the third circulation flow rate is between about 50 ml/min and about 250 ml/min, such as about 200 ml/min.

Optional step 1024 may be performed for a third predetermined period of time. In one specific example, the second period of time may be about 4 minutes, about 8 minutes, about 12 minutes, or even about 16 minutes. In other embodiments, the third predetermined period of time may be less than about 20 minutes, less than about 15 minutes, less than about 10 minutes, or even less than about 5 minutes. In some embodiments, the third predetermined period of time may be greater than about 2 minutes, greater than about 4 minutes, greater than about 6 minutes, greater than about 8 minutes, greater than about 10 minutes, greater than about 12 minutes, greater than about 14 minutes, greater than about 16 minutes, greater than about 18 minutes, or even greater than about 20 minutes. Step 1024 may be performed in embodiments to provide time to allow the reagent to coat portions of the bioreactor. For example, when the bioreactor comprises hollow fibers, step 1024 may be performed to allow the reagent time to coat interior surfaces of the hollow fibers.

Flow 1000 then passes to optional step 1028, where fluid with the reagent is circulated at a fourth flow rate, which may be less than the third flow rate. In embodiments, the fourth flow rate may be less than about 250 ml/min, less than about 200 ml/min, or even less than about 150 ml/min. In other embodiments, the second circulation rate may be greater than about 25 ml/min, greater than about 50 ml/min, or even greater than about 75 ml/min. In one embodiment, the fourth circulation flow rate is between about 25 ml/min and about 200 ml/min, such as about 150 ml/min.

Optional step 1028 may be performed for a fourth predetermined period of time. In one specific example, the second period of time may be about 4 minutes, about 8 minutes, about 12 minutes, or even about 16 minutes. In other embodiments, the fourth predetermined period of time may be less than about 20 minutes, less than about 15 minutes, less than about 10 minutes, or even less than about 5 minutes. In some embodiments, the fourth predetermined period of time may be greater than about 2 minutes, greater than about 4 minutes, greater than about 6 minutes, greater than about 8 minutes, greater than about 10 minutes, greater than about 12 minutes, greater than about 14 minutes, greater than about 16 minutes, greater than about 18 minutes, or even greater than about 20 minutes. Step 1028 may be performed in embodiments to provide time to allow the reagent to coat portions of the bioreactor. For example, when the bioreactor comprises hollow fibers, step 1028 may be performed to allow the reagent time to coat interior surfaces of the hollow fibers.

Flow passes to optional step 1032, where fluid with the reagent is circulated at a fifth flow rate, which may be less than the fourth flow rate. In embodiments, the fifth flow rate may be less than about 200 ml/min, less than about 150 ml/min, or even less than about 100 ml/min. In other embodiments, the fifth circulation rate may be greater than about 25 ml/min, greater than about 50 ml/min, or even greater than about 75 ml/min. In one embodiment, the fifth circulation flow rate is between about 25 ml/min and about 150 ml/min, such as about 100 ml/min.

Optional step 1032 may be performed for a fifth predetermined period of time. In one specific example, the fifth period of time may be about 4 minutes, about 8 minutes, about 12 minutes, or even about 16 minutes. In other embodiments, the fifth predetermined period of time may be less than about 20 minutes, less than about 15 minutes, less than about 10 minutes, or even less than about 5 minutes. In some embodiments, the fifth predetermined period of time may be greater than about 2 minutes, greater than about 4 minutes, greater than about 6 minutes, greater than about 8 minutes, greater than about 10 minutes, greater than about 12 minutes, greater than about 14 minutes, greater than about 16 minutes, greater than about 18 minutes, or even greater than about 20 minutes. Step 1032 may be performed in embodiments to provide time to allow the reagent to coat portions of the bioreactor. For example, when the bioreactor comprises hollow fibers, step 1032 may be performed to allow the reagent time to coat interior surfaces of the hollow fibers.

Flow 1000 passes to optional step 1036, where fluid with the reagent is circulated at a sixth flow rate, which may be less than the fifth flow rate. In embodiments, the sixth flow rate may be less than about 100 ml/min, less than about 50 ml/min, or even less than about 25 ml/min. In other embodiments, the sixth circulation rate may be greater than about 5 ml/min, greater than about 10 ml/min, or even greater than about 15 ml/min. In one embodiment, the sixth circulation flow rate is between about 25 ml/min and about 100 ml/min, such as about 50 ml/min.

Optional step 1036 may be performed for a sixth predetermined period of time. In one specific example, the sixth period of time may be about 4 minutes, about 8 minutes, about 12 minutes, or even about 16 minutes. In other embodiments, the sixth predetermined period of time may be less than about 20 minutes, less than about 15 minutes, less than about 10 minutes, or even less than about 5 minutes. In some embodiments, the sixth predetermined period of time may be greater than about 2 minutes, greater than about 4 minutes, greater than about 6 minutes, greater than about 8 minutes, greater than about 10 minutes, greater than about 12 minutes, greater than about 14 minutes, greater than about 16 minutes, greater than about 18 minutes, or even greater than about 20 minutes. Step 1036 may be performed in embodiments to provide time to allow the reagent to coat portions of the bioreactor. For example, when the bioreactor comprises hollow fibers, step 1036 may be performed to allow the reagent time to coat interior surfaces of the hollow fibers.

Flow 1000 passes to optional step 1040, where fluid with the reagent is circulated at a seventh flow rate, which may be less than the sixth flow rate. In embodiments, the seventh flow rate may be less than about 100 ml/min, less than about 50 ml/min, or even less than about 25 ml/min. In other embodiments, the seventh circulation rate may be greater than about 10 ml/min, greater than about 15 ml/min, or even greater than about 20 ml/min. In one embodiment, the seventh circulation flow rate is between about 10 ml/min and about 50 ml/min, such as about 25 ml/min.

Optional step 1040 may be performed for a seventh predetermined period of time. In one specific example, the seventh period of time may be about 4 minutes, about 8 minutes, about 12 minutes, or even about 16 minutes. In other embodiments, the sixth predetermined period of time may be less than about 20 minutes, less than about 15 minutes, less than about 10 minutes, or even less than about 5 minutes. In some embodiments, the sixth predetermined period of time may be greater than about 2 minutes, greater than about 4 minutes, greater than about 6 minutes, greater than about 8 minutes, greater than about 10 minutes, greater than about 12 minutes, greater than about 14 minutes, greater than about 16 minutes, greater than about 18 minutes, or even greater than about 20 minutes. Step 1040 may be performed in embodiments to provide time to allow the reagent to coat portions of the bioreactor. For example, when the bioreactor comprises hollow fibers, step 1040 may be performed to allow the reagent time to coat interior surfaces of the hollow fibers (e.g., the lumen).

Flow 1000 then passes to step 1042 where introduction of the second wash fluid into the bioreactor is stopped. In embodiments, step 1042 may involve deactivating a pump, such as pump 554, 654 to stop the introduction of the second wash fluid in the fluid flow path and into the bioreactor (100, 501, and/or 601). In embodiments, stopping the introduction of the second wash fluid stops the process of ultrafiltration.

Flow 1000 then passes to step 1044, where a second fluid, that may not include the reagent, or have a lower concentration of the reagent, may be circulated through the bioreactor. In embodiments, step 1044 may be performed to wash any remaining reagent that has not coated a surface of the bioreactor out of the bioreactor and CES. As noted above, flow 1000 may be part of a larger process such as a process for growing and harvesting cells in a cell expansion system, such as flow 700. Therefore, in embodiments, step 1044 may be implemented as part of steps performed in the larger process, such as step 710 (FIG. 7). Flow 1000 then ends at 1048.

Figure 11:
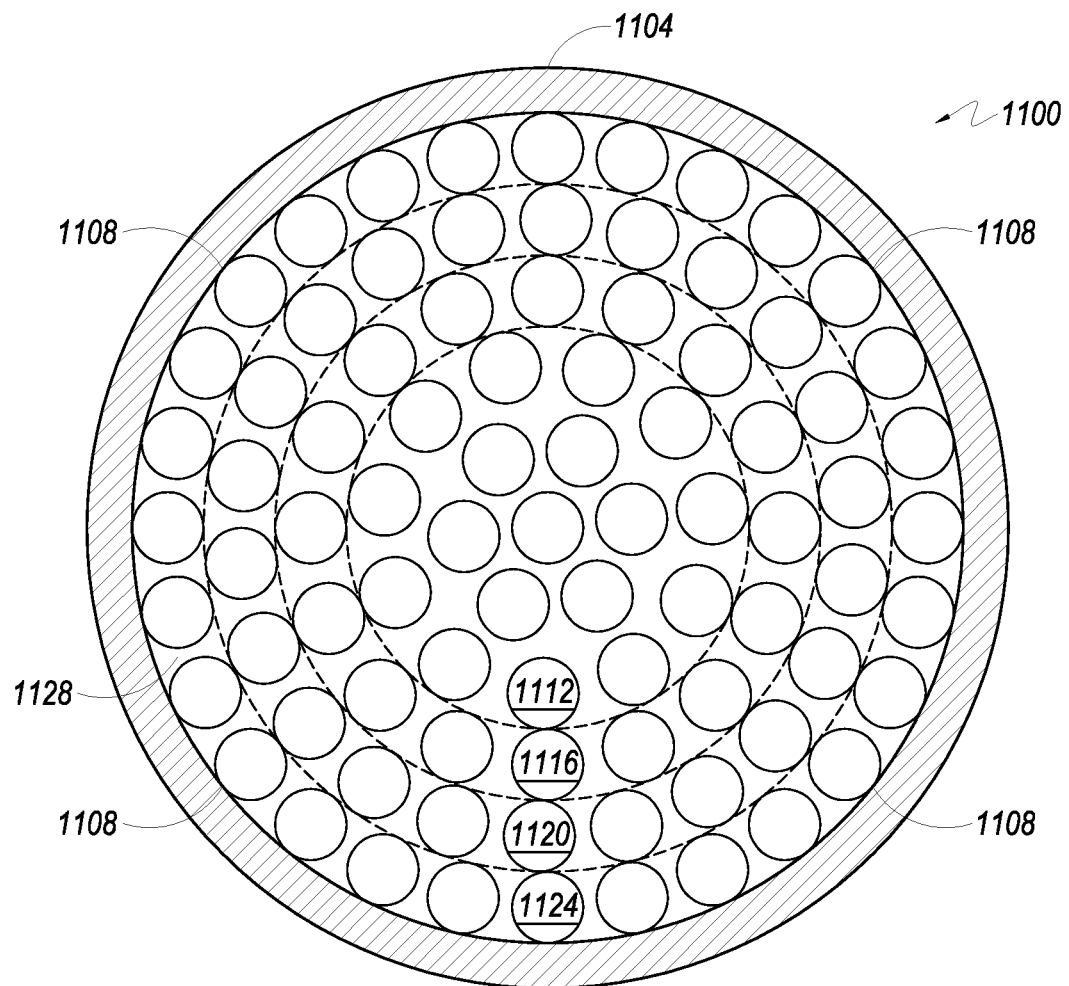
FIG. 11 illustrates a cross section of a bioreactor showing a plurality of hollow fibers and zones of hollow fibers through which liquid containing a reagent may circulate at different flow rates.
Figure 12:
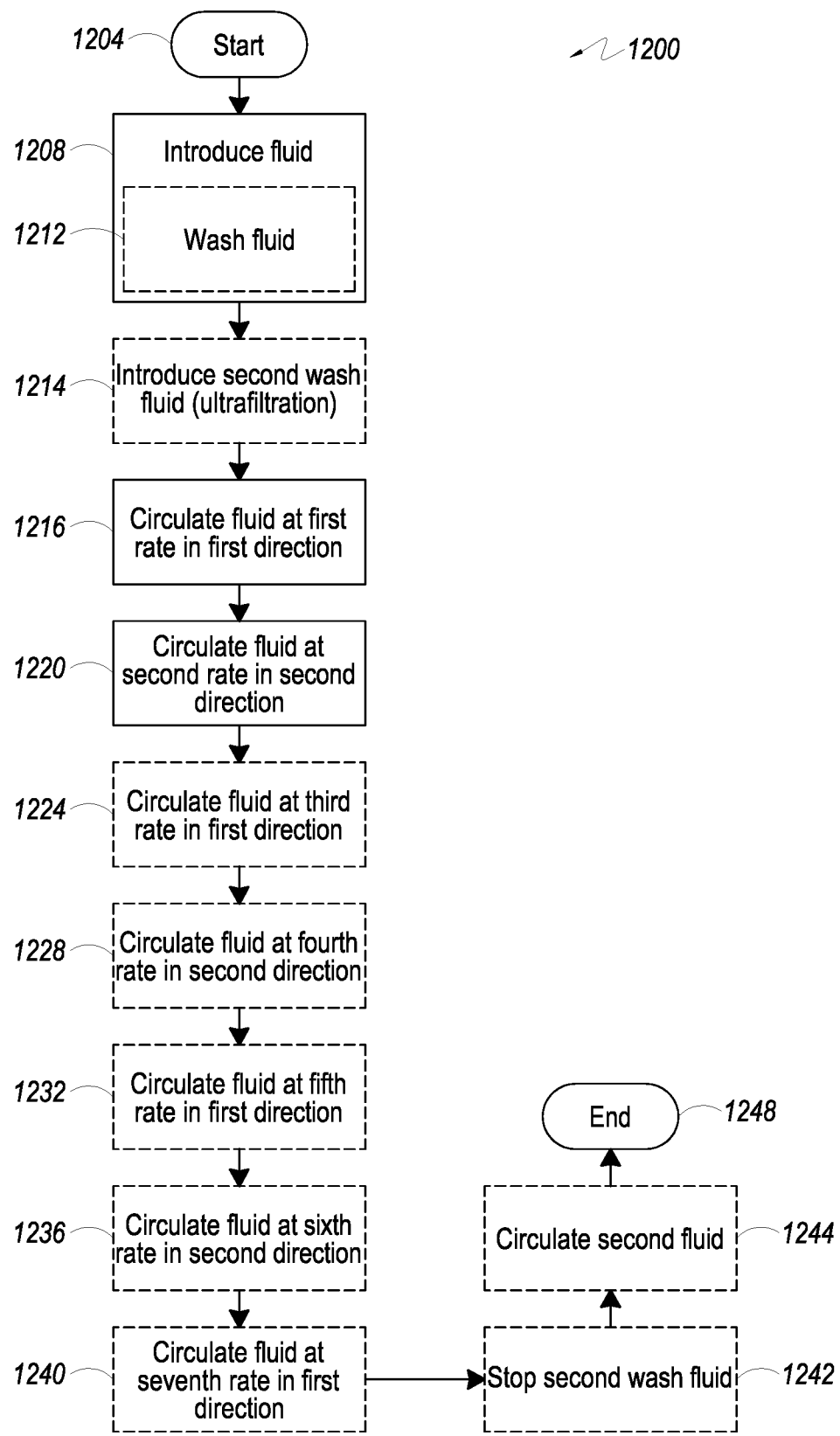
FIG. 12 illustrates a flow for a process of coating a bioreactor according to another embodiment.

Referring now to FIG. 11, a cross section 1100 (perpendicular to a central axis) of a bioreactor (e.g., bioreactor 100, 501, and/or 601) is shown. The cross section 1100 illustrates a plurality of hollow fibers 1108 which may be within a housing 1104. The cross section 1100 is taken from one end of a bioreactor and illustrates, in addition to the hollow fibers 1108 a matrix material 1128 (which may be referred to above as potting material) that holds the hollow fibers 1108 together.

Also shown in FIG. 11 are zones 1112, 1116, 1120 and 1124. These zones represent fibers that may have fluid circulating through them at different flow rates. Without being bound by theory, it is believed that circulation at relatively high flow rates, such as rates that may be used in circulation steps 1016 and/or 1020 (FIG. 10) may primarily flow through fibers in zone 1112. It is believed that the higher flow rates do not allow fluid to disperse enough to flow evenly into the hollow fibers in the outer zones. As the flow rate is reduced, such as in steps 1024, 1028, 1032, 1036, 1040, 1044, and 1048 it is believed that the fluid may disperse into hollow fibers in outer zones, such as 1116, 1120 and 1124.

It is believed that having steps 1016, 1020, 1024, 1028, 1032, 1036, 1040, 1044, and 1048 circulate at different flow rates, allows the fluid to flow through more of the hollow fibers 1108 than if just a single flow rate would be used. In one embodiment of a process that follows flow chart 1000, at steps 1016 and 1020 (at the flow rates described above), fluid may flow mainly through the hollow fibers in zone 1012. At steps 1024 and 1028 (at the flow rates described above), fluid may flow mainly through the hollow fibers in zones 1112 and 1116.

At steps 1032 and 1136 (at the flow rates described above), fluid may flow mainly through the hollow fibers in zone 1112, 1116, and 1120 because the rate is slower and the fluid may disperse more. At step 1040 (at the flow rates described above), fluid may flow through the hollow fibers in zones 1112, 1116, 1120, and 1124 because the flow rate is yet slower and fluid may disperse even more. Thus, it is believe that fluid with the reagent may flow into more of the hollow fibers using a sequence of different flow rates, than if a single high flow rate circulation is used.

Furthermore, it is also believed that the different flow rates may also affect the longitudinal distribution of the reagent along the bioreactor, e.g., along a hollow fiber. That is, a higher flow rate may allow the reagent to flow further along inside a hollow fiber. For example, at a higher flow rate, the reagent being carried by fluid may reach beyond half the length of the hollow fiber. At a lower flow rate, the reagent being carried by fluid may reach half the length of the hollow fiber. At even a lower flow rate, the reagent being carried by fluid may reach less than half the length of the hollow fiber. Accordingly, in some embodiments, it is believed that the use of different flow rates may provide some improvement in longitudinal distribution of the reagent along the length of the bioreactor, e.g., a hollow fiber.

Moreover, it is believed that the continuous addition of wash fluid (starting at step 1014 and ending at step 1042), to create ultrafiltration conditions, further promotes the coating of growth surfaces with the coating reagent. For example, as described above, the ultrafiltration moves the coating reagent toward an inside surface of hollow fiber walls, which may shorten the coating process, in addition to the more complete/uniform distribution of the coating agent provided by the other steps of flow 1000.

As noted above, steps in flow 1000 may be performed for predetermined periods of time. In embodiments, flow 1000 is designed to be performed within a period of time, e.g., 28 minutes, 56 minutes, 60 minutes, 90 minutes, and 120 minutes. For example, in embodiments, the predetermined period of times may be selected so that substantially all (or most) of the steps of flow 1000 may be performed in less than 90 minutes, such as less than 80 minutes, less than 70 minutes, less than 60 minutes, less than 50 minutes, less than 40 minutes, or even less than 30 minutes. In some embodiments, the steps of flow 1000 may be performed in greater than 10 minutes, greater than 20 minutes, greater than 30 minutes, greater than 40 minutes, or greater than 50 minutes. In selecting the periods of time, embodiments provide for each period to be the same in duration. In other embodiments, each period of time may have a different duration. In yet other embodiments, some periods of time may have the same duration while others have different durations. These are merely some examples and flow 1000 is not necessarily limited to being performed during any specific duration.

In one specific embodiment, flow 1000 may provide for performing each of steps 1016 through 1040 in less than 30 minutes. As one example, each of the steps may be performed for 4 minutes resulting in a 28 minute coating process. As yet another example, each of steps 1016 through 1040 may be performed for 8 minutes resulting in a 56 minute coating process. These are merely some non-limiting examples.

Referring now to flow 1200, it starts at step 1204 and proceeds to step 1208 where fluid that includes a reagent may be introduced into a cell expansion system and a bioreactor such as bioreactors 100, 501, and/or 601. In embodiments, step 1208 may be similar to step 808 and involve activating one or more pumps (564, 664) to introduce fluid with the reagent from a bag (562) or connection point (662) into a fluid flow path.

As part of introducing the fluid with the reagent into the cell expansion system, step 1208 may involve optional step 1212, where a wash fluid (e.g., PBS) may be used to chase the reagent from parts of the CES. For example, the wash fluid may move any reagent left behind in an ARC, such as ARC 556/656. The wash fluid may chase any lingering reagent into the bioreactor and/or a fluid flow path associated with the bioreactor e.g., 502/602.

Flow 1200 then passes to step 1214 where a second wash fluid may be introduced into the bioreactor. In embodiments, step 1214 may involve activating a pump, such as pumps 554,654 to introduce the second wash fluid from a bag (562) or connection point (662) into a fluid flow path and into the bioreactor (100, 501, and/or 601). In embodiments, the second wash fluid is introduced to create conditions for ultrafiltration, as described above. Ultrafiltration allows proteins or molecules (e.g., the coating reagent) that are too large to pass through the pores 818 (FIG. 8) of a hollow fiber 812 (FIG. 8) to adhere to the bioreactor fiber 812 and thus coat the walls while the solution flows through the pores 818. Where the solution flows through the pores 818 of the fiber 812 from the IC 816 to the EC side 820, positive ultrafiltration may result in the deposit of the coating agent or reagent on the inner walls, or IC side 816, of the fibers. In embodiments, the second wash fluid introduced at step 1214 may be continuously introduced as steps 1216 through 1240 are performed.

Flow 1200 passes to step 1216 where fluid that includes a reagent may be circulated through a bioreactor such as bioreactors 100, 501, and/or 601. In embodiments, step 1216 may involve activating one or more pumps to circulate fluid with the reagent through the bioreactor. For example, an IC circulation pump (e.g., 512 or 612) may be activated to circulate fluid through the IC side of a bioreactor at a first circulation flow rate. In at least one embodiment, fluid may pass through hollow fibers (e.g., the lumen). Step 1216 may involve circulating fluid at a first flow rate. The first flow rate may in embodiments be one of the first flow rates described above with respect to step 1016 (FIG. 10). Step 1216 may be performed for a first predetermined period of time. The first period of time may, in some embodiments, be one of the first periods of time described above with respect to step 1016 (FIG. 10).

In some embodiments, step 1216 may involve circulation in a specific direction. In other words, in some embodiments, step 1216 may involve activating a pump such as IC circulation pump (e.g., 512 or 612) in a specific direction, e.g., a counter clockwise or a clockwise direction. As one example, referring now to FIG. 6, step 1216 may involve activating pump 612 to circulate fluid through path 602 in a counter clock wise direction. That is, fluid may enter through port 601A and exit through port 601B.

Flow 1200 passes to step 1220, where fluid with the reagent is circulated at a second flow rate. In embodiments, the second flow rate may be one of the second flow rates described above with respect to step 1020 (FIG. 10). Step 1220 may be performed for a second predetermined period of time, which may be one of the second predetermined periods of time described above with respect to step 1020 (FIG. 10).

In some embodiments, step 1220 may involve circulation in a specific direction, such as a second direction opposite the first direction. Step 1220 may involve activating a pump such as IC circulation pump (e.g., 512 or 612) in a direction, e.g., a counter clockwise or a clockwise, opposite the first direction. Continuing with the example above, step 1216 may involve activating pump 612 to circulate fluid through path in a counter clock wise direction. Step 1220 may involve activating pump 612 to circulate fluid through path 602 in a clock wise direction. That is, fluid may enter through port 601B and exit through port 601A.

Flow 1200 then passes to optional step 1224, where fluid with the reagent is circulated at a third flow rate. In embodiments, the third flow rate may be one of the third flow rates described above with respect to step 1024 (FIG. 10). Step 1224 may be performed for a third predetermined period of time, which may be one of the third predetermined periods of time described above with respect to step 1024 (FIG. 10).

In some embodiments, step 1224 may involve circulation in a specific direction, such as the first direction. Step 1224 may involve activating a pump such as IC circulation pump (e.g., 512 or 612) in a direction, e.g., a counter clockwise or a clockwise. Continuing with the example above, step 1224 may involve activating pump 612 to circulate fluid through path in a counter clock wise direction. That is, fluid may enter through port 601A and exit through port 601B.

Flow 1200 then passes to optional step 1228, where fluid with the reagent is circulated at a fourth flow rate. In embodiments, the fourth flow rate may be one of the fourth flow rates described above with respect to step 1028 (FIG. 10). Step 1228 may be performed for a fourth predetermined period of time, which may be one of the fourth predetermined periods of time described above with respect to step 1028 (FIG. 10).

In some embodiments, step 1228 may involve circulation in a specific direction, such as opposite the first direction. Step 1228 may involve activating a pump such as IC circulation pump (e.g., 512 or 612) in a direction, e.g., a counter clockwise or a clockwise. Continuing with the example above, step 1228 may involve activating pump 612 to circulate fluid through path 602 in a clock wise direction. That is, fluid may enter through port 601B and exit through port 601A.

Flow 1200 then passes to optional step 1232, where fluid with the reagent is circulated at a fifth flow rate. In embodiments, the fifth flow rate may be one of the fifth flow rates described above with respect to step 1032 (FIG. 10). Step 1232 may be performed for a fifth predetermined period of time, which may be one of the fifth predetermined periods of time described above with respect to step 1032 (FIG. 10).

In some embodiments, step 1232 may involve circulation in a specific direction, such as the first direction. Step 1232 may involve activating a pump such as IC circulation pump (e.g., 512 or 612) in a direction, e.g., a counter clockwise or a clockwise. Continuing with the example above, step 1232 may involve activating pump 612 to circulate fluid through path 602 in a counter clock wise direction. That is, fluid may enter through port 601A and exit through port 601B.

Flow 1200 then passes to optional step 1236, where fluid with the reagent is circulated at a sixth flow rate. In embodiments, the sixth flow rate may be one of the sixth flow rates described above with respect to step 1036 (FIG. 10). Step 1236 may be performed for a sixth predetermined period of time, which may be one of the sixth predetermined periods of time described above with respect to step 1036 (FIG. 10).

In some embodiments, step 1236 may involve circulation in a specific direction, such as opposite the first direction. Step 1236 may involve activating a pump such as IC circulation pump (e.g., 512 or 612) in a direction, e.g., a counter clockwise or a clockwise. Continuing with the example above, step 1236 may involve activating pump 612 to circulate fluid through path 602 in a clock wise direction. That is, fluid may enter through port 601B and exit through port 601A.

Flow 1200 then passes to optional step 1240, where fluid with the reagent is circulated at a seventh flow rate. In embodiments, the seventh flow rate may be one of the seventh flow rates described above with respect to step 1040 (FIG. 10). Step 1240 may be performed for a seventh predetermined period of time, which may be one of the seventh predetermined periods of time described above with respect to step 1040 (FIG. 10).

In some embodiments, step 1240 may involve circulation in a specific direction, such as the first direction. Step 1240 may involve activating a pump such as IC circulation pump (e.g., 512 or 612) in a direction, e.g., a counter clockwise or a clockwise. Continuing with the example above, step 1240 may involve activating pump 612 to circulate fluid through path 602 in a counter clock wise direction. That is, fluid may enter through port 601A and exit through port 601B.

Flow 1200 then passes to step 1242 where introduction of the second wash fluid into the bioreactor is stopped. In embodiments, step 1242 may involve deactivating a pump, such as pump 554, 654 to stop the introduction of the second wash fluid into the fluid flow path and into the bioreactor (100, 501, and/or 601). In embodiments, stopping the introduction of the second wash fluid stops the process of ultrafiltration.

Flow 1200 then passes to step 1244, where a second fluid, that may not include the reagent, or have a lower concentration of the reagent, may be circulated through the bioreactor. In embodiments, step 1244 may be performed to wash any remaining reagent that has not coated a surface of the bioreactor out of the bioreactor and CES. As noted above, flow 1200 may be part of a larger process such as a process for growing and harvesting cells in a cell expansion system, such as flow 700. Therefore, in embodiments, step 1244 may be implemented as part of steps performed in the larger process, such as step 710 (FIG. 7). Flow 1200 then ends at 1248.

Without being bound by theory, it is believed that having steps 1216, 1220, 1224, 1228, 1232, 1236, 1240, 1244, and 1248 circulate at different flow rates, allows the fluid to flow through more of the hollow fibers e.g., 1108 (FIG. 11) than if just a single flow rate would be used. In one embodiment of a process that follows flow chart 1200, at steps 1216 and 1220 (at the flow rates described above), fluid may flow mainly through the hollow fibers in zone 1212. At steps 1224 and 1228 (at the flow rates described above), fluid may flow mainly through the hollow fibers in zones 1112 and 1116.

At steps 1232 and 1236 (at the flow rates described above), fluid may flow mainly through the hollow fibers in zone 1112, 1116, and 1120 because the rate is slower and the fluid may disperse more. At step 1240 (at the flow rates described above), fluid may flow through the hollow fibers in zones 1112, 1116, 1120, and 1124 because the flow rate is yet slower and fluid may disperse even more. Thus, it is believe that fluid with the reagent may flow into more of the hollow fibers using a sequence of different flow rates, than if a single high flow rate circulation is used.

As noted above, it is also believed that the different flow rates may also affect the longitudinal distribution of the reagent along the bioreactor, e.g., along a hollow fiber. That is, a higher flow rate may allow the reagent to flow further along inside a hollow fiber. For example, at a higher flow rate, the reagent being carried by fluid may reach beyond half the length of the hollow fiber. At a lower flow rate, the reagent being carried by fluid may reach half the length of the hollow fiber. At even a lower flow rate, the reagent being carried by fluid may reach less than half the length of the hollow fiber. Accordingly, in some embodiments, it is believed that the use of different flow rates may provide some improvement in longitudinal distribution of the reagent along the length of the bioreactor, e.g., a hollow fiber. Additionally, with the changing of directions provided for in flow 1200, the reagent may be distributed along the length of the hollow fibers from both sides of a hollow fiber. The combination of flow rate changes and changes in direction, may allow for more even distribution of the reagent along the length of a hollow fiber.

Moreover, it is believed that the continuous addition of wash fluid (starting at step 1214 and ending at step 1242), to create ultrafiltration conditions, further promotes the coating of growth surfaces with the coating reagent. For example, as described above, the ultrafiltration moves the coating reagent toward an inside surface of hollow fiber walls, which may shorten the coating process, in addition to the more complete/uniform distribution of the coating agent provided by the other steps of flow 1200.

As noted above, steps in flow 1200 may be performed for predetermined periods of time. In embodiments, flow 1200 is designed to be performed within a period of time, e.g., relatively quickly. For example, in embodiments, the predetermined period of times may be selected so that substantially all (or most) of the steps of flow 1200 may be performed in less than 90 minutes, such as less than 80 minutes, less than 70 minutes, less than 60 minutes, less than 50 minutes, less than 40 minutes, or even less than 30 minutes. In some embodiments, the steps of flow 800 may be performed in greater than 10 minutes, greater than 20 minutes, greater than 30 minutes, greater than 40 minutes, or greater than 50 minutes. In selecting the periods of time, embodiments provide for each period to be the same in duration. In other embodiments, each period of time may have a different duration. In yet other embodiments, some periods of time may have the same duration while others have different durations. These are merely some examples and flow 1200 is not necessarily limited to being performed during any specific duration.

In one specific embodiment, flow 1200 may provide for performing each of steps 1216 through 1240 in less than 30 minutes. As one example, each of the steps may be performed for 4 minutes resulting in a 28 minute coating process. As yet another example, each of steps 1216 through 1240 may be performed for 8 minutes resulting in a 56 minute coating process. These are merely some non-limiting examples.

Figure 13:
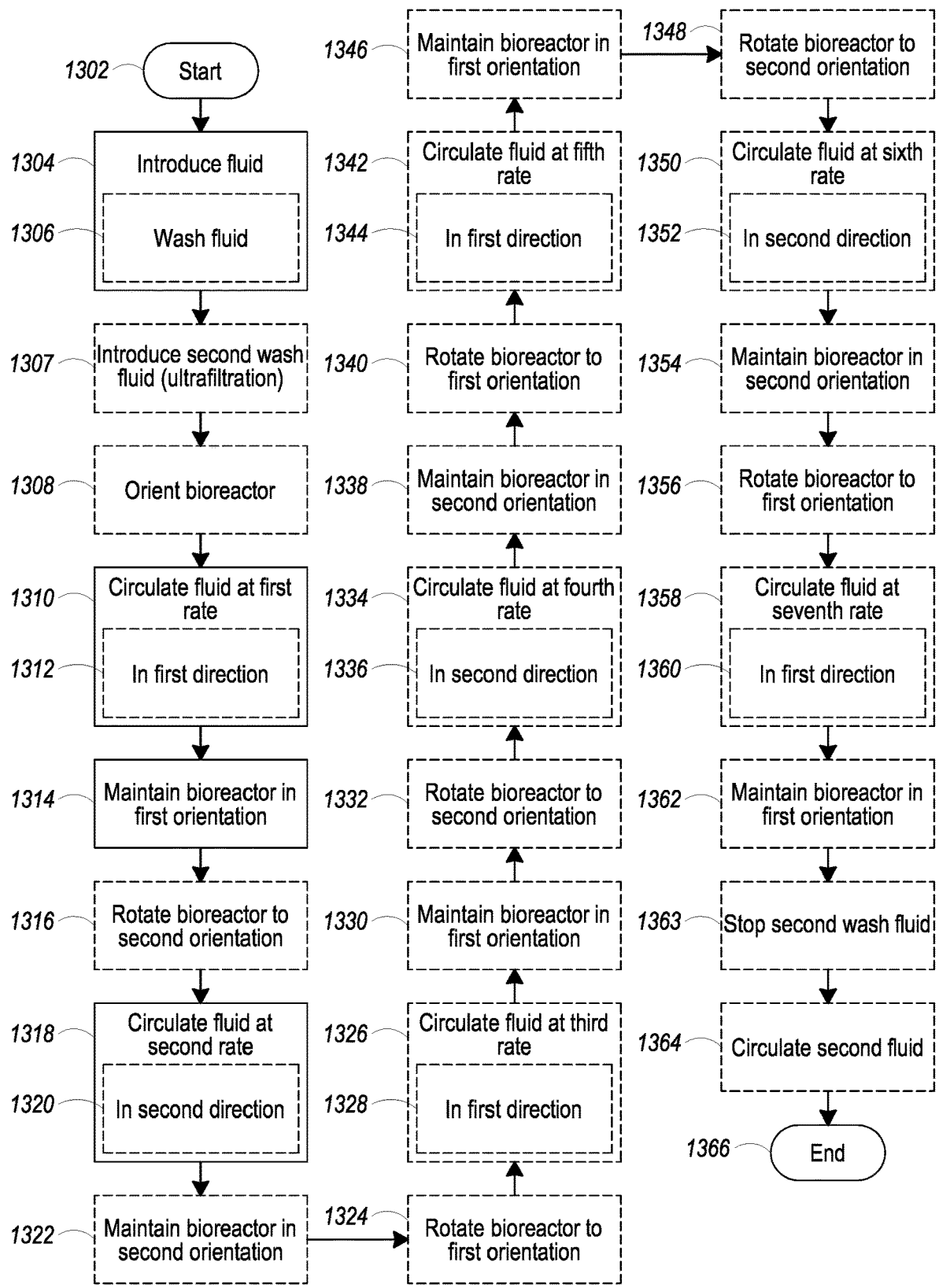
FIG. 13 illustrates a flow for a process of coating a bioreactor according to yet another embodiment.

Referring now to FIG. 13, flow 1300 starts at 1302 and passes to step 1304 where fluid that includes a reagent may be introduced into a cell expansion system and a bioreactor such as bioreactors 100, 300, 501, and/or 601. In embodiments, step 1304 may involve activating one or more pumps (564, 664) to introduce fluid with the reagent from a bag (562) or connection point (662) into a fluid flow path.

As part of introducing the fluid with the reagent into the cell expansion system, step 1304 may involve optional step 1306, where a wash fluid (e.g., PBS) may be used to chase the reagent from parts of the CES. For example, the wash fluid may move any reagent left behind in an ARC, such as ARC 556/656. The wash fluid may chase any lingering reagent into the bioreactor and/or a fluid flow path associated with the bioreactor e.g., 502/602.

Flow 1300 then passes to step 1307 where a second wash fluid may be introduced into the bioreactor. In embodiments, step 1307 may involve activating a pump, such as pumps 554, 654 to introduce the second wash fluid from a bag (562) or connection point (662) into a fluid flow path and into the bioreactor (100, 501, and/or 601). In embodiments, the second wash fluid is introduced to create conditions for ultrafiltration, as described above. Ultrafiltration allows proteins or molecules (e.g., the coating reagent) that are too large to pass through the pores 818 (FIG. 8) of a hollow fiber 812 (FIG. 8) to adhere to the bioreactor fiber 812 and thus coat the walls while the solution flows through the pores 818. Where the solution flows through the pores 818 of the fiber 812 from the IC 816 to the EC side 820, positive ultrafiltration may result in the deposit of the coating agent or reagent on the inner walls, or IC side 816, of the fibers. In embodiments, the second wash fluid introduced at step 1307 may be continuously introduced as steps 1308 through 1362 are performed.

Flow 1300 passes to step 1308 which may be performed to orient a bioreactor, e.g. bioreactor 100, 501, and/or 601, to an initial orientation. In embodiments, a bioreactor may already be oriented in an initial orientation, in which case step 1308 would not be performed. When performed, step 1308 may in some embodiments be performed by one or rotation mechanisms that may include one or more motors, gears, connectors, shafts, etc. that rotate the bioreactor to a first orientation. In embodiments, the orientation may be an initial horizontal orientation.

Figure 15:
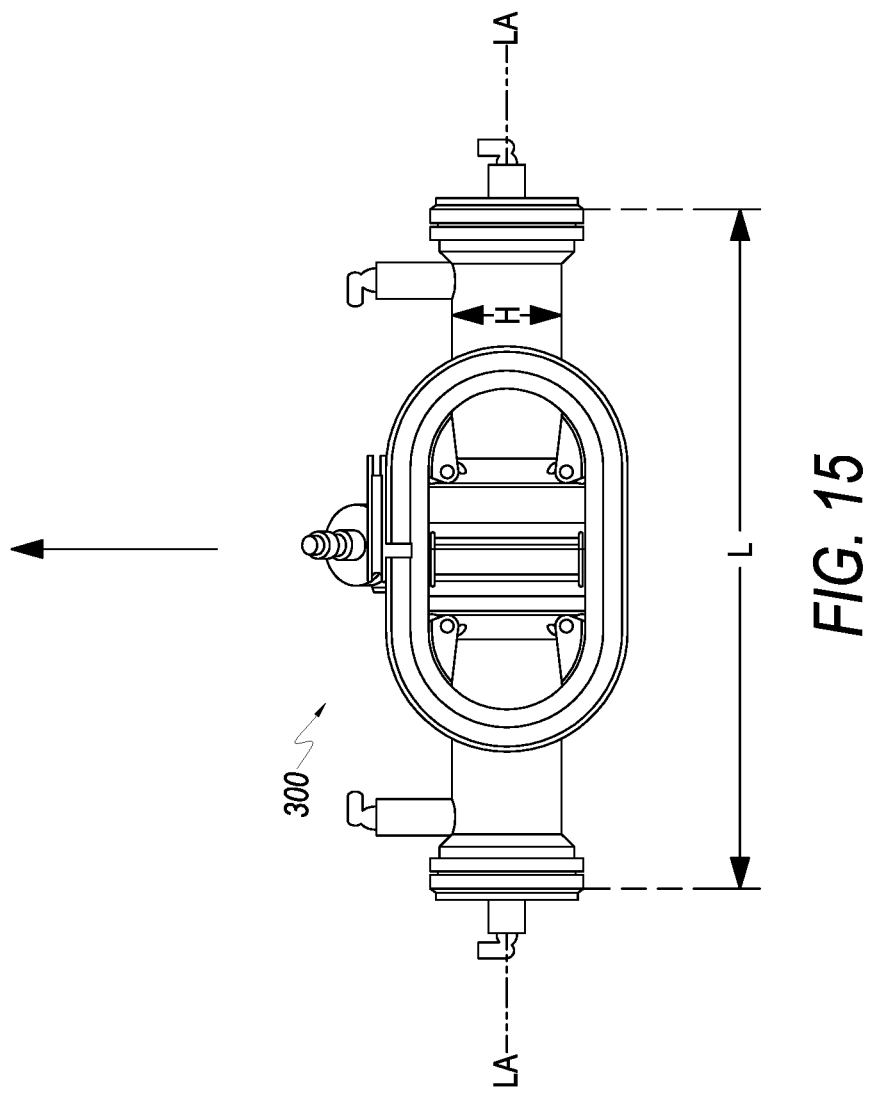
FIG. 15 illustrates a front elevation view of an embodiment of a bioreactor in a first orientation.
Figure 16:
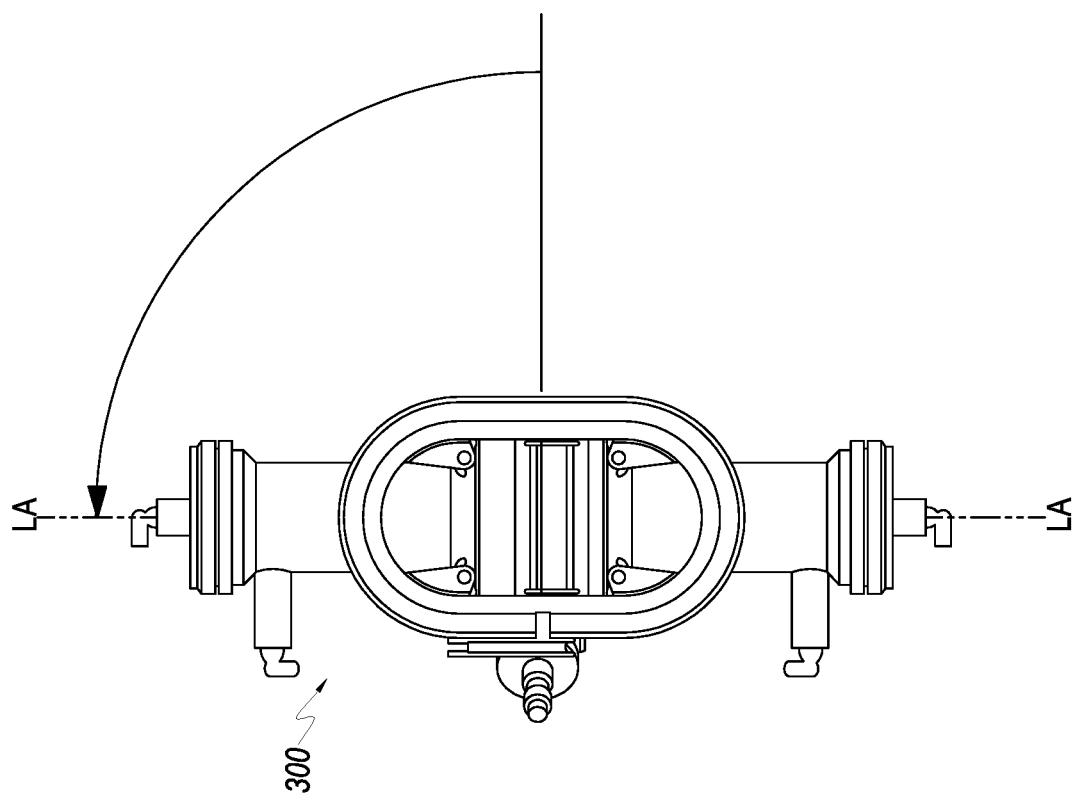
FIG. 16 illustrates a front elevation view of the bioreactor of FIG. 15, wherein the bioreactor is shown rotated about 90 degrees from the view of FIG. 15.
Figure 17:
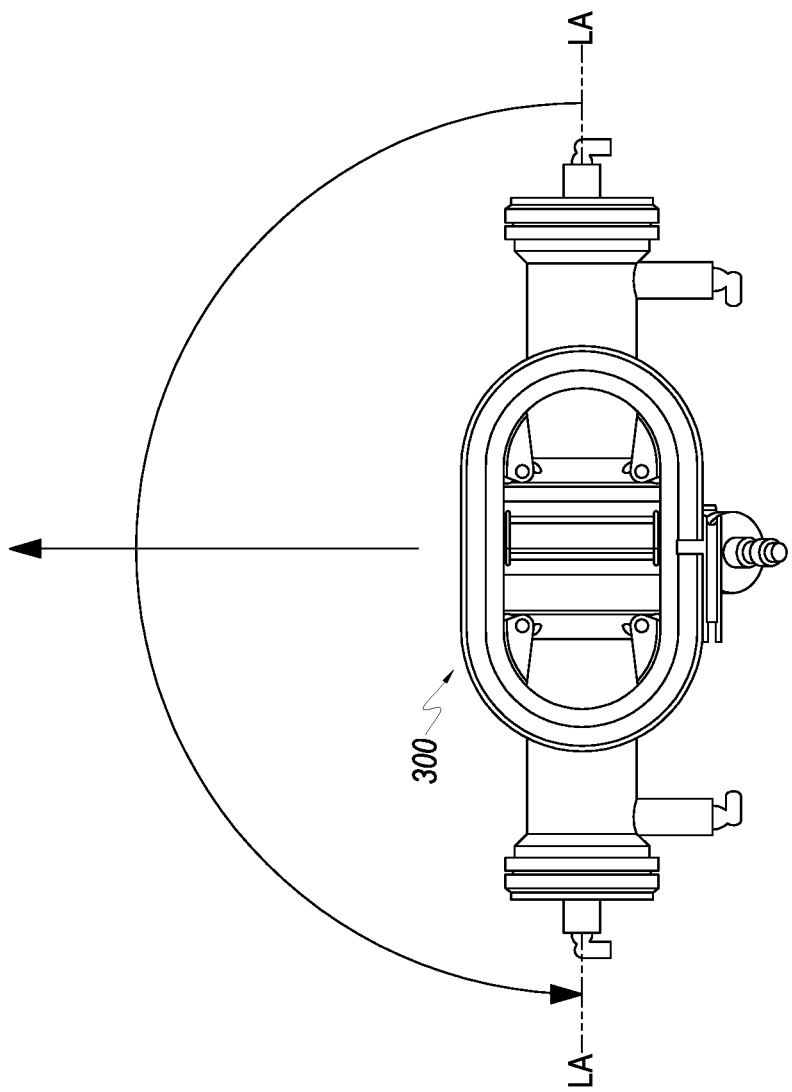
FIG. 17 is a front elevation view of the bioreactor of FIG. 15, wherein the bioreactor is shown rotated about 180 degrees from the view of FIG. 15.

Referring now to FIGS. 15-17, a bioreactor 300 (which in embodiments may be bioreactor 100, 501, and/or 601) is shown in different orientations. FIG. 15 illustrates the bioreactor 300 positioned in an initial orientation. As part of optional step 1308, bioreactor 300 may be oriented with its longitudinal axis LA-LA in a starting orientation, such as, for example, a first horizontal orientation as shown in FIG. 15.

Flow 1300 passes from optional step 1308 to step 1310 where fluid that includes a reagent may be circulated through a bioreactor such as bioreactors 100, 501, and/or 601. In embodiments, step 1310 may involve activating one or more pumps to circulate fluid with the reagent through the bioreactor. For example, an IC circulation pump (e.g., 512 or 612) may be activated to circulate fluid through the IC side of a bioreactor at a first circulation flow rate.

In at least one embodiment, fluid may pass through hollow fibers (e.g., the lumen). Step 1310 may involve circulating fluid at a first flow rate. The first flow rate may in embodiments be one of the first flow rates described above with respect to step 1016 (FIG. 10).

In other embodiments, fluid with the reagent may be circulated through the EC side of the bioreactor. Step 1310 may therefore, in embodiments, involve activating an EC circulation pump (e.g., 528 or 628) to circulate fluid through the EC side of bioreactor at a first circulation flow rate.

In embodiments, the reagent may be any protein, nutrient, or other material that is useful in creating conditions for expansion of cells. As described above, the reagent may be a protein that coats a surface in the bioreactor to which cell (e.g., adherent cells) may attach and grow. As one example, a glycoprotein (such as fibronectin, collagen, cryoprecipitate, etc.) may be the reagent that is circulated through a bioreactor, e.g., through the IC circuit of the bioreactor, to coat an inside surface of hollow fibers. The coating may promote the attachment of adherent cells that may later be added to the bioreactor and expanded in the bioreactor. This is merely one example and flow 1300 is not limited to this application.

In some embodiments, step 1310 may involve circulation in a specific direction. In other words, in some embodiments, step 1310 may involve activating a pump such as IC circulation pump (e.g., 512 or 612) in a first direction 1312, e.g., a counter clockwise or a clockwise direction. As one example, referring now to FIG. 6, step 1310 may involve activating pump 612 to circulate fluid through path 602 in a counter clock wise direction. That is, fluid may enter through port 601A and exit through port 601B.

Flow 1300 passes from step 1310 to step 1314 where the bioreactor is maintained in the first orientation, e.g., a horizontal orientation (FIG. 15). Step 1314 may be performed in combination with step 1310. In embodiments, the first period of time may be one of the first periods of time described above with respect to step 1016 (FIG. 10). Step 1314 may be performed in embodiments to provide time to allow the reagent to coat portions of the bioreactor. For example, when the bioreactor comprises hollow fibers, step 1314 may be performed to allow the reagent time to coat interior surfaces of the hollow fibers.

After step 1314, flow 1300 may pass to optional step 1316, where the bioreactor is rotated to a second orientation. In embodiments, the second orientation may be a horizontal orientation that is about 180 degrees from the original (e.g., first) orientation (e.g., FIG. 15). FIG. 13 illustrates bioreactor 300 rotated 90 degrees from the orientation shown in FIG. 15, with FIG. 17 illustrating bioreactor 300 rotated about 180 degrees from the orientation shown in FIG. 15. In embodiments, step 1316 may be performed to rotate the bioreactor to an orientation shown in FIG. 17 (e.g., a second horizontal orientation). If step 1316 is not performed, flow would pass from step 1314 to step 1318. In these embodiments, the bioreactor may remain in the first orientation (e.g., first horizontal orientation as shown in FIG. 15).

Flow passes to step 1318, wherein fluid with the reagent is circulated at a second flow rate, which may be less than the first flow rate. In embodiments, the second flow rate may be one of the second flow rates described above with respect to step 1020 (FIG. 10).

In some embodiments, step 1318 may involve circulation in a specific direction. In other words, in some embodiments, step 1318 may involve activating a pump such as IC circulation pump (e.g., 512 or 612) in a second direction 1320, e.g., a counter clockwise or a clockwise direction. Continuing with the example above, referring FIG. 6, step 1320 may involve activating pump 612 to circulate fluid through path 602 in a clock wise direction. That is, fluid may enter through port 601B and exit through port 601A.

Flow 1300 passes from step 1318 to optional step 1322 where the bioreactor is maintained in the second orientation, e.g., a second horizontal orientation (FIG. 17). Optional step 1322 may be performed in combination with optional step 1318. In embodiments, optional steps 1318 and 1322 may be performed for a second predetermined period of time. In embodiments, the second period of time may be one of the second periods of time described above with respect to step 1020 (FIG. 10). Step 1322 may be performed in embodiments to provide time to allow the reagent to coat portions of the bioreactor. For example, when the bioreactor comprises hollow fibers, step 1322 may be performed to allow the reagent time to coat interior surfaces of the hollow fibers.

After optional step 1322, flow 1300 may pass to optional step 1324, where the bioreactor is rotated back to the first orientation. In embodiments, the first orientation may be a horizontal orientation that is about the same as the original (e.g., first) orientation (e.g., FIG. 15).

Flow passes to step 1326, wherein fluid with the reagent is circulated at a third flow rate, which may be less than the second flow rate. In embodiments, the third flow rate may be one of the third flow rates described above with respect to step 1024 (FIG. 10).

In some embodiments, step 1326 may involve circulation in a specific direction. In other words, in some embodiments, step 1326 may involve activating a pump such as IC circulation pump (e.g., 512 or 612) in the first direction 1328 e.g., a counter clockwise or a clockwise direction. Continuing with the example above, referring to FIG. 6, step 1326 may involve activating pump 612 to circulate fluid through path 602 in a counter clock wise direction. That is, fluid may enter through port 601A and exit through port 601B.

Flow 1300 passes from step 1326 to optional step 1330 where the bioreactor is maintained in the first orientation, e.g., a first horizontal orientation (FIG. 15). Optional step 1330 may be performed in combination with optional step 1326. In embodiments, optional steps 1326 and 1330 may be performed for a third predetermined period of time. In embodiments, the third period of time may be one of the third periods of time described above with respect to step 1024 (FIG. 10). Step 1322 may be performed in embodiments to provide time to allow the reagent to coat portions of the bioreactor. For example, when the bioreactor comprises hollow fibers, step 1322 may be performed to allow the reagent time to coat interior surfaces of the hollow fibers.

After optional step 1326, flow 1300 may pass to optional step 1332, where the bioreactor is rotated back to the second orientation. In embodiments, the second orientation may be a horizontal orientation that is about 180 degrees from the first orientation (e.g., FIG. 17).

Flow 1300 then passes to optional step 1334, where fluid with the reagent is circulated at a fourth flow rate, which may be less than the third flow rate. In embodiments, the fourth flow rate may be one of the fourth flow rates described above with respect to step 1028 (FIG. 10).

In some embodiments, step 1334 may involve circulation in a specific direction. In other words, in some embodiments, step 1334 may involve activating a pump such as IC circulation pump (e.g., 512 or 612) in the second direction 1336 e.g., a counter clockwise or a clockwise direction. Continuing with the example above, referring to FIG. 6, step 1334 may involve activating pump 612 to circulate fluid through path 602 in a clock wise direction. That is, fluid may enter through port 601B and exit through port 601A.

Flow 1300 passes from step 1334 to optional step 1338 where the bioreactor is maintained in the second orientation, e.g., a second horizontal orientation (FIG. 17). Optional step 1338 may be performed in combination with optional step 1334. In embodiments, optional steps 1334 and 1338 may be performed for a fourth predetermined period of time. In embodiments, the fourth period of time may be one of the second periods of time described above with respect to step 1028 (FIG. 10). Step 1338 may be performed in embodiments to provide time to allow the reagent to coat portions of the bioreactor. For example, when the bioreactor comprises hollow fibers, step 1338 may be performed to allow the reagent time to coat interior surfaces of the hollow fibers.

After optional step 1338, flow 1300 may pass to optional step 1340, where the bioreactor is rotated back to the first orientation. In embodiments, the first orientation may be a horizontal orientation that is about the same as the original (e.g., first) orientation (e.g., FIG. 15).

Flow passes to step 1342, wherein fluid with the reagent is circulated at a fifth flow rate, which may be less than the fourth flow rate. In embodiments, the fifth flow rate may be one of the fifth flow rates described above with respect to step 1032 (FIG. 10).

In some embodiments, step 1342 may involve circulation in a specific direction. In other words, in some embodiments, step 1342 may involve activating a pump such as IC circulation pump (e.g., 512 or 612) in the first direction 1344 e.g., a counter clockwise or a clockwise direction. Continuing with the example above, referring to FIG. 6, step 1342 may involve activating pump 612 to circulate fluid through path 602 in a counter clock wise direction. That is, fluid may enter through port 601A and exit through port 601B.

Flow 1300 passes from step 1342 to optional step 1346 where the bioreactor is maintained in the first orientation, e.g., a first horizontal orientation (FIG. 15). Optional step 1346 may be performed in combination with optional step 1342. In embodiments, optional steps 1342 and 1346 may be performed for a fifth predetermined period of time. In embodiments, the fifth period of time may be one of the second periods of time described above with respect to step 1032 (FIG. 10). Step 1346 may be performed in embodiments to provide time to allow the reagent to coat portions of the bioreactor. For example, when the bioreactor comprises hollow fibers, step 1346 may be performed to allow the reagent time to coat interior surfaces of the hollow fibers.

After optional step 1346, flow 1300 may pass to optional step 1348, where the bioreactor is rotated back to the second orientation. In embodiments, the second orientation may be a horizontal orientation that is about 180 degrees from the original (e.g., first) orientation (e.g., FIG. 17).

Flow 1300 then passes to optional step 1350, where fluid with the reagent is circulated at a sixth flow rate, which may be less than the fifth flow rate. In embodiments, the fifth flow rate may be one of the fifth flow rates described above with respect to step 1032 (FIG. 10).

In some embodiments, step 1350 may involve circulation in a specific direction. In other words, in some embodiments, step 1350 may involve activating a pump such as IC circulation pump (e.g., 512 or 612) in the second direction 1352 e.g., a counter clockwise or a clockwise direction. Continuing with the example above, referring to FIG. 6, step 1350 may involve activating pump 612 to circulate fluid through path 602 in a clock wise direction. That is, fluid may enter through port 601B and exit through port 601A.

Flow 1300 passes from step 1350 to optional step 1354 where the bioreactor is maintained in the second orientation, e.g., a second horizontal orientation (FIG. 17). Optional step 1354 may be performed in combination with optional step 1350. In embodiments, optional steps 1350 and 1354 may be performed for a sixth predetermined period of time. In embodiments, the sixth period of time may be one of the sixth periods of time described above with respect to step 1036 (FIG. 10). Step 1354 may be performed in embodiments to provide time to allow the reagent to coat portions of the bioreactor. For example, when the bioreactor comprises hollow fibers, step 1354 may be performed to allow the reagent time to coat interior surfaces of the hollow fibers.

After optional step 1346, flow 1300 may pass to optional step 1348, where the bioreactor is rotated back to the first orientation. In embodiments, the first orientation may be a horizontal orientation that is substantially the same as the original (e.g., first) orientation (e.g., FIG. 15).

Flow passes to step 1358, wherein fluid with the reagent is circulated at a seventh flow rate, which may be less than the sixth flow rate. In embodiments, the seventh flow rate may be one of the fifth flow rates described above with respect to step 1040 (FIG. 10).

In some embodiments, step 1358 may involve circulation in a specific direction. In other words, in some embodiments, step 1358 may involve activating a pump such as IC circulation pump (e.g., 512 or 612) in the first direction 1360 e.g., a counter clockwise or a clockwise direction. Continuing with the example above, referring to FIG. 6, step 1358 may involve activating pump 612 to circulate fluid through path 602 in a counter clock wise direction. That is, fluid may enter through port 601A and exit through port 601B.

Flow 1300 passes from step 1358 to optional step 1362 where the bioreactor is maintained in the first orientation, e.g., a first horizontal orientation (FIG. 15). Optional step 1362 may be performed in combination with optional step 1358. In embodiments, optional steps 1358 and 1362 may be performed for a seventh predetermined period of time. In embodiments, the seventh period of time may be one of the seventh periods of time described above with respect to step 1040 (FIG. 10). Step 1362 may be performed in embodiments to provide time to allow the reagent to coat portions of the bioreactor. For example, when the bioreactor comprises hollow fibers, step 1362 may be performed to allow the reagent time to coat interior surfaces of the hollow fibers.

Flow 1300 then passes to step 1363 where introduction of the second wash fluid into the bioreactor is stopped. In embodiments, step 1363 may involve deactivating a pump, such as pump 554, 654 to stop the introduction of the second wash fluid into the fluid flow path and into the bioreactor (100, 501, and/or 601). In embodiments, stopping the introduction of the second wash fluid stops the process of ultrafiltration.

Flow 1300 then passes to step 1364, where a second fluid, that may not include the reagent, or have a lower concentration of the reagent, may be circulated through the bioreactor. In embodiments, step 1364 may be performed to wash any remaining reagent that has not coated a surface of the bioreactor out of the bioreactor and CES. As noted above, flow 1300 may be part of a larger process such as a process for growing and harvesting cells in a cell expansion system, such as flow 700. Therefore, in embodiments, step 1364 may be implemented as part of steps performed in the larger process, such as step 710 (FIG. 7). Flow 1300 then ends at 1366.

Without being bound by theory, it is believed that having steps 1310, 1318, 1326, 1334, 1342, 1350, and 1358 circulate at different flow rates, allows the fluid to flow through more of the hollow fibers e.g., 1108 (FIG. 11) than if just a single flow rate would be used. In one embodiment of a process that follows flow chart 1300, at steps 1310 and 1318 (at the flow rates described above), fluid may flow mainly through the hollow fibers in zone 1112. At steps 1326 and 1334 (at the flow rates described above), fluid may flow mainly through the hollow fibers in zones 1112 and 1116. At steps 1342 and 1350 (at the flow rates described above), fluid may flow mainly through the hollow fibers in zone 1112, 1116, and 1120 because the rate is slower and the fluid may disperse more. At step 1358 (at the flow rates described above), fluid may flow through the hollow fibers in zones 1112, 1116, 1120, and 1124 because the flow rate is yet slower and fluid may disperse even more. Thus, it is believe that fluid with the reagent may flow into more of the hollow fibers using a sequence of different flow rates, than if a single high flow rate circulation is used.

As noted above, it is also believed that the different flow rates may also affect the longitudinal distribution of the reagent along the bioreactor, e.g., along a hollow fiber. That is, a higher flow rate may allow the reagent to flow further along inside a hollow fiber. For example, at a higher flow rate, the reagent being carried by fluid may reach beyond half the length of the hollow fiber. At a lower flow rate, the reagent being carried by fluid may reach half the length of the hollow fiber. At even a lower flow rate, the reagent being carried by fluid may reach less than half the length of the hollow fiber. Accordingly, in some embodiments, it is believed that the use of different flow rates may provide some improvement in longitudinal distribution of the reagent along the length of the bioreactor, e.g., a hollow fiber. Additionally, with the changing of directions provided for in flow 1300, the reagent may be distributed along the length of the hollow fibers from both sides of a hollow fiber. The combination of flow rate changes and changes in direction, may allow for more even distribution of the reagent along the length of a hollow fiber.

Furthermore, flow 1300 provides for rotation of the bioreactor, as described above. It is also believed that rotation of the bioreactor, in addition to changes in direction and flow rates, provides a process where the reagent may be distributed/coated on hollow fibers more completely and/or uniformly.

Moreover, it is believed that the continuous addition of wash fluid (starting at step 1307 and ending at step 1363), to create ultrafiltration conditions, further promotes the coating of growth surfaces with the coating reagent. For example, as described above, the ultrafiltration moves the coating reagent toward an inside surface of hollow fiber walls, which may shorten the coating process, in addition to the more complete/uniform distribution of the coating agent provided by the other steps of flow 1300.

As noted above, steps in flow 1300 may be performed for predetermined periods of time. In embodiments, flow 1300 is designed to be performed within a period of time, e.g., relatively quickly. For example, in embodiments, the predetermined period of times may be selected so that substantially all (or most) of the steps of flow 1300 may be performed in less than 90 minutes, such as less than 80 minutes, less than 70 minutes, less than 60 minutes, less than 50 minutes, less than 40 minutes, or even less than 30 minutes. In some embodiments, the steps of flow 800 may be performed in greater than 10 minutes, greater than 20 minutes, greater than 30 minutes, greater than 40 minutes, or greater than 50 minutes. In selecting the periods of time, embodiments provide for each period to be the same in duration. In other embodiments, each period of time may have a different duration. In yet other embodiments, some periods of time may have the same duration while others have different durations. These are merely some examples and flow 1300 is not necessarily limited to being performed during any specific duration.

In one specific embodiment, flow 1300 may provide for performing all of steps 1310, 1318, 1326, 1334, 1342, 1350, and 1358 in less than 30 minutes. As one example, each of the steps may be performed for 4 minutes resulting in a 28 minute coating process. As yet another example, each of steps 1310, 1318, 1326, 1334, 1342, 1350, and 1358 may be performed for 8 minutes resulting in a 56 minute coating process. These are merely some non-limiting examples.

Figure 14:
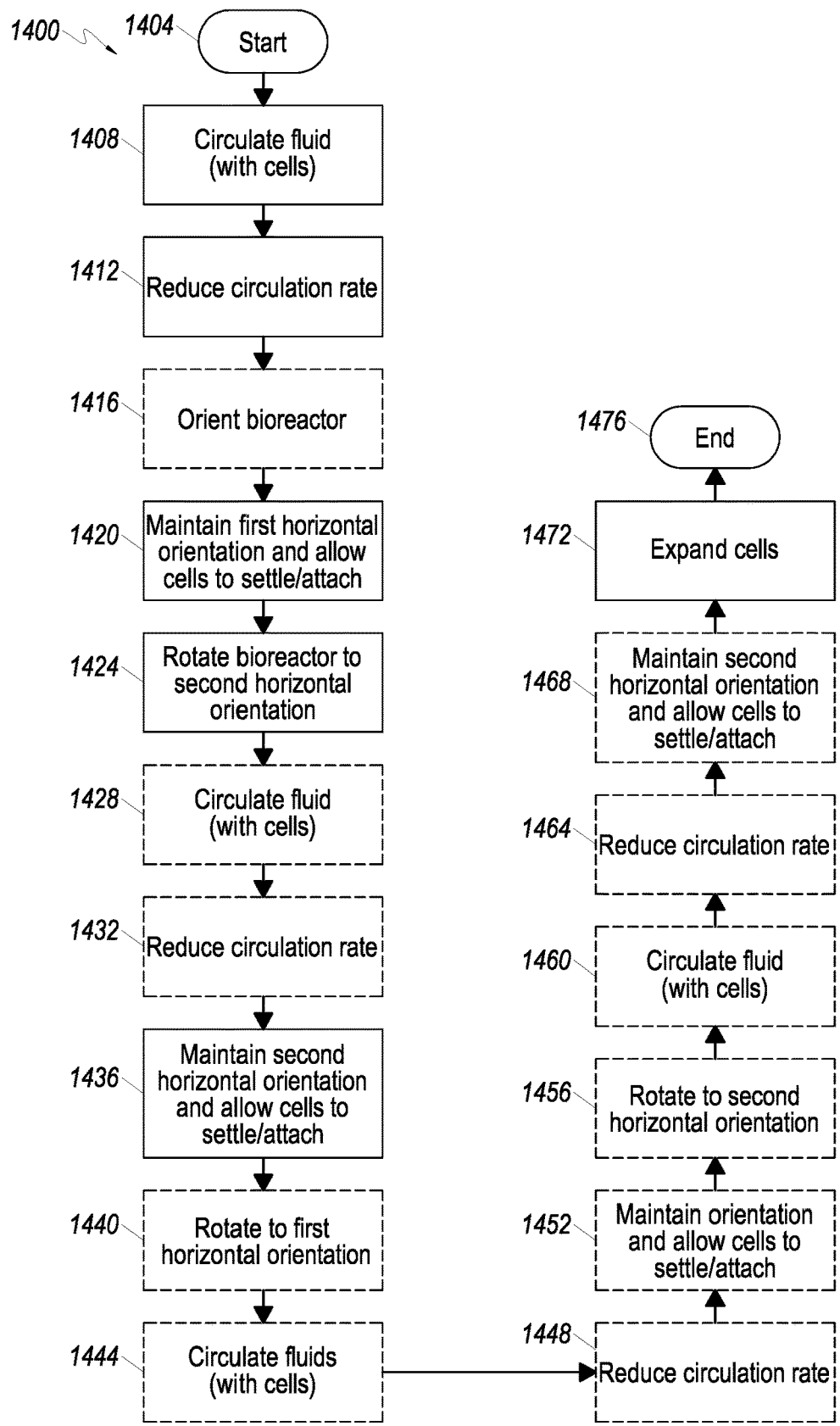
FIG. 14 is a flow chart of a process for loading, distributing, attaching, and expanding cells according to some embodiments.

Turning now to FIG. 14, flow 1400 begins at 1404 and passes to step 1408 where fluid that includes cells may be circulated through a bioreactor such as bioreactors 100, 300, 501, 601. In embodiments, step 1408 may involve activating one or more pumps to circulate fluid through the bioreactor 100, 300, 501, 601. For example, an IC circulation pump (e.g., 512 or 612) may be activated to circulate fluid through the IC side of the bioreactor at a first circulation flow rate. In at least one embodiment, fluid carrying the cells may pass through hollow fibers of the bioreactor from the IC side to the EC side. In other embodiments, cells may be loaded into the EC side of the bioreactor and have the fluid carrying the cells pass from the EC side to the IC side. In these embodiments, an EC circulation pump (e.g., 528, 628) may be activated to circulate fluid through the EC side of bioreactor at a first circulation flow rate.

In embodiments, the first circulation flow rate may be a relatively high flow rate. In embodiments, the first circulation flow rate may be less than about 500 ml/min, less than about 400 ml/min, or even less than about 300 ml/min. In other embodiments, the first circulation rate may be greater than about 50 ml/min, greater than about 100 ml/min, or even greater than about 150 ml/min. In one embodiment, the first circulation flow rate is between about 100 ml/min and about 300 ml/min, such as about 200 ml/min.

Step 1408 may in some embodiments involve also rotating the bioreactor in a particular sequence to facilitate distribution of the cells through the bioreactor and circulation paths of the CES to which the bioreactor may be fluidly associated. In other embodiments, the circulating step 1408 may involve rotating the bioreactor for some periods of time, but maintaining the bioreactor stationary for other periods of time.

After step 1408, the fluid circulation rate is reduced at step 1412. The circulation rate may be reduced to about zero (0) ml/min, or in other embodiments may be reduced to a rate that is above zero (0) ml/min but still allows cells to settle and attach to the bioreactor e.g., an inside surface of hollow fibers of bioreactor. In embodiments, step 1412 may involve stopping or turning off one or more pumps used in step 1408 to circulate the fluid.

Flow passes from step 1412 to optional step 1416, which may be performed to orient a bioreactor, e.g. bioreactor to an initial orientation. In embodiments, a bioreactor may already be oriented in an initial orientation, whereby step 1416 would not be performed. When performed, step 1416 may in some embodiments be performed by one or more motors.

Referring now to FIGS. 15-19, a bioreactor 300 is shown in FIG. 15 positioned in an initial orientation. As part of optional step 1416, bioreactor 300 may be oriented with its longitudinal axis LA-LA in a starting orientation, such as, for example, a first horizontal orientation as shown in FIG. 15.

Flow passes from 1416, to step 1420 where the bioreactor is maintained at a first orientation to allow cells to settle and in some embodiments attach to a first portion of bioreactor 300. Step 1420 may be performed for a first predetermined period of time.

Figure 20A:
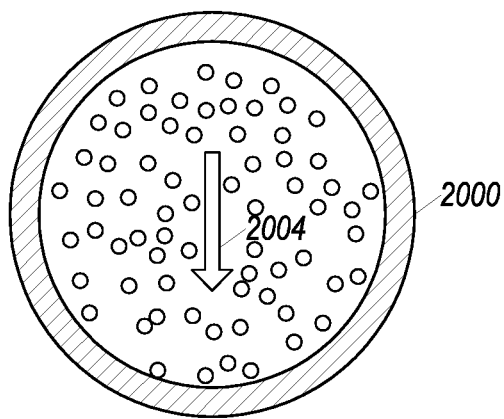
FIGS. 20A-20D illustrate a cross section (perpendicular to a central axis) of a hollow fiber that may be part of a bioreactor as it progresses through steps of a process for distributing, attaching, and expanding cells in the bioreactor according to another embodiment.
Figure 20B:
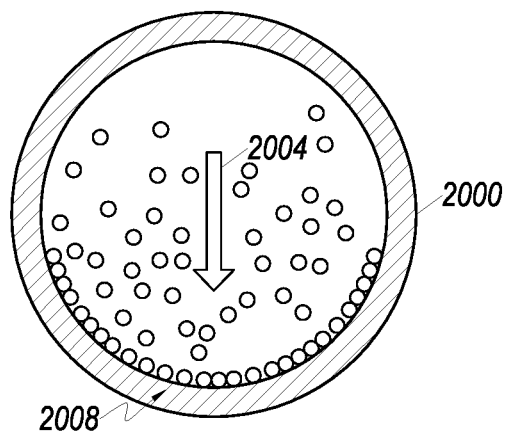
Figure 20C:
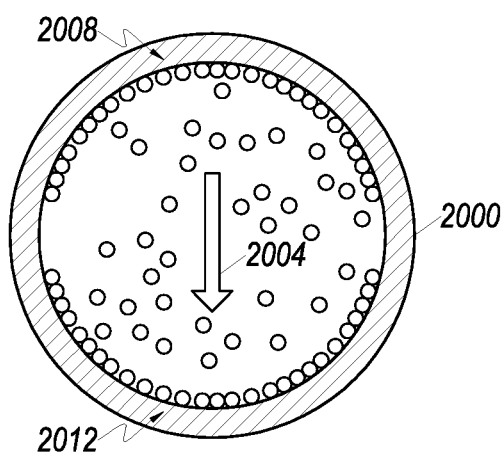
Figure 20D:
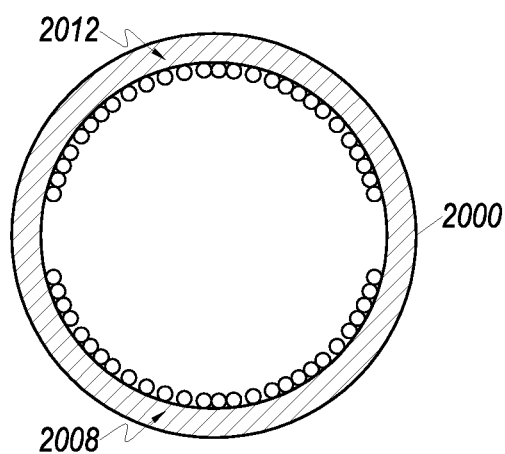
Figure 21A:
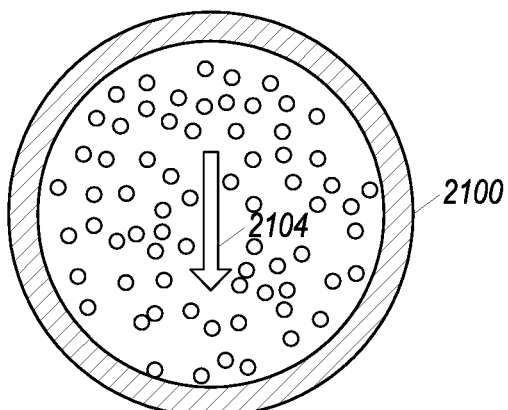
FIG. 21A-21F illustrate a cross section (perpendicular to a central axis) of a hollow fiber that may be part of a bioreactor as it progresses through steps of a process for distributing attaching and expanding cells in the bioreactor according to yet another embodiment.

Referring now to FIGS. 20A-20D and FIGS. 21A-21F these figures illustrate a cross-section of a hollow fiber 2000 (taken perpendicular to a central axis of the hollow fiber 2000 and a central axis of bioreactor 300) that may be one of the hollow fibers of bioreactor 300. These figures illustrate the possible locations of cells within the hollow fibers during some steps of flow chart 1400. As illustrated in FIG. 20A, before the circulation rate is reduced at step 1412, cells within individual hollow fiber 2000 may be distributed, in embodiments evenly, throughout the volume of hollow fiber 2000. When the circulation rate is reduced, the cells may begin to be influenced by gravity 2004 and begin to settle. FIG. 21A also illustrates a similar situation with respect to a hollow fiber 2100 and gravity 2104.

Figure 21B:
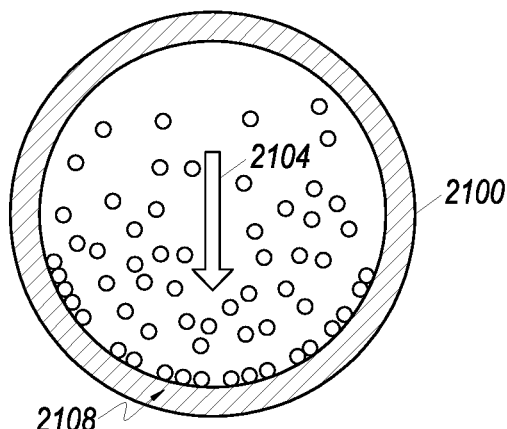

In embodiments, with the bioreactor 300 in the first horizontal orientation (FIG. 15), the cells within bioreactor 300 are allowed to settle onto a first portion of the bioreactor. As illustrated in FIGS. 20B and 21B, the first portion of bioreactor 300 may include at least a portion 2008 of hollow fiber 2000 and/or portion 2108 in hollow fiber 2100. In embodiments, the cells will be allowed to settle for a first predetermined period of time that may be selected to not only allow the cells to settle, but also to attach to portion 2008 of the hollow fiber 2000 (and 2108 of hollow fiber 2100).

In some embodiments, the first predetermined period of time may be long enough in duration to allow the cells to settle and attach to portion 2008 and 2108. In these embodiments, the cells may only need to travel the distance of the inner diameter of hollow fiber 2000 or 2100. For example, in embodiments where the hollow fiber has an inner diameter of between about 150 microns and about 300 microns, the first predetermined period of time may be less than about 20 minutes, less than about 15 minutes, or even less than about 10 minutes. In other embodiments, the first predetermined period of time may be greater than about 1 minute, greater than about 2 minutes, greater than about 3 minutes, or even greater than about 4 minutes. In one embodiment, the first period of time may be between about 3 minutes and about 8 minutes, such as about 5 minutes.

After step 1420, flow passes to step 1424, where the bioreactor 300 is rotated to a second horizontal orientation that is about 180 degrees from the first horizontal orientation. As shown in FIGS. 15-17, the bioreactor may be rotated by first being rotated from its first horizontal orientation (FIG. 15) to a first vertical orientation, which is about 90 degrees from the first horizontal orientation, e.g. axis LA LA in a vertical orientation (FIG. 16). Bioreactor 300 may then be rotated another 90 degrees (FIG. 17) to complete the rotation to the second horizontal orientation. Step 1424 may in some embodiments be performed by one or more motors connected to bioreactor 300. These motors may be part of a rocking device.

Figure 21C:
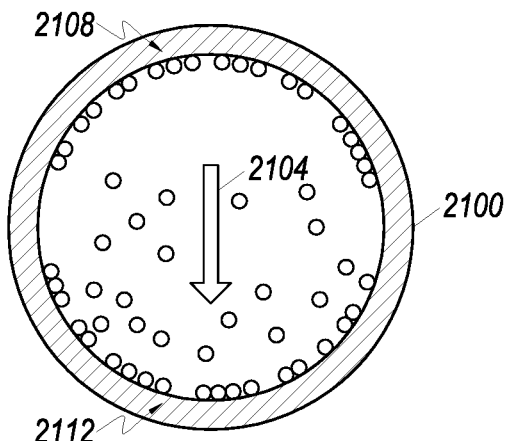
Figure 21D:
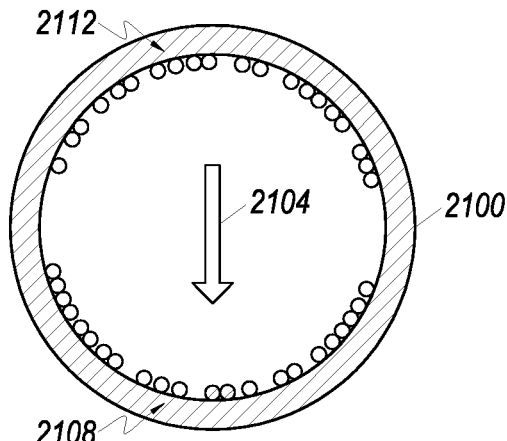
Figure 21E:
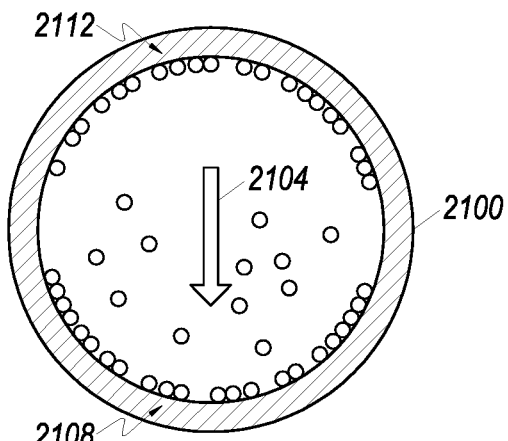

In some embodiments, flow 1400 will pass from step 1424 to step 1436 where the bioreactor 300 is maintained in the second horizontal orientation (FIG. 17) for a second predetermined period of time so that the cells are allowed to settle to a second portion of the bioreactor, such as portion 2012 of hollow fiber 2000 (FIG. 20C) or portion 2112 of hollow fiber 2100 (FIG. 21C).

In some embodiments, flow 1400 may include optional steps 1428 and 1432 prior to proceeding to step 1436. Similar to step 1408, step 1428 provides for circulating fluid through the bioreactor 300. In embodiments, step 1428 may involve activating one or more pumps to circulate fluid through the bioreactor 300. As noted above, an IC circulation pump (e.g., 512,612) may be activated to circulate fluid through the IC side of bioreactor 300 at a second circulation flow rate. In at least one embodiment, fluid carrying the cells may pass through hollow fibers of the bioreactor 300. In other embodiments, cells may be loaded into the EC side of the bioreactor 300 and have the fluid carrying the cells. In these embodiments, an EC circulation pump (e.g., 528, 628) may be activated to circulate fluid through the EC side of bioreactor 300 at a second circulation flow rate.

In embodiments, the second circulation flow rate may be less than the first circulation rate. In embodiments, the second circulation flow rate may be less than about 400 ml/min, less than about 300 ml/min, or even less than about 200 ml/min. In other embodiments, the second circulation rate may be greater than about 25 ml/min, greater than about 500 ml/min, or even greater than about 75 ml/min. In one embodiment, the second circulation flow rate is between about 50 ml/min and about 150 ml/min, such as about 100 ml/min.

In some embodiments, step 1428 may also involve circulation in a different direction than the circulation performed in step 1408. In other words, in some embodiments, step 708 may involve circulating fluid in a counter clockwise direction (see IC loop in FIGS. 5 and 6). In some embodiments, the circulation at step 1428 may be clockwise. In other words, the circulation may flow opposite to the circulation at step 1408. In other embodiments, the circulation in step 1408 may flow in the same direction as step 1408, clockwise or counter clockwise.

Optional step 1428 may in some embodiments involve also rotating the bioreactor 300 in a particular sequence to facilitate distribution of the cells through the bioreactor 300 and circulation paths of the CES to which the bioreactor 300 may be fluidly associated. In other embodiments, the circulating step 1428 may involve rotating the bioreactor 300 for some periods of time, but maintaining the bioreactor 300 stationary for other periods of time.

After optional step 1428, the fluid circulation rate is once again reduced at step 1432. The circulation rate may be reduced to about zero (0) ml/min, or in other embodiments may be reduced to a rate that is above zero (0) ml/min but still allows cells to settle and attach to the bioreactor 300, e.g., an inside surface of hollow fibers of bioreactor 300. In embodiments, step 1432 may involve stopping or turning off one or more pumps used in step 1428 to circulate the fluid.

Referring once again to step 1436, maintaining the bioreactor in the second horizontal orientation allows cells to settle on portion 2012 (or 2112 in FIG. 21C), which may be opposite portion 2008, e.g., portion 2008 (or 2108) may be referred to as a "bottom portion" and portion 2012 (or 2112 in FIG. 21C) may be referred to as a "top portion." FIGS. 20C and 20C illustrate cells settling onto portions 2012 and 2112, or in some embodiments vice versa. In embodiments, the cells will be allowed to settle for a second predetermined period of time that may be selected to not only allow the cells to settle, but also to attach to portion 2012 of the hollow fiber 2000 (or 2112 of fiber 2100).

In some embodiments, the second predetermined period of time may be long enough in duration allow the cells to settle and attach to portion 2012 (or 2112 in FIG. 21C). In these embodiments, the cells may only need to travel the distance of the inner diameter of hollow fiber 2000 or 2100. For example, in embodiments where the hollow fiber has an inner diameter of between about 150 microns and about 300 microns, the second predetermined period of time may be less than about 20 minutes, less than about 15 minutes, or even less than about 10 minutes. In other embodiments, the second predetermined period of time may be greater than about 1 minute, greater than about 2 minutes, greater than about 3 minutes, or even greater than about 4 minutes. In one embodiment, the second period of time may be between about 3 minutes and about 8 minutes, such as about 5 minutes.

In some embodiments, after step 1436, flow 1400 may pass to step 1472 where cells are expanded. Step 1472 may involve a number of substeps, such as circulating fluid into the bioreactor to feed and provide nutrients to the cells attached in the bioreactor. As can be appreciated, step 1472 may also involve providing oxygen to the cells so that they may multiply. Several other parameters in the bioreactor may be controlled in order to optimize the expansion, i.e. growth of the cells. In some embodiments, step 1472 may include circulating fluid to feed the cells for about 24 hours, about 36 hours, about 48 hours, about 60 hours, or even about 72 hours. In some embodiments, the feeding of the cells as part of step 1472 may be performed for less than about 120 hours, less than about 108 hours, less than about 96 hours, less than about 84 hours, or even less than about 72 hours. FIG. 20D illustrates hollow fiber 2000 for this embodiment. Flow then ends at 1476.

Figure 18:
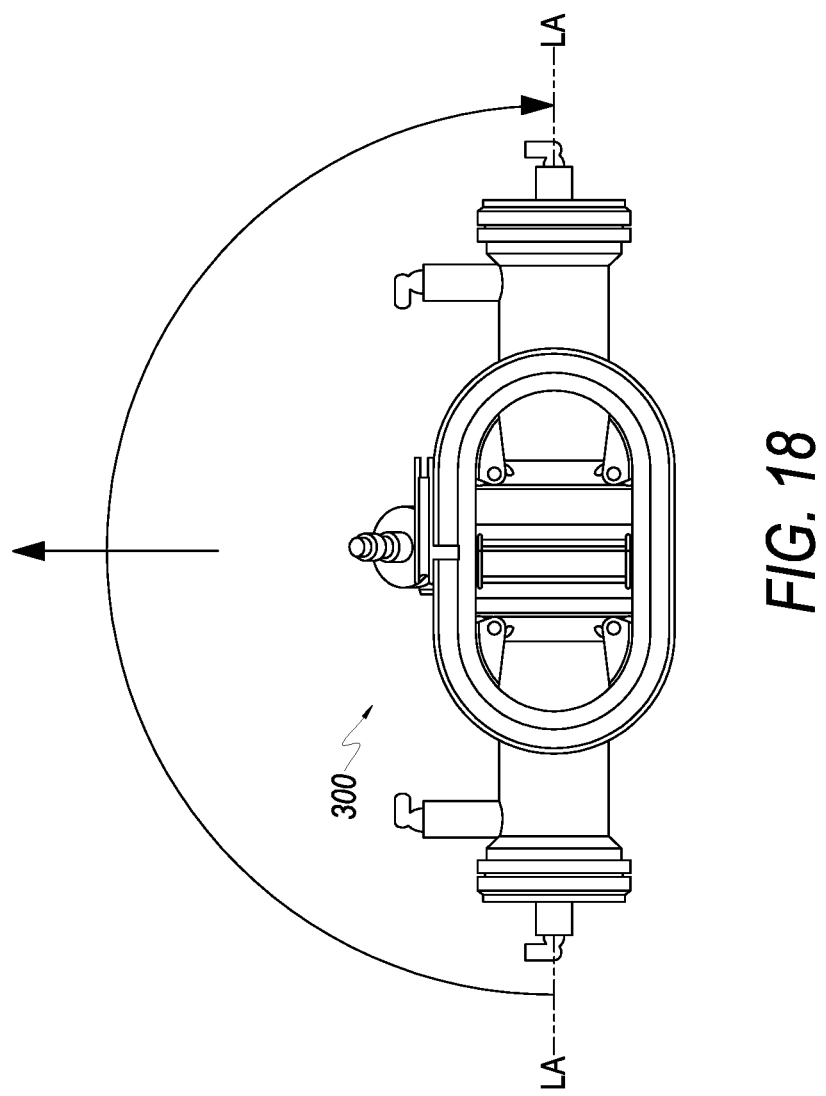
FIG. 18 is a front elevation view of the bioreactor of FIG. 15, wherein the bioreactor is shown rotated back to the original orientation shown in FIG. 15.
Figure 19:
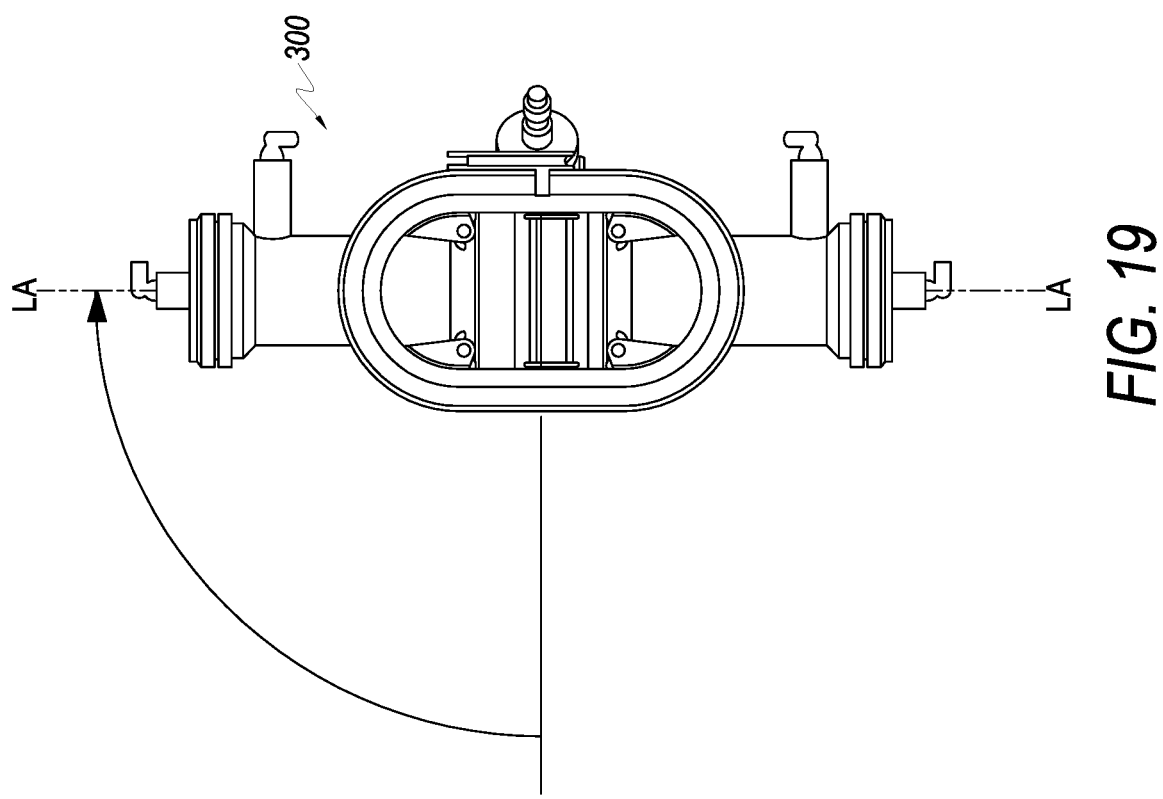
FIG. 19 illustrates a front elevation view of the bioreactor of FIG. 15, wherein the bioreactor is shown rotated about 90 degrees from the view of FIG. 15 and about 180 degrees from the view of FIG. 16.

In other embodiments, flow 1400 may pass to step 1440, where the bioreactor 300 is rotated back to its original first horizontal orientation. FIG. 18 illustrates bioreactor 300 once it has been rotated back to its first horizontal orientation. Step 1440 may be performed by one or more motors connected to bioreactor 300. These motors may be part of a rocking device. In embodiments, flow may pass from step 1440 to step 1472 where the cells are expanded. Flow then ends at 1476.

In other embodiments, flow 1400 passes from step 1440 to step 1444, or in other embodiments, flow may pass directly from step 1436, to step 1444 (when no additional rotation is performed), where fluid is again circulated but at a third circulation flow rate. Similar to steps 1408 and 1428, fluid is circulated through the bioreactor 300. In embodiments, step 1444 may involve activating one or more pumps to circulate fluid through the bioreactor 300. As noted above, an IC circulation pump (e.g., 512 or 612) may be activated to circulate fluid through the IC side of bioreactor 300 at a third circulation flow rate. In at least one embodiment, fluid carrying the cells may pass through (the lumen of) hollow fibers of the bioreactor 300. In other embodiments, cells may be loaded into the EC side of the bioreactor 300 and have the fluid carrying the cells. In these embodiments, an EC circulation pump (e.g., 528, 628) may be activated to circulate fluid through the EC side of bioreactor 300 at the third circulation flow rate.

In embodiments, the third circulation flow rate may be less than the second circulation rate. In embodiments, the third circulation flow rate may be less than about 200 ml/min, less than about 150 ml/min, or even less than about 100 ml/min. In other embodiments, the third circulation rate may be greater than about 10 ml/min, greater than about 20 ml/min, or even greater than about 30 ml/min. In one embodiment, the third circulation flow rate is between about 20 ml/min and about 100 ml/min, such as about 50 ml/min.

In some embodiments, step 1444 may also involve circulation in a different direction than the circulation performed in step 1428. In other words, in some embodiments, step 1428 may involve circulating fluid in a clockwise direction. In some embodiments, the circulation at step 1444 may be similar to step 1408 and be in a counter clockwise direction (see IC loop in FIGS. 5 and 6). In other words, the circulation at step 1444 may flow opposite to the circulation at step 1428, and the same as the direction of circulation of step 1408. In other embodiments, the circulation in steps 1408, 1428, 1444 may flow in the same direction, clockwise or counter clockwise.

Optional step 1444 may in some embodiments involve also rotating the bioreactor 300 in a particular sequence to facilitate distribution of the cells through the bioreactor 300 and circulation paths of the CES to which the bioreactor 300 may be fluidly associated. In other embodiments, the circulating step 1444 may involve rotating the bioreactor 300 for some periods of time, but maintaining the bioreactor 300 stationary for other periods of time.

Flow passes from 1444 to step 1448, where, the fluid circulation rate is once again reduced. The circulation rate may be reduced to about zero (0) ml/min, or in other embodiments may be reduced to a rate that is above zero (0) ml/min but still allows cells to settle and attach to the bioreactor 300, e.g., an inside surface of hollow fibers of bioreactor 300. In embodiments, step 1448 may involve stopping or turning off one or more pumps used in step 1444 to circulate the fluid.

From step 1448, flow passes to step 1452 where the bioreactor is maintained in a horizontal orientation. In those embodiments that include step 1444 (rotate to first orientation), step 1452 will involve maintaining the first horizontal orientation. In those embodiments that do not include the rotation of step 1440, step 1452 will involve maintaining the second horizontal orientation. In any case, step 1452 is performed to allow cells to settle again, such as on portion 2108 (See FIGS. 21D and 21E; if the rotation step 1440 is performed). In embodiments, the cells will be allowed to settle for a third predetermined period of time that may be selected to not only allow the cells to settle, but also to attach.

In some embodiments, the third predetermined period of time may be long enough in duration to allow the cells to settle and attach to portion 2108. In these embodiments, the cells may only need to travel the distance of the inner diameter of hollow fiber 2100. For example, in embodiments where the hollow fiber 2100 has an inner diameter of between about 150 microns and about 300 microns, the third predetermined period of time may be less than about 20 minutes, less than about 15 minutes, or even less than about 10 minutes. In other embodiments, the third predetermined period of time may be greater than about 1 minute, greater than about 2 minutes, greater than about 3 minutes, or even greater than about 4 minutes. In one embodiment, the third period of time may be between about 3 minutes and about 8 minutes, such as about 5 minutes.

Figure 21F:
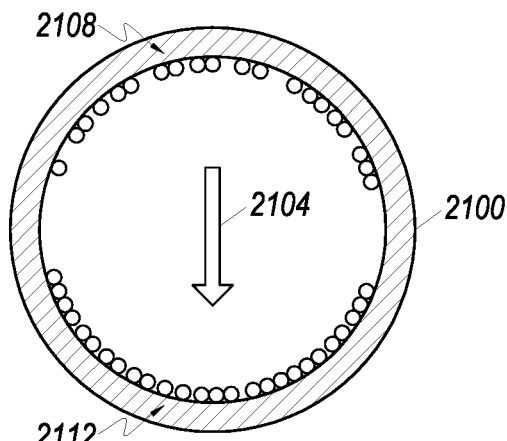

In some embodiments, flow 1400 may pass from step 1452 to step 1472 where the cells are expanded. FIG. 21F illustrates fiber 2100 in these embodiments. Flow would then end at 1476.

In other embodiments, as described below, flow 1400 may include additional rotation (1456), circulation (1460), reduce circulation (1464), and maintain orientation (1468) steps before moving to step 1472 where cells are expanded. In these embodiments, flow 1400 may pass from step 1452 to step 1456, where the bioreactor 300 is rotated back to the second horizontal orientation, if it was rotated at step 1440 to the first horizontal orientation. FIG. 17 illustrates bioreactor 300 in the second horizontal orientation. Step 1456 may be performed by one or more motors connected to bioreactor 300. These motors may be part of a rocking device. In some embodiments, this step may be unnecessary, if step 1440 was not performed to rotate the bioreactor to the first horizontal orientation.

Flow 1400 passes to step 1460 where fluid is again circulated but at a fourth circulation flow rate. Similar to steps 1408, 1428, and 1444, fluid is circulated through the bioreactor 300. In embodiments, step 1444 may involve activating one or more pumps to circulate fluid through the bioreactor 300, as noted above, an IC circulation pump (e.g., 512, 612) may be activated to circulate fluid through the IC side of bioreactor 300 at a fourth circulation flow rate. In at least one embodiment, fluid carrying the cells may pass through hollow fibers of the bioreactor 300. In other embodiments, cells may be loaded into the EC side of the bioreactor 300 and have the fluid carrying the cells. In these embodiments, an EC circulation pump (e.g., 528, 628) may be activated to circulate fluid through the EC side of bioreactor 300 at the fourth circulation flow rate.

In embodiments, the fourth circulation flow rate may be less than the third circulation rate. In embodiments, the fourth circulation flow rate may be less than about 100 ml/min, less than about 75 ml/min, or even less than about 50 ml/min. In other embodiments, the fourth circulation rate may be greater than about 5 ml/min, greater than about 10 ml/min, or even greater than about 15 ml/min. In one embodiment, the fourth circulation flow rate is between about 15 ml/min and about 35 ml/min, such as about 25 ml/min.

In some embodiments, step 1460 may also involve circulation in a different direction than the circulation performed in step 1444. In other words, in some embodiments, step 1444 may involve circulating fluid in a counter clockwise direction. In some embodiments, the circulation at step 1460 may be similar to step 1428 and be in a clockwise direction. In other words, the circulation at step 1460 may flow opposite to the circulation at step 1444, and the same as the direction of circulation of step 1428. In other embodiments, the circulation in steps 1408, 1428, 1444 and 1460 may flow in the same direction, clockwise or counter clockwise.

Step 1460 may in some embodiments involve also rotating the bioreactor 300 in a particular sequence to facilitate distribution of the cells through the bioreactor 300 and circulation paths of the CES to which the bioreactor 300 may be fluidly associated. In other embodiments, the circulating step 1460 may involve rotating the bioreactor 300 for some periods of time, but maintaining the bioreactor 300 stationary for other periods of time.

Flow passes from 1460 to step 1464, where, the fluid circulation rate is once again reduced. The circulation rate may be reduced to about zero (0) ml/min, or in other embodiments may be reduced to a rate that is above zero (0) ml/min but still allows cells to settle and attach to the bioreactor 300, e.g., an inside surface of hollow fibers of bioreactor 300. In embodiments, step 1464 may involve stopping or turning off one or more pumps used in step 1460 to circulate the fluid.

From step 1464, flow passes to step 1468 where the bioreactor is maintained in the second horizontal orientation to allow cells to settle on for example portion 2112 again (see FIG. 21F). In embodiments, the cells will be allowed to settle for a fourth predetermined period of time that may be selected to not only allow the cells to settle, but also to attach once again.

In some embodiments, the fourth predetermined period of time may be long enough in duration to allow the cells to settle and attach. In these embodiments, the cells may only need to travel the distance of the inner diameter of the hollow fiber, e.g., fiber 2100. For example, in embodiments where the hollow fiber 2100 has an inner diameter of between about 150 microns and about 300 microns, the fourth predetermined period of time may be less than about 20 minutes, less than about 15 minutes, or even less than about 10 minutes. In other embodiments, the fourth predetermined period of time may be greater than about 1 minute, greater than about 2 minutes, greater than about 3 minutes, or even greater than about 4 minutes. In one embodiment, the fourth period of time may be between about 3 minutes and about 8 minutes, such as about 5 minutes.

After step 1468, flow 1400 passes to step 1472 where the cells settled and attached to the bioreactor 300, e.g., to hollow fibers of the bioreactor, are expanded, i.e., multiplied. Flow 1400 then ends at 1476.

Without being bound by theory, it is believe that in embodiments, the cell expansion is improved if the steps of flow 1400 are performed. It is believed that these embodiments help to ensure that more portions of the bioreactor, e.g., surface of hollow fibers in the bioreactor, are seeded with cells prior to cell expansion. This may provide for more cells to initially be seeded, and ultimately may improve cell yield and reduce cell doubling time, as compared to conventional processes.

Although flow 1400 includes specific number of steps that provide for rotating, circulating, reducing circulation, and maintaining the orientation of the bioreactor, other embodiments are not limited to these specific number of steps. In other embodiments, even after step 1468, the bioreactor may be rotated again, circulation can be restarted again, followed by another period of reducing circulation to allow cells to settle and maintain the orientation for a period of time to allow cells to attach to portion of a bioreactor. These steps may be performed any number of times. In embodiments, each time the circulation is restarted, it is at a lower rate than the previous circulation. In other embodiments, the circulation rates may be the same each time circulation is started. In yet other embodiments, the direction of circulation may be changed, with circulation in a first direction, followed by stopping the circulation to allow the cells to settle and attach, circulation in a direction opposite the first direction (clockwise vs. counter clockwise) and again stopping the circulation to allow the cells to settle.

Referring back to FIG. 11, zones 1112, 1116, 1120 and 1124 represent fibers that may have fluid circulating through them at different flow rates. In other words, without being bound by theory, it is believed that circulation at relatively high flow rates, such as rates that may be used in circulation steps 1408 or 1428 (FIG. 14) may primarily flow through fibers in zone 1112. It is believed that the higher flow rates do not allow fluid to disperse enough to flow evenly into the hollow fibers in the outer zones. As the flow rate is reduced, such as in steps 1444 and 1460, it is believed that the fluid may disperse into hollow fibers in outer zones, such as 1116, 1120 and 1124.

It is believed that having steps 1408, 1428, 1444 and 1452 circulate at different flow rates, allows the fluid to flow through more of the hollow fibers 1108 than if just a single flow rate would be used. In one embodiment of a process that follows flow chart 1400, at step 1408 (at the flow rates described above), fluid may flow through the hollow fibers in zone 1112. At step 1428 (at the flow rates described above), fluid may flow through the hollow fibers in both zones 1112 and 1116 because the rate is slower and the fluid may disperse more. At step 1444 (at the flow rates described above), fluid may flow through the hollow fibers in zones 1112, 1116, and 1120 because the flow rate is yet slower and fluid may disperse even more. At step 1452 (at the flow rates described above), fluid may flow through the hollow fibers in all the zones 1112, 1116, 1120 and 1124 because the flow rates are even slower and the fluid may disperse through all of the fibers in the various zones. Thus, it is believe that fluid with the cells may flow into more of the hollow fibers using a sequence of different flow rates, than if a single high flow rate circulation is used.

Furthermore, it is also believed that the different flow rates may also affect the longitudinal distribution of cells along the bioreactor, e.g., along a hollow fiber. That is, a higher flow rate may allow cells to flow further along inside a hollow fiber. For example, at a higher flow rate, a cell being carried by fluid may reach beyond half the length of the hollow fiber. At a lower flow rate, a cell being carried by fluid may reach half the length of the hollow fiber. At even a lower flow rate, a cell being carried by fluid may reach less than half the length of the hollow fiber. Accordingly, in some embodiments, it is believed that the use of different flow rates may provide some improvement in longitudinal distribution of cells along the length of the bioreactor, e.g., a hollow fiber.

Figure 22:
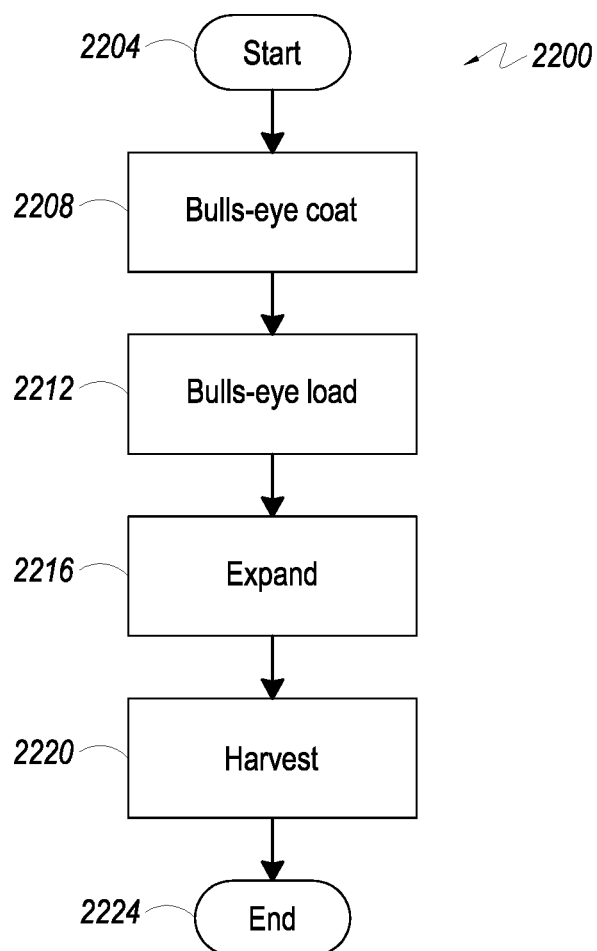
FIG. 22 is a flow chart of a process for coating, loading, distributing, attaching, and expanding cells according to some embodiments.

Referring now to FIG. 22, flow 2200 illustrates a process of expanding cells according to some embodiments of the present disclosure. Flow 2200 starts at 2204 and passes to step 2208 where a bulls-eye coat process is performed on a CES (e.g., CES 500 and/or CES 600) to coat portions of a bioreactor (bioreactors 501, 601). In embodiments, step 2208 may involve performing steps of one or more of the processes described above with respect to flows 1000, 1200, and/or 1300, which may be referred to as bulls-eye coating processes. As described in detail above, flows 1000, 1200, and/or 1300 provide for changing flow rates, changing direction of flows, and/or rotating of a bioreactor to improve the distribution of a coating reagent in a bioreactor. As described above, changing flow rates, changing direction of flows, and/or rotating of a bioreactor may allow interior surfaces of hollow fibers (in a hollow fiber bioreactor) to be more completely coated during a coating process.

From step 2208, flow 2200 passes to steps 2212 where a bulls-eye cell load process is performed on the CES (e.g., CES 500 and/or CES 600) to load cells into the bioreactor (bioreactors 501, 601). In embodiments, step 2212 may involve performing steps of one or more of the processes described above with respect to flow 1400, which may be referred to as a bulls-eye cell loading process. As described in detail above, flow 1400 provides for changing flow rates, changing direction of flows, and/or rotating of a bioreactor to improve the distribution of cells loaded/attached in a bioreactor. As described above, changing flow rates, changing direction of flows, and/or rotating of a bioreactor may allow cells to be more uniformly distributed on interior surfaces of hollow fibers (in a hollow fiber bioreactor).

After step 2212, flow passes to step 2216 where cell are expanded. In embodiments, the expanding of cells may involve a number of steps. For example, step 2216 may involve performing one or more of the steps described above with respect to step 718 in flow 700 (FIG. 7), e.g., feeding of cells.

At step 2220 cells expanded at step 2216 are harvested. In embodiments, the harvesting of cells may involve a number of steps. For example, step 2220 may involve performing one or more of the steps described above with respect to step 722 in flow 700 (FIG. 7). Flow 2220 ends at 2224.

With respect to the processes illustrated in FIGS. 7-10, 12-14, and 22, the operational steps depicted are offered for purposes of illustration and may be rearranged, combined into other steps, used in parallel with other steps, etc., according to embodiments of the present disclosure. Fewer or additional steps may be used in embodiments without departing from the spirit and scope of the present disclosure. Also, steps (and any sub-steps), such as priming, coating a bioreactor, loading cells, for example, may be performed automatically in some embodiments, such as by a processor executing custom and/or pre-programmed tasks stored in memory.

Examples and further description of tasks and protocols, including custom tasks and pre-programmed tasks, for use with a cell expansion system are provided in U.S. patent application Ser. No. 13/269,323 ("Configurable Methods and Systems of Growing and Harvesting Cells in a Hollow Fiber Bioreactor System," filed Oct. 7, 2011, now U.S. Pat. No. 9,725,689) and U.S. patent application Ser. No. 13/269,351 ("Customizable Methods and Systems of Growing and Harvesting Cells in a Hollow Fiber Bioreactor System," filed Oct. 7, 2011, now U.S. Pat. No. 9,677,042), which applications are hereby incorporated by reference herein in their entireties for all that they teach and for all purposes.

Figure 23:
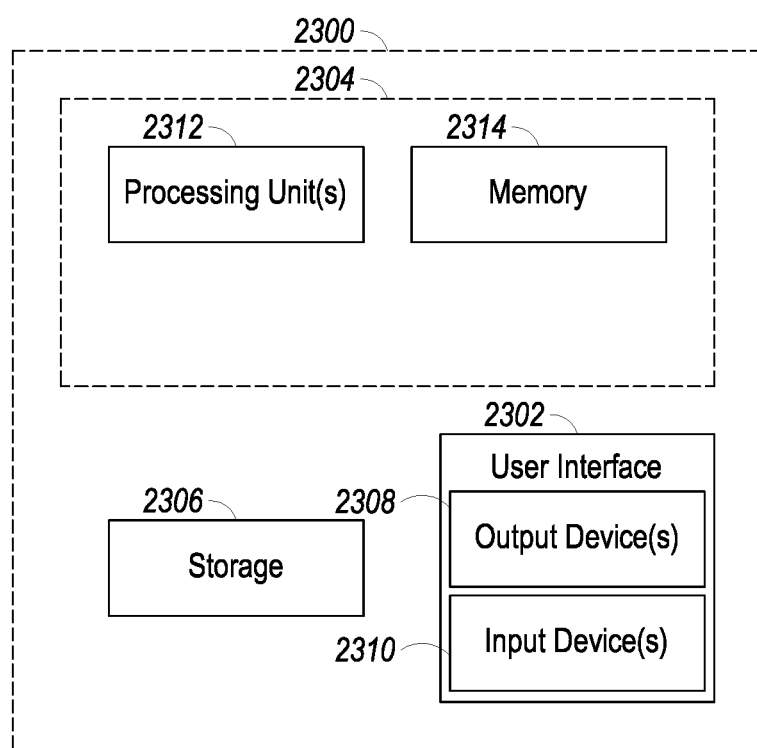
FIG. 23 illustrates an example processing system of a cell expansion system upon which embodiments of the present disclosure may be implemented.
Figure 24:
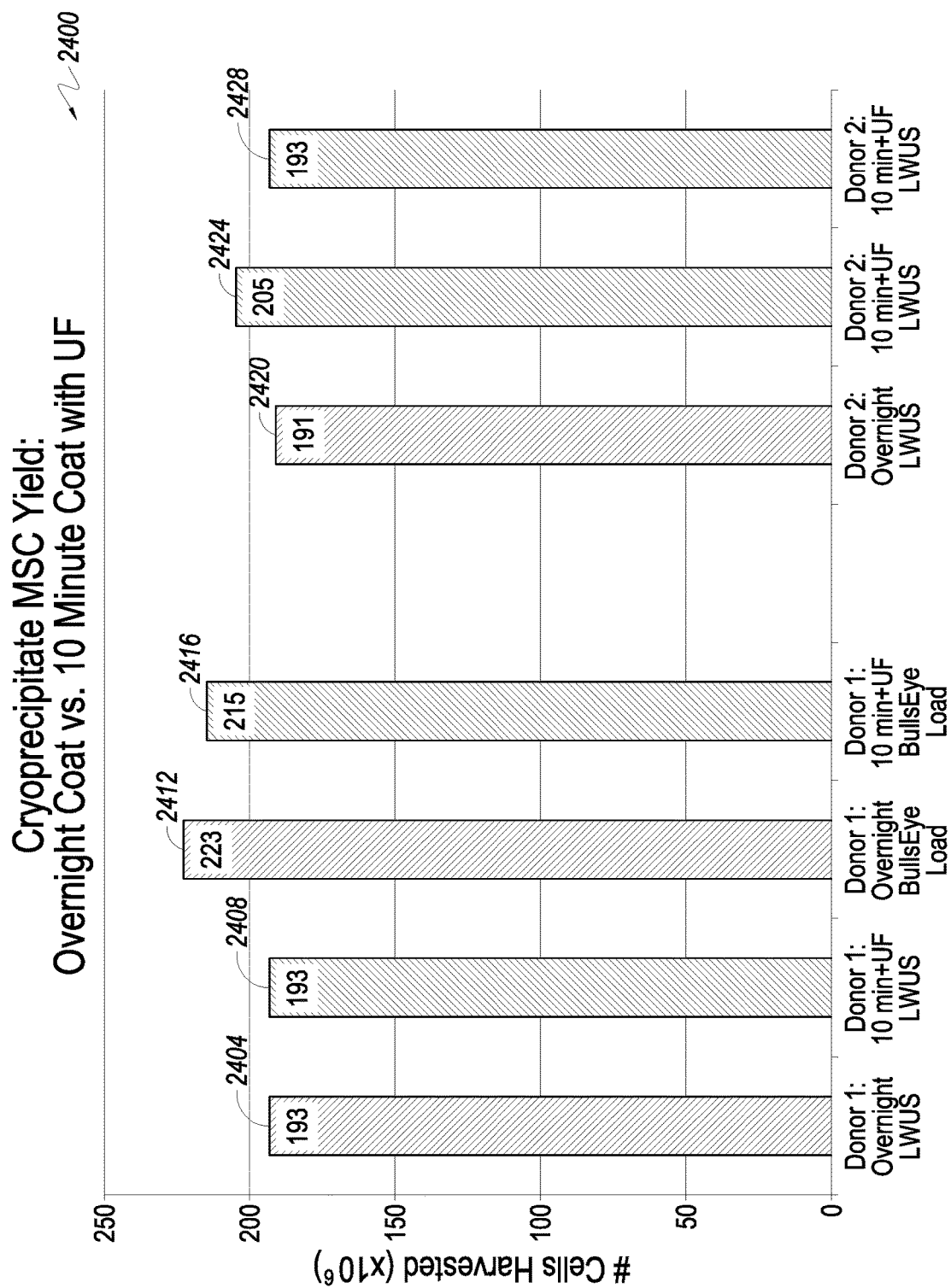
FIG. 24 depicts example cell yields using a coating application(s) in accordance with embodiments of the present disclosure.
Figure 25A:
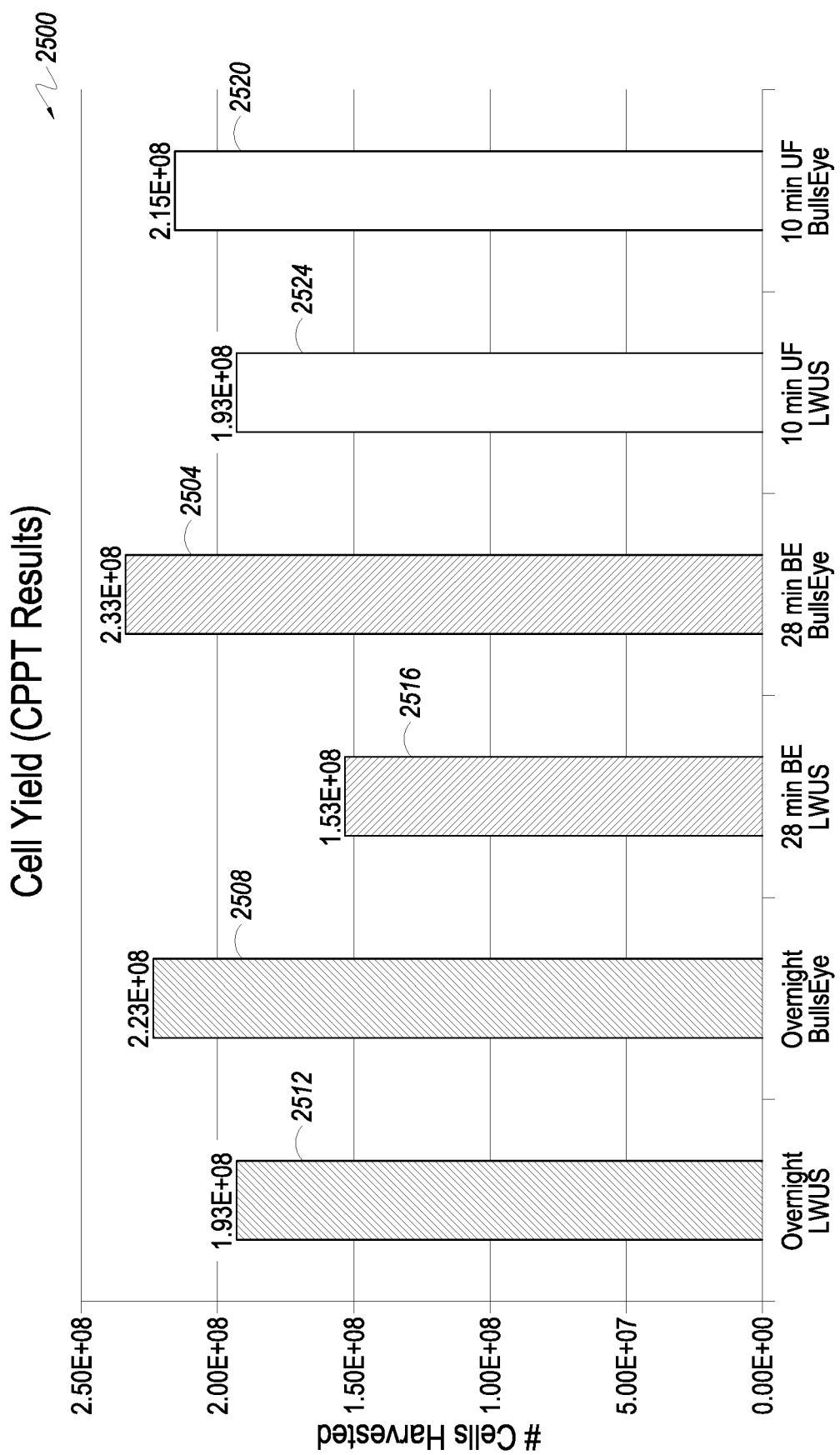
FIG. 25A illustrates example results of expanding cells using various coating and cell loading procedures in accordance with embodiments of the present disclosure.
Figure 25B:
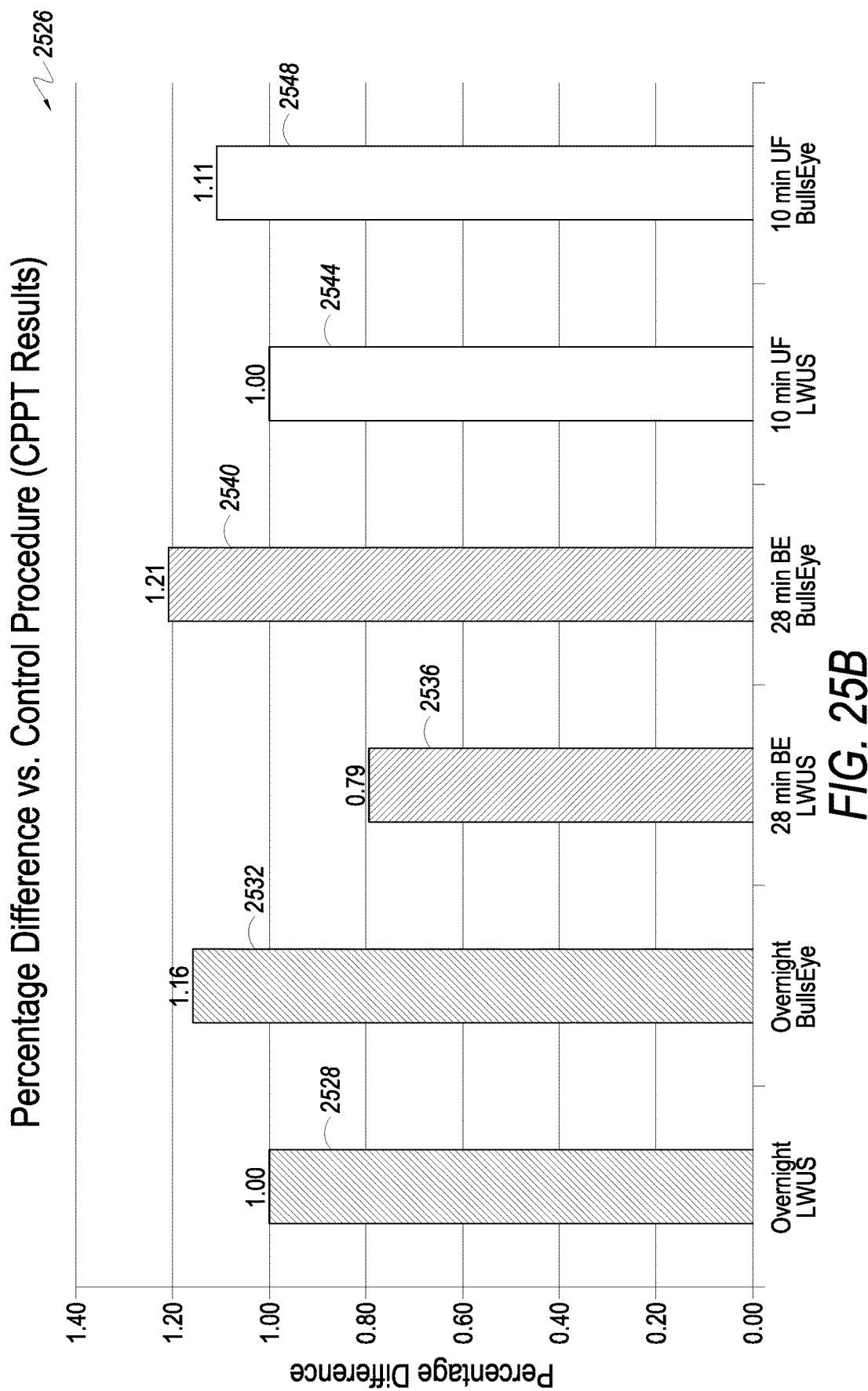
FIG. 25B depicts example results of expanding cells using various coating and cell loading procedures in accordance with embodiments of the present disclosure.
Figure 26A:
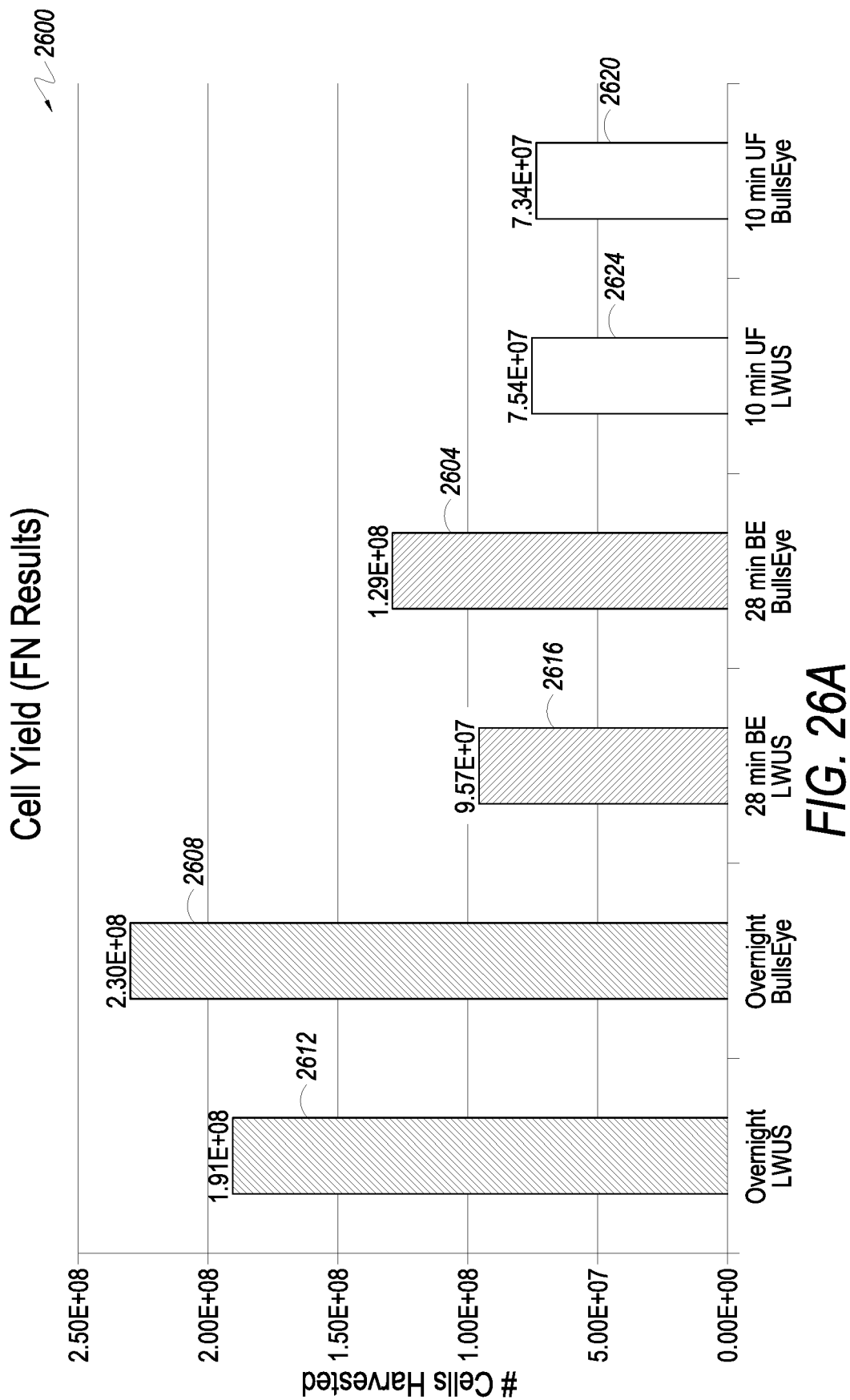
FIG. 26A illustrates example results of expanding cells using various coating and cell loading procedures in accordance with embodiments of the present disclosure.
Figure 26B:
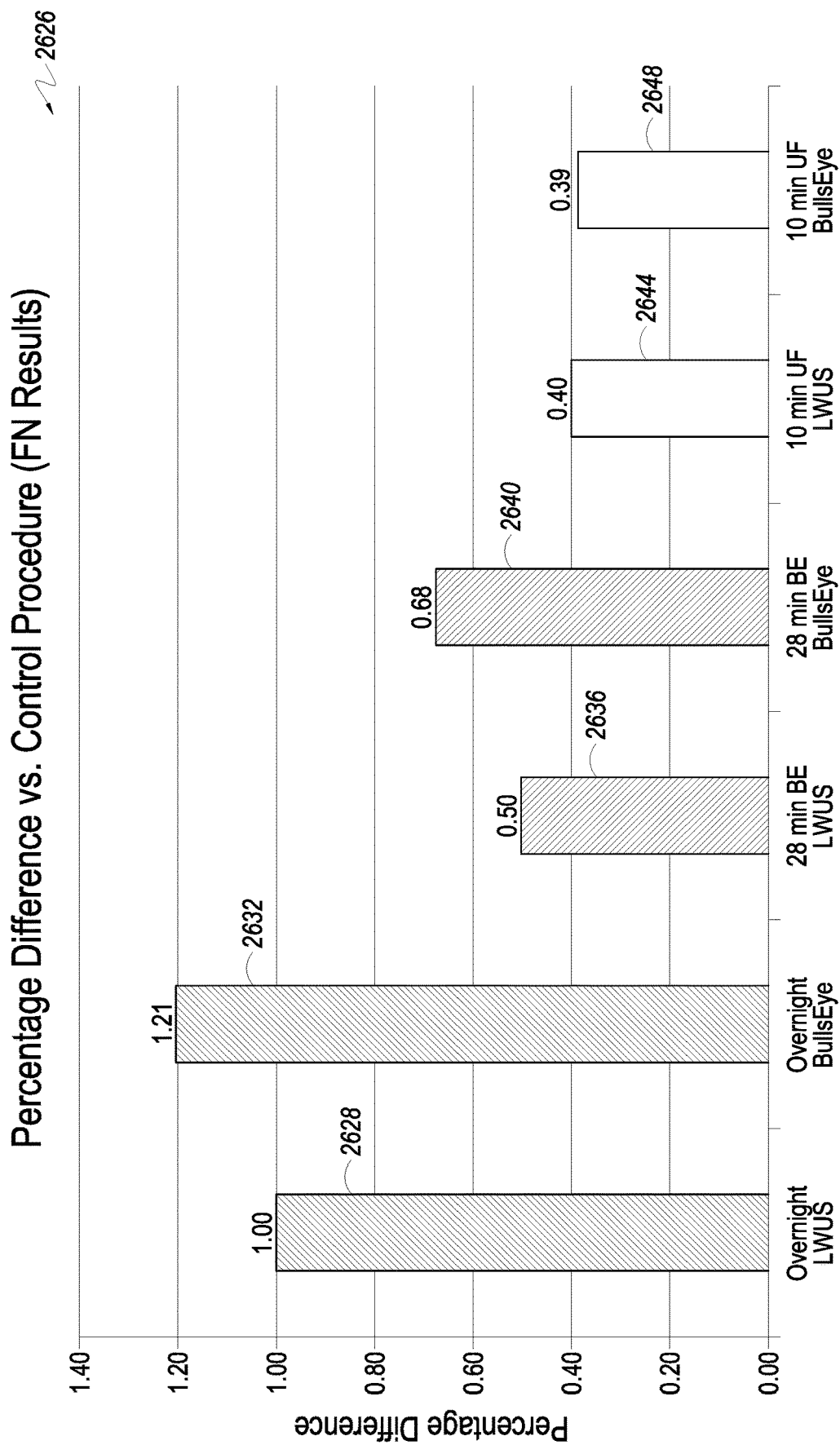
FIG. 26B depicts example results of expanding cells using various coating and cell loading procedures in accordance with embodiments of the present disclosure.
Figure 27A:
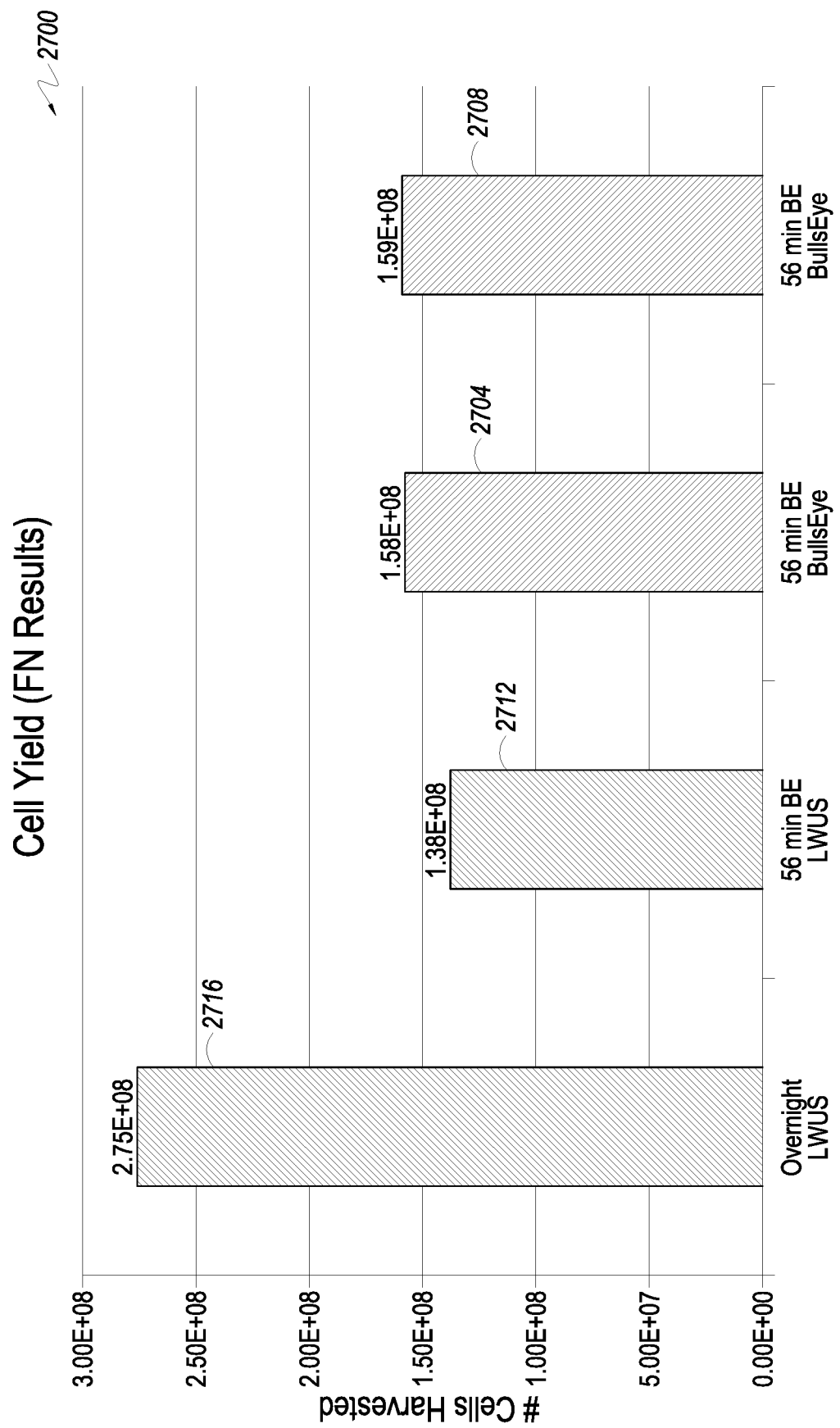
FIG. 27A illustrates example results of expanding cells using various coating and cell loading procedures in accordance with embodiments.
Figure 27B:
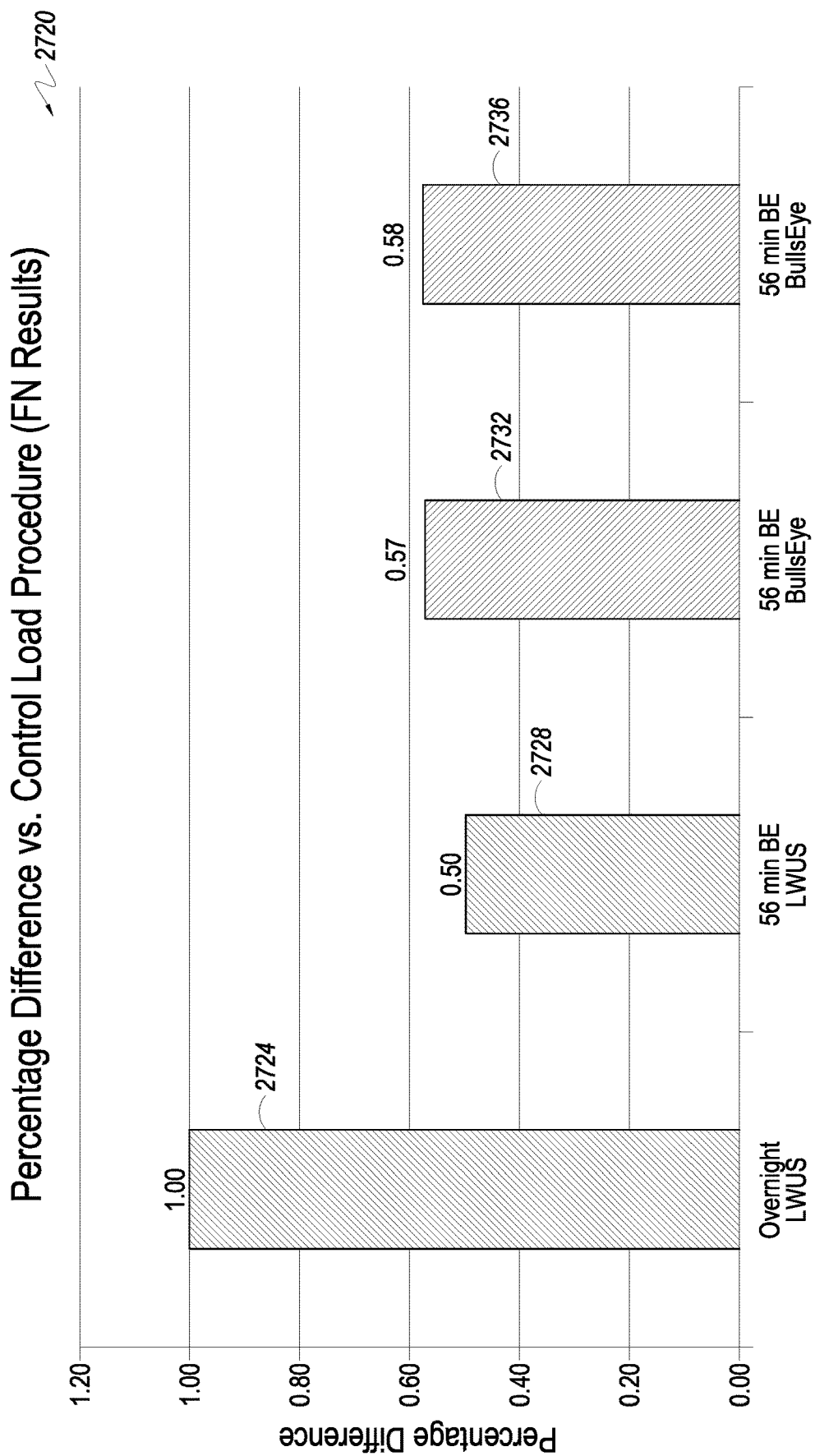
FIG. 27B depicts example results of expanding cells using various coating and cell loading procedures in accordance with embodiments.

Next, FIG. 23 illustrates example components of a computing system 2300 upon which embodiments of the present disclosure may be implemented. Computing system 2300 may be used in embodiments, for example, where a cell expansion system uses a processor to execute tasks, such as custom tasks or pre-programmed tasks performed as part of a process, such as process 700, 800, 900, 916, 1000, 1200, 1300, 1400 and/or 2200 described above. In embodiments, pre-programmed tasks may include, "IC/EC Washout" task and/or "Feed Cells" task, for example.

The computing system 2300 may include a user interface 2302, a processing system 2304, and/or storage 2306. The user interface 2302 may include output device(s) 2308, and/or input device(s) 2310 as understood by a person of skill in the art. Output device(s) 2308 may include one or more touch screens, in which the touch screen may comprise a display area for providing one or more application windows. The touch screen may also be an input device 2310 that may receive and/or capture physical touch events from a user or operator, for example. The touch screen may comprise a liquid crystal display (LCD) having a capacitance structure that allows the processing system 2304 to deduce the location(s) of touch event(s), as understood by those of skill in the art. The processing system 2304 may then map the location of touch events to UI elements rendered in predetermined locations of an application window. The touch screen may also receive touch events through one or more other electronic structures, according to embodiments. Other output devices 2308 may include a printer, speaker, etc. Other input devices 2310 may include a keyboard, other touch input devices, mouse, voice input device, etc., as understood by a person of skill in the art.

Processing system 2304 may include a processing unit 2312 and/or a memory 2314, according to embodiments of the present disclosure. The processing unit 2312 may be a general purpose processor operable to execute instructions stored in memory 2314. Processing unit 2312 may include a single processor or multiple processors, according to embodiments. Further, in embodiments, each processor may be a multi-core processor having one or more cores to read and execute separate instructions. The processors may include general purpose processors, application specific integrated circuits (ASICs), field programmable gate arrays (FPGAs), other integrated circuits, etc., as understood by a person of skill in the art.

The memory 2314 may include any short-term or long-term storage for data and/or processor executable instructions, according to embodiments. The memory 2314 may include, for example, Random Access Memory (RAM), Read-Only Memory (ROM), or Electrically Erasable Programmable Read-Only Memory (EEPROM), as understood by a person of skill in the art. Other storage media may include, for example, CD-ROM, tape, digital versatile disks (DVD) or other optical storage, tape, magnetic disk storage, magnetic tape, other magnetic storage devices, etc., as understood by a person of skill in the art.

Storage 2306 may be any long-term data storage device or component. Storage 2306 may include one or more of the systems described in conjunction with the memory 2314, according to embodiments. The storage 2306 may be permanent or removable. In embodiments, storage 2306 stores data generated or provided by the processing system 2304.

EXAMPLES

Results for some examples of protocols/methods/processes that may be used with a cell expansion system, such as CES 500 (FIG. 5) and/or CES 600 (FIG. 6) that implement aspects of the embodiments such as those shown in FIGS. 700, 800, 900, and/or 916, 1000, 1200, 1300, 1400 and/or 2200 are described below. Although specific features may be described in the examples, such examples are provided merely for illustrative and descriptive purposes. For example, while examples may provide for the expansion of MSCs, other cell types may be used in other embodiments. The present embodiments are not limited to the examples provided herein.

It is noted that the example protocols/methods/processes are provided for illustrative purposes and are not intended to limit other embodiments, which may include different or additional steps, parameters, or other features. The example protocols/methods/processes, including the steps (and any sub-steps), may be performed automatically in some embodiments, such as by a processor executing custom tasks or pre-programmed tasks stored in memory. In other embodiments, the steps (and any sub-steps) may be performed through the combination of automated and manual execution of operations. In further embodiments, the steps (and any sub-steps) may be performed by an operator(s) or user(s) or through other manual means.

Some examples provide example data from embodiments providing for the expansion of cells using various coating procedures, various cell loading procedures, various coating materials (e.g., cryoprecipitate (CPPT), fibronectin (FN)), and/or combination(s) of such procedures and/or materials. Such procedures include, for example: positive ultrafiltration coating procedure; positive ultrafiltration coating procedure with a bulls-eye (BE) cell load procedure; positive ultrafiltration coating procedure with a load cells with uniform suspension (LWUS) cell loading procedure; overnight coating with cryoprecipitate; overnight coating with fibronectin; bulls-eye coating procedure; 28-minute bulls-eye coating procedure; etc. Examples and further description of a bulls-eye coating procedure(s) are provided in an application U.S. patent application Ser. No. 15/616,745, now U.S. Pat. No. 10,577,575, entitled, "Coating a Bioreactor," filed on Jun. 7, 2017, which similar to the present application, also claims priority to U.S. Provisional Application Ser. No. 62/347,012, entitled "Coating a Bioreactor," and filed on Jun. 7, 2016. Examples of other coating processes/steps that, in embodiments, may be utilized in combination with the embodiments described herein are described in U.S. patent application Ser. No. 15/616,635, entitled "METHODS AND SYSTEMS FOR COATING A CELL GROWTH SURFACE," filed Jun. 7, 2017, which similar to the present application also claims priority to U.S. Provisional Patent Application No. 62/347,025, entitled "GROWTH SURFACE COATING," filed Jun. 7, 2016. These applications are hereby incorporated by reference in their entireties for all that they teach and for all purposes. As described above, examples and further description of a bulls-eye cell loading procedure(s) are provided in U.S. patent application Ser. No. 14/542,276 (U.S. Pat. No. 9,617,506), entitled, "Expanding Cells in a Bioreactor," issued on Apr. 11, 2017, which is hereby incorporated by reference herein in its entirety for all that it teaches and for all purposes.

Example 1

Below is an example of a protocol that may be used for implementing embodiments of flows 1000, 1200, and/or 1300 on CES systems such as CES 500, 600. Although specific settings are shown and described below, other embodiments may provide for different values.

Day: 0 Bulls-Eye Coat Bioreactor

Purpose: coats the bioreactor membrane with a reagent.

Step 1: loads a reagent into the IC loop until the bag is empty.

Step 2: chases the reagent from the ARC into the IC loop.

Step 3: coats the bioreactor using +UFR.

Before starting this task, the following preconditions may be satisfied:

Coating is preceded by system prime with RT PBS; and
Include 40 mL or more of air in the cell inlet bag.

Table 24 describes the bags of solution attached to each line when performing Coat Bioreactor. These solutions and corresponding volumes are based on some settings for this task.

TABLE 24

Solutions for Coat Bioreactor

| Bag | Solution in Bag | Volume (estimation) |
|---|---|---|
| Cell Inlet | None | N/A |
| Reagent | CPPT or Fibronectin | 6-25 mL CPPT in 100 mL total volume w/PBS or 5 mg Fibronectin in 100 mL total volume w/PBS |
| IC Media | None | N/A |
| Wash | PBS | 1 L |
| EC Media | None | N/A |

Coat Bioreactor pathway: Task>System Management>Coat Bioreactor

1 Enter the values for each setting for step 1 shown in Table 25.

TABLE 25

Step 1 for Coat Bioreactor

| Setting | Factory | Laboratory | Modifications |
|---|---|---|---|
| IC Inlet | Reagent | | |
| IC Inlet Rate | 10 mL/min | | |
| IC Circulation Rate | 100 mL/min | | |
| EC Inlet | None | | |
| EC Inlet Rate | 0 mL/min | | |
| EC Circulation Rate | 30 mL/min | | |
| Outlet | EC Outlet | | |
| Rocker Control | Stationary (0°) | | |
| Stop Condition | Empty Bag | | |

2 Enter the values for each setting for step 2 shown in Table 26.

TABLE 26

Step 2 Settings for Coat Bioreactor

| Setting | Factory | Laboratory | Modifications |
|---|---|---|---|
| IC Inlet | Wash | | |
| IC Inlet Rate | 10 mL/min | | |
| IC Circulation Rate | 100 mL/min | | |
| EC Inlet | None | | |
| EC Inlet Rate | 0 mL/min | | |
| EC Circulation Rate | 30 mL/min | | |
| Outlet | EC Outlet | | |
| Rocker Control | Stationary (0°) | | |
| Stop Condition | IC Volume (22 mL) | | |

3 Enter the values for each setting for step 3 shown in Table 27.

TABLE 27

Step 3 Settings for Coat Bioreactor

| Setting | Factory | Laboratory Modifications |
|---|---|---|
| IC Inlet | None | |
| IC Inlet Rate | 0 mL/min | |
| IC Circulation Rate | ~~20 mL/min~~ | −300 mL/min |
| EC Inlet | Wash | |
| EC Inlet Rate | 0.1 mL/min | |
| EC Circulation Rate | 30 mL/min | |
| Outlet | EC Outlet | |
| Rocker Control | Stationary (180°) | |
| Stop Condition | ~~Manual~~ | 4 min |

4 Enter the values for each setting for step 4 shown in Table 28.

TABLE 28

Step 4 Settings for Coat Bioreactor

| Setting | Factory | Laboratory Modifications |
|---|---|---|
| IC Inlet | None | |
| IC Inlet Rate | 0 mL/min | |
| IC Circulation Rate | 0 mL/min | 250 mL/min |
| EC Inlet | Wash | |
| EC Inlet Rate | 0.1 mL/min | |
| EC Circulation Rate | 30 mL/min | |
| Outlet | EC Outlet | |
| Rocker Control | Stationary (0°) | |
| Stop Condition | ~~Manual~~ | 4 min |

5 Enter the values for each setting for step 5 shown in Table 29.

TABLE 29

Step 5 Settings for Coat Bioreactor

| Setting | Factory | Laboratory Modifications |
|---|---|---|
| IC Inlet | None | |
| IC Inlet Rate | 0 mL/min | |
| IC Circulation Rate | ~~20 mL/min~~ | −200 mL/min |
| EC Inlet | Wash | |
| EC Inlet Rate | 0.1 mL/min | |
| EC Circulation Rate | 30 mL/min | |
| Outlet | EC Outlet | |
| Rocker Control | Stationary (180°) | |
| Stop Condition | ~~Manual~~ | 4 min |

6 Enter the values for each setting for step 6 shown in Table 30.

TABLE 30

Step 6 Settings for Coat Bioreactor

| Setting | Factory | Laboratory Modifications |
|---|---|---|
| IC Inlet | None | |
| IC Inlet Rate | 0 mL/min | |
| IC Circulation Rate | ~~20 mL/min~~ | 150 mL/min |
| EC Inlet | Wash | |
| EC Inlet Rate | 0.1 mL/min | |
| EC Circulation Rate | 30 mL/min | |
| Outlet | EC Outlet | |
| Rocker Control | Stationary (0°) | |
| Stop Condition | ~~Manual~~ | 4 min |

7 Enter the values for each setting for step 7 shown in Table 31.

TABLE 31

Step 7 Settings for Coat Bioreactor

| Setting | Factory | Laboratory Modifications |
|---|---|---|
| IC Inlet | None | |
| IC Inlet Rate | 0 mL/min | |
| IC Circulation Rate | ~~20 mL/min~~ | −100 mL/min |
| EC Inlet | Wash | |
| EC Inlet Rate | 0.1 mL/min | |
| EC Circulation Rate | 30 mL/min | |
| Outlet | EC Outlet | |
| Rocker Control | Stationary (180°) | |
| Stop Condition | ~~Manual~~ | 4 min |

8 Enter the values for each setting for step 8 shown in Table 32.

TABLE 32

Step 8 Settings for Coat Bioreactor

| Setting | Factory | Laboratory Modifications |
|---|---|---|
| IC Inlet | None | |
| IC Inlet Rate | 0 mL/min | |
| IC Circulation Rate | ~~20 mL/min~~ | 50 mL/min |
| EC Inlet | Wash | |
| EC Inlet Rate | 0.1 mL/min | |
| EC Circulation Rate | 30 mL/min | |
| Outlet | EC Outlet | |
| Rocker Control | Stationary (0°) | |
| Stop Condition | ~~Manual~~ | 4 min |

9 Enter the values for each setting for step 9 shown in Table 33.

TABLE 33

Step 9 Settings for Coat Bioreactor

| Setting | Factory | Laboratory Modifications |
|---|---|---|
| IC Inlet | None | |
| IC Inlet Rate | 0 mL/min | |
| IC Circulation Rate | ~~20 mL/min~~ | −25 mL/min |
| EC Inlet | Wash | |
| EC Inlet Rate | 0.1 mL/min | |
| EC Circulation Rate | 30 mL/min | |
| Outlet | EC Outlet | |
| Rocker Control | Stationary (180°) | |
| Stop Condition | ~~Manual~~ | 4 min |

Example 2

Example results of expanding cells using a coating procedure(s) with, for example, the above methods 800, 1000, and/or 1100 and/or with systems 500, 600, are shown in graph 1600 of FIG. 16, in accordance with embodiments of the present disclosure. For example, such cell growth surface coating and resulting cell expansion may use the QUANTUM® Cell Expansion System manufactured by Terumo BCT, Inc. in Lakewood, Colo. FIG. 16 illustrates example results for coating a cell growth surface through a coating procedure with ultrafiltration, e.g., about 10-minute positive ultrafiltration coating procedure (10 min +UF), versus an overnight circulating coating procedure. As shown in graph 1600 of FIG. 16, example results may be provided for using cryoprecipitate (CPPT) as a coating agent.

Example comparison results may also be provided (not shown in FIG. 16) for using fibronectin (FN) as a coating agent. In this example, two donors, e.g., Donor 1 and Donor 2, may be used to determine an MSC harvest yield. Donor 1 data includes both a Load Cells with Uniform Suspension cell loading procedure (LWUS) and a bulls-eye cell loading procedure (BullsEye Load). Donor 2 data includes results for using a load with uniform suspension cell loading procedure (LWUS).

For Donor 1 and Donor 2, 5×106 MSC may be loaded into a bioreactor, e.g., bioreactor 501, 601, preconditioned with cell culture media comprised of αMEM+GlutaMAX (Gibco CAT #32561102) and 10% FBS (Hyclone CAT #5H30070.03). Donor 1 MSC may be cultured for 6.8 days and Donor 2 MSC may be cultured for 6.9 days. For Donor 1, n=1 (where n=number of machines or CESs, e.g., QUANTUM® Systems) for both overnight-coated and 10-minute coated bioreactors. For Donor 2, n=1 for the overnight-coated CES, e.g., QUANTUM® System, and n=2 for the two 10-minute coated CESs, e.g., QUANTUM® Systems.

Harvest yields for Donor 1 QUANTUM® System runs may both be observed to be 1.93×108 MSC. For example, overnight coating with load with uniform suspension cell loading procedure (LWUS) may yield 193×106 MSC 1604; and 10-minute ultrafiltration coating with load with uniform suspension cell loading procedure (LWUS) may yield 193×106 MSC 1608. To confirm efficacy of the 10-minute coating technique with other cell load protocols, an additional comparison may be made between QUANTUM® Systems loaded using the bulls-eye cell loading procedure (BullsEye Load). The Donor 1 MSC yield for the Overnight coated with bulls-eye cell loading may be observed to be 223×106 MSC 1612, and MSC yield for the 10-minute ultrafiltration coat with bulls-eye cell loading procedure (BullsEye Load) may be observed to be 215×106 MSC 1616. The Donor 2 MSC expansion may be observed to yield 191×106 MSC 1620 from the Overnight coated QUANTUM® System (n=1) with load with uniform suspension cell loading procedure (LWUS), and 205×106 MSC 1624 and 193×106 MSC 1628, respectively, for the two runs of 10-minute ultrafiltration coated QUANTUM® Systems (n=2) with load with uniform suspension cell loading procedure (LWUS).

Example results (not shown in FIG. 16) may also be provided for using fibronectin (FN) as a coating agent with similar methods and systems as described above. Cell yields for 10-minute ultrafiltration FN coated QUANTUM® Systems may be observed to be in the range of 40% to 50% of Overnight-coated harvests.

Example 3

Example results of expanding cells by coating a cell growth surface of a cell expansion system, such as CES 500 (FIG. 5) and/or CES 600 (FIG. 6), for example, with various coating procedures are illustrated in FIGS. 17A and 17B. For example, such cell growth surface coating and resulting cell expansion may use the QUANTUM® Cell Expansion System manufactured by Terumo BCT, Inc. in Lakewood, Colo. FIGS. 17A and 17B illustrate example results for coating a cell growth surface through a coating procedure with ultrafiltration, e.g., about 10-minute ultrafiltration coating procedure (10 min UF), versus coating using an overnight circulating coating procedure or a bulls-eye coating procedure, e.g., a 28-minute modified bulls-eye coating procedure (28 min BE). For example, a 10-minute positive ultrafiltration coating procedure may be used. In such procedures, 5 million MSCs may be loaded into the system, and 25 mL of a cryoprecipitate solution may be used for coating the cell growth surface of a hollow fiber bioreactor. The 28-minute bulls-eye coating time period used to coat the hollow fibers, e.g., fibers 812 (FIG. 8B), may be divided into seven (7) different time periods, each division being four (4) minutes long. During each 4-minute divisional time period, the circulation rate for the IC loop 502, 602 may be changed by adjusting the rate and/or direction of the circulation pump 512, 612. For example, the direction and/or circulation rate for the pump 512, 612 for each subsequent time division may be −300 mL/min, 250 mL/min, −200 mL/min, 150 mL/min, −100 mL/min, 50 mL/min, and −25 mL/min. The results from using these coating procedures with cryoprecipitate (CPPT) may be as shown in FIGS. 17A and 17B.

FIGS. 17A and 17B illustrate example results of using CPPT to coat the cell growth surface of a plurality of hollow fibers using various coating and cell loading procedures, and combinations thereof. As shown in graph 1700 of FIG. 17A, the 28-minute bulls-eye coating procedure (28 min BE) with bulls-eye cell loading procedure (BullsEye) may outperform the following procedures: the 28-minute bulls-eye coating procedure (28 min BE) with load with uniform suspension cell loading procedure (LWUS); the Overnight (o/n) coating procedure with load with uniform suspension cell loading procedure (LWUS); the Overnight coating procedure with bulls-eye cell loading procedure (BullsEye); the 10-minute ultrafiltration coating procedure (10 min UF) with load with uniform suspension cell loading procedure (LWUS); and the 10-minute ultrafiltration coating procedure (10 min UF) with bulls-eye cell loading procedure (BullsEye).

As shown in graph 1700 of FIG. 17A, the 28-minute bulls-eye coating procedure (28 min BE) procedure with bulls-eye cell loading procedure (BullsEye) may yield 2.33×108 cells 1704 while the Overnight coating procedure with bulls-eye cell loading procedure (BullsEye) may yield 2.23×108 cells 1708. The Overnight coating procedure with load with uniform suspension cell loading procedure (LWUS) may yield 1.93×108 cells 1712, while the 28-minute bulls-eye coating (28 min BE) procedure with load with uniform suspension cell loading procedure (LWUS) may yield 1.53×108 cells 1716. A 10-minute ultrafiltration procedure (10 min UF) with bulls-eye cell loading procedure (BullsEye) may result in 2.15×108 cells 1720, while a 10-minute ultrafiltration coating procedure (10 min UF) LWUS procedure may yield 1.93×108 cells 1724.

These example yields are compared in FIG. 17B. Graph 1726 of FIG. 17B illustrates a percentage difference versus control procedure using cryoprecipitate (CPPT) as a coating agent in various coating procedures and cell loading procedures, and combinations thereof. As shown in graph 1726 of FIG. 17B, compared to the Overnight coating procedure with load with uniform suspension cell loading procedure (LWUS) 1728, the Overnight coating procedure with bulls-eye cell loading procedure (BullsEye) may yield 16% 1732 more cells; the 28-minute bulls-eye coating (28 min BE) procedure with load with uniform suspension cell loading procedure (LWUS) may yield 21% 1736 fewer cells; the 28-minute bulls-eye coating procedure (28 min BE) with bulls-eye cell loading procedure (BullsEye) may yield 21% 1740 more cells; the 10-minute ultrafiltration coating procedure (10 min) with load with uniform suspension cell loading procedure (LWUS) may yield substantially the same number 1744 of cells; and the 10-minute ultrafiltration coating procedure (10 min) with bulls-eye cell loading procedure (BullsEye) may yield 11% 1748 more cells.

Example 4

Example results of expanding cells by coating a cell growth surface of a cell expansion system, such as CES 500 (FIG. 5) and/or CES 600 (FIG. 6), for example, with various coating procedures are illustrated in FIGS. 18A and 18B. For example, such cell growth surface coating and resulting cell expansion may use the QUANTUM® Cell Expansion System manufactured by Terumo BCT, Inc. in Lakewood, Colo. FIGS. 18A and 18B illustrate example results for coating a cell growth surface through a coating procedure with ultrafiltration, e.g., about 10-minute ultrafiltration coating procedure (10 min UF), versus coating using an overnight circulating coating procedure, or a bulls-eye coating (BE) procedure, e.g., a 28-minute modified bulls-eye coating procedure (28 min BE). For example, a 10-minute positive ultrafiltration coating procedure may be used. In such procedures, 5 million MSCs may be loaded into the system, and a 5 mg fibronectin (FN) solution may be used for coating the cell growth surface of a hollow fiber bioreactor. In an embodiment, such 5 mg FN solution may be circulated at 20 mL/minute. In the QUANTUM® System, such 5 mg FN solution may be circulated at 20 mL/minute in the 189 mL IC loop, according to an embodiment. The 28-minute bulls-eye coating time period used to coat the hollow fibers, e.g., fibers 908 (FIG. 9), may be divided into seven (7) different time periods, each division being four (4) minutes long. During each 4-minute divisional time period, the circulation rate for the IC loop 502, 602 may be changed by adjusting the rate and/or direction of the circulation pump 512, 612. For example, the direction and/or circulation rate for the pump 512, 612 for each subsequent time division may be −300 mL/min, 250 mL/min, −200 mL/min, 150 mL/min, −100 mL/min, 50 mL/min, and −25 mL/min. The results from using these coating procedures with fibronectin (FN) may be as shown in FIGS. 18A and 18B.

FIGS. 18A and 18B illustrate example results of using FN to coat the cell growth surface of a plurality of hollow fibers using various coating and cell loading procedures, and combinations thereof.

The Overnight coating procedure with bulls-eye cell loading procedure (BullsEye) may outperform the following: the Overnight coating procedure with load with uniform suspension cell loading procedure (LWUS); the 28-minute bulls-eye coating (28 min BE) procedure with load with uniform suspension cell loading procedure (LWUS); the 28-minute bulls-eye coating (28 min BE) procedure with bulls-eye cell loading procedure (BullsEye); the 10-minute ultrafiltration coating procedure (10 min UF) with load with uniform suspension cell loading procedure (LWUS); and the 10-minute ultrafiltration coating procedure (10 min UF) with bulls-eye cell loading procedure (BullsEye). As shown in graph 1800 of FIG. 18A, the 28-minute bulls-eye coating procedure (28 min BE) with bulls-eye cell loading procedure (BullsEye) may yield 1.29×108 cells 1804, while the Overnight coating procedure with bulls-eye cell loading procedure (BullsEye) may yield 2.30×108 cells 1808. The Overnight coating procedure with load with uniform suspension cell loading procedure (LWUS) may yield 1×108 cells 1812, while the 28-minute bulls-eye coating procedure (28 min BE) with load with uniform suspension cell loading procedure (LWUS) may yield 9.57×107 cells 1816. A 10-minute ultrafiltration coating procedure (10 min UF) with a bulls-eye cell loading procedure (BullsEye) may result in 7.34× 107 cells 1820, while a 10-minute ultrafiltration procedure (10 min UF) with load with uniform suspension cell loading procedure (LWUS) may yield 7.54×107 cells 1824.

These example yields are compared in FIG. 18B. Graph 1826 of FIG. 18B illustrates a percentage difference versus control procedure using fibronectin (FN) as a coating agent using in various coating procedures and cell loading procedures, and combinations thereof. As shown in graph 1826 of FIG. 18B, compared to the Overnight coating procedure with load with uniform suspension cell loading procedure (LWUS) 1828, the Overnight coating procedure with bulls-eye cell loading procedure (BullsEye) may yield 21% 1832 more cells; the 28-minute bulls-eye coating procedure with load with uniform suspension cell loading procedure (LWUS) may yield 50% 1836 fewer cells; the 28-minute bulls-eye coating procedure (28 min BE) with bulls-eye cell loading procedure (BullsEye) may yield 32% 1840 fewer cells; the 10-minute ultrafiltration coating procedure (10 min) with load with uniform suspension cell loading procedure (LWUS) may yield 60% 1844 fewer cells; and the 10-minute ultrafiltration coating procedure (10 min) with bulls-eye cell loading procedure (BullsEye) may yield 61% 1848 fewer cells.

Example 5

Example results of expanding cells by coating a cell growth surface of a cell expansion system, such as CES 500 (FIG. 5) and/or CES 600 (FIG. 6), for example, with various coating procedures are illustrated in FIGS. 19A and 19B. For example, such cell growth surface coating and resulting cell expansion may use the QUANTUM® Cell Expansion System manufactured by Terumo BCT, Inc. in Lakewood, Colo. FIGS. 19A and 19B illustrate example results for coating a cell growth surface through a coating procedure with coating using an overnight circulating coating procedure versus a bulls-eye coating procedure, e.g., a 56-minute modified bulls-eye coating procedure (56 min BE). In such procedures, 5 million MSCs may be loaded into the system, and a 5 mg fibronectin (FN) solution may be used for coating the cell growth surface of a hollow fiber bioreactor. In an embodiment, such 5 mg FN solution may be circulated at 20 mL/minute. In the QUANTUM® System, such 5 mg FN solution may be circulated at 20 mL/minute in the 189 mL IC loop, according to an embodiment. The 56-minute bulls-eye coating (56 min BE) time period used to coat the hollow fibers, e.g., fibers 908 (FIG. 9), may be divided into seven (7) different time periods, each division being minutes (8) minutes long. During each 8-minute divisional time period, the circulation rate for the IC loop 502, 602 may be changed by adjusting the rate and/or direction of the circulation pump 512, 612. For example, the direction and/or circulation rate for the pump 512, 612 for each subsequent time division may be −300 mL/min, 250 mL/min, −200 mL/min, 150 mL/min, −100 mL/min, 50 mL/min, and −25 mL/min. The results from using these coating procedures with fibronectin (FN) may be as shown in FIGS. 19A and 19B.

FIGS. 19A and 19B illustrate example results of using FN to coat the cell growth surface of a plurality of hollow fibers using various coating and cell loading procedures, and combinations thereof.

The Overnight coating procedure with uniform suspension cell loading procedure (LWUS) may outperform the following: the 56-minute bulls-eye coating (56 min BE) procedure with uniform suspension cell loading procedure (LWUS) and the 56-minute bulls-eye coating procedure (56 min BE) with BullsEye loading procedure. As shown in graph 1900 of FIG. 19A, the 56-minute bulls-eye coating procedure (56 min BE) with bulls-eye cell loading procedure (BullsEye) may yield 1.58×108 cells 1904 in a first run and 1.59×108 cells 1908 in a second run. The 56-minute bulls-eye coating procedure (56 min BE) with uniform suspension cell loading (LWUS) may yield 1.38×108 cells 1912. The Overnight coating procedure with uniform suspension cell loading procedure (LWUS) may yield 2.75×108 cells 1916.

These example yields are compared in FIG. 19B. Graph 1920 of FIG. 19B illustrates a percentage difference versus control procedure using fibronectin (FN) as a coating agent using various coating procedures and cell loading procedures, and combinations thereof. As shown in graph 1920 of FIG. 19B, compared to the Overnight coating procedure with load with uniform suspension cell loading procedure (LWUS) 1924, the 56-minute bulls-eye coating procedure (56 min BE) with uniform suspension cell loading procedure (LWUS) may yield 50% 1928 fewer cells; the 56-minute bulls-eye coating procedure (56 min BE) with bulls-eye cell loading procedure (BullsEye) may yield 43% 1932 fewer cells in a first run, and 42% 1936 fewer cells in a second run.

Example 6

The objective of this study is to characterize the expansion of human bone marrow derived mesenchymal stem cells (hMSCs) using two unique cell seeding methodologies in the QUANTUM® cell expansion system.

The current cell loading procedure used on the QUANTUM cell expansion system for pre-selected hMSCs distributes the cells in the bioreactor via uniform cell suspension. The cells are loaded into the IC Circulation loop of the QUANTUM cell expansion system and then circulated at relatively high flow rates (200 mL/min) for two minutes. This circulation method, coinciding with deliberate bioreactor motion, results in a uniform suspension of cells. Once the cells are uniformly suspended, circulation and bioreactor motion stops and the cells settle onto the bioreactor surface.

One limitation of this cell loading procedure is that only the trough of the bioreactor fiber is seeded with cells. hMSCs are frequently seeded at a specified cell density (e.g., 500 cells/cm2). In order to achieve a specified seed density, only approximately 50% of the bioreactor surface area can be considered when determining the appropriate number of cells to load. At 500 cells/cm2, the QUANTUM cell expansion system bioreactor can be seeded with 10.5E+06 cells (500 cells/cm2×21000 cm2). However, only 50% of the bioreactor surface area can be considered "seed able" due to the aforementioned mechanics of the current cell load protocol. In addition, expanding cells attempting to migrate to the "unseedable" surface of the bioreactor must overcome gravity in order to utilize that surface. It is theorized here that migrating cells may take the path of least resistance; resulting in rapid confluence within the cell population compared to those expanded in its flask counter-part.

A total of seven sterilized QUANTUM CES Disposable sets with a bioreactor may be fibronectin coated (5 mg) overnight. All QUANTUM systems may be seeded with pre-cultured hMSCs. One QUANTUM cell expansion system may use the current Load with Circulation Task and serve as the experiment control. Three QUANTUM cell expansion systems may use "Load with Circulation Task: Modification 1" (Modification 1) and three QUANTUM cell expansion systems may use "Load with Circulation Task: Modification 2" (Modification 2).

Disposable Sets: All bioreactors may be integrated into a QUANTUM cell expansion system (CES) disposable set and sterilized with ethylene oxide.

Cell Source and Density: The bioreactor that may be used may have a 2.1 m2 inner (IC) surface area. As a result, an adjustment to seeding densities for control flasks may need to be made based on the bioreactor volume fraction of the IC loop. All bioreactors may be uniformly loaded with a maximum of 20E+06 pre-selected MSCs (existing passages 1-3) from a direct re-load of the same cell source. Cells from a single donor are preferred. Seed three (3) T25 control flasks with hMSCs at the same density per cm2 as the bioreactor for comparative purposes.

CES Media IC Input Q Management & Harvest: The media feed rate (IC Input Q) may be doubled when the glucose levels fall below 70 mg/dL; the IC Input Q may be doubled a second time in the course of one day if the glucose values continue to fall below 70 mg/dL. All disposable sets may be harvested at the same time and no later than Day 8 to limit potential aggregation. Cell harvest time may be determined as a result of the metabolic characteristics displayed by the cell cultures. The target harvest time may be post-log phase growth of the cells.

Post-Harvest Evaluation: Evaluations may be performed on each of the harvest products. These evaluations may include cell count and viability.

Quantum CES Cell Load Modification 1

The current cell load procedure may be performed with the following modifications shown in bold. After allowing the cells to attach for 5 minutes, all bioreactors may be rotated 180 degrees to allow unattached cells to settle to the top of the hollow fiber membrane for an additional 5 minutes. Then bioreactor may be rotated back to the home horizontal position and proceed with the expansion protocol. The rationale for the modification is to distribute the cells over the entire surface area of the bioreactor hollow fiber.

Day: 0 Attach Cells with One (1) Rotation

Purpose: enables adherent cells to attach to the bioreactor membrane while allowing flow on the EC circulation loop. The pump flow rate to the IC loop may be set to zero.

Table 34 describes the bags of solution that may be attached to each line when performing Attach Cells. These solutions and corresponding volumes are based on the default settings for this task.

TABLE 34

Solutions for Attach Cells Modification 1
Table 34: Solutions for Attach Cells
Table 34: Solutions for Attach Cells

| Bag | Solution in Bag | Volume (estimate based on factory default) |
|---|---|---|
| Cell Inlet | None | N/A |
| Reagent | None | N/A |
| IC Media | Media with Protein | 6 mL/hour |
| Wash | None | N/A |
| EC Media | None | N/A |

Cells pathway: Task>Load and Attach>Attach Cells

Enter the values for each setting for Attach Cells shown in Protocol Table 35-37.

TABLE 35

Task > Load and Attach > Attach Cells, Step 1 Modification 1
Table 35: Task Settings for Attach Cells, Step 1

| Setting | Factory Default | Laboratory Default | Modifications |
|---|---|---|---|
| IC Inlet | None | | |
| IC Inlet Rate | 0 | | |
| IC Circulation Rate | 0 | | |
| EC Inlet | EC Media | IC Media | |
| EC Inlet Rate | 0 | | |
| EC Circulation Rate | 0 | | |
| Outlet | EC Waste | | |
| Rocker Control | Stationary (0°) | | Stationary 180° |
| Stop Condition | Manual | | Time: 5 minutes |

TABLE 36

Task > Load and Attach > Attach Cells, Step 2 Modification 1
Table 36: Task Settings for Attach Cells, Step 2

| Setting | Factory Default | Laboratory Default | Modifications |
|---|---|---|---|
| IC Inlet | None | | |
| IC Inlet Rate | 0 | | |
| IC Circulation Rate | 0 | | |
| EC Inlet | EC Media | IC Media | |
| EC Inlet Rate | 0 | | |
| EC Circulation Rate | 0 | | |
| Outlet | EC Waste | | |
| Rocker Control | Stationary (0°) | | |
| Stop Condition | Manual | | Time: 5 minutes |

TABLE 37

Task > Load and Attach > Attach Cells, Step 3 Modification 1
Table 37: Task Settings for Attach Cells, Step 3

| Setting | Factory Default | Laboratory Default | Modifications |
|---|---|---|---|
| IC Inlet | None | | |
| IC Inlet Rate | 0 | | |
| IC Circulation Rate | 0 | | |
| EC Inlet | EC Media | IC Media | |
| EC Inlet Rate | 0.1 | | |
| EC Circulation Rate | 30 | | |
| Outlet | EC Waste | | |
| Rocker Control | Stationary (0°) | | Stationary 180° |
| Stop Condition | Manual | | |

Quantum CES Cell Load Modification 2

The current cell load procedure, pre-selected MSC Expansion Protocol, may be performed with the following modifications shown in bold. Cells may be attached to the top of the hollow fiber by rotating the bioreactor to the 180 degree position during the cell attachment phase (18-24 hours). Then rotate the bioreactor back to the home position and proceed with the expansion protocol. The rationale for the modification is to allow gravity to influence the direction of cell migration toward the empty growth surface during cell expansion.

The force of gravity may be used to "influence" the cell migration during expansion. This may be accomplished by seeding the cells as described in the current cell load procedure, then during expansion the bioreactor may be rotated 180°. In this configuration the unoccupied growth surface of the bioreactor is below the seeded cells. The cells may then expand in the direction of least resistance (e.g., downward, aided by gravity).

Day: 0 Attach Cells with One (1) Rotation

Purpose: enables adherent cells to attach to the bioreactor membrane while allowing flow on the EC circulation loop. The pump flow rate to the IC loop may be set to zero.

Table 38 describes the bags of solution that may be attached to each line when performing Attach Cells. These solutions and corresponding volumes are based on the default settings for this task.

TABLE 38

Solutions for Attach Cells Modification 2
Table 38: Solutions for Attach Cells

| Bag | Solution in Bag | Volume (estimate based on factory default) |
|---|---|---|
| Cell Inlet | None | N/A |
| Reagent | None | N/A |
| IC Media | Media with Protein | 6 mL/hour |
| Wash | None | N/A |
| EC Media | None | N/A |

Cells pathway: Task>Load and Attach>Attach Cells

TABLE 39

Task > Load and Attach > Attach Cells Modification 2
Table 39: Task Settings for Attach Cells, Step 1

| Setting | Factory Default | Laboratory Default | Modifications |
|---|---|---|---|
| IC Inlet | None | | |
| IC Inlet Rate | 0 | | |
| IC Circulation Rate | 0 | | |
| EC Inlet | EC Media | IC Media | |
| EC Inlet Rate | 0.1 | | |
| EC Circulation Rate | 30 | | |
| Outlet | EC Waste | | |
| Rocker Control | Stationary (0°) | | Stationary 180° |
| Stop Condition | Manual | | |

The results may be as follows:

TABLE 40

| Quantum Run | Modification | hMSC Seeding | hMSC Seeding//cm$^2$ | Harvest hMSC | Harvest hMSC/cm$^2$ | Percent Increase |
|---|---|---|---|---|---|---|
| Q621 | Control | 1.05E+07 | 500 | 2.56E+08 | 12,194 | 0% |
| Q622 | Mod 1 | 1.05E+07 | 500 | 3.02E+08 | 14,376 | 18% |
| Q623 | Mod 1 | 1.05E+07 | 500 | | | |
| Q624 | Mod 1 | 1.05E+07 | 500 | 3.49E+08 | 16,596 | 51% |

TABLE 41

| Quantum Run | Modification | hMSC Seeding | hMSC Seeding//cm² | Harvest hMSC | Harvest hMSC/cm² | Percent Increase |
|---|---|---|---|---|---|---|
| | Control | 1.05E+07 | 500 | 2.56E+08 | 12,194 | 0% |
| Average | Mod 1 | 1.05E+07 | 500 | 3.40E+08 | 16,197 | 35% |

TABLE 42

| Load Condition | # of Cells Seeded | # Cells Harvested | Doubling Time (hrs) |
|---|---|---|---|
| Control | $10.5 \times 10^6$ | $256 \times 10^6$ | 34.9 |
| Gravity Influenced Expansion (Modification 2) | $10.5 \times 10^6$ | $345 \times 10^6$ | 30.9 |
| Gravity Influenced Expansion (Modification 2) | $10.5 \times 10^6$ | $347 \times 10^6$ | 31.9 |
| Gravity Influenced Expansion (Modification 2) | $10.5 \times 10^6$ | $388 \times 10^6$ | 31.9 |

Example 7

The Bull's Eye cell loading procedure is a series of steps designed to increase cell yield by allowing for a more even distribution of cells within the bioreactor of the QUANTUM® cell expansion system and by reducing the number of cells lost during a seeding process.

The Bull's Eye cell loading technique for the QUANTUM cell expansion system provides a series of steps that include and add to the 'Load Cells with Uniform Suspension' protocol (QUANTUM Cell Expansion System Operator's Manual for Software Version 2.0) that is commonly used to seed the bioreactor. In Load Cells with Uniform Suspension (LCWUS), suspended cells have a single opportunity to enter and attach to the internal surface of one fiber of the bioreactor after the cell suspension is circulated through the IC loop at 200 mL/min. Bull's Eye may allow cells that do not attach after the initial suspension and those that may be left in the IC loop rather than in the bioreactor to be re-suspended and transported to a different fiber within the bioreactor for subsequent attachment.

The Bull's Eye load may operate on the principle that a cell suspension introduced to the bioreactor via circulation of the IC loop may pass through a different set of bioreactor fibers depending on the rate of circulation of that cell suspension in the IC loop.

Following an initial 200 mL/min suspension cycle in loading cells with uniform suspension (LCWUS), the cell suspension in the IC loop may be circulated alternately in the positive and negative directions at sequentially lower circulation rates: −100 mL/min, 50 mL/min, −25 mL/min. Each progressively slower cycle of the IC loop may allow those cells still left in suspension an additional opportunity to enter and attach to the inner surface of a bioreactor fiber.

Each cycling of the fluid in the IC loop may be followed by a 7-minute cell-attachment period during which the IC circulation rate may be zero. MSC cells have been demonstrated to attach within 5 minutes to the inner surface of a fiber in a bioreactor used in the QUANTUM cell expansion system. As such, the 7-minute attachment may allow for 5 minutes for cell attachment, and 2 extra minutes to allow for slower-attaching cells. The four total cycles of cell suspension and cell attachment in the IC loop may be followed by a 24 hr attachment period after which an appropriate cell feeding schedule may be input as desired.

Day: −1 Coat Bioreactor

Purpose: coats the bioreactor membrane with a reagent.

Step 1: loads a reagent into the IC loop until the bag is empty.

Step 2: chases the reagent from the ARC into the IC loop.

Step 3: circulates the reagent in the IC loop.

Before starting this task, the following preconditions may be satisfied:

Include at least 40 mL of air in the cell inlet bag.

Table 43 describes the bags of solution that may be used to attach to each line when performing Coat Bioreactor. These solutions and corresponding volumes may be based on the default settings for this task.

TABLE 43

Solutions for Coat Bioreactor

| Bag | Solution in Bag | Volume (estimation based on factory default values) |
|---|---|---|
| Cell Inlet | None | N/A |
| Reagent | Fibronectin | 5 mg Fibronectin in 100 mL PBS |
| IC Media | None | N/A |
| Wash | PBS | 0.1 L + 6 mL/hr (overnight) |
| EC Media | None | N/A |

Coat Bioreactor pathway: Task>System Management>Coat Bioreactor

Enter the values for each setting for step 1 shown in Table 44.

TABLE 44

Step 1 for Coat Bioreactor

| Setting | Factory Default | Laboratory Default | Modifications |
|---|---|---|---|
| IC Inlet | Reagent | | |
| IC Inlet Rate | 10 mL/min | | |
| IC Circulation Rate | 100 mL/min | | |
| EC Inlet | None | | |
| EC Inlet Rate | 0 mL/min | | |
| EC Circulation Rate | 30 mL/min | | |
| Outlet | EC Outlet | | |
| Rocker Control | Stationary (0°) | | |
| Stop Condition | Empty Bag | | |

Enter the values for each setting for step 2 shown in Table 45.

TABLE 45

Step 2 Setting for Coat Bioreactor

| Setting | Factory Default | Laboratory Default | Modifications |
|---|---|---|---|
| IC Inlet | Wash | | |
| IC Inlet Rate | 10 mL/min | | |
| IC Circulation Rate | 100 mL/min | | |
| EC Inlet | None | | |
| EC Inlet Rate | 0 mL/min | | |
| EC Circulation Rate | 30 mL/min | | |
| Outlet | EC Outlet | | |
| Rocker Control | Stationary (0°) | | |
| Stop Condition | IC Volume (22 mL) | | |

Enter the values for each setting for step 3 shown in Table 46.

TABLE 46

Step 3 Settings for Coat Bioreactor

| Setting | Factory Default | Laboratory Default | Modifications |
|---|---|---|---|
| IC Inlet | None | | |
| IC Inlet Rate | 0 mL/min | | |
| IC Circulation Rate | 20 mL/min | | |
| EC Inlet | Wash | | |
| EC Inlet Rate | 0.1 mL/min | | |
| EC Circulation Rate | 30 mL/min | | |
| Outlet | EC Outlet | | |
| Rocker Control | Stationary (0°) | | |
| Stop Condition | Manual | | |

Day: 0 IC EC Washout

Purpose: used to replace the fluid on both the IC circulation loop and the EC circulation loop. The replacement volume is specified by the number of IC Volumes and EC Volumes exchanged. Table 47 describes the bags of solution that may be attached to each line when performing IC EC Washout. These solutions and corresponding volumes may be based on the default settings for this task.

TABLE 47

Solutions for IC EC Washout

| Bag | Solution in Bag | Volume (estimation based on factory default values) |
|---|---|---|
| Cell Inlet | None | N/A |
| Reagent | None | N/A |
| IC Media | Media with Protein | 1.4 L |
| Wash | None | N/A |
| EC Media | None | N/A |

IC EC Washout pathway: Task>Washout>IC EC Washout

Confirm the values for each setting for IC EC Washout shown in Table 48.

TABLE 48

Task Settings for IC EC Washout

| Setting | Factory Default | Laboratory Default | Modifications |
|---|---|---|---|
| IC Inlet | IC Media | | |
| IC Inlet Rate | 100 mL/min | | |
| IC Circulation Rate | −17 mL/min | | |
| EC Inlet | EC Media | IC Media | |
| EC Inlet Rate | 148 mL/min | | |
| EC Circulation Rate | −1.7 mL/min | | |
| Outlet | IC and EC Outlet | | |
| Rocker Control | In Motion (−90°, 180°, 1 sec) | | |
| Stop Condition | Exchange (2.5 IC Volumes) (2.5 EC Volumes) | | |

Day: 0 Condition Media

Follow the instructions in this task to allow the media to reach equilibrium with the provided gas supply before loading the cells. This task may include two separate steps:

Step 1: provides rapid contact between the media and the gas supply by using a high EC circulation rate.

Step 2: maintains the system in a proper state until the operator is ready to load the cells.

Table 49 describes the bags of solution that may be attached to each line when performing Condition Media. These solutions and corresponding volumes may be based on the default settings for this task.

TABLE 49

Solutions for Condition Media

| Line | Solution in Bag | Volume (estimation based on factory default values) |
|---|---|---|
| Cell Inlet | None | N/A |
| Reagent | None | N/A |
| IC Media | None | N/A |
| Wash | None | N/A |
| EC Media | Media without Protein | 0.1 L plus 6 mL/hour |

Condition Media pathway: Task>System Management>Condition Media

Enter the values for each setting for step 1 shown in Table 50.

TABLE 50

Step 1 Settings for Condition Media

| Setting | Factory Default | Laboratory Default | Modifications |
|---|---|---|---|
| IC Inlet | None | | |
| IC Inlet Rate | 0 mL/min | | |
| IC Circulation Rate | 100 mL/min | | |
| EC Inlet | EC Media | IC Media | |
| EC Inlet Rate | 0.1 mL/min | | |
| EC Circulation Rate | 250 mL/min | | |
| Outlet | EC Outlet | | |
| Rocker Control | Stationary (0°) | | |
| Stop Condition | Time (10 min) | | |

Enter the values for each setting for step 2 shown in Table 51.

TABLE 51

Step 2 Settings for Condition Media

| Setting | Factory Default | Laboratory Default | Modifications |
|---|---|---|---|
| IC Inlet | None | | |
| IC Inlet Rate | 0 mL/min | | |
| IC Circulation Rate | 100 mL/min | | |
| EC Inlet | EC Media | IC Media | |
| EC Inlet Rate | 0.1 mL/min | | |
| EC Circulation Rate | 30 mL/min | | |
| Outlet | EC Outlet | | |
| Rocker Control | Stationary (0°) | | |
| Stop Condition | Manual | | |

Day: 0 Load Cells with Uniform Suspension

Purpose: loads the cells into the bioreactor from the cell inlet bag until the bag is empty. This task only uses IC circulation to distribute the cells and does not attempt to chase the cells from the line into the bioreactor. This task may include three separate steps.

Step 1: loads the cells from the cell inlet bag into the bioreactor.

Step 2: chases the cells from the ARC to the bioreactor. Larger chase volumes spread the cells and move them towards the IC outlet.

Step 3: promotes distribution of cells across membrane via IC circulation and no IC inlet thus no ultrafiltration.

Before starting this task, the following preconditions may be satisfied:

Include at least 40 mL of air in the cell inlet bag.

Table 52 describes the bags of solution that may be attached to each line when performing Load Cells With Uniform Suspension. These solutions and corresponding volumes may be based on the default settings for this task.

TABLE 52

Solutions for Load Cells With Uniform Suspension

| Line | Solution in Bag | Volume (estimation based on factory default values) |
|---|---|---|
| Cell Inlet | Cells | N/A |
| Reagent | None | N/A |
| IC Media | Media with Protein | 0.2 L |
| Wash | None | N/A |
| EC Media | None | N/A |

Load Cells with Uniform suspension pathway: Task>Load and Attach>Load Cells with Uniform Suspension Confirm the values for each setting for step 1 shown in Table 53.

TABLE 53

Step 1 Settings for Load Cells With Uniform Suspension

| Setting | Factory Default | Laboratory Default | Modifications |
|---|---|---|---|
| IC Inlet | Cell | | |
| IC Inlet Rate | 50 mL/min | | 25 mL/min |
| IC Circulation Rate | 200 mL/min | | 150 mL/min |
| EC Inlet | None | | |
| EC Inlet Rate | 0 mL/min | | |

TABLE 53-continued

Step 1 Settings for Load Cells With Uniform Suspension

| Setting | Factory Default | Laboratory Default | Modifications |
|---|---|---|---|
| EC Circulation Rate | 30 mL/min | | |
| Outlet | EC Outlet | | |
| Rocker Control | In Motion (−90°, 180°, 1 sec) | | |
| Stop Condition | Empty Bag | | |

Confirm the values for each setting for step 2 shown in Table 54.

TABLE 54

Step 2 Settings for Load Cells with Uniform Suspension

| Setting | Factory Default | Laboratory Default | Modifications |
|---|---|---|---|
| IC Inlet | IC Media | | |
| IC Inlet Rate | 50 mL/min | | 25 mL/min |
| IC Circulation Rate | 200 mL/min | | 150 mL/min |
| EC Inlet | None | | |
| EC Inlet Rate | 0 mL/min | | |
| EC Circulation Rate | 30 mL/min | | |
| Outlet | EC Outlet | | |
| Rocker Control | In Motion (−90°, 180°, 1 sec) | | |
| Stop Condition | IC Volume (22 mL) | | |

Confirm the values for each setting for step 3 shown in Table 55.

TABLE 55

Step 3 Settings for Load Cells with Uniform Suspension

| Setting | Factory Default | Laboratory Default | Modifications |
|---|---|---|---|
| IC Inlet | None | | |
| IC Inlet Rate | 0 mL/min | | |
| IC Circulation Rate | 200 mL/min | | |
| EC Inlet | None | | |
| EC Inlet Rate | 0 mL/min | | |
| EC Circulation Rate | 30 mL/min | | |
| Outlet | EC Outlet | | |
| Rocker Control | In Motion (−90°, 180°, 1 sec) | | |
| Stop Condition | Time (2.0 min) | | |

Day: 0 Bull's Eye Attachment

Purpose: allows adherent cells to attach to the bioreactor membrane while allowing flow on the EC circulation loop. The pump flow rate to the IC loop may be set to zero.

Step 1: Allows cells 7 minutes to attach to the inner surface of the bioreactor at 180°.

Step 2: Circulates the IC fluid and the remaining suspended cells at a high rate in a direction opposite to the initial load.

Step 3: This step is a second 7.0 minute allowance for further cell attachment. Those cells that were relocated from the IC loop or from a different region of the bioreactor will be given a chance to settle and adhere to the bioreactor.

Step 4: Again re-circulates those cells remaining in the IC loop and those cells that have yet to attach to a surface.

Circulation may be in the positive direction and the circulation rate may be lower this time to avoid removing those cells that have already attached and to seed preferentially regions of the bioreactor that may not have been seeded in previous steps.

Step 5: This step is a third 7.0 minute allowance for further cell attachment. Those cells that were relocated from the IC loop or from a different region of the bioreactor will be given a chance to settle and adhere to the bioreactor.

Step 6: re-circulates those cells remaining in the IC loop and those cells that have yet to attach to a surface. Circulation may be in the negative direction and the circulation rate is lower this time to avoid removing those cells that have already attached.

Step 7: 24 hour attach cells phase. Cells may have 24 hours to anchor solidly to the bioreactor before feeding begins.

Table 56 describes the bags of solution that may be attached to each line when performing Bull's Eye Attachment. These solutions and corresponding volumes may be based on the default settings for this task.

TABLE 56

Solutions for Bull's Eye Attachment

| Bag | Solution in Bag | Volume (estimation based on factory default values) |
|---|---|---|
| Cell Inlet | None | N/A |
| Reagent | None | N/A |
| IC Media | Media with Protein | 6 mL/hour |
| Wash | None | N/A |
| EC Media | None | N/A |

Bull's Eye attachment Cells pathway: Task>Custom>Custom

Enter the values for each setting shown in Table 57.

TABLE 57

Step 1 Task Settings for Bull's Eye Attachment

| Setting | Factory Default | Laboratory Default | Modifications |
|---|---|---|---|
| IC Inlet | None | | |
| IC Inlet Rate | 0 mL/min | | |
| IC Circulation Rate | 0 mL/min | | |
| EC Inlet | EC Media | | |
| EC Inlet Rate | 0.1 mL/min | | |
| EC Circulation Rate | 30 mL/min | | |
| Outlet | EC Outlet | | |
| Rocker Control | Stationary (0°) | Stationary (180°) | |
| Stop Condition | Time (7.0 min) | | |

Enter the values for each setting shown in Table 58.

TABLE 58

Step 2 Task Settings for Bull's Eye Attachment

| Setting | Factory Default | Laboratory Default | Modifications |
|---|---|---|---|
| IC Inlet | None | | |
| IC Inlet Rate | 0 mL/min | | |
| IC Circulation Rate | 0 mL/min | | −100 mL/min |
| EC Inlet | None | | |
| EC Inlet Rate | 0 mL/min | | |
| EC Circulation Rate | 0 mL/min | | 30 mL/min |
| Outlet | EC Outlet | | |
| Rocker Control | Stationary | | In Motion (−90°, 180°, 1 sec) |
| Stop Condition | Manual | | Time (2.0 min) |

Enter the values for each setting shown in Table 59.

TABLE 59

Step 3 Task Settings for Bull's Eye Attachment

| Setting | Factory Default | Laboratory Default | Modifications |
|---|---|---|---|
| IC Inlet | None | | |
| IC Inlet Rate | 0 mL/min | | |
| IC Circulation Rate | 0 mL/min | | |
| EC Inlet | EC Media | IC Media | |
| EC Inlet Rate | 0.1 mL/min | | |
| EC Circulation Rate | 30 mL/min | | |
| Outlet | EC Outlet | | |
| Rocker Control | Stationary (0°) | | |
| Stop Condition | Time (7.0 min) | | |

Enter the values for each setting shown in Table 60.

TABLE 60

Step 4 Task Settings for Bull's Eye Attachment

| Setting | Factory Default | Laboratory Default | Modifications |
|---|---|---|---|
| IC Inlet | None | | |
| IC Inlet Rate | 0 mL/min | | |
| IC Circulation Rate | 0 mL/min | | 50 mL/min |
| EC Inlet | None | | |
| EC Inlet Rate | 0 mL/min | | |
| EC Circulation Rate | 0 mL/min | | 30 mL/min |
| Outlet | EC Outlet | | |
| Rocker Control | Stationary | | In Motion (−90°, 180°, 1 sec) |
| Stop Condition | Manual | | Time (4.0 min) |

Enter the values for each setting shown in Table 61.

TABLE 61

Step 5 Task Settings for Bull's Eye Attachment

| Setting | Factory Default | Laboratory Default | Modifications |
|---|---|---|---|
| IC Inlet | None | | |
| IC Inlet Rate | 0 mL/min | | |
| IC Circulation Rate | 0 mL/min | | |
| EC Inlet | EC Media | | |
| EC Inlet Rate | 0.1 mL/min | | |
| EC Circulation Rate | 30 mL/min | | |

TABLE 61-continued

Step 5 Task Settings for Bull's Eye Attachment

| Setting | Factory Default | Laboratory Default | Modifications |
|---|---|---|---|
| Outlet | EC Outlet | | |
| Rocker Control | Stationary (0°) | | |
| Stop Condition | Time (7.0 min) | | |

Enter the values for each setting shown in Table 62.

TABLE 62

Step 6 Task Settings for Bull's Eye Attachment

| Setting | Factory Default | Laboratory Default | Modifications |
|---|---|---|---|
| IC Inlet | None | | |
| IC Inlet Rate | 0 mL/min | | |
| IC Circulation Rate | 0 mL/min | | −25 mL/min |
| EC Inlet | None | | |
| EC Inlet Rate | 0 mL/min | | |
| EC Circulation Rate | 0 mL/min | | 30 mL/min |
| Outlet | EC Outlet | | |
| Rocker Control | Stationary | | In Motion (−90°, 180°, 1 sec) |
| Stop Condition | Manual | | Time (8.0 min) |

Enter the values for each setting shown in Table 63.

TABLE 63

Task Settings for Bull's Eye Attachment

| Setting | Factory Default | Laboratory Default | Modifications |
|---|---|---|---|
| IC Inlet | None | | |
| IC Inlet Rate | 0 mL/min | | |
| IC Circulation Rate | 0 mL/min | | |
| EC Inlet | EC Media | IC Media | |
| EC Inlet Rate | 0.1 mL/min | | |
| EC Circulation Rate | 30 mL/min | | |
| Outlet | EC Outlet | | |
| Rocker Control | Stationary (0°) | | |
| Stop Condition | Manual | | Time (1440.0 min) |

Day: 1 Feed Cells

Purpose: continuously adds a low flow rate to the IC circulation loop and/or the EC circulation loop. There are several outlet settings that can be used to remove the fluid added to the system during this task.

Table 64 describes the bags of solution that may be attached to each line when performing Feed Cells. These solutions and corresponding volumes may be based on the default settings for this task.

TABLE 64

Solutions for Feed Cells

| Bag | Solution in Bag | Volume (estimation based on factory default values) |
|---|---|---|
| Cell Inlet | None | N/A |
| Reagent | None | N/A |
| IC Media | Media with Protein | 6 mL/hour |

TABLE 64-continued

Solutions for Feed Cells

| Bag | Solution in Bag | Volume (estimation based on factory default values) |
|---|---|---|
| Wash | None | N/A |
| EC Media | None | N/A |

Confirm the values for each setting for step 1 for shown in Table 65.

TABLE 65

Task Settings for Feed Cells

| Setting | Factory Default | Laboratory Default | Modifications |
|---|---|---|---|
| IC Inlet | IC Media | | |
| IC Inlet Rate | 0.1 mL/min | | |
| IC Circulation Rate | 20 mL/min | | |
| EC Inlet | None | | |
| EC Inlet Rate | 0 mL/min | | |
| EC Circulation Rate | 30 mL/min | | |
| Outlet | IC Outlet | | |
| Rocker Control | Stationary (0°) | | |
| Stop Condition | Manual | | |

Increase IC Inlet rate as needed.

Release Adherent Cells And Harvest

Purpose: releases cells from the membrane, leaving the cells in the IC loop and transfers cells in suspension from the IC circulation loop, including cells in the bioreactor, into the harvest bag.

Step 1: performs the IC EC Washout task in preparation for adding a reagent. For example, the system replaces IC EC media with PBS to remove protein, Ca++, and Mg++ in preparation for adding trypsin.

Step 2: loads a reagent into the system until the bag is empty.

Step 3: chases the reagent into the IC loop.

Step 4: mixes the reagent within the IC loop.

Step 5: transfers cells in suspension from the IC circulation loop, including cells in the bioreactor, to the harvest bag.

Before starting this task, the following preconditions may be satisfied:

Include at least 40 mL of air on the cell inlet bag.

Table 66 describes the bags of solution that may be attached to each line when performing Release Adherent Cells And Harvest. These solutions and corresponding volumes may be based on the default settings for this task.

TABLE 66

Solutions for Release Adherent Cells And Harvest

| Bag | Solution in Bag | Volume (estimation based on factory default values) |
|---|---|---|
| Cell Inlet | None | N/A |
| Reagent | Trypsin | 180 mL |
| IC Media | Media with Protein | 0.6 L |
| Wash | PBS | 1.4 L |
| EC Media | None | N/A |

Release Adherent Cells pathway: Task>Release and Harvest>Release Adherent Cells And Harvest Confirm the values for each setting for step 1 shown in Table 67.

TABLE 67

Step 1 Settings for Release Adherent Cells And Harvest

| Setting | Factory Default | Laboratory Default | Modifications |
|---|---|---|---|
| IC Inlet | Wash | | |
| IC Inlet Rate | 100 mL/min | | |
| IC Circulation Rate | −17 mL/min | | |
| EC Inlet | Wash | | |
| EC Inlet Rate | 148 mL/min | | |
| EC Circulation Rate | −1.7 mL/min | | |
| Outlet | IC and EC Outlet | | |
| Rocker Control | In Motion (−90°, 180°, 1 sec) | | |
| Stop Condition | Exchange (2.5 IC Volumes) (2.5 EC Volumes) | | |

Confirm the values for each setting for step 2 shown in Table 68.

TABLE 68

Step 2 Settings for Release Adherent Cells And Harvest

| Setting | Factory Default | Laboratory Default | Modifications |
|---|---|---|---|
| IC Inlet | Reagent | | |
| IC Inlet Rate | 50 mL/min | | |
| IC Circulation Rate | 300 mL/min | | |
| EC Inlet | None | | |
| EC Inlet Rate | 0 mL/min | | |
| EC Circulation Rate | 30 mL/min | | |
| Outlet | EC Outlet | | |
| Rocker Control | In Motion (−90°, 180°, 1 sec) | | |
| Stop Condition | Empty Bag | | |

Confirm the values for each setting for step 3 shown in Table 69.

TABLE 69

Step 3 Settings for Release Adherent Cells And Harvest

| Setting | Factory Default | Laboratory Default | Modifications |
|---|---|---|---|
| IC Inlet | Wash | | |
| IC Inlet Rate | 50 mL/min | | |
| C Circulation Rate | 300 mL/min | | |
| EC Inlet | None | | |
| EC Inlet Rate | 0 mL/min | | |
| EC Circulation Rate | 30 mL/min | | |

TABLE 69-continued

Step 3 Settings for Release Adherent Cells And Harvest

| Setting | Factory Default | Laboratory Default | Modifications |
|---|---|---|---|
| Outlet | EC Outlet | | |
| Rocker Control | In Motion (−90°, 180°, 1 sec) | | |
| Stop Condition | IC Volume (22 mL) | | |

Confirm the values for each setting for step 4 shown in Table 70.

TABLE 70

Step 4 Settings for Release Adherent Cells And Harvest

| Setting | Factory Default | Laboratory Default | Modifications |
|---|---|---|---|
| IC Inlet | None | | |
| IC Inlet Rate | 0 mL/min | | |
| IC Circulation Rate | 300 mL/min | | |
| EC Inlet | None | | |
| EC Inlet Rate | 0 mL/min | | |
| EC Circulation Rate | 30 mL/min | | |
| Outlet | EC Outlet | | |
| Rocker Control | In Motion (−90°, 180°, 1 sec) | | |
| Stop Condition | Time (4 min) | | |

Confirm the values for each setting for step 5 shown in Table 71.

TABLE 71

Step 5 Settings for Release Adherent Cells And Harvest

| Setting | Factory Default | Laboratory Default | Modifications |
|---|---|---|---|
| IC Inlet | IC Media | | |
| IC Inlet Rate | 400 mL/min | | |
| IC Circulation Rate | −70 mL/min | | |
| EC Inlet | EC Media | IC Media | |
| EC Inlet Rate | 60 mL/min | | |
| EC Circulation Rate | 30 mL/min | | |
| Outlet | Harvest | | |
| Rocker Control | In Motion (−90°, 180°, 1 sec) | | |
| Stop Condition | IC Volume (378 mL) | | |

The results of the study may be as follows:

TABLE 72

| Load | Time (days) | #Cells Loaded | #Cells Harvested | Viability | Agg (0-5) | 69% Adjusted Doubling Time (Hrs) | Un-adjusted Doubling Time (Hrs) | Mean Flask Doubling Time (Hrs) |
|---|---|---|---|---|---|---|---|---|
| BullsEye | 4.8 | 1.52E+06 | 1.97E+08 | 98.1% | 2 | 27.2 | 31.2 | 24.1 |
| BullsEye | 4.8 | 1.52E+06 | 2.05E+08 | 98.0% | 2 | 26.8 | 30.7 | 24.1 |
| BullsEye | 4.8 | .52E+06 | 2.01E+08 | 99.3% | 2 | 27.1 | 31.0 | 24.1 |
| Control | 4.8 | 1.52E+06 | 1.38E+08 | 99.3% | 2 | 31.0 | 36.2 | 24.1 |

The Bull's Eye load may be evaluated using MSC from four different donors. Yields from Bull's Eye loaded harvests may be consistently higher than the yields loaded using LCWUS and cultured under identical conditions. The mean cell yield increase using Bull's Eye (n=6) vs. LCWUS (n=4) may be 25%.

Viability of MSC samples from the IC loop taken immediately after performing the Bull's Eye load may be 100%. Viability of MSC from Bull's Eye harvests may be over 98% for all samples. MSC from Bull's Eye harvests may display typical morphology in culture, and all MSC biomarkers measured by flow cytometry may conform to ISCT standards.

Example 8

The same protocol as described above with respect to EXAMPLE 7 may be used to study modifications to the Bulls Eye attachment protocol. The modifications to the Bulls Eye attachment (Bulls Eye II), and to the protocol described above, include eliminating the attachments phases after the circulation rates: 100 ml/min; −50 ml/min; and 25 ml/min. That is, instead of having 7 minute stop conditions as described above, there is no stop condition so that the next circulation rate follows the previous circulation rate. A control, as well as an original Bulls Eye run (Bulls Eye I) may also be performed as a comparison.

The results of this study may be as follows:

TABLE 73

| Load | Time (days) | #Cells Loaded | #Cells Harvested | Viability | Agg (0-5) | 69% Adjusted Doubling Time (Hrs) | Un-adjusted Doubling Time (Hrs) | Mean Flask Doubling Time (Hrs) |
|---|---|---|---|---|---|---|---|---|
| BullsEye I | 4.9 | 1.52E+07 | 2.60E+08 | 99.2% | 0 | 25.4 | 28.7 | 26.0 (500 cells/cm2) |
| Control | 4.9 | 1.52E+07 | 1.94E+08 | 97.5% | 1 | 27.9 | 32.0 | 5.5 (345 cells/cm2) |
| BullsEye II | 4.9 | 1.52E+07 | 2.10E+08 | 98.1% | 1 | 27.2 | 31.1 | ? |
| BullsEye II | 4.9 | 1.52E+07 | 2.07E+08 | 98.7% | 1 | 27.3 | 31.2 | ? |

It will be apparent to those skilled in the art that various modifications and variations can be made to the methods and structure of the present invention without departing from its scope. Thus it should be understood that the present invention is not be limited to the specific examples given. Rather, the present invention is intended to cover modifications and variations within the scope of the following claims and their equivalents.

As used herein, "at least one," "one or more," and "and/or" are open-ended expressions that are both conjunctive and disjunctive in operation. For example, each of the expressions "at least one of A, B and C," "at least one of A, B, or C," "one or more of A, B, and C," "one or more of A, B, or C" and "A, B, and/or C" can mean A alone, B alone, C alone, A and B together, A and C together, B and C together, or A, B and C together.

While example embodiments and applications of the present invention have been illustrated and described, it is to be understood that the invention is not limited to the precise configuration and resources described above. Various modifications, changes, and variations apparent to those skilled in the art may be made in the arrangement, operation, and details of the methods and systems of the present invention disclosed herein without departing from the scope of the present invention.

What is claimed is:

1. A system for growing cells, the system comprising:
a bioreactor comprising a hollow fiber membrane with a plurality of hollow fibers;
a first pump;
a second pump;
a processor; and
a memory including processor executable instructions that when executed by the processor perform the steps of:
activating the first pump to introduce a first fluid into the bioreactor, and while introducing the first fluid into the bioreactor:
activating the second pump to circulate a second fluid at a first flow rate through the bioreactor, wherein the second fluid comprises a reagent, wherein the first fluid promotes coating of the bioreactor with the reagent;
while circulating the second fluid, maintaining the bioreactor in a first orientation for a first period of time to allow at least a first portion of the reagent to coat the bioreactor by ultrafiltration; and
after the first period of time, changing the flow rate of the second pump to circulate the second fluid at a second flow rate slower than the first flow rate through the bioreactor for a second period of time to allow a second portion of the reagent to coat the bioreactor by ultrafiltration;

stopping the first pump; and activating the second pump to circulate a third fluid through the bioreactor to remove a portion of the reagent not coated on the bioreactor.

2. The system of claim 1, further comprising a rocking device including a motor for rotating the bioreactor from the first orientation to a second orientation.

3. The system of claim 2, wherein the first orientation is about 180 degrees from the second orientation.

4. The system of claim 2, wherein the memory includes processor executable instructions that when executed by the processor cause the rocking device to rotate the bioreactor from the first orientation to the second orientation after the first period of time and before circulating the second fluid at the second flow rate.

5. The system of claim 1, wherein the second fluid at the second flow rate travels in a direction opposite to a direction of the second fluid at the first flow rate within the bioreactor.

6. The system of claim 1, wherein the first and second portions of the reagent are coated on an intracapillary surface of the hollow fibers.

7. The system of claim 1, wherein the first and second portions of the reagent are coated on an extracapillary surface of the hollow fibers.

8. The system of claim 1, wherein a direction of ultrafiltration is based on a cell growth surface of the bioreactor on which cells are grown.

9. The system of claim 1, wherein the memory includes processor executable instructions that when executed by the processor activate the second pump to load cells into the bioreactor.

10. The system of claim 6, wherein the first and second portions of the reagent aid attachment of the cells to the hollow fibers.

11. The system of claim 7, wherein the memory includes processor executable instructions that when executed by the processor activate the second pump to feed the cells.

12. A system for growing cells, the system comprising:
a bioreactor comprising a hollow fiber membrane with a plurality of hollow fibers;
a first pump;
a second pump;
processing circuitry configured to:
activate the first pump to introduce a first fluid into the bioreactor;
activate the second pump to circulate a second fluid at a first flow rate through the bioreactor, wherein the second fluid comprises a reagent, wherein the first fluid promotes coating of the bioreactor with the reagent;
while circulating the second fluid, maintain the bioreactor in a first orientation for a first period of time to allow at least a first portion of the reagent to coat the bioreactor by ultrafiltration;
after the first period of time, change the flow rate of the second pump to circulate the second fluid at a second flow rate slower than the first flow rate through the bioreactor for a second period of time to allow a second portion of the reagent to coat the bioreactor by ultrafiltration;
stop the first pump; and
activate the second pump to circulate a third fluid through the bioreactor to remove a portion of the reagent not coated on the bioreactor.

13. The system of claim 12, further comprising a rocking device including a motor for rotating the bioreactor from the first orientation to a second orientation.

14. The system of claim 13, wherein the first orientation is about 180 degrees from the second orientation.

15. The system of claim 13, wherein the processing circuitry is configured to control the rocking device to rotate the bioreactor from the first orientation to the second orientation after the first period of time and before circulating the second fluid at the second flow rate.

16. The system of claim 12, wherein the second fluid at the second flow rate travels in a direction opposite to a direction of the second fluid at the first flow rate within the bioreactor.

17. The system of claim 12, wherein the first and second portions of the reagent are coated on an intracapillary surface of the hollow fibers.

18. The system of claim 12, wherein the first and second portions of the reagent are coated on an extracapillary surface of the hollow fibers.

* * * * *